US012344662B2

(12) United States Patent
Sentman et al.

(10) Patent No.: US 12,344,662 B2
(45) **Date of Patent: *Jul. 1, 2025**

(54) CHIMERIC ANTIGEN RECEPTORS FOR TREATMENT OF NEURODEGENERATIVE DISEASES AND DISORDERS

(71) Applicant: THE TRUSTEES OF DARTMOUTH COLLEGE, Hanover, NH (US)

(72) Inventors: Charles Sentman, Grantham, NH (US); David Graber, Hanover, NH (US); W. James Cook, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 1307 days.

This patent is subject to a terminal disclaimer.

(21) Appl. No.: 16/968,451

(22) PCT Filed: Feb. 11, 2019

(86) PCT No.: PCT/US2019/017489

§ 371 (c)(1),
(2) Date: Aug. 7, 2020

(87) PCT Pub. No.: WO2019/157440

PCT Pub. Date: Aug. 15, 2019

(65) Prior Publication Data

US 2020/0399354 A1 Dec. 24, 2020

Related U.S. Application Data

(60) Provisional application No. 62/628,632, filed on Feb. 9, 2018.

(51) Int. Cl.

| | |
|---|---|
| ***C07K 16/18*** | (2006.01) |
| ***A61K 40/11*** | (2025.01) |
| ***A61K 40/22*** | (2025.01) |
| ***A61K 40/31*** | (2025.01) |
| ***A61K 40/41*** | (2025.01) |
| ***A61P 25/16*** | (2006.01) |
| ***A61P 25/28*** | (2006.01) |
| ***C07K 14/705*** | (2006.01) |
| ***C07K 14/725*** | (2006.01) |
| ***C12N 5/0783*** | (2010.01) |

(52) U.S. Cl.

CPC .............. *C07K 16/18* (2013.01); *A61K 40/11* (2025.01); *A61K 40/22* (2025.01); *A61K 40/31* (2025.01); *A61K 40/414* (2025.01); *A61K 40/416* (2025.01); *A61P 25/16* (2018.01); *A61P 25/28* (2018.01); *C07K 14/7051* (2013.01); *C07K 14/70521* (2013.01); *C12N 5/0637* (2013.01); *C07K 2317/622* (2013.01); *C07K 2319/03* (2013.01)

(58) Field of Classification Search

CPC ................ C07K 16/18; C07K 14/7051; C07K 14/70521; C07K 2317/622; C07K 2319/03; A61K 35/17; A61P 25/16; A61P 25/28; C12N 5/0637

See application file for complete search history.

(56) References Cited

U.S. PATENT DOCUMENTS

| | | | |
|---|---|---|---|
| 2010/0135974 A1 | 6/2010 | Eshhar et al. | |
| 2017/0137783 A1* | 5/2017 | Bedoya .............. | A61K 2239/59 |
| 2017/0274095 A1 | 9/2017 | Meyer et al. | |
| 2018/0186855 A1 | 7/2018 | Rosenthal | |

FOREIGN PATENT DOCUMENTS

| | | | |
|---|---|---|---|
| JP | 2015513394 | 5/2015 | |
| WO | 2016/106198 | 6/2016 | |
| WO | 2017/058752 | 4/2017 | |
| WO | WO-2017075119 A1 * | 5/2017 | ........... A61K 39/395 |

OTHER PUBLICATIONS

Schwartz, M., "Can immunotherapy treat neurodegeneration?" Science 357(6348): 254-255. doi: 10.1126/science.aai8231. (Year: 2017).*

Armstrong, R., "What causes neurodegenerative disease?," Folia Neuropathol 58(2): 93-112. doi: 10.5114/fn.2020.96707. (Year: 2020).*

Calabrese, G., et al., "Protein interaction networks in neurodegenerative diseases: From physiological function to aggregation," J Biol Chem 298(7): 102062. doi: 10.1016/j.jbc.2022.102062. (Year: 2022).*

Marchetti, L., and Engelhardt, B., "Immune cell trafficking across the blood-brain barrier in the absence and presence of neuroinflammation," Vasc Biol 2(1): H1-H8. doi: 10.1530/VB-19-0033. (Year: 2020).*

Dawson, Nicholas A J, and Megan K Levings. "Antigen-specific regulatory T cells: are police CARs the answer?." Translational research : the journal of laboratory and clinical medicine vol. 187 (2017): 53-58. doi:10.1016/j.trsl.2017.06.009.

Gonzalez et al. "T-cell-mediated regulation of neuroinflammation involved in neurodegenerative diseases." Journal of neuroinflammation. Dec. 1, 2014 ;11 (1 ):201.

(Continued)

*Primary Examiner* — Tracy Vivlemore
*Assistant Examiner* — Eric J Rogers
(74) *Attorney, Agent, or Firm* — Robin L. Teskin; Baker, Donelson, Bearman, Caldwell & Berkowitz PC

(57) ABSTRACT

The present disclosure generally relates to novel chimeric antigen receptors ("CARs"), modified regulatory T cells ("Tregs") expressing such CARs and/or Tregs which are engineered to express neurodegenerative disease modifying molecules, e.g., which express molecules which prevent oxidative/inflammatory activity, or which promote neuronal growth/survival such as nerve growth factors or non-classical neurotrophic factors. The present disclosure also generally relates to compositions containing such modified Tregs, and methods of use thereof as therapeutics, in particular for treating and preventing neurodegenerative diseases and symptoms associated with therewith, and/or for slowing the onset of such neurodegenerative diseases, particularly in persons at risk because of genetic factors or in persons exhibiting early signs of developing such a neurodegenerative disease.

19 Claims, 23 Drawing Sheets

Specification includes a Sequence Listing.

(56) References Cited

OTHER PUBLICATIONS

Fransson, Moa et al. "CAR/FoxP3-engineered T regulatory cells target the CNS and suppress EAE upon intranasal delivery." Journal of neuroinflammation vol. 9 112. May 30, 2012, doi:10.1186/1742-2094-9-112.
Fymat A., "Immunotherapy of brain cancers and neurological disorders", J Cancer Prev Curr Res. 2017;8(6):395-400.

* cited by examiner

Pre-Transduction

Post-Transduction

Pre-tCD19 Sort

Post-Transduction

Post-tCD19 Sort

SEQUENCE LISTING

<160> NUMBER OF SEQ ID NOS: 260

<210> SEQ ID NO 1
<211> LENGTH: 266
<212> TYPE: PRT
<213> ORGANISM: Artificial Sequence
<220> FEATURE:
<223> OTHER INFORMATION: DG01 SCFV

<400> SEQUENCE: 1

Met Glu Trp Thr Trp Val Phe Leu Phe Leu Leu Ser Val Thr Ala Gly
1 5 10 15

Val His Ser Gln Val Gln Leu Val Glu Ser Gly Gly Gly Val Val Gln
20 25 30

Pro Gly Arg Ser Leu Arg Leu Ser Cys Ala Ala Ser Gly Phe Ala Phe
35 40 45

Ser Ser Tyr Gly Met His Trp Val Arg Gln Ala Pro Gly Lys Gly Leu
50 55 60

Glu Trp Val Ala Val Ile Trp Phe Asp Gly Thr Lys Lys Tyr Tyr Thr
65 70 75 80

Asp Ser Val Lys Gly Arg Phe Thr Ile Ser Arg Asp Asn Ser Lys Asn
85 90 95

Thr Leu Tyr Leu Gln Met Asn Thr Leu Arg Ala Glu Asp Thr Ala Val
100 105 110

Tyr Tyr Cys Ala Arg Asp Arg Gly Ile Gly Ala Arg Arg Gly Pro Tyr
115 120 125

Tyr Met Asp Val Trp Gly Lys Gly Thr Thr Val Thr Val Ser Ser Ala
130 135 140

Gly Gly Gly Gly Ser Gly Gly Gly Gly Ser Gly Gly Gly Gly Ser Asp
145 150 155 160

Ile Gln Met Thr Gln Ser Pro Ser Ser Leu Ser Ala Ser Val Gly Asp
165 170 175

```
Arg Val Thr Ile Thr Cys Arg Ala Ser Gln Ser Ile Ser Ser Tyr Leu
            180                 185                 190

Asn Trp Tyr Gln Gln Lys Pro Gly Lys Ala Pro Lys Leu Leu Ile Tyr
        195                 200                 205

Ala Ala Ser Ser Leu Gln Ser Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Ser Thr Pro Leu Thr
                245                 250                 255

Phe Gly Gly Gly Thr Lys Val Glu Ile Lys
            260                 265


<210> SEQ ID NO 2
<211> LENGTH: 266
<212> TYPE: PRT
<213> ORGANISM: Artificial Sequence
<220> FEATURE:
<223> OTHER INFORMATION: DG02 SCFV

<400> SEQUENCE: 2

Met Glu Trp Thr Trp Val Phe Leu Phe Leu Leu Ser Val Thr Ala Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Asp Val Val Met Thr Gln
145                 150                 155                 160

Ser Pro Leu Ser Leu Pro Val Thr Pro Gly Glu Pro Ala Ser Ile Ser
                165                 170                 175

Cys Lys Ser Ser Gln Ser Leu Leu Asp Ser Asp Gly Lys Thr Tyr Leu
            180                 185                 190

Asn Trp Leu Leu Gln Lys Pro Gly Gln Ser Pro Gln Arg Leu Ile Tyr
        195                 200                 205

Leu Val Ser Lys Leu Asp Ser Gly Val Pro Asp Arg Phe Ser Gly Ser
    210                 215                 220

Gly Ser Gly Thr Asp Phe Thr Leu Lys Ile Ser Arg Val Glu Ala Glu
225                 230                 235                 240

Asp Val Gly Val Tyr Tyr Cys Trp Gln Gly Thr His Phe Pro Arg Thr
                245                 250                 255

Phe Gly Gln Gly Thr Lys Val Glu Ile Lys
            260                 265
```

<210> SEQ ID NO 3
<211> LENGTH: 259
<212> TYPE: PRT
<213> ORGANISM: Artificial Sequence
<220> FEATURE:
<223> OTHER INFORMATION: DG03 SCFV

<400> SEQUENCE: 3

```
Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Gly Met Ser Trp Val Arg Gln Ala Pro Gly Lys Gly Leu
    50                  55                  60

Glu Leu Val Ala Ser Ile Asn Ser Asn Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Gly Asp Tyr Trp Gly Gln Gly Thr Thr Val Thr
        115                 120                 125

Val Ser Ser Ala Gly Gly Gly Gly Ser Gly Gly Gly Gly Ser Gly Gly
    130                 135                 140

Gly Gly Ser Asp Ile Val Met Thr Gln Ser Pro Leu Ser Leu Pro Val
145                 150                 155                 160

Thr Pro Gly Glu Pro Ala Ser Ile Ser Cys Arg Ser Ser Gln Ser Leu
                165                 170                 175

Val Tyr Ser Asn Gly Asp Thr Tyr Leu His Trp Tyr Leu Gln Lys Pro
            180                 185                 190

Gly Gln Ser Pro Gln Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

Leu Lys Ile Ser Arg Val Glu Ala Glu Asp Val Gly Val Tyr Tyr Cys
225                 230                 235                 240

Ser Gln Ser Thr His Val Pro Trp Thr Phe Gly Gln Gly Thr Lys Val
                245                 250                 255

Glu Ile Lys
```

<210> SEQ ID NO 4
<211> LENGTH: 269
<212> TYPE: PRT
<213> ORGANISM: Artificial Sequence
<220> FEATURE:
<223> OTHER INFORMATION: DG04 SCFV

<400> SEQUENCE: 4

```
Met Glu Trp Thr Trp Val Phe Leu Phe Leu Leu Ser Val Thr Ala Gly
1               5                   10                  15

Val His Ser Gln Val Glu Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45
```

Ser Ser Tyr Ala Met Ser Trp Val Arg Gln Ala Pro Gly Lys Gly Leu
50 55 60

Glu Trp Val Ser Ala Ile Asn Ala Ser Gly Thr Arg Thr Tyr Tyr Ala
65 70 75 80

Asp Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ala Arg Gly Lys Gly Asn Thr His Lys Pro Tyr Gly Tyr
115 120 125

Val Arg Tyr Phe Asp Val Trp Gly Gln Gly Thr Leu Val Thr Val Ser
130 135 140

Ser Ala Gly Gly Gly Gly Ser Gly Gly Gly Gly Ser Gly Gly Gly Gly
145 150 155 160

Ser Asp Ile Val Leu Thr Gln Ser Pro Ala Thr Leu Ser Leu Ser Pro
165 170 175

Gly Glu Arg Ala Thr Leu Ser Cys Arg Ala Ser Gln Ser Val Ser Ser
180 185 190

Ser Tyr Leu Ala Trp Tyr Gln Gln Lys Pro Gly Gln Ala Pro Arg Leu
195 200 205

Leu Ile Tyr Gly Ala Ser Ser Arg Ala Thr Gly Val Pro Ala Arg Phe
210 215 220

Ser Gly Ser Gly Ser Gly Thr Asp Phe Thr Leu Thr Ile Ser Ser Leu
225 230 235 240

Glu Pro Glu Asp Phe Ala Thr Tyr Tyr Cys Leu Gln Ile Tyr Asn Met
245 250 255

Pro Ile Thr Phe Gly Gln Gly Thr Lys Val Glu Ile Lys
260 265

<210> SEQ ID NO 5
<211> LENGTH: 261
<212> TYPE: PRT
<213> ORGANISM: Artificial Sequence
<220> FEATURE:
<223> OTHER INFORMATION: DG05 SCFV

<400> SEQUENCE: 5

Met Glu Trp Thr Trp Val Phe Leu Phe Leu Leu Ser Val Thr Ala Gly
1 5 10 15

Val His Ser Glu Val Gln Leu Val Gln Ser Gly Gly Gly Leu Val Lys
20 25 30

Pro Gly Gly Ser Leu Arg Leu Ser Cys Ala Gly Ser Gly Phe Thr Phe
35 40 45

Ser Ser Tyr Ser Met His Trp Leu Arg Gln Ala Pro Gly Lys Gly Leu
50 55 60

Glu Trp Val Ser Ala Ile Gly Thr Ala Gly Gly Thr Tyr Tyr Ala Asp
65 70 75 80

Ser Val Lys Gly Arg Phe Thr Ile Ser Arg Asp Asn Ala Lys Asn Ser
85 90 95

Leu Tyr Leu Gln Met Asn Ser Leu Arg Ala Glu Asp Thr Ala Val Tyr
100 105 110

Tyr Cys Ala Arg Glu Tyr Phe Phe Gly Ser Gly Asn Tyr Gly Tyr Trp
115 120 125

Gly Gln Gly Thr Leu Val Thr Val Ser Ser Ala Gly Gly Gly Gly Ser
130 135 140

Gly Gly Gly Gly Ser Gly Gly Gly Gly Ser Glu Ile Val Leu Thr Gln
145 150 155 160

Ser Pro Ala Thr Leu Ser Leu Ser Pro Gly Glu Arg Ala Thr Leu Ser
165 170 175

Cys Arg Ala Ser Gln Ser Val Ser Ser Tyr Leu Ala Trp Tyr Gln Gln
180 185 190

Lys Pro Gly Gln Ala Pro Arg Leu Leu Ile Tyr Asp Ala Ser Asn Arg
195 200 205

Ala Thr Gly Ile Pro Ala Arg Phe Ser Gly Ser Gly Ser Gly Thr Asp
210 215 220

Phe Thr Leu Thr Ile Ser Ser Leu Glu Pro Glu Asp Phe Ala Val Tyr
225 230 235 240

Tyr Cys Gln Gln Arg Ser Asn Trp Pro Pro Thr Phe Gly Gln Gly Thr
245 250 255

Lys Val Glu Ile Lys
260

<210> SEQ ID NO 6
<211> LENGTH: 259
<212> TYPE: PRT
<213> ORGANISM: Artificial Sequence
<220> FEATURE:
<223> OTHER INFORMATION: DG06 SCFV

<400> SEQUENCE: 6

Met Glu Trp Thr Trp Val Phe Leu Phe Leu Leu Ser Val Thr Ala Gly
1 5 10 15

Val His Ser Gln Val Gln Leu Val Glu Ser Gly Gly Gly Val Val Gln
20 25 30

Pro Gly Arg Ser Leu Arg Leu Ser Cys Ala Ala Ser Gly Phe Thr Phe
35 40 45

Ser Asn Tyr Gly Ile His Trp Val Arg Gln Ala Pro Gly Lys Gly Leu
50 55 60

Glu Trp Val Ala Ile Ile Trp His Asp Gly Ser Asn Ser Tyr Tyr Val
65 70 75 80

Asp Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Phe Cys Ala Arg Ile Ile Gly Gly Ala Phe Asp Ile Trp Gly Gln
115 120 125

Gly Thr Met Val Thr Val Ser Ser Ala Gly Gly Gly Gly Ser Gly Gly
130 135 140

Gly Gly Ser Gly Gly Gly Gly Ser Asp Ile Gln Met Thr Gln Ser Pro
145 150 155 160

Ser Ser Leu Ser Ala Ser Val Gly Asp Arg Val Thr Ile Thr Cys Arg
165 170 175

Ala Ser Gln Gly Ile Ser Ser Trp Leu Ala Trp Tyr Gln Gln Lys Pro
180 185 190

Glu Lys Ala Pro Lys Ser Leu Ile Tyr Ala Ala Ser Ser Leu Gln Ser
195 200 205

Gly Val Pro Ser Arg Phe Ser Gly Ser Gly Ser Gly Thr Asp Phe Thr
210 215 220

Leu Thr Ile Ser Ser Leu Gln Pro Glu Asp Phe Ala Thr Tyr Tyr Cys
225 230 235 240

```
Gln Gln Tyr Asn Ser Tyr Pro Ile Thr Phe Gly Gln Gly Thr Arg Leu
                245                 250                 255

Glu Ile Lys


<210> SEQ ID NO 7
<211> LENGTH: 256
<212> TYPE: PRT
<213> ORGANISM: Artificial Sequence
<220> FEATURE:
<223> OTHER INFORMATION: DG07 SCFV

<400> SEQUENCE: 7

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Ile
        35                  40                  45

Ser Gly Tyr Trp Met Ser Trp Val Arg Gln Ala Pro Gly Lys Gly Leu
    50                  55                  60

Glu Trp Val Ala Asn Ile Lys Gln Asp Gly Gly Glu Lys Tyr Tyr Gly
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Met Ala Gly Gly Leu Asp Tyr Trp Gly Gln Gly Thr
        115                 120                 125

Leu Val Thr Val Ser Ser Ala Gly Gly Gly Gly Ser Gly Gly Gly Gly
    130                 135                 140

Ser Gly Gly Gly Gly Ser Glu Ile Val Leu Thr Gln Ser Pro Ala Thr
145                 150                 155                 160

Leu Ser Leu Ser Pro Gly Glu Arg Ala Thr Leu Ser Cys Arg Ala Ser
                165                 170                 175

Gln Ser Val Ser Ser Tyr Leu Ala Trp Tyr Gln Gln Lys Pro Gly Gln
            180                 185                 190

Ala Pro Arg Leu Leu Ile Tyr Asp Ala Ser Asn Arg Ala Thr Gly Ile
        195                 200                 205

Pro Ala Arg Phe Ser Gly Ser Gly Ser Gly Thr Asp Phe Thr Leu Thr
    210                 215                 220

Ile Ser Ser Leu Glu Pro Glu Asp Phe Ala Val Tyr Tyr Cys Gln Gln
225                 230                 235                 240

Arg Ser Asn Trp Tyr Thr Phe Gly Gln Gly Thr Lys Leu Glu Ile Lys
                245                 250                 255


<210> SEQ ID NO 8
<211> LENGTH: 264
<212> TYPE: PRT
<213> ORGANISM: Artificial Sequence
<220> FEATURE:
<223> OTHER INFORMATION: DG08 SCFV

<400> SEQUENCE: 8

Met Glu Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30
```

-continued

```
Pro Gly Ala Ser Val Arg Leu Ser Cys Arg Ala Ser Gly Tyr Asn Phe
        35                  40                  45

Ile Asp Phe His Ile His Trp Val Arg Gln Ala Pro Gly Glu Gly Leu
    50                  55                  60

Glu Trp Met Gly Trp Ser Asn Pro Gln Ser Gly Asn Ser Ser Ser Ala
65                  70                  75                  80

Gln Arg Phe Gln Gly Arg Val Thr Met Thr Thr Asp Thr Ser Met Ser
                85                  90                  95

Ala Ala Tyr Met Asp Leu Asn Trp Leu Thr Leu Asp Asp Thr Ala Val
            100                 105                 110

Tyr Tyr Cys Thr Arg Pro His Asp Gly Ala Gly Asn Tyr Arg Phe Asp
        115                 120                 125

Thr Trp Gly Gln Gly Thr Leu Val Thr Val Ser Ser Ala Gly Gly Gly
    130                 135                 140

Gly Ser Gly Gly Gly Gly Ser Gly Gly Gly Gly Ser Ser Tyr Glu Leu
145                 150                 155                 160

Thr Gln Pro Pro Ser Val Ser Val Ala Pro Gly Gln Thr Ala Arg Ile
                165                 170                 175

Thr Cys Ser Gly Asp Ala Leu Pro Lys His Tyr Ala His Trp Tyr Gln
            180                 185                 190

Gln Lys Pro Gly Gln Val Pro Ile Val Val Ile Tyr Lys Asp Thr Glu
        195                 200                 205

Arg Pro Ser Gly Ile Pro Glu Arg Phe Ser Gly Ser Thr Ser Gly Thr
    210                 215                 220

Thr Val Thr Leu Thr Ile Ser Gly Val Gln Ala Glu Asp Glu Ala His
225                 230                 235                 240

Tyr Tyr Cys Gln Ser Ala Asp Val Ser Ser Thr Tyr Val Val Phe Gly
                245                 250                 255

Gly Gly Thr Lys Leu Thr Val Leu
            260


<210> SEQ ID NO 9
<211> LENGTH: 256
<212> TYPE: PRT
<213> ORGANISM: Artificial Sequence
<220> FEATURE:
<223> OTHER INFORMATION: DG09 SCFV

<400> SEQUENCE: 9

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Glu
            20                  25                  30

Pro Gly Gly Ser Leu Arg Leu Ser Cys Ala Val Ser Gly Phe Asp Phe
        35                  40                  45

Glu Lys Ala Trp Met Ser Trp Val Arg Gln Ala Pro Gly Gln Gly Leu
    50                  55                  60

Gln Trp Val Ala Arg Ile Lys Ser Thr Ala Asp Gly Gly Thr Thr Ser
65                  70                  75                  80

Tyr Ala Ala Pro Val Glu Gly Arg Phe Ile Ile Ser Arg Asp Asp Ser
                85                  90                  95

Arg Asn Met Leu Tyr Leu Gln Met Asn Ser Leu Lys Thr Glu Asp Thr
            100                 105                 110

Ala Val Tyr Tyr Cys Thr Ser Ala His Trp Gly Gln Gly Thr Leu Val
        115                 120                 125
```

```
Thr Val Ser Ser Ala Gly Gly Gly Gly Ser Gly Gly Gly Gly Ser Gly
    130                 135                 140

Gly Gly Gly Ser Ser Tyr Glu Leu Thr Gln Pro Pro Ser Val Ser Val
145                 150                 155                 160

Ser Pro Gly Gln Thr Ala Arg Ile Thr Cys Ser Gly Glu Ala Leu Pro
                165                 170                 175

Met Gln Phe Ala His Trp Tyr Gln Gln Arg Pro Gly Lys Ala Pro Val
            180                 185                 190

Ile Val Val Tyr Lys Asp Ser Glu Arg Pro Ser Gly Val Pro Glu Arg
        195                 200                 205

Phe Ser Gly Ser Ser Ser Gly Thr Thr Ala Thr Leu Thr Ile Thr Gly
    210                 215                 220

Val Gln Ala Glu Asp Glu Ala Asp Tyr Tyr Cys Gln Ser Pro Asp Ser
225                 230                 235                 240

Thr Asn Thr Tyr Glu Val Phe Gly Gly Gly Thr Lys Leu Thr Val Leu
                245                 250                 255


<210> SEQ ID NO 10
<211> LENGTH: 272
<212> TYPE: PRT
<213> ORGANISM: Artificial Sequence
<220> FEATURE:
<223> OTHER INFORMATION: DG10 SCFV

<400> SEQUENCE: 10

Met Glu Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly Lys Arg Lys Tyr Ser
65                  70                  75                  80

Gln Lys Phe Gln Asp Arg Val Thr Ile Asn Arg Asp Thr Ser Ala Ser
                85                  90                  95

Thr Ile Tyr Met Glu Leu Ser Ser Leu Gly Ser Glu Asp Thr Ala Val
            100                 105                 110

Tyr Tyr Cys Ala Arg Glu Glu Asp His Ala Gly Ser Gly Ser Tyr Leu
        115                 120                 125

Ser Met Asp Val Trp Gly Gln Gly Ser Thr Val Thr Val Ser Ser Ala
    130                 135                 140

Gly Gly Gly Gly Ser Gly Gly Gly Gly Ser Gly Gly Gly Gly Ser Asp
145                 150                 155                 160

Ile Val Met Thr Gln Ser Pro Asp Ser Leu Ala Val Ser Leu Gly Glu
                165                 170                 175

Arg Ala Thr Ile Asn Cys Lys Ser Ser Gln Asn Val Leu Tyr Ser Ser
            180                 185                 190

Asn Asn Lys Asn Tyr Leu Ala Trp Tyr Gln Gln Lys Pro Gly His Pro
        195                 200                 205

Pro Lys Leu Leu Ile Tyr Trp Ala Ser Thr Arg Glu Ser Gly Val Pro
    210                 215                 220

Asp Arg Phe Ser Gly Ser Gly Ser Gly Thr Asp Phe Thr Leu Thr Ile
225                 230                 235                 240
```

Thr Ser Leu Gln Thr Glu Asp Val Ala Val Tyr Tyr Cys Gln Gln Tyr
245 250 255

Tyr Ser Ser Pro Leu Thr Phe Gly Gly Gly Thr Lys Val Glu Ile Lys
260 265 270

<210> SEQ ID NO 11
<211> LENGTH: 268
<212> TYPE: PRT
<213> ORGANISM: Artificial Sequence
<220> FEATURE:
<223> OTHER INFORMATION: DG11 SCFV

<400> SEQUENCE: 11

Met Glu Trp Thr Trp Val Phe Leu Phe Leu Leu Ser Val Thr Ala Gly
1 5 10 15

Val His Ser Glu Val Gln Leu Val Glu Thr Gly Gly Gly Leu Val Gln
20 25 30

Pro Lys Gly Ser Leu Lys Leu Ser Cys Ala Thr Ser Gly Phe Thr Phe
35 40 45

Asn Thr Tyr Ala Met Asn Trp Val Arg Gln Ala Pro Gly Lys Gly Leu
50 55 60

Glu Trp Val Ala Arg Ile Arg Thr Lys Ser Asn Asp Tyr Ala Thr Tyr
65 70 75 80

Tyr Ala Asp Ser Val Lys Gly Arg Ile Thr Ile Ser Arg Asp Asp Ser
85 90 95

Gln Ser Met Leu Tyr Leu Gln Met Asn Asn Leu Lys Thr Glu Asp Thr
100 105 110

Ala Met Tyr Tyr Cys Val Arg Val Gly Tyr Arg Pro Tyr Ala Met Asp
115 120 125

Tyr Trp Gly Gln Gly Thr Ser Val Thr Val Ser Ser Ala Gly Gly Gly
130 135 140

Gly Ser Gly Gly Gly Gly Ser Gly Gly Gly Gly Ser Asp Val Leu Met
145 150 155 160

Thr Gln Thr Pro Leu Ser Leu Pro Val Ser Leu Gly Asp Gln Ala Ser
165 170 175

Ile Ser Cys Arg Ser Ser Gln Asn Ile Val His Ser Asn Gly Asn Thr
180 185 190

Tyr Leu Glu Trp Tyr Leu Gln Lys Pro Gly Gln Ser Pro Thr Leu Leu
195 200 205

Ile Tyr Lys Val Ser Asn Arg Phe Ser Gly Val Pro Asp Arg Phe Ser
210 215 220

Gly Ser Gly Ser Gly Thr Asp Phe Thr Leu Lys Ile Ser Arg Val Glu
225 230 235 240

Ala Glu Asp Leu Gly Val Tyr Tyr Cys Phe Gln Gly Ser His Val Pro
245 250 255

Leu Thr Phe Gly Ala Gly Thr Lys Leu Glu Leu Lys
260 265

<210> SEQ ID NO 12
<211> LENGTH: 42
<212> TYPE: PRT
<213> ORGANISM: Artificial Sequence
<220> FEATURE:
<223> OTHER INFORMATION: 4-1BB CO-STIMULATORY DOMAIN

<400> SEQUENCE: 12

Lys Arg Gly Arg Lys Lys Leu Leu Tyr Ile Phe Lys Gln Pro Phe Met

-continued

```
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 13
<211> LENGTH: 15
<212> TYPE: PRT
<213> ORGANISM: Artificial Sequence
<220> FEATURE:
<223> OTHER INFORMATION: (G4S)3 LINKER

<400> SEQUENCE: 13

Gly Gly Gly Gly Ser Gly Gly Gly Gly Ser Gly Gly Gly Gly Ser
1               5                   10                  15


<210> SEQ ID NO 14
<211> LENGTH: 26
<212> TYPE: PRT
<213> ORGANISM: Artificial Sequence
<220> FEATURE:
<223> OTHER INFORMATION: T2A

<400> SEQUENCE: 14

Arg Ala Lys Arg Ser Gly Ser Gly Glu Gly Arg Gly Ser Leu Ile Thr
1               5                   10                  15

Cys Gly Asp Val Glu Glu Asn Pro Gly Pro
            20                  25


<210> SEQ ID NO 15
<211> LENGTH: 27
<212> TYPE: PRT
<213> ORGANISM: Artificial Sequence
<220> FEATURE:
<223> OTHER INFORMATION: P2A

<400> SEQUENCE: 15

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25


<210> SEQ ID NO 16
<211> LENGTH: 112
<212> TYPE: PRT
<213> ORGANISM: Artificial Sequence
<220> FEATURE:
<223> OTHER INFORMATION: CD3Z

<400> SEQUENCE: 16

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
```

-continued

```
                85                  90                  95

Thr Lys Asp Thr Tyr Asp Ala Leu His Met Gln Ala Leu Pro Pro Arg
            100                 105                 110


<210> SEQ ID NO 17
<211> LENGTH: 770
<212> TYPE: PRT
<213> ORGANISM: Artificial Sequence
<220> FEATURE:
<223> OTHER INFORMATION: HUMAN AMYLOID BETA, ISOFORM APP770 (IDENTIFIER:
      P05067-1)

<400> SEQUENCE: 17

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335
```

-continued

```
Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
```

```
        755                 760                 765

Gln Asn
    770


<210> SEQ ID NO 18
<211> LENGTH: 154
<212> TYPE: PRT
<213> ORGANISM: Artificial Sequence
<220> FEATURE:
<223> OTHER INFORMATION: HUMAN SUPEROXIDE DISMUTASE, IDENTIFIER:
      P00441-1

<400> SEQUENCE: 18

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150


<210> SEQ ID NO 19
<211> LENGTH: 140
<212> TYPE: PRT
<213> ORGANISM: Artificial Sequence
<220> FEATURE:
<223> OTHER INFORMATION: H HUMAN ALPHA-SYNUCLEIN, ISOFORM 1 (IDENTIFIER:
      P37840-1)

<400> SEQUENCE: 19

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
```

```
        115                 120                 125

Ser Glu Glu Gly Tyr Gln Asp Tyr Glu Pro Glu Ala
    130                 135                 140


<210> SEQ ID NO 20
<211> LENGTH: 467
<212> TYPE: PRT
<213> ORGANISM: Artificial Sequence
<220> FEATURE:
<223> OTHER INFORMATION: DG01.28.Z CAR

<400> SEQUENCE: 20

Met Glu Trp Thr Trp Val Phe Leu Phe Leu Leu Ser Val Thr Ala Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Ala Phe
        35                  40                  45

Ser Ser Tyr Gly Met His Trp Val Arg Gln Ala Pro Gly Lys Gly Leu
    50                  55                  60

Glu Trp Val Ala Val Ile Trp Phe Asp Gly Thr Lys Lys Tyr Tyr Thr
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Thr Leu Arg Ala Glu Asp Thr Ala Val
            100                 105                 110

Tyr Tyr Cys Ala Arg Asp Arg Gly Ile Gly Ala Arg Arg Gly Pro Tyr
        115                 120                 125

Tyr Met Asp Val Trp Gly Lys Gly Thr Thr Val Thr Val Ser Ser Ala
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Arg Ala Ser Gln Ser Ile Ser Ser Tyr Leu
            180                 185                 190

Asn Trp Tyr Gln Gln Lys Pro Gly Lys Ala Pro Lys Leu Leu Ile Tyr
        195                 200                 205

Ala Ala Ser Ser Leu Gln Ser Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln Gln Ser Tyr Ser Thr Pro Leu Thr
                245                 250                 255

Phe Gly Gly Gly Thr Lys Val Glu Ile Lys Ala Ser Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
```

```
            340                 345                 350

Arg Ser Lys Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro
465


<210> SEQ ID NO 21
<211> LENGTH: 467
<212> TYPE: PRT
<213> ORGANISM: Artificial Sequence
<220> FEATURE:
<223> OTHER INFORMATION: DG02.28.Z CAR

<400> SEQUENCE: 21

Met Glu Trp Thr Trp Val Phe Leu Phe Leu Leu Ser Val Thr Ala Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Gly Arg Thr Tyr Tyr Ser
65                  70                  75                  80

Asp Asn Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Asp Val Val Met Thr Gln
145                 150                 155                 160

Ser Pro Leu Ser Leu Pro Val Thr Pro Gly Glu Pro Ala Ser Ile Ser
                165                 170                 175

Cys Lys Ser Ser Gln Ser Leu Leu Asp Ser Asp Gly Lys Thr Tyr Leu
            180                 185                 190

Asn Trp Leu Leu Gln Lys Pro Gly Gln Ser Pro Gln Arg Leu Ile Tyr
        195                 200                 205

Leu Val Ser Lys Leu Asp Ser Gly Val Pro Asp Arg Phe Ser Gly Ser
    210                 215                 220

Gly Ser Gly Thr Asp Phe Thr Leu Lys Ile Ser Arg Val Glu Ala Glu
```

-continued

```
225                 230                 235                 240

Asp Val Gly Val Tyr Tyr Cys Trp Gln Gly Thr His Phe Pro Arg Thr
                245                 250                 255

Phe Gly Gln Gly Thr Lys Val Glu Ile Lys Ala Ser Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Lys Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro
465


<210> SEQ ID NO 22
<211> LENGTH: 460
<212> TYPE: PRT
<213> ORGANISM: Artificial Sequence
<220> FEATURE:
<223> OTHER INFORMATION: DG03.28.Z CAR

<400> SEQUENCE: 22

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Gly Met Ser Trp Val Arg Gln Ala Pro Gly Lys Gly Leu
    50                  55                  60

Glu Leu Val Ala Ser Ile Asn Ser Asn Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Gly Asp Tyr Trp Gly Gln Gly Thr Thr Val Thr
```

```
        115                 120                 125

Val Ser Ser Ala Gly Gly Gly Gly Ser Gly Gly Gly Gly Ser Gly Gly
    130                 135                 140

Gly Gly Ser Asp Ile Val Met Thr Gln Ser Pro Leu Ser Leu Pro Val
145                 150                 155                 160

Thr Pro Gly Glu Pro Ala Ser Ile Ser Cys Arg Ser Ser Gln Ser Leu
                165                 170                 175

Val Tyr Ser Asn Gly Asp Thr Tyr Leu His Trp Tyr Leu Gln Lys Pro
            180                 185                 190

Gly Gln Ser Pro Gln Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

Leu Lys Ile Ser Arg Val Glu Ala Glu Asp Val Gly Val Tyr Tyr Cys
225                 230                 235                 240

Ser Gln Ser Thr His Val Pro Trp Thr Phe Gly Gln Gly Thr Lys Val
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Arg Leu Leu His Ser Asp Tyr Met Asn
305                 310                 315                 320

Met Thr Pro Arg Arg Pro Gly Pro Thr Arg Lys His Tyr Gln Pro Tyr
                325                 330                 335

Ala Pro Pro Arg Asp Phe Ala Ala Tyr Arg Ser Lys Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro
    450                 455                 460


<210> SEQ ID NO 23
<211> LENGTH: 470
<212> TYPE: PRT
<213> ORGANISM: Artificial Sequence
<220> FEATURE:
<223> OTHER INFORMATION: DG04.28.Z CAR

<400> SEQUENCE: 23

Met Glu Trp Thr Trp Val Phe Leu Phe Leu Leu Ser Val Thr Ala Gly
1               5                   10                  15

Val His Ser Gln Val Glu Leu Val Glu Ser Gly Gly Gly Leu Val Gln
```

-continued

```
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Asn Ala Ser Gly Thr Arg Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Lys Gly Asn Thr His Lys Pro Tyr Gly Tyr
        115                 120                 125

Val Arg Tyr Phe Asp Val Trp Gly Gln Gly Thr Leu Val Thr Val Ser
    130                 135                 140

Ser Ala Gly Gly Gly Gly Ser Gly Gly Gly Gly Ser Gly Gly Gly Gly
145                 150                 155                 160

Ser Asp Ile Val Leu Thr Gln Ser Pro Ala Thr Leu Ser Leu Ser Pro
                165                 170                 175

Gly Glu Arg Ala Thr Leu Ser Cys Arg Ala Ser Gln Ser Val Ser Ser
            180                 185                 190

Ser Tyr Leu Ala Trp Tyr Gln Gln Lys Pro Gly Gln Ala Pro Arg Leu
        195                 200                 205

Leu Ile Tyr Gly Ala Ser Ser Arg Ala Thr Gly Val Pro Ala Arg Phe
    210                 215                 220

Ser Gly Ser Gly Ser Gly Thr Asp Phe Thr Leu Thr Ile Ser Ser Leu
225                 230                 235                 240

Glu Pro Glu Asp Phe Ala Thr Tyr Tyr Cys Leu Gln Ile Tyr Asn Met
                245                 250                 255

Pro Ile Thr Phe Gly Gln Gly Thr Lys Val Glu Ile Lys Ala Ser Val
            260                 265                 270

Lys Gly Lys His Leu Cys Pro Ser Pro Leu Phe Pro Gly Pro Ser Lys
        275                 280                 285

Pro Phe Trp Val Leu Val Val Val Gly Gly Val Leu Ala Cys Tyr Ser
    290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335

Gly Pro Thr Arg Lys His Tyr Gln Pro Tyr Ala Pro Pro Arg Asp Phe
            340                 345                 350

Ala Ala Tyr Arg Ser Lys Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445
```

```
Tyr Gln Gly Leu Ser Thr Ala Thr Lys Asp Thr Tyr Asp Ala Leu His
    450                 455                 460

Met Gln Ala Leu Pro Pro
465                 470
```

<210> SEQ ID NO 24
<211> LENGTH: 462
<212> TYPE: PRT
<213> ORGANISM: Artificial Sequence
<220> FEATURE:
<223> OTHER INFORMATION: DG05.28.Z CAR

<400> SEQUENCE: 24

```
Met Glu Trp Thr Trp Val Phe Leu Phe Leu Leu Ser Val Thr Ala Gly
1               5                   10                  15

Val His Ser Glu Val Gln Leu Val Gln Ser Gly Gly Gly Leu Val Lys
            20                  25                  30

Pro Gly Gly Ser Leu Arg Leu Ser Cys Ala Gly Ser Gly Phe Thr Phe
        35                  40                  45

Ser Ser Tyr Ser Met His Trp Leu Arg Gln Ala Pro Gly Lys Gly Leu
    50                  55                  60

Glu Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Glu Tyr Phe Phe Gly Ser Gly Asn Tyr Gly Tyr Trp
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Val Ser Ser Tyr Leu Ala Trp Tyr Gln Gln
            180                 185                 190

Lys Pro Gly Gln Ala Pro Arg Leu Leu Ile Tyr Asp Ala Ser Asn Arg
        195                 200                 205

Ala Thr Gly Ile Pro Ala Arg Phe Ser Gly Ser Gly Ser Gly Thr Asp
    210                 215                 220

Phe Thr Leu Thr Ile Ser Ser Leu Glu Pro Glu Asp Phe Ala Val Tyr
225                 230                 235                 240

Tyr Cys Gln Gln Arg Ser Asn Trp Pro Pro Thr Phe Gly Gln Gly Thr
                245                 250                 255

Lys Val Glu Ile Lys Ala Ser Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Arg Leu Leu His Ser Asp Tyr
305                 310                 315                 320

Met Asn Met Thr Pro Arg Arg Pro Gly Pro Thr Arg Lys His Tyr Gln
                325                 330                 335
```

```
Pro Tyr Ala Pro Pro Arg Asp Phe Ala Ala Tyr Arg Ser Lys Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro
    450                 455                 460


<210> SEQ ID NO 25
<211> LENGTH: 460
<212> TYPE: PRT
<213> ORGANISM: Artificial Sequence
<220> FEATURE:
<223> OTHER INFORMATION: DG06.28.Z CAR

<400> SEQUENCE: 25

Met Glu Trp Thr Trp Val Phe Leu Phe Leu Leu Ser Val Thr Ala Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Ile His Trp Val Arg Gln Ala Pro Gly Lys Gly Leu
    50                  55                  60

Glu Trp Val Ala Ile Ile Trp His Asp Gly Ser Asn Ser Tyr Tyr Val
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Phe Cys Ala Arg Ile Ile Gly Gly Ala Phe Asp Ile Trp Gly Gln
        115                 120                 125

Gly Thr Met Val Thr Val Ser Ser Ala Gly Gly Gly Gly Ser Gly Gly
    130                 135                 140

Gly Gly Ser Gly Gly Gly Gly Ser Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Gly Ile Ser Ser Trp Leu Ala Trp Tyr Gln Gln Lys Pro
            180                 185                 190

Glu Lys Ala Pro Lys Ser Leu Ile Tyr Ala Ala Ser Ser Leu Gln Ser
        195                 200                 205

Gly Val Pro Ser Arg Phe Ser Gly Ser Gly Ser Gly Thr Asp Phe Thr
    210                 215                 220

Leu Thr Ile Ser Ser Leu Gln Pro Glu Asp Phe Ala Thr Tyr Tyr Cys
225                 230                 235                 240
```

```
Gln Gln Tyr Asn Ser Tyr Pro Ile Thr Phe Gly Gln Gly Thr Arg Leu
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Arg Leu Leu His Ser Asp Tyr Met Asn
305                 310                 315                 320

Met Thr Pro Arg Arg Pro Gly Pro Thr Arg Lys His Tyr Gln Pro Tyr
                325                 330                 335

Ala Pro Pro Arg Asp Phe Ala Ala Tyr Arg Ser Lys Leu Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro
    450                 455                 460


<210> SEQ ID NO 26
<211> LENGTH: 457
<212> TYPE: PRT
<213> ORGANISM: Artificial Sequence
<220> FEATURE:
<223> OTHER INFORMATION: DG07.28.Z CAR

<400> SEQUENCE: 26

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Ile
        35                  40                  45

Ser Gly Tyr Trp Met Ser Trp Val Arg Gln Ala Pro Gly Lys Gly Leu
    50                  55                  60

Glu Trp Val Ala Asn Ile Lys Gln Asp Gly Gly Glu Lys Tyr Tyr Gly
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Met Ala Gly Gly Leu Asp Tyr Trp Gly Gln Gly Thr
        115                 120                 125

Leu Val Thr Val Ser Ser Ala Gly Gly Gly Gly Ser Gly Gly Gly Gly
    130                 135                 140
```

```
Ser Gly Gly Gly Gly Ser Glu Ile Val Leu Thr Gln Ser Pro Ala Thr
145                 150                 155                 160

Leu Ser Leu Ser Pro Gly Glu Arg Ala Thr Leu Ser Cys Arg Ala Ser
                165                 170                 175

Gln Ser Val Ser Ser Tyr Leu Ala Trp Tyr Gln Gln Lys Pro Gly Gln
            180                 185                 190

Ala Pro Arg Leu Leu Ile Tyr Asp Ala Ser Asn Arg Ala Thr Gly Ile
        195                 200                 205

Pro Ala Arg Phe Ser Gly Ser Gly Ser Gly Thr Asp Phe Thr Leu Thr
    210                 215                 220

Ile Ser Ser Leu Glu Pro Glu Asp Phe Ala Val Tyr Tyr Cys Gln Gln
225                 230                 235                 240

Arg Ser Asn Trp Tyr Thr Phe Gly Gln Gly Thr Lys Leu Glu Ile Lys
                245                 250                 255

Ala Ser Val Lys Gly Lys His Leu Cys Pro Ser Pro Leu Phe Pro Gly
            260                 265                 270

Pro Ser Lys Pro Phe Trp Val Leu Val Val Val Gly Gly Val Leu Ala
        275                 280                 285

Cys Tyr Ser Leu Leu Val Thr Val Ala Phe Ile Ile Phe Trp Val Arg
    290                 295                 300

Ser Lys Arg Ser Arg Leu Leu His Ser Asp Tyr Met Asn Met Thr Pro
305                 310                 315                 320

Arg Arg Pro Gly Pro Thr Arg Lys His Tyr Gln Pro Tyr Ala Pro Pro
                325                 330                 335

Arg Asp Phe Ala Ala Tyr Arg Ser Lys Leu Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro
    450                 455
```

<210> SEQ ID NO 27
<211> LENGTH: 465
<212> TYPE: PRT
<213> ORGANISM: Artificial Sequence
<220> FEATURE:
<223> OTHER INFORMATION: DG08.28.Z CAR

<400> SEQUENCE: 27

```
Met Glu Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Arg Leu Ser Cys Arg Ala Ser Gly Tyr Asn Phe
        35                  40                  45
```

```
Ile Asp Phe His Ile His Trp Val Arg Gln Ala Pro Gly Glu Gly Leu
    50                  55                  60

Glu Trp Met Gly Trp Ser Asn Pro Gln Ser Gly Asn Ser Ser Ser Ala
65                  70                  75                  80

Gln Arg Phe Gln Gly Arg Val Thr Met Thr Thr Asp Thr Ser Met Ser
                85                  90                  95

Ala Ala Tyr Met Asp Leu Asn Trp Leu Thr Leu Asp Asp Thr Ala Val
            100                 105                 110

Tyr Tyr Cys Thr Arg Pro His Asp Gly Ala Gly Asn Tyr Arg Phe Asp
        115                 120                 125

Thr Trp Gly Gln Gly Thr Leu Val Thr Val Ser Ser Ala Gly Gly Gly
    130                 135                 140

Gly Ser Gly Gly Gly Gly Ser Gly Gly Gly Gly Ser Ser Tyr Glu Leu
145                 150                 155                 160

Thr Gln Pro Pro Ser Val Ser Val Ala Pro Gly Gln Thr Ala Arg Ile
                165                 170                 175

Thr Cys Ser Gly Asp Ala Leu Pro Lys His Tyr Ala His Trp Tyr Gln
            180                 185                 190

Gln Lys Pro Gly Gln Val Pro Ile Val Val Ile Tyr Lys Asp Thr Glu
        195                 200                 205

Arg Pro Ser Gly Ile Pro Glu Arg Phe Ser Gly Ser Thr Ser Gly Thr
    210                 215                 220

Thr Val Thr Leu Thr Ile Ser Gly Val Gln Ala Glu Asp Glu Ala His
225                 230                 235                 240

Tyr Tyr Cys Gln Ser Ala Asp Val Ser Ser Thr Tyr Val Val Phe Gly
                245                 250                 255

Gly Gly Thr Lys Leu Thr Val Leu Ala Ser Val Lys Gly Lys His Leu
            260                 265                 270

Cys Pro Ser Pro Leu Phe Pro Gly Pro Ser Lys Pro Phe Trp Val Leu
        275                 280                 285

Val Val Val Gly Gly Val Leu Ala Cys Tyr Ser Leu Leu Val Thr Val
    290                 295                 300

Ala Phe Ile Ile Phe Trp Val Arg Ser Lys Arg Ser Arg Leu Leu His
305                 310                 315                 320

Ser Asp Tyr Met Asn Met Thr Pro Arg Arg Pro Gly Pro Thr Arg Lys
                325                 330                 335

His Tyr Gln Pro Tyr Ala Pro Pro Arg Asp Phe Ala Ala Tyr Arg Ser
            340                 345                 350

Lys Leu Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460
```

Pro
465

<210> SEQ ID NO 28
<211> LENGTH: 457
<212> TYPE: PRT
<213> ORGANISM: Artificial Sequence
<220> FEATURE:
<223> OTHER INFORMATION: DG09.28.Z CAR

<400> SEQUENCE: 28

Met Glu Trp Thr Trp Val Phe Leu Phe Leu Leu Ser Val Thr Ala Gly
1 5 10 15

Val His Ser Glu Val Gln Leu Val Glu Ser Gly Gly Gly Leu Val Glu
20 25 30

Pro Gly Gly Ser Leu Arg Leu Ser Cys Ala Val Ser Gly Phe Asp Phe
35 40 45

Glu Lys Ala Trp Met Ser Trp Val Arg Gln Ala Pro Gly Gln Gly Leu
50 55 60

Gln Trp Val Ala Arg Ile Lys Ser Thr Ala Asp Gly Gly Thr Thr Ser
65 70 75 80

Tyr Ala Ala Pro Val Glu Gly Arg Phe Ile Ile Ser Arg Asp Asp Ser
85 90 95

Arg Asn Met Leu Tyr Leu Gln Met Asn Ser Leu Lys Thr Glu Asp Thr
100 105 110

Ala Val Tyr Tyr Cys Thr Ser Ala His Trp Gly Gln Gly Thr Leu Val
115 120 125

Thr Val Ser Ser Ala Gly Gly Gly Gly Ser Gly Gly Gly Gly Ser Gly
130 135 140

Gly Gly Gly Ser Ser Tyr Glu Leu Thr Gln Pro Pro Ser Val Ser Val
145 150 155 160

Ser Pro Gly Gln Thr Ala Arg Ile Thr Cys Ser Gly Glu Ala Leu Pro
165 170 175

Met Gln Phe Ala His Trp Tyr Gln Gln Arg Pro Gly Lys Ala Pro Val
180 185 190

Ile Val Val Tyr Lys Asp Ser Glu Arg Pro Ser Gly Val Pro Glu Arg
195 200 205

Phe Ser Gly Ser Ser Ser Gly Thr Thr Ala Thr Leu Thr Ile Thr Gly
210 215 220

Val Gln Ala Glu Asp Glu Ala Asp Tyr Tyr Cys Gln Ser Pro Asp Ser
225 230 235 240

Thr Asn Thr Tyr Glu Val Phe Gly Gly Gly Thr Lys Leu Thr Val Leu
245 250 255

Ala Ser Val Lys Gly Lys His Leu Cys Pro Ser Pro Leu Phe Pro Gly
260 265 270

Pro Ser Lys Pro Phe Trp Val Leu Val Val Val Gly Gly Val Leu Ala
275 280 285

Cys Tyr Ser Leu Leu Val Thr Val Ala Phe Ile Ile Phe Trp Val Arg
290 295 300

Ser Lys Arg Ser Arg Leu Leu His Ser Asp Tyr Met Asn Met Thr Pro
305 310 315 320

Arg Arg Pro Gly Pro Thr Arg Lys His Tyr Gln Pro Tyr Ala Pro Pro
325 330 335

Arg Asp Phe Ala Ala Tyr Arg Ser Lys Leu Arg Val Lys Phe Ser Arg
340 345 350

```
Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro
    450                 455


<210> SEQ ID NO 29
<211> LENGTH: 473
<212> TYPE: PRT
<213> ORGANISM: Artificial Sequence
<220> FEATURE:
<223> OTHER INFORMATION: DG10.28.Z CAR

<400> SEQUENCE: 29

Met Glu Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Ala Met His Trp Val Arg Gln Ala Pro Gly Gln Arg Leu
    50                  55                  60

Glu Trp Met Gly Trp Ile Asn Ala Gly Asn Gly Lys Arg Lys Tyr Ser
65                  70                  75                  80

Gln Lys Phe Gln Asp Arg Val Thr Ile Asn Arg Asp Thr Ser Ala Ser
                85                  90                  95

Thr Ile Tyr Met Glu Leu Ser Ser Leu Gly Ser Glu Asp Thr Ala Val
            100                 105                 110

Tyr Tyr Cys Ala Arg Glu Glu Asp His Ala Gly Ser Gly Ser Tyr Leu
        115                 120                 125

Ser Met Asp Val Trp Gly Gln Gly Ser Thr Val Thr Val Ser Ser Ala
    130                 135                 140

Gly Gly Gly Gly Ser Gly Gly Gly Gly Ser Gly Gly Gly Gly Ser Asp
145                 150                 155                 160

Ile Val Met Thr Gln Ser Pro Asp Ser Leu Ala Val Ser Leu Gly Glu
                165                 170                 175

Arg Ala Thr Ile Asn Cys Lys Ser Ser Gln Asn Val Leu Tyr Ser Ser
            180                 185                 190

Asn Asn Lys Asn Tyr Leu Ala Trp Tyr Gln Gln Lys Pro Gly His Pro
        195                 200                 205

Pro Lys Leu Leu Ile Tyr Trp Ala Ser Thr Arg Glu Ser Gly Val Pro
    210                 215                 220

Asp Arg Phe Ser Gly Ser Gly Ser Gly Thr Asp Phe Thr Leu Thr Ile
225                 230                 235                 240

Thr Ser Leu Gln Thr Glu Asp Val Ala Val Tyr Tyr Cys Gln Gln Tyr
                245                 250                 255
```

```
Tyr Ser Ser Pro Leu Thr Phe Gly Gly Gly Thr Lys Val Glu Ile Lys
            260                 265                 270

Ala Ser Val Lys Gly Lys His Leu Cys Pro Ser Pro Leu Phe Pro Gly
        275                 280                 285

Pro Ser Lys Pro Phe Trp Val Leu Val Val Val Gly Gly Val Leu Ala
    290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
            340                 345                 350

Arg Asp Phe Ala Ala Tyr Arg Ser Lys Leu Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro
465                 470


<210> SEQ ID NO 30
<211> LENGTH: 469
<212> TYPE: PRT
<213> ORGANISM: Artificial Sequence
<220> FEATURE:
<223> OTHER INFORMATION: DG11.28.Z CAR

<400> SEQUENCE: 30

Met Glu Trp Thr Trp Val Phe Leu Phe Leu Leu Ser Val Thr Ala Gly
1               5                   10                  15

Val His Ser Glu Val Gln Leu Val Glu Thr Gly Gly Gly Leu Val Gln
            20                  25                  30

Pro Lys Gly Ser Leu Lys Leu Ser Cys Ala Thr Ser Gly Phe Thr Phe
        35                  40                  45

Asn Thr Tyr Ala Met Asn Trp Val Arg Gln Ala Pro Gly Lys Gly Leu
    50                  55                  60

Glu Trp Val Ala Arg Ile Arg Thr Lys Ser Asn Asp Tyr Ala Thr Tyr
65                  70                  75                  80

Tyr Ala Asp Ser Val Lys Gly Arg Ile Thr Ile Ser Arg Asp Asp Ser
                85                  90                  95

Gln Ser Met Leu Tyr Leu Gln Met Asn Asn Leu Lys Thr Glu Asp Thr
            100                 105                 110

Ala Met Tyr Tyr Cys Val Arg Val Gly Tyr Arg Pro Tyr Ala Met Asp
        115                 120                 125

Tyr Trp Gly Gln Gly Thr Ser Val Thr Val Ser Ser Ala Gly Gly Gly
    130                 135                 140
```

-continued

Gly Ser Gly Gly Gly Gly Ser Gly Gly Gly Gly Ser Asp Val Leu Met
145 150 155 160

Thr Gln Thr Pro Leu Ser Leu Pro Val Ser Leu Gly Asp Gln Ala Ser
165 170 175

Ile Ser Cys Arg Ser Ser Gln Asn Ile Val His Ser Asn Gly Asn Thr
180 185 190

Tyr Leu Glu Trp Tyr Leu Gln Lys Pro Gly Gln Ser Pro Thr Leu Leu
195 200 205

Ile Tyr Lys Val Ser Asn Arg Phe Ser Gly Val Pro Asp Arg Phe Ser
210 215 220

Gly Ser Gly Ser Gly Thr Asp Phe Thr Leu Lys Ile Ser Arg Val Glu
225 230 235 240

Ala Glu Asp Leu Gly Val Tyr Tyr Cys Phe Gln Gly Ser His Val Pro
245 250 255

Leu Thr Phe Gly Ala Gly Thr Lys Leu Glu Leu Lys Ala Ser Val Lys
260 265 270

Gly Lys His Leu Cys Pro Ser Pro Leu Phe Pro Gly Pro Ser Lys Pro
275 280 285

Phe Trp Val Leu Val Val Val Gly Gly Val Leu Ala Cys Tyr Ser Leu
290 295 300

Leu Val Thr Val Ala Phe Ile Ile Phe Trp Val Arg Ser Lys Arg Ser
305 310 315 320

Arg Leu Leu His Ser Asp Tyr Met Asn Met Thr Pro Arg Arg Pro Gly
325 330 335

Pro Thr Arg Lys His Tyr Gln Pro Tyr Ala Pro Pro Arg Asp Phe Ala
340 345 350

Ala Tyr Arg Ser Lys Leu Arg Val Lys Phe Ser Arg Ser Ala Asp Ala
355 360 365

Pro Ala Tyr Gln Gln Gly Gln Asn Gln Leu Tyr Asn Glu Leu Asn Leu
370 375 380

Gly Arg Arg Glu Glu Tyr Asp Val Leu Asp Lys Arg Arg Gly Arg Asp
385 390 395 400

Pro Glu Met Gly Gly Lys Pro Arg Arg Lys Asn Pro Gln Glu Gly Leu
405 410 415

Tyr Asn Glu Leu Gln Lys Asp Lys Met Ala Glu Ala Tyr Ser Glu Ile
420 425 430

Gly Met Lys Gly Glu Arg Arg Arg Gly Lys Gly His Asp Gly Leu Tyr
435 440 445

Gln Gly Leu Ser Thr Ala Thr Lys Asp Thr Tyr Asp Ala Leu His Met
450 455 460

Gln Ala Leu Pro Pro
465

<210> SEQ ID NO 31
<211> LENGTH: 19
<212> TYPE: PRT
<213> ORGANISM: Artificial Sequence
<220> FEATURE:
<223> OTHER INFORMATION: SIGNAL SEQUENCE

<400> SEQUENCE: 31

Met Glu Trp Thr Trp Val Phe Leu Phe Leu Leu Ser Val Thr Ala Gly
1 5 10 15

Val His Ser

```
<210> SEQ ID NO 32
<211> LENGTH: 18
<212> TYPE: PRT
<213> ORGANISM: Artificial Sequence
<220> FEATURE:
<223> OTHER INFORMATION: HUMAN CD28 HINGE

<400> SEQUENCE: 32

Val Lys Gly Lys His Leu Cys Pro Ser Pro Leu Phe Pro Gly Pro Ser
1               5                   10                  15

Lys Pro


<210> SEQ ID NO 33
<211> LENGTH: 15
<212> TYPE: PRT
<213> ORGANISM: Artificial Sequence
<220> FEATURE:
<223> OTHER INFORMATION: MOUSE CD28 HINGE

<400> SEQUENCE: 33

Ile Lys Glu Lys His Leu Cys His Thr Gln Ser Ser Pro Lys Leu
1               5                   10                  15


<210> SEQ ID NO 34
<211> LENGTH: 45
<212> TYPE: PRT
<213> ORGANISM: Artificial Sequence
<220> FEATURE:
<223> OTHER INFORMATION: HUMAN CD8A HINGE

<400> SEQUENCE: 34

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 35
<211> LENGTH: 30
<212> TYPE: PRT
<213> ORGANISM: Artificial Sequence
<220> FEATURE:
<223> OTHER INFORMATION: HUMAN DAP10 HINGE

<400> SEQUENCE: 35

Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro
            20                  25                  30


<210> SEQ ID NO 36
<211> LENGTH: 27
<212> TYPE: PRT
<213> ORGANISM: Artificial Sequence
<220> FEATURE:
<223> OTHER INFORMATION: HUMAN CD28 TM

<400> SEQUENCE: 36

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 37
<211> LENGTH: 27
<212> TYPE: PRT
<213> ORGANISM: Artificial Sequence
<220> FEATURE:
<223> OTHER INFORMATION: MOUSE CD28 TM

<400> SEQUENCE: 37

```
Phe Trp Ala Leu Val Val Val Ala Gly Val Leu Phe Cys Tyr Gly Leu
1               5                   10                  15

Leu Val Thr Val Ala Leu Cys Val Ile Trp Thr
            20                  25
```

<210> SEQ ID NO 38
<211> LENGTH: 24
<212> TYPE: PRT
<213> ORGANISM: Artificial Sequence
<220> FEATURE:
<223> OTHER INFORMATION: HUMAN CD8A TM

<400> SEQUENCE: 38

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 39
<211> LENGTH: 21
<212> TYPE: PRT
<213> ORGANISM: Artificial Sequence
<220> FEATURE:
<223> OTHER INFORMATION: HUMAN DAP10 TM

<400> SEQUENCE: 39

```
Leu Leu Ala Gly Leu Val Ala Ala Asp Ala Val Ala Ser Leu Leu Ile
1               5                   10                  15

Val Gly Ala Val Phe
            20
```

<210> SEQ ID NO 40
<211> LENGTH: 451
<212> TYPE: PRT
<213> ORGANISM: Artificial Sequence
<220> FEATURE:
<223> OTHER INFORMATION: DG05-CD28tm-DAP10-CD3Z

<400> SEQUENCE: 40

```
Met Glu Trp Thr Trp Val Phe Leu Phe Leu Leu Ser Val Thr Ala Gly
1               5                   10                  15

Val His Ser Glu Val Gln Leu Val Gln Ser Gly Gly Gly Leu Val Lys
            20                  25                  30

Pro Gly Gly Ser Leu Arg Leu Ser Cys Ala Gly Ser Gly Phe Thr Phe
        35                  40                  45

Ser Ser Tyr Ser Met His Trp Leu Arg Gln Ala Pro Gly Lys Gly Leu
    50                  55                  60

Glu Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Glu Tyr Phe Phe Gly Ser Gly Asn Tyr Gly Tyr Trp
```

```
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Val Ser Ser Tyr Leu Ala Trp Tyr Gln Gln
            180                 185                 190

Lys Pro Gly Gln Ala Pro Arg Leu Leu Ile Tyr Asp Ala Ser Asn Arg
        195                 200                 205

Ala Thr Gly Ile Pro Ala Arg Phe Ser Gly Ser Gly Ser Gly Thr Asp
    210                 215                 220

Phe Thr Leu Thr Ile Ser Ser Leu Glu Pro Glu Asp Phe Ala Val Tyr
225                 230                 235                 240

Tyr Cys Gln Gln Arg Ser Asn Trp Pro Pro Thr Phe Gly Gln Gly Thr
                245                 250                 255

Lys Val Glu Ile Lys Ala Ser Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Leu Cys Ala Arg Pro Arg Arg
305                 310                 315                 320

Ser Pro Ala Gln Glu Asp Gly Lys Val Tyr Ile Asn Met Pro Gly Arg
                325                 330                 335

Gly Lys Leu Arg Val Lys Phe Ser Arg Ser Ala Asp Ala Pro Ala Tyr
            340                 345                 350

Gln Gln Gly Gln Asn Gln Leu Tyr Asn Glu Leu Asn Leu Gly Arg Arg
        355                 360                 365

Glu Glu Tyr Asp Val Leu Asp Lys Arg Arg Gly Arg Asp Pro Glu Met
    370                 375                 380

Gly Gly Lys Pro Arg Arg Lys Asn Pro Gln Glu Gly Leu Tyr Asn Glu
385                 390                 395                 400

Leu Gln Lys Asp Lys Met Ala Glu Ala Tyr Ser Glu Ile Gly Met Lys
                405                 410                 415

Gly Glu Arg Arg Arg Gly Lys Gly His Asp Gly Leu Tyr Gln Gly Leu
            420                 425                 430

Ser Thr Ala Thr Lys Asp Thr Tyr Asp Ala Leu His Met Gln Ala Leu
        435                 440                 445

Pro Pro Arg
    450
```

<210> SEQ ID NO 41
<211> LENGTH: 491
<212> TYPE: PRT
<213> ORGANISM: Artificial Sequence
<220> FEATURE:
<223> OTHER INFORMATION: DG05-CD28tm-CD44-CD3Z

<400> SEQUENCE: 41

```
Met Glu Trp Thr Trp Val Phe Leu Phe Leu Leu Ser Val Thr Ala Gly
1               5                   10                  15

Val His Ser Glu Val Gln Leu Val Gln Ser Gly Gly Gly Leu Val Lys
```

```
            20                  25                  30

Pro Gly Gly Ser Leu Arg Leu Ser Cys Ala Gly Ser Gly Phe Thr Phe
        35                  40                  45

Ser Ser Tyr Ser Met His Trp Leu Arg Gln Ala Pro Gly Lys Gly Leu
    50                  55                  60

Glu Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Glu Tyr Phe Phe Gly Ser Gly Asn Tyr Gly Tyr Trp
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Val Ser Ser Tyr Leu Ala Trp Tyr Gln Gln
            180                 185                 190

Lys Pro Gly Gln Ala Pro Arg Leu Leu Ile Tyr Asp Ala Ser Asn Arg
        195                 200                 205

Ala Thr Gly Ile Pro Ala Arg Phe Ser Gly Ser Gly Ser Gly Thr Asp
    210                 215                 220

Phe Thr Leu Thr Ile Ser Ser Leu Glu Pro Glu Asp Phe Ala Val Tyr
225                 230                 235                 240

Tyr Cys Gln Gln Arg Ser Asn Trp Pro Pro Thr Phe Gly Gln Gly Thr
                245                 250                 255

Lys Val Glu Ile Lys Ala Ser Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Ser Arg Arg Arg Cys Gly Gln Lys Lys Lys Leu Val
305                 310                 315                 320

Ile Asn Ser Gly Asn Gly Ala Val Glu Asp Arg Lys Pro Ser Gly Leu
                325                 330                 335

Asn Gly Glu Ala Ser Lys Ser Gln Glu Met Val His Leu Val Asn Lys
            340                 345                 350

Glu Ser Ser Glu Thr Pro Asp Gln Phe Met Thr Ala Asp Glu Thr Arg
        355                 360                 365

Asn Leu Gln Asn Val Asp Met Lys Ile Gly Val Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445
```

```
Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 42
<211> LENGTH: 426
<212> TYPE: PRT
<213> ORGANISM: Artificial Sequence
<220> FEATURE:
<223> OTHER INFORMATION: DG05-CD28tm-CD3Z

<400> SEQUENCE: 42

Met Glu Trp Thr Trp Val Phe Leu Phe Leu Leu Ser Val Thr Ala Gly
1               5                   10                  15

Val His Ser Glu Val Gln Leu Val Gln Ser Gly Gly Gly Leu Val Lys
            20                  25                  30

Pro Gly Gly Ser Leu Arg Leu Ser Cys Ala Gly Ser Gly Phe Thr Phe
        35                  40                  45

Ser Ser Tyr Ser Met His Trp Leu Arg Gln Ala Pro Gly Lys Gly Leu
    50                  55                  60

Glu Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Glu Tyr Phe Phe Gly Ser Gly Asn Tyr Gly Tyr Trp
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Val Ser Ser Tyr Leu Ala Trp Tyr Gln Gln
            180                 185                 190

Lys Pro Gly Gln Ala Pro Arg Leu Leu Ile Tyr Asp Ala Ser Asn Arg
        195                 200                 205

Ala Thr Gly Ile Pro Ala Arg Phe Ser Gly Ser Gly Ser Gly Thr Asp
    210                 215                 220

Phe Thr Leu Thr Ile Ser Ser Leu Glu Pro Glu Asp Phe Ala Val Tyr
225                 230                 235                 240

Tyr Cys Gln Gln Arg Ser Asn Trp Pro Pro Thr Phe Gly Gln Gly Thr
                245                 250                 255

Lys Val Glu Ile Lys Ala Ser Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Arg Arg Val Lys Phe Ser Arg
305                 310                 315                 320
```

```
Ser Ala Asp Ala Pro Ala Tyr Gln Gln Gly Gln Asn Gln Leu Tyr Asn
            325                 330                 335

Glu Leu Asn Leu Gly Arg Arg Glu Glu Tyr Asp Val Leu Asp Lys Arg
        340                 345                 350

Arg Gly Arg Asp Pro Glu Met Gly Gly Lys Pro Arg Arg Lys Asn Pro
    355                 360                 365

Gln Glu Gly Leu Tyr Asn Glu Leu Gln Lys Asp Lys Met Ala Glu Ala
370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
                405                 410                 415

Ala Leu His Met Gln Ala Leu Pro Pro Arg
            420                 425


<210> SEQ ID NO 43
<211> LENGTH: 349
<212> TYPE: PRT
<213> ORGANISM: Artificial Sequence
<220> FEATURE:
<223> OTHER INFORMATION: DG05-CD28

<400> SEQUENCE: 43

Met Glu Trp Thr Trp Val Phe Leu Phe Leu Leu Ser Val Thr Ala Gly
1               5                   10                  15

Val His Ser Glu Val Gln Leu Val Gln Ser Gly Gly Gly Leu Val Lys
            20                  25                  30

Pro Gly Gly Ser Leu Arg Leu Ser Cys Ala Gly Ser Gly Phe Thr Phe
        35                  40                  45

Ser Ser Tyr Ser Met His Trp Leu Arg Gln Ala Pro Gly Lys Gly Leu
    50                  55                  60

Glu Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Glu Tyr Phe Phe Gly Ser Gly Asn Tyr Gly Tyr Trp
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Val Ser Ser Tyr Leu Ala Trp Tyr Gln Gln
            180                 185                 190

Lys Pro Gly Gln Ala Pro Arg Leu Leu Ile Tyr Asp Ala Ser Asn Arg
        195                 200                 205

Ala Thr Gly Ile Pro Ala Arg Phe Ser Gly Ser Gly Ser Gly Thr Asp
    210                 215                 220

Phe Thr Leu Thr Ile Ser Ser Leu Glu Pro Glu Asp Phe Ala Val Tyr
225                 230                 235                 240

Tyr Cys Gln Gln Arg Ser Asn Trp Pro Pro Thr Phe Gly Gln Gly Thr
                245                 250                 255
```

```
Lys Val Glu Ile Lys Ala Ser Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Arg Leu Leu His Ser Asp Tyr
305                 310                 315                 320

Met Asn Met Thr Pro Arg Arg Pro Gly Pro Thr Arg Lys His Tyr Gln
                325                 330                 335

Pro Tyr Ala Pro Pro Arg Asp Phe Ala Ala Tyr Arg Ser
            340                 345


<210> SEQ ID NO 44
<211> LENGTH: 319
<212> TYPE: PRT
<213> ORGANISM: Artificial Sequence
<220> FEATURE:
<223> OTHER INFORMATION: DG05-CD28tm

<400> SEQUENCE: 44

Met Glu Trp Thr Trp Val Phe Leu Phe Leu Leu Ser Val Thr Ala Gly
1               5                   10                  15

Val His Ser Glu Val Gln Leu Val Gln Ser Gly Gly Gly Leu Val Lys
            20                  25                  30

Pro Gly Gly Ser Leu Arg Leu Ser Cys Ala Gly Ser Gly Phe Thr Phe
        35                  40                  45

Ser Ser Tyr Ser Met His Trp Leu Arg Gln Ala Pro Gly Lys Gly Leu
    50                  55                  60

Glu Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Glu Tyr Phe Phe Gly Ser Gly Asn Tyr Gly Tyr Trp
        115                 120                 125

Gly Gln Gly Thr Leu Val Thr Val Ser Ser Ala Gly Gly Gly Gly Ser
    130                 135                 140

Gly Gly Gly Gly Ser Gly Gly Gly Gly Ser Glu Ile Val Leu Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Val Ser Ser Tyr Leu Ala Trp Tyr Gln Gln
            180                 185                 190

Lys Pro Gly Gln Ala Pro Arg Leu Leu Ile Tyr Asp Ala Ser Asn Arg
        195                 200                 205

Ala Thr Gly Ile Pro Ala Arg Phe Ser Gly Ser Gly Ser Gly Thr Asp
    210                 215                 220

Phe Thr Leu Thr Ile Ser Ser Leu Glu Pro Glu Asp Phe Ala Val Tyr
225                 230                 235                 240

Tyr Cys Gln Gln Arg Ser Asn Trp Pro Pro Thr Phe Gly Gln Gly Thr
                245                 250                 255

Lys Val Glu Ile Lys Ala Ser Val Lys Gly Lys His Leu Cys Pro Ser
            260                 265                 270
```

```
Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Arg Leu Leu His Ser Asp
305                 310                 315


<210> SEQ ID NO 45
<211> LENGTH: 449
<212> TYPE: PRT
<213> ORGANISM: Artificial Sequence
<220> FEATURE:
<223> OTHER INFORMATION: DG03-CD28tm-DAP10-CD3Z

<400> SEQUENCE: 45

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Gly Met Ser Trp Val Arg Gln Ala Pro Gly Lys Gly Leu
    50                  55                  60

Glu Leu Val Ala Ser Ile Asn Ser Asn Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Gly Asp Tyr Trp Gly Gln Gly Thr Thr Val Thr
        115                 120                 125

Val Ser Ser Ala Gly Gly Gly Gly Ser Gly Gly Gly Gly Ser Gly Gly
    130                 135                 140

Gly Gly Ser Asp Ile Val Met Thr Gln Ser Pro Leu Ser Leu Pro Val
145                 150                 155                 160

Thr Pro Gly Glu Pro Ala Ser Ile Ser Cys Arg Ser Ser Gln Ser Leu
                165                 170                 175

Val Tyr Ser Asn Gly Asp Thr Tyr Leu His Trp Tyr Leu Gln Lys Pro
            180                 185                 190

Gly Gln Ser Pro Gln Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

Leu Lys Ile Ser Arg Val Glu Ala Glu Asp Val Gly Val Tyr Tyr Cys
225                 230                 235                 240

Ser Gln Ser Thr His Val Pro Trp Thr Phe Gly Gln Gly Thr Lys Val
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Leu Cys Ala Arg Pro Arg Arg Ser Pro
305                 310                 315                 320
```

```
Ala Gln Glu Asp Gly Lys Val Tyr Ile Asn Met Pro Gly Arg Gly Lys
                325                 330                 335

Leu Arg Val Lys Phe Ser Arg Ser Ala Asp Ala Pro Ala Tyr Gln Gln
            340                 345                 350

Gly Gln Asn Gln Leu Tyr Asn Glu Leu Asn Leu Gly Arg Arg Glu Glu
        355                 360                 365

Tyr Asp Val Leu Asp Lys Arg Arg Gly Arg Asp Pro Glu Met Gly Gly
    370                 375                 380

Lys Pro Arg Arg Lys Asn Pro Gln Glu Gly Leu Tyr Asn Glu Leu Gln
385                 390                 395                 400

Lys Asp Lys Met Ala Glu Ala Tyr Ser Glu Ile Gly Met Lys Gly Glu
                405                 410                 415

Arg Arg Arg Gly Lys Gly His Asp Gly Leu Tyr Gln Gly Leu Ser Thr
            420                 425                 430

Ala Thr Lys Asp Thr Tyr Asp Ala Leu His Met Gln Ala Leu Pro Pro
        435                 440                 445

Arg


<210> SEQ ID NO 46
<211> LENGTH: 489
<212> TYPE: PRT
<213> ORGANISM: Artificial Sequence
<220> FEATURE:
<223> OTHER INFORMATION: DG03-CD28tm-CD44-CD3Z

<400> SEQUENCE: 46

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Gly Met Ser Trp Val Arg Gln Ala Pro Gly Lys Gly Leu
    50                  55                  60

Glu Leu Val Ala Ser Ile Asn Ser Asn Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Gly Asp Tyr Trp Gly Gln Gly Thr Thr Val Thr
        115                 120                 125

Val Ser Ser Ala Gly Gly Gly Gly Ser Gly Gly Gly Gly Ser Gly Gly
    130                 135                 140

Gly Gly Ser Asp Ile Val Met Thr Gln Ser Pro Leu Ser Leu Pro Val
145                 150                 155                 160

Thr Pro Gly Glu Pro Ala Ser Ile Ser Cys Arg Ser Ser Gln Ser Leu
                165                 170                 175

Val Tyr Ser Asn Gly Asp Thr Tyr Leu His Trp Tyr Leu Gln Lys Pro
            180                 185                 190

Gly Gln Ser Pro Gln Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220
```

-continued

```
Leu Lys Ile Ser Arg Val Glu Ala Glu Asp Val Gly Val Tyr Tyr Cys
225                 230                 235                 240

Ser Gln Ser Thr His Val Pro Trp Thr Phe Gly Gln Gly Thr Lys Val
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Ser Arg Arg Arg Cys Gly Gln Lys Lys Lys Leu Val Ile Asn
305                 310                 315                 320

Ser Gly Asn Gly Ala Val Glu Asp Arg Lys Pro Ser Gly Leu Asn Gly
                325                 330                 335

Glu Ala Ser Lys Ser Gln Glu Met Val His Leu Val Asn Lys Glu Ser
            340                 345                 350

Ser Glu Thr Pro Asp Gln Phe Met Thr Ala Asp Glu Thr Arg Asn Leu
        355                 360                 365

Gln Asn Val Asp Met Lys Ile Gly Val Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 47
<211> LENGTH: 469
<212> TYPE: PRT
<213> ORGANISM: Artificial Sequence
<220> FEATURE:
<223> OTHER INFORMATION: DG03-CD28tm-4-1-BB-CD3Z

<400> SEQUENCE: 47

```
Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Gly Met Ser Trp Val Arg Gln Ala Pro Gly Lys Gly Leu
    50                  55                  60

Glu Leu Val Ala Ser Ile Asn Ser Asn Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95
```

-continued

```
Ser Leu Tyr Leu Gln Met Asn Ser Leu Arg Ala Glu Asp Thr Ala Val
            100                 105                 110

Tyr Tyr Cys Ala Ser Gly Asp Tyr Trp Gly Gln Gly Thr Thr Val Thr
        115                 120                 125

Val Ser Ser Ala Gly Gly Gly Gly Ser Gly Gly Gly Gly Ser Gly Gly
    130                 135                 140

Gly Gly Ser Asp Ile Val Met Thr Gln Ser Pro Leu Ser Leu Pro Val
145                 150                 155                 160

Thr Pro Gly Glu Pro Ala Ser Ile Ser Cys Arg Ser Ser Gln Ser Leu
                165                 170                 175

Val Tyr Ser Asn Gly Asp Thr Tyr Leu His Trp Tyr Leu Gln Lys Pro
            180                 185                 190

Gly Gln Ser Pro Gln Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

Leu Lys Ile Ser Arg Val Glu Ala Glu Asp Val Gly Val Tyr Tyr Cys
225                 230                 235                 240

Ser Gln Ser Thr His Val Pro Trp Thr Phe Gly Gln Gly Thr Lys Val
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Leu Glu Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Lys Leu Arg Val Lys Phe Ser Arg Ser Ala Asp Ala Pro
        355                 360                 365

Ala Tyr Gln Gln Gly Gln Asn Gln Leu Tyr Asn Glu Leu Asn Leu Gly
    370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465
```

<210> SEQ ID NO 48
<211> LENGTH: 424
<212> TYPE: PRT
<213> ORGANISM: Artificial Sequence
<220> FEATURE:
<223> OTHER INFORMATION: DG03-CD28tm-CD3Z

<400> SEQUENCE: 48

Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Gly Met Ser Trp Val Arg Gln Ala Pro Gly Lys Gly Leu
    50                  55                  60

Glu Leu Val Ala Ser Ile Asn Ser Asn Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Gly Asp Tyr Trp Gly Gln Gly Thr Thr Val Thr
        115                 120                 125

Val Ser Ser Ala Gly Gly Gly Gly Ser Gly Gly Gly Gly Ser Gly Gly
    130                 135                 140

Gly Gly Ser Asp Ile Val Met Thr Gln Ser Pro Leu Ser Leu Pro Val
145                 150                 155                 160

Thr Pro Gly Glu Pro Ala Ser Ile Ser Cys Arg Ser Ser Gln Ser Leu
                165                 170                 175

Val Tyr Ser Asn Gly Asp Thr Tyr Leu His Trp Tyr Leu Gln Lys Pro
            180                 185                 190

Gly Gln Ser Pro Gln Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

Leu Lys Ile Ser Arg Val Glu Ala Glu Asp Val Gly Val Tyr Tyr Cys
225                 230                 235                 240

Ser Gln Ser Thr His Val Pro Trp Thr Phe Gly Gln Gly Thr Lys Val
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val Arg Ser Lys Arg Ser Arg Arg Val Lys Phe Ser Arg Ser Ala
305                 310                 315                 320

Asp Ala Pro Ala Tyr Gln Gln Gly Gln Asn Gln Leu Tyr Asn Glu Leu
                325                 330                 335

Asn Leu Gly Arg Arg Glu Glu Tyr Asp Val Leu Asp Lys Arg Arg Gly
            340                 345                 350

Arg Asp Pro Glu Met Gly Gly Lys Pro Arg Arg Lys Asn Pro Gln Glu
        355                 360                 365

Gly Leu Tyr Asn Glu Leu Gln Lys Asp Lys Met Ala Glu Ala Tyr Ser
    370                 375                 380

Glu Ile Gly Met Lys Gly Glu Arg Arg Arg Gly Lys Gly His Asp Gly
385                 390                 395                 400

Leu Tyr Gln Gly Leu Ser Thr Ala Thr Lys Asp Thr Tyr Asp Ala Leu 405 410 415

His Met Gln Ala Leu Pro Pro Arg
420

<210> SEQ ID NO 49
<211> LENGTH: 347
<212> TYPE: PRT
<213> ORGANISM: Artificial Sequence
<220> FEATURE:
<223> OTHER INFORMATION: DG03-CD28

<400> SEQUENCE: 49

Met Glu Trp Thr Trp Val Phe Leu Phe Leu Leu Ser Val Thr Ala Gly
1 5 10 15

Val His Ser Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Gly Met Ser Trp Val Arg Gln Ala Pro Gly Lys Gly Leu
50 55 60

Glu Leu Val Ala Ser Ile Asn Ser Asn Gly Gly Ser Thr Tyr Tyr Pro
65 70 75 80

Asp Ser Val Lys Gly Arg Phe Thr Ile Ser Arg Asp Asn Ala Lys Asn
85 90 95

Ser Leu Tyr Leu Gln Met Asn Ser Leu Arg Ala Glu Asp Thr Ala Val
100 105 110

Tyr Tyr Cys Ala Ser Gly Asp Tyr Trp Gly Gln Gly Thr Thr Val Thr
115 120 125

Val Ser Ser Ala Gly Gly Gly Gly Ser Gly Gly Gly Gly Ser Gly Gly
130 135 140

Gly Gly Ser Asp Ile Val Met Thr Gln Ser Pro Leu Ser Leu Pro Val
145 150 155 160

Thr Pro Gly Glu Pro Ala Ser Ile Ser Cys Arg Ser Ser Gln Ser Leu
165 170 175

Val Tyr Ser Asn Gly Asp Thr Tyr Leu His Trp Tyr Leu Gln Lys Pro
180 185 190

Gly Gln Ser Pro Gln Leu Leu Ile Tyr Lys Val Ser Asn Arg Phe Ser
195 200 205

Gly Val Pro Asp Arg Phe Ser Gly Ser Gly Ser Gly Thr Asp Phe Thr
210 215 220

Leu Lys Ile Ser Arg Val Glu Ala Glu Asp Val Gly Val Tyr Tyr Cys
225 230 235 240

Ser Gln Ser Thr His Val Pro Trp Thr Phe Gly Gln Gly Thr Lys Val
245 250 255

Glu Ile Lys Ala Ser Val Lys Gly Lys His Leu Cys Pro Ser Pro Leu
260 265 270

Phe Pro Gly Pro Ser Lys Pro Phe Trp Val Leu Val Val Val Gly Gly
275 280 285

Val Leu Ala Cys Tyr Ser Leu Leu Val Thr Val Ala Phe Ile Ile Phe
290 295 300

Trp Val Arg Ser Lys Arg Ser Arg Leu Leu His Ser Asp Tyr Met Asn
305 310 315 320

Met Thr Pro Arg Arg Pro Gly Pro Thr Arg Lys His Tyr Gln Pro Tyr
325 330 335

Ala Pro Pro Arg Asp Phe Ala Ala Tyr Arg Ser 340 345

<210> SEQ ID NO 50
<211> LENGTH: 306
<212> TYPE: PRT
<213> ORGANISM: Artificial Sequence
<220> FEATURE:
<223> OTHER INFORMATION: DG03-CD28tm

<400> SEQUENCE: 50

```
Met Glu Trp Thr Trp Val Phe Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Gly Met Ser Trp Val Arg Gln Ala Pro Gly Lys Gly Leu
    50                  55                  60

Glu Leu Val Ala Ser Ile Asn Ser Asn Gly Gly Ser Thr Tyr Tyr Pro
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Gly Asp Tyr Trp Gly Gln Gly Thr Thr Val Thr
        115                 120                 125

Val Ser Ser Ala Gly Gly Gly Gly Ser Gly Gly Gly Gly Ser Gly Gly
    130                 135                 140

Gly Gly Ser Asp Ile Val Met Thr Gln Ser Pro Leu Ser Leu Pro Val
145                 150                 155                 160

Thr Pro Gly Glu Pro Ala Ser Ile Ser Cys Arg Ser Ser Gln Ser Leu
                165                 170                 175

Val Tyr Ser Asn Gly Asp Thr Tyr Leu His Trp Tyr Leu Gln Lys Pro
            180                 185                 190

Gly Gln Ser Pro Gln Leu Leu Ile Tyr Lys Val Ser Asn Arg Phe Ser
        195                 200                 205

Gly Val Pro Asp Arg Phe Ser Gly Ser Gly Ser Gly Thr Asp Phe Thr
    210                 215                 220

Leu Lys Ile Ser Arg Val Glu Ala Glu Asp Val Gly Val Tyr Tyr Cys
225                 230                 235                 240

Ser Gln Ser Thr His Val Pro Trp Thr Phe Gly Gln Gly Thr Lys Val
                245                 250                 255

Glu Ile Lys Ala Ser Val Lys Gly Lys His Leu Cys Pro Ser Pro Leu
            260                 265                 270

Phe Pro Gly Pro Ser Lys Pro Phe Trp Val Leu Val Val Val Gly Gly
        275                 280                 285

Val Leu Ala Cys Tyr Ser Leu Leu Val Thr Val Ala Phe Ile Ile Phe
    290                 295                 300

Trp Val
305
```

<210> SEQ ID NO 51
<211> LENGTH: 90
<212> TYPE: PRT
<213> ORGANISM: Artificial Sequence
<220> FEATURE:
<223> OTHER INFORMATION: Construct for expression of the NDMM Nrf2

(Keap1 inhibitor peptide)

<400> SEQUENCE: 51

```
Met Met Asp Leu Glu Leu Pro Pro Pro Gly Leu Pro Ser Gln Gln Asp
1               5                   10                  15

Met Asp Leu Ile Asp Ile Leu Trp Arg Gln Asp Ile Asp Leu Gly Val
            20                  25                  30

Ser Arg Glu Val Phe Asp Phe Ser Gln Arg Arg Lys Glu Tyr Glu Leu
        35                  40                  45

Glu Lys Gln Lys Lys Leu Glu Lys Glu Arg Gln Glu Gln Leu Gln Lys
    50                  55                  60

Glu Gln Glu Lys Ala Phe Phe Ala Gln Leu Gln Leu Asp Glu Glu Thr
65                  70                  75                  80

Gly Glu Phe Leu Pro Ile Gln Pro Ala Gln
                85                  90
```

<210> SEQ ID NO 52
<211> LENGTH: 527
<212> TYPE: PRT
<213> ORGANISM: Artificial Sequence
<220> FEATURE:
<223> OTHER INFORMATION: Construct for expression of the NDMM human catalase

<400> SEQUENCE: 52

```
Met Ala Asp Ser Arg Asp Pro Ala Ser Asp Gln Met Gln His Trp Lys
1               5                   10                  15

Glu Gln Arg Ala Ala Gln Lys Ala Asp Val Leu Thr Thr Gly Ala Gly
            20                  25                  30

Asn Pro Val Gly Asp Lys Leu Asn Val Ile Thr Val Gly Pro Arg Gly
        35                  40                  45

Pro Leu Leu Val Gln Asp Val Val Phe Thr Asp Glu Met Ala His Phe
    50                  55                  60

Asp Arg Glu Arg Ile Pro Glu Arg Val Val His Ala Lys Gly Ala Gly
65                  70                  75                  80

Ala Phe Gly Tyr Phe Glu Val Thr His Asp Ile Thr Lys Tyr Ser Lys
                85                  90                  95

Ala Lys Val Phe Glu His Ile Gly Lys Lys Thr Pro Ile Ala Val Arg
            100                 105                 110

Phe Ser Thr Val Ala Gly Glu Ser Gly Ser Ala Asp Thr Val Arg Asp
        115                 120                 125

Pro Arg Gly Phe Ala Val Lys Phe Tyr Thr Glu Asp Gly Asn Trp Asp
    130                 135                 140

Leu Val Gly Asn Asn Thr Pro Ile Phe Phe Ile Arg Asp Pro Ile Leu
145                 150                 155                 160

Phe Pro Ser Phe Ile His Ser Gln Lys Arg Asn Pro Gln Thr His Leu
                165                 170                 175

Lys Asp Pro Asp Met Val Trp Asp Phe Trp Ser Leu Arg Pro Glu Ser
            180                 185                 190

Leu His Gln Val Ser Phe Leu Phe Ser Asp Arg Gly Ile Pro Asp Gly
        195                 200                 205

His Arg His Met Asn Gly Tyr Gly Ser His Thr Phe Lys Leu Val Asn
    210                 215                 220

Ala Asn Gly Glu Ala Val Tyr Cys Lys Phe His Tyr Lys Thr Asp Gln
225                 230                 235                 240

Gly Ile Lys Asn Leu Ser Val Glu Asp Ala Ala Arg Leu Ser Gln Glu
```

-continued

```
                245                 250                 255

Asp Pro Asp Tyr Gly Ile Arg Asp Leu Phe Asn Ala Ile Ala Thr Gly
            260                 265                 270

Lys Tyr Pro Ser Trp Thr Phe Tyr Ile Gln Val Met Thr Phe Asn Gln
        275                 280                 285

Ala Glu Thr Phe Pro Phe Asn Pro Phe Asp Leu Thr Lys Val Trp Pro
    290                 295                 300

His Lys Asp Tyr Pro Leu Ile Pro Val Gly Lys Leu Val Leu Asn Arg
305                 310                 315                 320

Asn Pro Val Asn Tyr Phe Ala Glu Val Glu Gln Ile Ala Phe Asp Pro
                325                 330                 335

Ser Asn Met Pro Pro Gly Ile Glu Ala Ser Pro Asp Lys Met Leu Gln
            340                 345                 350

Gly Arg Leu Phe Ala Tyr Pro Asp Thr His Arg His Arg Leu Gly Pro
        355                 360                 365

Asn Tyr Leu His Ile Pro Val Asn Cys Pro Tyr Arg Ala Arg Val Ala
    370                 375                 380

Asn Tyr Gln Arg Asp Gly Pro Met Cys Met Gln Asp Asn Gln Gly Gly
385                 390                 395                 400

Ala Pro Asn Tyr Tyr Pro Asn Ser Phe Gly Ala Pro Glu Gln Gln Pro
                405                 410                 415

Ser Ala Leu Glu His Ser Ile Gln Tyr Ser Gly Glu Val Arg Arg Phe
            420                 425                 430

Asn Thr Ala Asn Asp Asp Asn Val Thr Gln Val Arg Ala Phe Tyr Val
        435                 440                 445

Asn Val Leu Asn Glu Glu Gln Arg Lys Arg Leu Cys Glu Asn Ile Ala
    450                 455                 460

Gly His Leu Lys Asp Ala Gln Ile Phe Ile Gln Lys Lys Ala Val Lys
465                 470                 475                 480

Asn Phe Thr Glu Val His Pro Asp Tyr Gly Ser His Ile Gln Ala Leu
                485                 490                 495

Leu Asp Lys Tyr Asn Ala Glu Lys Pro Lys Asn Ala Ile His Thr Phe
            500                 505                 510

Val Gln Ser Gly Ser His Leu Ala Ala Arg Glu Lys Ala Asn Leu
        515                 520                 525


<210> SEQ ID NO 53
<211> LENGTH: 247
<212> TYPE: PRT
<213> ORGANISM: Artificial Sequence
<220> FEATURE:
<223> OTHER INFORMATION: Construct for expression of the NDMM BDNF

<400> SEQUENCE: 53

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
```

```
                85                  90                  95

Ser Ser Gln Val Pro Leu Glu Pro Pro Leu Leu Phe Leu Leu Glu Glu
            100                 105                 110

Tyr Lys Asn Tyr Leu Asp Ala Ala Asn Met Ser Met Arg Val Arg Arg
        115                 120                 125

His Ser Asp Pro Ala Arg Arg Gly Glu Leu Ser Val Cys Asp Ser Ile
    130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245


<210> SEQ ID NO 54
<211> LENGTH: 195
<212> TYPE: PRT
<213> ORGANISM: Artificial Sequence
<220> FEATURE:
<223> OTHER INFORMATION: Construct for expression of the NDMM IGF-1

<400> SEQUENCE: 54

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Trp Pro Lys Thr His Pro Gly Gly Glu
145                 150                 155                 160

Gln Lys Glu Gly Thr Glu Ala Ser Leu Gln Ile Arg Gly Lys Lys Lys
                165                 170                 175

Glu Gln Arg Arg Glu Ile Gly Ser Arg Asn Ala Glu Cys Arg Gly Lys
            180                 185                 190

Lys Gly Lys
```

-continued

195

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

-continued

000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

-continued

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

-continued

000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 798

<212> TYPE: DNA
<213> ORGANISM: Artificial Sequence
<220> FEATURE:
<223> OTHER INFORMATION: DG01 SCFV

<400> SEQUENCE: 201
atggaatgga cctgggtgtt cctgtttctg ctgtccgtga ccgctggcgt gcacagccag 60
gtgcagctgg tggaaagcgg cggaggagtc gtgcagcctg gcagaagcct gaggctgagc 120
tgtgccgcca gcggcttcgc cttcagctcc tacggcatgc actgggtgag acaggcccct 180
ggcaagggac tggagtgggt ggctgtgatc tggttcgacg gcaccaagaa gtactacacc 240
gacagcgtca agggcaggtt caccatctcc agggacaata gcaagaatac cctgtacctc 300
caaatgaaca ccctgagggc cgaggacacc gccgtgtatt actgcgccag ggatagggga 360
atcggcgcca ggagaggccc ctactacatg gacgtgtggg gcaagggcac aacagtgacc 420
gtttcttctg ctggaggagg aggttctgga ggaggaggaa gcggaggagg aggctccgac 480
atccagatga cacagtcccc cagctccctg tccgccagcg tgggcgatag agtgaccatc 540
acctgcaggg ccagccagag catctccagc tacctgaact ggtatcaaca gaagcccggc 600
aaagccccca aactgctgat ctacgctgcc agcagcctgc agagcggcgt gccttccaga 660
ttcagcggct ccggcagcgg caccgatttc acactgacca tctccagcct gcagcccgag 720
gacttcgcca cctactactg ccagcagagc tacagcaccc ccctgacctt tggcggaggc 780
accaaggtgg agatcaaa 798

<210> SEQ ID NO 202
<211> LENGTH: 798
<212> TYPE: DNA
<213> ORGANISM: Artificial Sequence
<220> FEATURE:
<223> OTHER INFORMATION: DG02 SCFV

<400> SEQUENCE: 202
atggaatgga cctgggtgtt tctgttcctg ctgagcgtga cagccggcgt gcacagcgag 60
gtgcagctgc tggagagcgg aggaggactg gtgcaacccg gcggaagcct cagactgagc 120
tgtgccgcca gcggcttcac cttcagcaac tatggcatga gctgggtgag gcaggcccct 180
ggcaaaggcc tcgaatgggt ggcttccatt aggagcggcg gcggcaggac ctattacagc 240
gacaacgtga agggcaggtt caccatctcc agggacaata gcaagaacac cctgtacctg 300
cagatgaact ccctgagggc cgaggatacc gccgtgtact actgcgtgag gtacgaccac 360
tacagcggct ccagcgacta ttggggacag ggcaccctgg tgacagtgtc cagcgccgga 420
ggaggcggca gcggcggcgg cggcagcggc ggcggcggaa gcgatgtggt gatgacccag 480 tccccccctga gcctgcctgt gacacctgga gagcccgcca gcatcagctg taagagcagc 540
cagagcctcc tggacagcga cggcaaaacc tacctgaact ggctcctgca gaagcccgga 600
caaagccccc agaggctgat ctacctggtg agcaaactgg acagcggcgt gcctgacaga 660
ttctccggct ccggcagcgg caccgacttc acactgaaga tcagcagagt ggaggctgag 720
gacgtgggcg tctactactg ctggcagggc acccacttcc ccaggacctt cggccaggga 780
accaaggtgg agatcaag 798

<210> SEQ ID NO 203
<211> LENGTH: 777
<212> TYPE: DNA
<213> ORGANISM: Artificial Sequence
<220> FEATURE:

<223> OTHER INFORMATION: DG03 SCFV

<400> SEQUENCE: 203
atggaatgga cctgggtgtt cctgtttctg ctctccgtga ccgccggagt gcacagcgag 60
gtgcagctgg tcgaaagcgg cggaggactg gtgcagcctg gcggcagcct gagactgagc 120
tgtgccgcct ccggcttcac ctttagcagc tacggaatgt cctgggtgag acaggctcct 180
ggcaagggcc tggaactggt ggccagcatc aatagcaacg gcggcagcac ctactaccct 240
gatagcgtga agggcaggtt caccatctcc agggacaacg ccaagaacag cctgtacctg 300
cagatgaaca gcctcagggc cgaggacaca gccgtgtact actgcgccag cggcgactat 360
tggggacagg gaacaaccgt gaccgtcagc agcgccggcg gcggcggcag cggcggcggc 420
ggcagcggcg gcggcggctc cgatatcgtg atgacccaga gccccctgtc cctgcctgtc 480
acacctggcg aacccgccag cattagctgc aggtccagcc agagcctggt gtacagcaat 540
ggcgacacct acctgcactg gtacctgcag aagcctggcc agagcccccca gctgctgatc 600 tacaaggtga gcaacaggtt ctccggagtg cctgacaggt tcagcggctc cggcagcgga 660
accgatttca ccctcaagat cagcagagtg gaggccgagg acgtgggcgt ctactattgt 720
agccagagca cccacgtgcc ctggaccttt ggccagggca ccaaggtgga gatcaaa 777

<210> SEQ ID NO 204
<211> LENGTH: 807
<212> TYPE: DNA
<213> ORGANISM: Artificial Sequence
<220> FEATURE:
<223> OTHER INFORMATION: DG04 SCFV

<400> SEQUENCE: 204
atggaatgga cctgggtgtt tctgttcctc ctgagcgtga ccgccggagt gcacagccaa 60
gtggagctgg tggagagcgg aggaggactg gtgcagcctg gaggctccct gaggctgagc 120
tgtgctgcca gcggcttcac cttcagctcc tatgctatga gctgggtgag acaggcccct 180
ggcaaaggcc tggagtgggt gagcgccatc aacgcctccg gcaccaggac ctactatgcc 240
gactccgtga agggcaggtt caccatctcc agggacaaca gcaagaacac cctgtacctg 300
cagatgaaca gcctgagggc tgaagacacc gccgtgtact actgtgccag gggcaagggc 360
aacacacaca agccctatgg ctacgtgaga tacttcgacg tgtggggaca gggcaccctg 420
gtgacagtga gcagcgccgg aggaggaggt tctggaggag gaggaagcgg cggaggagga 480
agcgacatcg tgctgacaca atccccccgcc acactgtccc tgtcccctgg cgagagggcc 540
acactgagct gcagggccag ccagagcgtg tcctcctcct acctggcctg gtaccagcag 600
aaacctggcc aggcccccag gctgctgatc tatggcgcca gcagcagagc cacaggagtg 660
cctgccagat ttagcggcag cggcagcggc accgacttta ccctgaccat ttccagcctg 720
gagcccgagg acttcgccac ctactactgc ctgcagatct acaacatgcc tatcaccttc 780
ggccagggca caaaagtgga aatcaag 807

<210> SEQ ID NO 205
<211> LENGTH: 783
<212> TYPE: DNA
<213> ORGANISM: Artificial Sequence
<220> FEATURE:
<223> OTHER INFORMATION: DG05 SCFV

<400> SEQUENCE: 205
atggaatgga cctgggtgtt tctgttcctc ctgtccgtga ccgccggagt gcactccgaa 60
gtgcagctgg tgcagtccgg cggaggactg gtgaaacccg gaggaagcct cagactgagc 120
tgcgccggca gcggctttac cttctccagc tactccatgc actggctgag acaggcccct 180
ggcaagggcc tggaatgggt cagcgccatc ggcaccgccg gaggcacata ctatgccgac 240
agcgtgaagg gcaggttcac catcagcagg gacaacgcca agaacagcct gtacctgcag 300
atgaactctc tgagggccga ggataccgct gtgtactact gcgccaggga gtacttcttt 360
ggcagcggca actacggata ctggggccag ggcaccctgg tgacagtgag ctccgccgga 420
ggaggaggaa gcggaggagg cggaagcgga ggaggcggca gcgaaatcgt gctgacccag 480
agccctgcca ccctgagcct gagccctggc gaaagggcca ccctgagctg cagagccagc 540
cagagcgtga gcagctacct ggcctggtac cagcagaagc ccggacaggc ccccagactg 600
ctgatctacg acgccagcaa cagagccacc ggcattcccg ccagattctc cggcagcggc 660
agcggaaccg acttcacact gaccatcagc tccttagaac ccgaggactt cgccgtgtac 720
tactgtcagc agagaagcaa ctggcctccc accttcggcc agggcacaaa ggtggagatc 780
aag 783

<210> SEQ ID NO 206
<211> LENGTH: 777
<212> TYPE: DNA
<213> ORGANISM: Artificial Sequence
<220> FEATURE:
<223> OTHER INFORMATION: DG06 SCFV

<400> SEQUENCE: 206
atggaatgga cctgggtgtt cctgttcctc ctgagcgtga ccgctggcgt ccacagccag 60
gtgcagctgg tggaaagcgg aggcggagtg gtgcagcctg gaaggtccct cagactgagc 120
tgcgctgcca gcggcttcac cttcagcaac tacggcatcc actgggtgag acaagccccc 180
ggcaaaggcc tggagtgggt ggccatcatc tggcacgacg gcagcaactc ctactacgtg 240
gactccgtga agggcaggtt cacaatcagc agagacaaca gcaagaatac cctgtacctg 300
cagatgaaca gcctcagggc cgaagatacc gccgtgtact tctgcgccag gatcatcggc 360
ggcgcctttg acatttgggg ccaaggcact atggttaccg tgagcagcgc tggcggaggc 420
ggcagcggcg gcggcggcag cggcggcggc ggaagcgaca tccagatgac ccagagccct 480
tccagcctca gcgcctccgt gggagacaga gtgaccatca cctgcagggc cagccagggc 540
atctccagct ggctggcctg gtaccagcag aagcctgaga aagcccccaa gagcctgatc 600
tacgctgcct ccagcctgca gtccggcgtg ccttccagat tctccggcag cggcagcggc 660
accgacttta ccctgaccat ttccagcctg caacccgagg acttcgccac ctactactgc 720
cagcagtaca acagctaccc catcaccttt ggccagggca ccagactgga gatcaag 777

<210> SEQ ID NO 207
<211> LENGTH: 768
<212> TYPE: DNA
<213> ORGANISM: Artificial Sequence
<220> FEATURE:
<223> OTHER INFORMATION: DG07 SCFV

<400> SEQUENCE: 207
atggaatgga cctgggtgtt cctgttcctg ctgtccgtga ccgccggagt ccacagcgag 60
gtgcagctgg tggaaagcgg cggaggactg gtgcagcctg gaggcagcct gaggctgagc 120
tgtgctgcca gcggcttctc catcagcggc tactggatgt cctgggtgag gcaggcccct 180

```
ggaaagggct tagaatgggt ggccaacatc aaacaggacg gcggcgagaa gtactacgga    240

gacagcgtca agggcagatt caccatcagc agggacaacg ccaagaacag cctgtacctg    300

cagatgaaca gcctgagggc cgaggacacc gctgtgtact actgcgtgat ggccggaggc    360

ctggattatt ggggccaggg cacactggtg acagtgagca gcgccggcgg cggcggcagc    420

ggcggcggcg gcagcggcgg cggcggcagc gagatcgtgc tgacccagag ccctgccaca    480

ctgagcctga gccccggcga aagagccacc ctcagctgca gggccagcca gagcgtgagc    540

agctacctgg cctggtacca gcagaagccc ggacaggccc ctaggctgct gatctacgat    600

gccagcaaca gagccaccgg catccctgct aggttcagcg gttctggcag cggcaccgac    660

ttcaccctga ccatcagcag cctggagcct gaggacttcg ctgtctacta ctgccagcag    720

aggagcaact ggtatacctt cggccaggga accaagctgg agatcaag                 768
```

<210> SEQ ID NO 208
<211> LENGTH: 792
<212> TYPE: DNA
<213> ORGANISM: Artificial Sequence
<220> FEATURE:
<223> OTHER INFORMATION: DG08 SCFV

<400> SEQUENCE: 208

```
atggaatgga cctgggtgtt cctgttcctg ctcagcgtga ccgccggagt gcactcccag     60

gtgcagctgg tgcagagcgg cgccgaagtg aaaaagcccg gcgccagcgt gagactctcc    120

tgtagagcca gcggctacaa cttcatcgac ttccacatcc actgggtgag acaggcccct    180

ggagagggcc tggagtggat gggctggagc aacccccaga gcggcaatag cagcagcgcc    240

cagaggttcc agggcagagt gaccatgacc accgatacct ccatgagcgc cgcctacatg    300

gacctgaact ggctgaccct ggacgacacc gccgtgtact actgcaccag gcctcacgac    360

ggcgctggca actacaggtt cgacacctgg ggacagggaa ccctggtgac agtcagcagc    420

gcgggaggtg gtggtagcgg tggtgggggt tccggtggag gtggcagttc atatgagctt    480

acacaacccc caagtgtgag cgtggctcct ggccagacag ccaggatcac ctgcagcgga    540

gacgccctgc ccaaacacta cgcccactgg tatcagcaga aacccggcca ggtgcccatc    600

gtggtgatct acaaggacac cgagagacct agcggcatcc ccgagagatt cagcggcagc    660

accagcggca ccacagtcac cctgaccatc tccggcgtgc aggccgagga tgaagcccac    720

tactactgcc aaagcgccga cgtgtcctcc acctatgtgg tgttcggcgg cggcaccaag    780

ctgaccgtcc tc                                                        792
```

<210> SEQ ID NO 209
<211> LENGTH: 768
<212> TYPE: DNA
<213> ORGANISM: Artificial Sequence
<220> FEATURE:
<223> OTHER INFORMATION: DG09 SCFV

<400> SEQUENCE: 209

```
atggagtgga cttgggtatt cctgtttttg ttgtccgtaa ctgctggggt acactcagag     60

gtgcagctgg tagagtctgg aggggggctc gtcgaaccag gcggctctct caggctttcc    120

tgtgccgtaa gcgggtttga ttttgagaaa gcatggatgt cctgggtaag gcaagctcca    180

gggcagggac tccagtgggt agcgcggata aagtcaacag ctgatggcgg aaccacctct    240

tatgcagcac cggttgaggg aaggttcatc atctcacgag acgattcccg caacatgttg    300

tatctgcaga tgaacagttt gaaaactgaa gacacagctg tttactactg tacttcagcg    360
```

-continued

```
cattggggac agggtactct tgtgacggtc tctagcgccg gggggggagg ctctggaggg    420

gggggttcag ggggtggtgg cagctcctat gagctgactc aaccgccttc agtaagcgta    480

agccctggtc agaccgctag aataacctgt agtggagagg ccctgccgat gcaattcgcc    540

cactggtatc agcagaggcc tggaaaagcc ccagtgattg tcgtttacaa agattccgaa    600

cgccctagcg gggttcccga acgctttagc ggtagttcaa gcgggacaac agcaaccctt    660

acgataaccg gtgtacaagc ggaagacgaa gcggattact attgccaatc acctgatagt    720

acaaatactt atgaggtatt tggcggggga acgaagttga ctgtactg                 768


<210> SEQ ID NO 210
<211> LENGTH: 816
<212> TYPE: DNA
<213> ORGANISM: Artificial Sequence
<220> FEATURE:
<223> OTHER INFORMATION: DG10 SCFV

<400> SEQUENCE: 210

atggaatgga cctgggtgtt cctcttcctc ctgtccgtca ccgctggcgt gcacagccag     60

gtgcagctgg tccagagcgg agccgaggtg aaaaagcccg gcgcctccgt gaaggtcagc    120

tgcaaggcct ccggctacac cttcaccaac tacgccatgc actgggtgag acaggcccct    180

ggccagagac tggagtggat gggctggatc aacgccggca acggcaagag aaagtacagc    240

cagaagtttc aggacagggt gaccatcaac agggacacca gcgcctccac catctacatg    300

gagctgtcca gcctgggcag cgaggatacc gccgtgtact actgtgccag agaggaggat    360

cacgctggca gcggcagcta cctgagcatg gacgtctggg gacagggcag caccgtgaca    420

gtgagcagcg ctggaggcgg cggctccggc ggcggaggaa gcggaggcgg aggctccgac    480

atcgtgatga cccagtcccc cgatagcctg gctgtgagcc tgggcgagag ggccacaatc    540

aactgtaaga gcagccagaa cgtgctgtac tcctccaaca acaagaacta cctggcctgg    600

taccagcaga aacctggcca tccccccaag ctgctgatct actgggccag caccagggag    660

agcggagtgc ctgacaggtt tagcggcagc ggcagcggca cagactttac cctgaccatc    720

acctccctgc agaccgagga cgtggccgtg tactattgcc agcagtacta cagctcccct    780

ctgaccttcg gcggcggcac caaagtggag atcaaa                              816


<210> SEQ ID NO 211
<211> LENGTH: 804
<212> TYPE: DNA
<213> ORGANISM: Artificial Sequence
<220> FEATURE:
<223> OTHER INFORMATION: DG11 SCFV

<400> SEQUENCE: 211

atggagtgga cttgggtatt ccttttcctc ctctccgtga cagcgggtgt gcactctgaa     60

gtacaacttg tagagaccgg tgggggattg gtgcaaccca agggttccct gaaactctca    120

tgtgctacct ctggttttac tttcaacacc tatgcaatga attgggttag gcaagcaccc    180

ggtaaaggac ttgagtgggt ggcacggata cgcactaaga gtaatgacta tgctacgtac    240

tacgcagact ccgtaaaagg ccggatcacc atatctcgag acgatagcca gtctatgctg    300

tatcttcaaa tgaacaacct caaaacggaa gatacggcga tgtattactg cgtgcgagtt    360

ggttataggc cttatgctat ggattactgg ggacagggca cgtctgtcac ggtaagttct    420

gccggagggg ggggcagcgg aggaggagga tctggcggag gggctccga tgtccttatg     480
```

acacagactc ccctcagttt gcccgtgtcc ttgggggacc aggcttctat atcatgccgc 540
agttcccaaa atatcgtcca ttcaaatggc aatacttacc ttgagtggta tttgcagaag 600
cctggacaga gcccgacgct tctgatctat aaggtaagca acaggttcag tggtgtaccc 660
gacagattta gtggaagtgg gtccggaact gatttcactc ttaagattag tcgggtagag 720
gctgaagacc ttggggtgta ttattgcttt caagggagtc acgtccctct tacatttggt 780
gctgggacta agttggagct gaag 804

<210> SEQ ID NO 212
<211> LENGTH: 126
<212> TYPE: DNA
<213> ORGANISM: Artificial Sequence
<220> FEATURE:
<223> OTHER INFORMATION: 4-1BB CO-STIMULATORY DOMAIN

<400> SEQUENCE: 212
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 213
<211> LENGTH: 45
<212> TYPE: DNA
<213> ORGANISM: Artificial Sequence
<220> FEATURE:
<223> OTHER INFORMATION: (G4S)3 LINKER

<400> SEQUENCE: 213
ggcggaggcg gatcaggagg aggaggatca ggcggaggag gatca 45

<210> SEQ ID NO 214
<211> LENGTH: 78
<212> TYPE: DNA
<213> ORGANISM: Artificial Sequence
<220> FEATURE:
<223> OTHER INFORMATION: T2A

<400> SEQUENCE: 214
agagccaaaa ggtctggctc cggtgagggc agaggaagtc ttataacatg cggtgacgtg 60
gaggagaatc ccggccct 78

<210> SEQ ID NO 215
<211> LENGTH: 81
<212> TYPE: DNA
<213> ORGANISM: Artificial Sequence
<220> FEATURE:
<223> OTHER INFORMATION: P2A

<400> SEQUENCE: 215
agagccaaaa ggtccggaag cggcgccacc aacttcagcc tgctgaagca ggccggcgac 60
gtggaagaga atcctggccc c 81

<210> SEQ ID NO 216
<211> LENGTH: 336
<212> TYPE: DNA
<213> ORGANISM: Artificial Sequence
<220> FEATURE:
<223> OTHER INFORMATION: CD3Z

<400> SEQUENCE: 216
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220
<211> LENGTH: 1401
<212> TYPE: DNA
<213> ORGANISM: Artificial Sequence
<220> FEATURE:
<223> OTHER INFORMATION: DG01.28.Z CAR

<400> SEQUENCE: 220
atggaatgga cctgggtgtt cctgtttctg ctgtccgtga ccgctggcgt gcacagccag 60
gtgcagctgg tggaaagcgg cggaggagtc gtgcagcctg gcagaagcct gaggctgagc 120
tgtgccgcca gcggcttcgc cttcagctcc tacggcatgc actgggtgag acaggcccct 180
ggcaagggac tggagtgggt ggctgtgatc tggttcgacg gcaccaagaa gtactacacc 240
gacagcgtca agggcaggtt caccatctcc agggacaata gcaagaatac cctgtacctc 300
caaatgaaca ccctgagggc cgaggacacc gccgtgtatt actgcgccag ggatagggga 360
atcggcgcca ggagaggccc ctactacatg gacgtgtggg gcaagggcac aacagtgacc 420
gtttcttctg ctggaggagg aggttctgga ggaggaggaa gcggaggagg aggctccgac 480
atccagatga cacagtcccc cagctccctg tccgccagcg tgggcgatag agtgaccatc 540
acctgcaggg ccagccagag catctccagc tacctgaact ggtatcaaca gaagcccggc 600
aaagccccca aactgctgat ctacgctgcc agcagcctgc agagcggcgt gccttccaga 660
ttcagcggct ccggcagcgg caccgatttc acactgacca tctccagcct gcagcccgag 720
gacttcgcca cctactactg ccagcagagc tacagcaccc ccctgacctt tggcggaggc 780
accaaggtgg agatcaaagc tagcgtgaaa gggaaacacc tttgtccaag tcccctattt 840
cccggacctt ctaagccctt ttgggtgctg gtggtggttg gtggagtcct ggcttgctat 900
agcttgctag taacagtggc ctttattatt ttctgggtga ggagtaagag gagcaggctc 960
ctgcacagtg actacatgaa catgactccc cgccgccccg ggcccacccg caagcattac 1020
cagccctatg ccccaccacg cgacttcgca gcctatcgct ccaagcttag agtgaagttc 1080
agcaggagcg cagacgcccc cgcgtaccag cagggccaga accagctcta taacgagctc 1140

-continued

```
aatctaggac gaagagagga gtacgatgtt ttggacaaga gacgtggccg ggaccctgag   1200

atggggggaa agccgagaag gaagaaccct caggaaggcc tgtacaatga actgcagaaa   1260

gataagatgg cggaggccta cagtgagatt gggatgaaag gcgagcgccg gaggggcaag   1320

gggcacgatg gcctttacca gggtctcagt acagccacca aggacaccta cgacgccctt   1380

cacatgcagg ccctgccccc t                                             1401
```

<210> SEQ ID NO 221
<211> LENGTH: 1401
<212> TYPE: DNA
<213> ORGANISM: Artificial Sequence
<220> FEATURE:
<223> OTHER INFORMATION: DG02.28.Z CAR

<400> SEQUENCE: 221

```
atggaatgga cctgggtgtt tctgttcctg ctgagcgtga cagccggcgt gcacagcgag     60

gtgcagctgc tggagagcgg aggaggactg gtgcaacccg gcggaagcct cagactgagc    120

tgtgccgcca gcggcttcac cttcagcaac tatggcatga gctgggtgag gcaggcccct    180

ggcaaaggcc tcgaatgggt ggcttccatt aggagcggcg gcggcaggac ctattacagc    240

gacaacgtga agggcaggtt caccatctcc agggacaata gcaagaacac cctgtacctg    300

cagatgaact ccctgagggc cgaggatacc gccgtgtact actgcgtgag gtacgaccac    360

tacagcggct ccagcgacta ttggggacag ggcaccctgg tgacagtgtc cagcgccgga    420

ggaggcggca gcggcggcgg cggcagcggc ggcggcggaa gcgatgtggt gatgacccag    480

tccccccctga gcctgcctgt gacacctgga gagcccgcca gcatcagctg taagagcagc    540

cagagcctcc tggacagcga cggcaaaacc tacctgaact ggctcctgca gaagcccgga    600

caaagccccc agaggctgat ctacctggtg agcaaactgg acagcggcgt gcctgacaga    660

ttctccggct ccggcagcgg caccgacttc acactgaaga tcagcagagt ggaggctgag    720

gacgtgggcg tctactactg ctggcagggc acccacttcc ccaggacctt cggccaggga    780

accaaggtgg agatcaaggc tagcgtgaaa gggaaacacc tttgtccaag tcccctattt    840

cccggacctt ctaagccctt ttgggtgctg gtggtggttg gtggagtcct ggcttgctat    900

agcttgctag taacagtggc ctttattatt ttctgggtga ggagtaagag gagcaggctc    960

ctgcacagtg actacatgaa catgactccc cgccgccccg ggcccacccg caagcattac   1020

cagccctatg ccccaccacg cgacttcgca gcctatcgct ccaagcttag agtgaagttc   1080

agcaggagcg cagacgcccc cgcgtaccag cagggccaga accagctcta taacgagctc   1140

aatctaggac gaagagagga gtacgatgtt ttggacaaga gacgtggccg ggaccctgag   1200

atggggggaa agccgagaag gaagaaccct caggaaggcc tgtacaatga actgcagaaa   1260

gataagatgg cggaggccta cagtgagatt gggatgaaag gcgagcgccg gaggggcaag   1320

gggcacgatg gcctttacca gggtctcagt acagccacca aggacaccta cgacgccctt   1380

cacatgcagg ccctgccccc t                                             1401
```

<210> SEQ ID NO 222
<211> LENGTH: 1380
<212> TYPE: DNA
<213> ORGANISM: Artificial Sequence
<220> FEATURE:
<223> OTHER INFORMATION: DG03.28.Z CAR

<400> SEQUENCE: 222

-continued

```
atggaatgga cctgggtgtt cctgtttctg ctctccgtga ccgccggagt gcacagcgag      60

gtgcagctgg tcgaaagcgg cggaggactg gtgcagcctg gcggcagcct gagactgagc     120

tgtgccgcct ccggcttcac ctttagcagc tacggaatgt cctgggtgag acaggctcct     180

ggcaagggcc tggaactggt ggccagcatc aatagcaacg gcggcagcac ctactaccct     240

gatagcgtga agggcaggtt caccatctcc agggacaacg ccaagaacag cctgtacctg     300

cagatgaaca gcctcagggc cgaggacaca gccgtgtact actgcgccag cggcgactat     360

tggggacagg gaacaaccgt gaccgtcagc agcgccggcg gcggcggcag cggcggcggc     420

ggcagcggcg gcggcggctc cgatatcgtg atgacccaga gccccctgtc cctgcctgtc     480

acacctggcg aacccgccag cattagctgc aggtccagcc agagcctggt gtacagcaat     540

ggcgacacct acctgcactg gtacctgcag aagcctggcc agagccccca gctgctgatc     600

tacaaggtga gcaacaggtt ctccggagtg cctgacaggt tcagcggctc cggcagcgga     660

accgatttca ccctcaagat cagcagagtg gaggccgagg acgtgggcgt ctactattgt     720

agccagagca cccacgtgcc ctggaccttt ggccagggca ccaaggtgga gatcaaagct     780

agcgtgaaag ggaaacacct ttgtccaagt cccctatttc ccggaccttc taagcccttt     840

tgggtgctgg tggtggttgg tggagtcctg gcttgctata gcttgctagt aacagtggcc     900

tttattattt tctgggtgag gagtaagagg agcaggctcc tgcacagtga ctacatgaac     960

atgactcccc gccgccccgg gcccacccgc aagcattacc agccctatgc cccaccacgc    1020

gacttcgcag cctatcgctc caagcttaga gtgaagttca gcaggagcgc agacgccccc    1080

gcgtaccagc agggccagaa ccagctctat aacgagctca atctaggacg aagagaggag    1140

tacgatgttt tggacaagag acgtggccgg gaccctgaga tggggggaaa gccgagaagg    1200

aagaaccctc aggaaggcct gtacaatgaa ctgcagaaag ataagatggc ggaggcctac    1260

agtgagattg ggatgaaagg cgagcgccgg aggggcaagg ggcacgatgg cctttaccag    1320

ggtctcagta cagccaccaa ggacacctac gacgcccttc acatgcaggc cctgccccct    1380
```

<210> SEQ ID NO 223
<211> LENGTH: 1410
<212> TYPE: DNA
<213> ORGANISM: Artificial Sequence
<220> FEATURE:
<223> OTHER INFORMATION: DG04.28.Z CAR

<400> SEQUENCE: 223

```
atggaatgga cctgggtgtt tctgttcctc ctgagcgtga ccgccggagt gcacagccaa      60

gtggagctgg tggagagcgg aggaggactg gtgcagcctg gaggctccct gaggctgagc     120

tgtgctgcca gcggcttcac cttcagctcc tatgctatga gctgggtgag acaggcccct     180

ggcaaaggcc tggagtgggt gagcgccatc aacgcctccg gcaccaggac ctactatgcc     240

gactccgtga agggcaggtt caccatctcc agggacaaca gcaagaacac cctgtacctg     300

cagatgaaca gcctgagggc tgaagacacc gccgtgtact actgtgccag ggcaagggc     360

aacacacaca agccctatgg ctacgtgaga tacttcgacg tgtggggaca gggcaccctg     420

gtgacagtga gcagcgccgg aggaggaggt tctggaggag gaggaagcgg cggaggagga     480

agcgacatcg tgctgacaca atcccccgcc acactgtccc tgtcccctgg cgagagggcc     540

acactgagct gcagggccag ccagagcgtg tcctcctcct acctggcctg gtaccagcag     600

aaacctggcc aggcccccag gctgctgatc tatggcgcca gcagcagagc cacaggagtg     660

cctgccagat ttagcggcag cggcagcggc accgacttta ccctgaccat ttccagcctg     720
```

```
gagcccgagg acttcgccac ctactactgc ctgcagatct acaacatgcc tatcaccttc    780

ggccagggca caaaagtgga aatcaaggct agcgtgaaag ggaaacacct ttgtccaagt    840

cccctatttc ccggaccttc taagcccttt tgggtgctgg tggtggttgg tggagtcctg    900

gcttgctata gcttgctagt aacagtggcc tttattattt tctgggtgag gagtaagagg    960

agcaggctcc tgcacagtga ctacatgaac atgactcccc gccgccccgg gcccacccgc   1020

aagcattacc agccctatgc cccaccacgc gacttcgcag cctatcgctc caagcttaga   1080

gtgaagttca gcaggagcgc agacgccccc gcgtaccagc agggccagaa ccagctctat   1140

aacgagctca atctaggacg aagagaggag tacgatgttt tggacaagag acgtggccgg   1200

gaccctgaga tgggggggaaa gccgagaagg aagaaccctc aggaaggcct gtacaatgaa   1260

ctgcagaaag ataagatggc ggaggcctac agtgagattg ggatgaaagg cgagcgccgg   1320

aggggcaagg ggcacgatgg cctttaccag ggtctcagta cagccaccaa ggacacctac   1380

gacgcccttc acatgcaggc cctgcccccct                                   1410
```

<210> SEQ ID NO 224
<211> LENGTH: 1386
<212> TYPE: DNA
<213> ORGANISM: Artificial Sequence
<220> FEATURE:
<223> OTHER INFORMATION: DG05.28.Z CAR

<400> SEQUENCE: 224

```
atggaatgga cctgggtgtt tctgttcctc ctgtccgtga ccgccggagt gcactccgaa     60

gtgcagctgg tgcagtccgg cggaggactg gtgaaacccg gaggaagcct cagactgagc    120

tgcgccggca gcggctttac cttctccagc tactccatgc actggctgag acaggcccct    180

ggcaagggcc tggaatgggt cagcgccatc ggcaccgccg gaggcacata ctatgccgac    240

agcgtgaagg gcaggttcac catcagcagg gacaacgcca agaacagcct gtacctgcag    300

atgaactctc tgagggccga ggataccgct gtgtactact gcgccaggga gtacttcttt    360

ggcagcggca actacggata ctggggccag ggcaccctgg tgacagtgag ctccgccgga    420

ggaggaggaa gcggaggagg cggaagcgga ggaggcggca gcgaaatcgt gctgacccag    480

agccctgcca ccctgagcct gagccctggc gaaagggcca ccctgagctg cagagccagc    540

cagagcgtga gcagctacct ggcctggtac cagcagaagc ccggacaggc ccccagactg    600

ctgatctacg acgccagcaa cagagccacc ggcattcccg ccagattctc cggcagcggc    660

agcggaaccg acttcacact gaccatcagc tccttagaac ccgaggactt cgccgtgtac    720

tactgtcagc agagaagcaa ctggcctccc accttcggcc agggcacaaa ggtggagatc    780

aaggctagcg tgaaagggaa acacctttgt ccaagtcccc tatttcccgg accttctaag    840

ccctttttggg tgctggtggt ggttggtgga gtcctggctt gctatagctt gctagtaaca    900

gtggccttta ttattttctg ggtgaggagt aagaggagca ggctcctgca cagtgactac    960

atgaacatga ctccccgccg ccccgggccc acccgcaagc attaccagcc ctatgcccca   1020

ccacgcgact tcgcagccta tcgctccaag cttagagtga agttcagcag gagcgcagac   1080

gcccccgcgt accagcaggg ccagaaccag ctctataacg agctcaatct aggacgaaga   1140

gaggagtacg atgttttgga caagagacgt ggccgggacc ctgagatggg gggaaagccg   1200

agaaggaaga accctcagga aggcctgtac aatgaactgc agaaagataa gatggcggag   1260

gcctacagtg agattgggat gaaaggcgag cgccggaggg gcaaggggca cgatggcctt   1320
```

taccagggtc tcagtacagc caccaaggac acctacgacg cccttcacat gcaggccctg 1380
ccccct 1386

<210> SEQ ID NO 225
<211> LENGTH: 1380
<212> TYPE: DNA
<213> ORGANISM: Artificial Sequence
<220> FEATURE:
<223> OTHER INFORMATION: DG06.28.Z CAR

<400> SEQUENCE: 225
atggaatgga cctgggtgtt cctgttcctc ctgagcgtga ccgctggcgt ccacagccag 60
gtgcagctgg tggaaagcgg aggcggagtg gtgcagcctg gaaggtccct cagactgagc 120
tgcgctgcca gcggcttcac cttcagcaac tacggcatcc actgggtgag acaagccccc 180
ggcaaaggcc tggagtgggt ggccatcatc tggcacgacg gcagcaactc ctactacgtg 240
gactccgtga agggcaggtt cacaatcagc agagacaaca gcaagaatac cctgtacctg 300
cagatgaaca gcctcagggc cgaagatacc gccgtgtact tctgcgccag gatcatcggc 360
ggcgcctttg acatttgggg ccaaggcact atggttaccg tgagcagcgc tggcggaggc 420
ggcagcggcg gcggcggcag cggcggcggc ggaagcgaca tccagatgac ccagagccct 480
tccagcctca gcgcctccgt gggagacaga gtgaccatca cctgcagggc cagccagggc 540
atctccagct ggctggcctg gtaccagcag aagcctgaga aagcccccaa gagcctgatc 600
tacgctgcct ccagcctgca gtccggcgtg ccttccagat tctccggcag cggcagcggc 660
accgacttta ccctgaccat ttccagcctg caacccgagg acttcgccac ctactactgc 720
cagcagtaca acagctaccc catcaccttt ggccagggca ccagactgga gatcaaggct 780
agcgtgaaag ggaaacacct ttgtccaagt cccctatttc ccggaccttc taagcccttt 840
tgggtgctgg tggtggttgg tggagtcctg gcttgctata gcttgctagt aacagtggcc 900
tttattattt tctgggtgag gagtaagagg agcaggctcc tgcacagtga ctacatgaac 960
atgactcccc gccgccccgg gcccacccgc aagcattacc agccctatgc cccaccacgc 1020
gacttcgcag cctatcgctc caagcttaga gtgaagttca gcaggagcgc agacgccccc 1080
gcgtaccagc agggccagaa ccagctctat aacgagctca atctaggacg aagagaggag 1140
tacgatgttt tggacaagag acgtggccgg gaccctgaga tgggggggaaa gccgagaagg 1200 aagaaccctc aggaaggcct gtacaatgaa ctgcagaaag ataagatggc ggaggcctac 1260
agtgagattg ggatgaaagg cgagcgccgg aggggcaagg ggcacgatgg cctttaccag 1320
ggtctcagta cagccaccaa ggacacctac gacgcccttc acatgcaggc cctgcccccct 1380

<210> SEQ ID NO 226
<211> LENGTH: 1371
<212> TYPE: DNA
<213> ORGANISM: Artificial Sequence
<220> FEATURE:
<223> OTHER INFORMATION: DG07.28.Z CAR

<400> SEQUENCE: 226
atggaatgga cctgggtgtt cctgttcctg ctgtccgtga ccgccggagt ccacagcgag 60
gtgcagctgg tggaaagcgg cggaggactg gtgcagcctg gaggcagcct gaggctgagc 120
tgtgctgcca gcggcttctc catcagcggc tactggatgt cctgggtgag gcaggcccct 180
ggaaagggct tagaatgggt ggccaacatc aaacaggacg gcggcgagaa gtactacgga 240
gacagcgtca agggcagatt caccatcagc agggacaacg ccaagaacag cctgtacctg 300
cagatgaaca gcctgagggc cgaggacacc gctgtgtact actgcgtgat ggccggaggc 360
ctggattatt ggggccaggg cacactggtg acagtgagca gcgccggcgg cggcggcagc 420
ggcggcggcg gcagcggcgg cggcggcagc gagatcgtgc tgacccagag ccctgccaca 480
ctgagcctga gccccggcga aagagccacc ctcagctgca gggccagcca gagcgtgagc 540
agctacctgg cctggtacca gcagaagccc ggacaggccc ctaggctgct gatctacgat 600
gccagcaaca gagccaccgg catccctgct aggttcagcg gttctggcag cggcaccgac 660
ttcaccctga ccatcagcag cctggagcct gaggacttcg ctgtctacta ctgccagcag 720
aggagcaact ggtatacctt cggccaggga accaagctgg agatcaaggc tagcgtgaaa 780
gggaaacacc tttgtccaag tcccctattt cccggacctt ctaagccctt ttgggtgctg 840
gtggtggttg gtggagtcct ggcttgctat agcttgctag taacagtggc ctttattatt 900
ttctgggtga ggagtaagag gagcaggctc ctgcacagtg actacatgaa catgactccc 960
cgccgccccg ggcccacccg caagcattac cagccctatg ccccaccacg cgacttcgca 1020
gcctatcgct ccaagcttag agtgaagttc agcaggagcg cagacgcccc cgcgtaccag 1080
cagggccaga accagctcta taacgagctc aatctaggac gaagagagga gtacgatgtt 1140
ttggacaaga gacgtggccg ggaccctgag atggggggaa agccgagaag gaagaaccct 1200
caggaaggcc tgtacaatga actgcagaaa gataagatgg cggaggccta cagtgagatt 1260
gggatgaaag gcgagcgccg gaggggcaag gggcacgatg gcctttacca gggtctcagt 1320
acagccacca aggacaccta cgacgccctt cacatgcagg ccctgccccc t 1371

<210> SEQ ID NO 227
<211> LENGTH: 1395
<212> TYPE: DNA
<213> ORGANISM: Artificial Sequence
<220> FEATURE:
<223> OTHER INFORMATION: DG08.28.Z CAR

<400> SEQUENCE: 227
atggaatgga cctgggtgtt cctgttcctg ctcagcgtga ccgccggagt gcactcccag 60
gtgcagctgg tgcagagcgg cgccgaagtg aaaaagcccg gcgccagcgt gagactctcc 120
tgtagagcca gcggctacaa cttcatcgac ttccacatcc actgggtgag acaggcccct 180
ggagagggcc tggagtggat gggctggagc aacccccaga gcggcaatag cagcagcgcc 240
cagaggttcc agggcagagt gaccatgacc accgatacct ccatgagcgc cgcctacatg 300
gacctgaact ggctgaccct ggacgacacc gccgtgtact actgcaccag gcctcacgac 360
ggcgctggca actacaggtt cgacacctgg ggacagggaa ccctggtgac agtcagcagc 420
gcgggaggtg gtggtagcgg tggtgggggt tccggtggag gtggcagttc atatgagctt 480
acacaacccc caagtgtgag cgtggctcct ggccagacag ccaggatcac ctgcagcgga 540
gacgccctgc ccaaacacta cgcccactgg tatcagcaga aacccggcca ggtgcccatc 600
gtggtgatct acaaggacac cgagagacct agcggcatcc ccgagagatt cagcggcagc 660
accagcggca ccacagtcac cctgaccatc tccggcgtgc aggccgagga tgaagcccac 720
tactactgcc aaagcgccga cgtgtcctcc acctatgtgg tgttcggcgg cggcaccaag 780
ctgaccgtcc tcgctagcgt gaaagggaaa cacctttgtc caagtcccct atttcccgga 840
ccttctaagc ccttttgggt gctggtggtg gttggtggag tcctggcttg ctatagcttg 900
ctagtaacag tggcctttat tattttctgg gtgaggagta agaggagcag gctcctgcac 960
agtgactaca tgaacatgac tccccgccgc cccgggccca cccgcaagca ttaccagccc 1020
tatgccccac cacgcgactt cgcagcctat cgctccaagc ttagagtgaa gttcagcagg 1080
agcgcagacg cccccgcgta ccagcagggc cagaaccagc tctataacga gctcaatcta 1140
ggacgaagag aggagtacga tgttttggac aagagacgtg gccgggaccc tgagatgggg 1200
ggaaagccga gaaggaagaa ccctcaggaa ggcctgtaca atgaactgca gaaagataag 1260
atggcggagg cctacagtga gattgggatg aaaggcgagc gccggagggg caaggggcac 1320
gatggccttt accagggtct cagtacagcc accaaggaca cctacgacgc ccttcacatg 1380
caggccctgc cccct 1395

<210> SEQ ID NO 228
<211> LENGTH: 1371
<212> TYPE: DNA
<213> ORGANISM: Artificial Sequence
<220> FEATURE:
<223> OTHER INFORMATION: DG09.28.Z CAR

<400> SEQUENCE: 228
atggagtgga cttgggtatt cctgtttttg ttgtccgtaa ctgctggggt acactcagag 60
gtgcagctgg tagagtctgg aggggggctc gtcgaaccag gcggctctct caggctttcc 120
tgtgccgtaa gcgggtttga ttttgagaaa gcatggatgt cctgggtaag gcaagctcca 180
gggcagggac tccagtgggt agcgcggata aagtcaacag ctgatggcgg aaccacctct 240
tatgcagcac cggttgaggg aaggttcatc atctcacgag acgattcccg caacatgttg 300
tatctgcaga tgaacagttt gaaaactgaa gacacagctg tttactactg tacttcagcg 360
cattggggac agggtactct tgtgacggtc tctagcgccg gggggggagg ctctggaggg 420
gggggttcag gggtggtgg cagctcctat gagctgactc aaccgccttc agtaagcgta 480
agccctggtc agaccgctag aataacctgt agtggagagg ccctgccgat gcaattcgcc 540
cactggtatc agcagaggcc tggaaaagcc ccagtgattg tcgtttacaa agattccgaa 600
cgccctagcg ggttcccga acgctttagc ggtagttcaa gcgggacaac agcaaccctt 660
acgataaccg gtgtacaagc ggaagacgaa gcggattact attgccaatc acctgatagt 720
acaaatactt atgaggtatt tggcgggggga acgaagttga ctgtactggc tagcgtgaaa 780
gggaaacacc tttgtccaag tcccctattt cccggacctt ctaagccctt ttgggtgctg 840
gtggtggttg gtggagtcct ggcttgctat agcttgctag taacagtggc ctttattatt 900
ttctgggtga ggagtaagag gagcaggctc ctgcacagtg actacatgaa catgactccc 960
cgccgccccg ggcccacccg caagcattac cagccctatg ccccaccacg cgacttcgca 1020
gcctatcgct ccaagcttag agtgaagttc agcaggagcg cagacgcccc cgcgtaccag 1080
cagggccaga accagctcta taacgagctc aatctaggac gaagagagga gtacgatgtt 1140
ttggacaaga gacgtggccg ggaccctgag atgggggggaa agccgagaag gaagaaccct 1200
caggaaggcc tgtacaatga actgcagaaa gataagatgg cggaggccta cagtgagatt 1260
gggatgaaag gcgagcgccg gaggggcaag gggcacgatg gcctttacca gggtctcagt 1320
acagccacca aggacaccta cgacgccctt cacatgcagg ccctgccccc t 1371

<210> SEQ ID NO 229
<211> LENGTH: 1419
<212> TYPE: DNA
<213> ORGANISM: Artificial Sequence
<220> FEATURE:
<223> OTHER INFORMATION: DG10.28.Z CAR

<400> SEQUENCE: 229
atggaatgga cctgggtgtt cctcttcctc ctgtccgtca ccgctggcgt gcacagccag 60
gtgcagctgg tccagagcgg agccgaggtg aaaaagcccg gcgcctccgt gaaggtcagc 120
tgcaaggcct ccggctacac cttcaccaac tacgccatgc actgggtgag acaggcccct 180
ggccagagac tggagtggat gggctggatc aacgccggca acggcaagag aaagtacagc 240
cagaagtttc aggacagggt gaccatcaac agggacacca gcgcctccac catctacatg 300
gagctgtcca gcctgggcag cgaggatacc gccgtgtact actgtgccag agaggaggat 360
cacgctggca gcggcagcta cctgagcatg gacgtctggg gacagggcag caccgtgaca 420
gtgagcagcg ctggaggcgg cggctccggc ggcggaggaa gcggaggcgg aggctccgac 480
atcgtgatga cccagtcccc cgatagcctg gctgtgagcc tgggcgagag ggccacaatc 540
aactgtaaga gcagccagaa cgtgctgtac tcctccaaca acaagaacta cctggcctgg 600
taccagcaga aacctggcca tccccccaag ctgctgatct actgggccag caccagggag 660
agcggagtgc ctgacaggtt tagcggcagc ggcagcggca cagactttac cctgaccatc 720
acctccctgc agaccgagga cgtggccgtg tactattgcc agcagtacta cagctcccct 780
ctgaccttcg gcggcggcac caaagtggag atcaaagcta gcgtgaaagg gaaacacctt 840
tgtccaagtc ccctatttcc cggaccttct aagccctttt gggtgctggt ggtggttggt 900
ggagtcctgg cttgctatag cttgctagta acagtggcct ttattatttt ctgggtgagg 960
agtaagagga gcaggctcct gcacagtgac tacatgaaca tgactccccg ccgccccggg 1020
cccacccgca agcattacca gccctatgcc ccaccacgcg acttcgcagc ctatcgctcc 1080
aagcttagag tgaagttcag caggagcgca gacgcccccg cgtaccagca gggccagaac 1140
cagctctata acgagctcaa tctaggacga agagaggagt acgatgtttt ggacaagaga 1200
cgtggccggg accctgagat ggggggaaag ccgagaagga agaaccctca ggaaggcctg 1260
tacaatgaac tgcagaaaga taagatggcg gaggcctaca gtgagattgg gatgaaaggc 1320
gagcgccgga ggggcaaggg gcacgatggc ctttaccagg gtctcagtac agccaccaag 1380
gacacctacg acgcccttca catgcaggcc ctgcccccct 1419

<210> SEQ ID NO 230
<211> LENGTH: 1407
<212> TYPE: DNA
<213> ORGANISM: Artificial Sequence
<220> FEATURE:
<223> OTHER INFORMATION: DG11.28.Z CAR

<400> SEQUENCE: 230
atggagtgga cttgggtatt ccttttcctc ctctccgtga cagcgggtgt gcactctgaa 60
gtacaacttg tagagaccgg tgggggattg gtgcaaccca agggttccct gaaactctca 120
tgtgctacct ctggttttac tttcaacacc tatgcaatga attgggttag gcaagcaccc 180
ggtaaaggac ttgagtgggt ggcacggata cgcactaaga gtaatgacta tgctacgtac 240
tacgcagact ccgtaaaagg ccggatcacc atatctcgag acgatagcca gtctatgctg 300
tatcttcaaa tgaacaacct caaaacggaa gatacggcga tgtattactg cgtgcgagtt 360
ggttataggc cttatgctat ggattactgg ggacagggca cgtctgtcac ggtaagttct 420
gccggagggg ggggcagcgg aggaggagga tctggcggag ggggctccga tgtccttatg 480
acacagactc ccctcagttt gcccgtgtcc ttgggggacc aggcttctat atcatgccgc 540

-continued

```
agttcccaaa atatcgtcca ttcaaatggc aatacttacc ttgagtggta tttgcagaag    600

cctggacaga gcccgacgct tctgatctat aaggtaagca acaggttcag tggtgtaccc    660

gacagattta gtggaagtgg gtccggaact gatttcactc ttaagattag tcgggtagag    720

gctgaagacc ttggggtgta ttattgcttt caagggagtc acgtccctct tacatttggt    780

gctgggacta agttggagct gaaggctagc gtgaaaggga aacacctttg tccaagtccc    840

ctatttcccg gaccttctaa gcccttttgg gtgctggtgg tggttggtgg agtcctggct    900

tgctatagct tgctagtaac agtggccttt attattttct gggtgaggag taagaggagc    960

aggctcctgc acagtgacta catgaacatg actccccgcc gccccgggcc cacccgcaag   1020

cattaccagc cctatgcccc accacgcgac ttcgcagcct atcgctccaa gcttagagtg   1080

aagttcagca ggagcgcaga cgcccccgcg taccagcagg gccagaacca gctctataac   1140

gagctcaatc taggacgaag agaggagtac gatgttttgg acaagagacg tggccgggac   1200

cctgagatgg ggggaaagcc gagaaggaag aaccctcagg aaggcctgta caatgaactg   1260

cagaaagata agatggcgga ggcctacagt gagattggga tgaaaggcga gcgccggagg   1320

ggcaaggggc acgatggcct ttaccagggt ctcagtacag ccaccaagga cacctacgac   1380

gcccttcaca tgcaggccct gccccct                                        1407
```

<210> SEQ ID NO 231
<211> LENGTH: 54
<212> TYPE: DNA
<213> ORGANISM: Artificial Sequence
<220> FEATURE:
<223> OTHER INFORMATION: SIGNAL SEQUENCE

<400> SEQUENCE: 231

```
atggaatgga cctgggtctt tctcttcctc ctgtcagtaa ctgcaggtgt ccac           54
```

<210> SEQ ID NO 232
<211> LENGTH: 54
<212> TYPE: DNA
<213> ORGANISM: Artificial Sequence
<220> FEATURE:
<223> OTHER INFORMATION: HUMAN CD28 HINGE

<400> SEQUENCE: 232

```
gtgaaaggga aacacctttg tccaagtccc ctatttcccg gaccttctaa gccc           54
```

<210> SEQ ID NO 233
<211> LENGTH: 45
<212> TYPE: DNA
<213> ORGANISM: Artificial Sequence
<220> FEATURE:
<223> OTHER INFORMATION: MOUSE CD28 HINGE

<400> SEQUENCE: 233

```
ataaaagaga aacatctttg tcatactcag tcatctccta agctg                     45
```

<210> SEQ ID NO 234
<211> LENGTH: 135
<212> TYPE: DNA
<213> ORGANISM: Artificial Sequence
<220> FEATURE:
<223> OTHER INFORMATION: HUMAN CD8A HINGE

<400> SEQUENCE: 234

```
accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120
```

gacttcgcct gtgat 135

<210> SEQ ID NO 235
<211> LENGTH: 90
<212> TYPE: DNA
<213> ORGANISM: Artificial Sequence
<220> FEATURE:
<223> OTHER INFORMATION: HUMAN DAP10 HINGE

<400> SEQUENCE: 235
cagacgaccc caggagagag atcatcactc cctgcctttt accctggcac ttcaggctcc 60
tgttccggat gtgggtccct ctctctgccg 90

<210> SEQ ID NO 236
<211> LENGTH: 81
<212> TYPE: DNA
<213> ORGANISM: Artificial Sequence
<220> FEATURE:
<223> OTHER INFORMATION: HUMAN CD28 TM

<400> SEQUENCE: 236
ttttgggtgc tggtggtggt tggtggagtc ctggcttgct atagcttgct agtaacagtg 60
gcctttatta ttttctgggt g 81

<210> SEQ ID NO 237
<211> LENGTH: 81
<212> TYPE: DNA
<213> ORGANISM: Artificial Sequence
<220> FEATURE:
<223> OTHER INFORMATION: MOUSE CD28 TM

<400> SEQUENCE: 237
ttttgggcac tggtcgtggt tgctggagtc ctgttttgtt atggcttgct agtgacagtg 60
gctctttgtg ttatctggac a 81

<210> SEQ ID NO 238
<211> LENGTH: 72
<212> TYPE: DNA
<213> ORGANISM: Artificial Sequence
<220> FEATURE:
<223> OTHER INFORMATION: HUMAN CD8A TM

<400> SEQUENCE: 238
atctacatct gggcgccctt ggccgggact tgtggggtcc ttctcctgtc actggttatc 60
accctttact gc 72

<210> SEQ ID NO 239
<211> LENGTH: 63
<212> TYPE: DNA
<213> ORGANISM: Artificial Sequence
<220> FEATURE:
<223> OTHER INFORMATION: HUMAN DAP10 TM

<400> SEQUENCE: 239
ctcctggcag gcctcgtggc tgctgatgcg gtggcatcgc tgctcatcgt gggggcggtg 60
ttc 63

<210> SEQ ID NO 240
<211> LENGTH: 1353
<212> TYPE: DNA
<213> ORGANISM: Artificial Sequence
<220> FEATURE:

<223> OTHER INFORMATION: DG05-CD28tm-DAP10-CD3Z

<400> SEQUENCE: 240
atggaatgga cctgggtgtt tctgttcctc ctgtccgtga ccgccggagt gcactccgaa 60
gtgcagctgg tgcagtccgg cggaggactg gtgaaacccg gaggaagcct cagactgagc 120
tgcgccggca gcggctttac cttctccagc tactccatgc actggctgag acaggcccct 180
ggcaagggcc tggaatgggt cagcgccatc ggcaccgccg gaggcacata ctatgccgac 240
agcgtgaagg gcaggttcac catcagcagg gacaacgcca agaacagcct gtacctgcag 300
atgaactctc tgagggccga ggataccgct gtgtactact gcgccaggga gtacttcttt 360
ggcagcggca actacggata ctggggccag ggcaccctgg tgacagtgag ctccgccgga 420
ggaggaggaa gcggaggagg cggaagcgga ggaggcggca gcgaaatcgt gctgacccag 480
agccctgcca ccctgagcct gagccctggc gaaagggcca ccctgagctg cagagccagc 540
cagagcgtga gcagctacct ggcctggtac cagcagaagc ccggacaggc ccccagactg 600
ctgatctacg acgccagcaa cagagccacc ggcattcccg ccagattctc cggcagcggc 660
agcggaaccg acttcacact gaccatcagc tccttagaac ccgaggactt cgccgtgtac 720
tactgtcagc agagaagcaa ctggcctccc accttcggcc agggcacaaa ggtggagatc 780
aaggctagcg tgaaagggaa acacctttgt ccaagtcccc tatttcccgg accttctaag 840
cccttttggg tgctggtggt ggttggtgga gtcctggctt gctatagctt gctagtaaca 900
gtggccttta ttattttctg ggtgaggagt aagaggagcc tgtgcgcacg cccacgccgc 960
agccccgccc aagaagatgg caaagtctac atcaacatgc caggcagggg caagcttaga 1020
gtgaagttca gcaggagcgc agacgccccc gcgtaccagc agggccagaa ccagctctat 1080
aacgagctca atctaggacg aagagaggag tacgatgttt tggacaagag acgtggccgg 1140
gaccctgaga tgggggggaaa gccgagaagg aagaaccctc aggaaggcct gtacaatgaa 1200
ctgcagaaag ataagatggc ggaggcctac agtgagattg ggatgaaagg cgagcgccgg 1260
aggggcaagg ggcacgatgg cctttaccag ggtctcagta cagccaccaa ggacacctac 1320
gacgcccttc acatgcaggc cctgcccccct cgc 1353

<210> SEQ ID NO 241
<211> LENGTH: 1473
<212> TYPE: DNA
<213> ORGANISM: Artificial Sequence
<220> FEATURE:
<223> OTHER INFORMATION: DG05-CD28tm-CD44-CD3Z

<400> SEQUENCE: 241
atggaatgga cctgggtgtt tctgttcctc ctgtccgtga ccgccggagt gcactccgaa 60
gtgcagctgg tgcagtccgg cggaggactg gtgaaacccg gaggaagcct cagactgagc 120
tgcgccggca gcggctttac cttctccagc tactccatgc actggctgag acaggcccct 180
ggcaagggcc tggaatgggt cagcgccatc ggcaccgccg gaggcacata ctatgccgac 240
agcgtgaagg gcaggttcac catcagcagg gacaacgcca agaacagcct gtacctgcag 300
atgaactctc tgagggccga ggataccgct gtgtactact gcgccaggga gtacttcttt 360
ggcagcggca actacggata ctggggccag ggcaccctgg tgacagtgag ctccgccgga 420
ggaggaggaa gcggaggagg cggaagcgga ggaggcggca gcgaaatcgt gctgacccag 480
agccctgcca ccctgagcct gagccctggc gaaagggcca ccctgagctg cagagccagc 540
cagagcgtga gcagctacct ggcctggtac cagcagaagc ccggacaggc ccccagactg 600
ctgatctacg acgccagcaa cagagccacc ggcattcccg ccagattctc cggcagcggc 660
agcggaaccg acttcacact gaccatcagc tccttagaac ccgaggactt cgccgtgtac 720
tactgtcagc agagaagcaa ctggcctccc accttcggcc agggcacaaa ggtggagatc 780
aaggctagcg tgaaagggaa acacctttgt ccaagtcccc tatttcccgg accttctaag 840
cccttttggg tgctggtggt ggttggtgga gtcctggctt gctatagctt gctagtaaca 900
gtggccttta ttattttctg ggtgagtcga agaaggtgtg ggcagaagaa aaagctagtg 960
atcaacagtg gcaatggagc tgtggaggac agaaagccaa gtggactcaa cggagaggcc 1020
agcaagtctc aggaaatggt gcatttggtg aacaaggagt cgtcagaaac tccagaccag 1080
tttatgacag ctgatgagac aaggaacctg cagaatgtgg acatgaagat tggggtgaga 1140
gtgaagttca gcaggagcgc agacgccccc gcgtaccagc agggccagaa ccagctctat 1200
aacgagctca atctaggacg aagagaggag tacgatgttt tggacaagag acgtggccgg 1260
gaccctgaga tgggggggaaa gccgagaagg aagaaccctc aggaaggcct gtacaatgaa 1320
ctgcagaaag ataagatggc ggaggcctac agtgagattg ggatgaaagg cgagcgccgg 1380
aggggcaagg ggcacgatgg cctttaccag ggtctcagta cagccaccaa ggacacctac 1440
gacgcccttc acatgcaggc cctgcccccct cgc 1473

<210> SEQ ID NO 242
<211> LENGTH: 1278
<212> TYPE: DNA
<213> ORGANISM: Artificial Sequence
<220> FEATURE:
<223> OTHER INFORMATION: DG05-CD28tm-CD3Z

<400> SEQUENCE: 242
atggaatgga cctgggtgtt tctgttcctc ctgtccgtga ccgccggagt gcactccgaa 60
gtgcagctgg tgcagtccgg cggaggactg gtgaaacccg gaggaagcct cagactgagc 120
tgcgccggca gcggctttac cttctccagc tactccatgc actggctgag acaggcccct 180
ggcaagggcc tggaatgggt cagcgccatc ggcaccgccg gaggcacata ctatgccgac 240
agcgtgaagg gcaggttcac catcagcagg gacaacgcca agaacagcct gtacctgcag 300
atgaactctc tgagggccga ggataccgct gtgtactact gcgccaggga gtacttcttt 360
ggcagcggca actacggata ctggggccag ggcaccctgg tgacagtgag ctccgccgga 420
ggaggaggaa gcggaggagg cggaagcgga ggaggcggca gcgaaatcgt gctgacccag 480
agccctgcca ccctgagcct gagccctggc gaaagggcca ccctgagctg cagagccagc 540
cagagcgtga gcagctacct ggcctggtac cagcagaagc ccggacaggc ccccagactg 600
ctgatctacg acgccagcaa cagagccacc ggcattcccg ccagattctc cggcagcggc 660
agcggaaccg acttcacact gaccatcagc tccttagaac ccgaggactt cgccgtgtac 720
tactgtcagc agagaagcaa ctggcctccc accttcggcc agggcacaaa ggtggagatc 780
aaggctagcg tgaaagggaa acacctttgt ccaagtcccc tatttcccgg accttctaag 840
cccttttggg tgctggtggt ggttggtgga gtcctggctt gctatagctt gctagtaaca 900
gtggccttta ttattttctg ggtgaggagt aagaggagca ggagagtgaa gttcagcagg 960
agcgcagacg cccccgcgta ccagcagggc cagaaccagc tctataacga gctcaatcta 1020
ggacgaagag aggagtacga tgttttggac aagagacgtg gccgggaccc tgagatgggg 1080
ggaaagccga gaaggaagaa ccctcaggaa ggcctgtaca atgaactgca gaaagataag 1140

-continued atggcggagg cctacagtga gattgggatg aaaggcgagc gccggagggg caaggggcac 1200
gatggccttt accagggtct cagtacagcc accaaggaca cctacgacgc ccttcacatg 1260
caggccctgc cccctcgc 1278

<210> SEQ ID NO 243
<211> LENGTH: 1047
<212> TYPE: DNA
<213> ORGANISM: Artificial Sequence
<220> FEATURE:
<223> OTHER INFORMATION: DG05-CD28

<400> SEQUENCE: 243
atggaatgga cctgggtgtt tctgttcctc ctgtccgtga ccgccggagt gcactccgaa 60
gtgcagctgg tgcagtccgg cggaggactg gtgaaacccg gaggaagcct cagactgagc 120
tgcgccggca gcggctttac cttctccagc tactccatgc actggctgag acaggcccct 180
ggcaagggcc tggaatgggt cagcgccatc ggcaccgccg gaggcacata ctatgccgac 240
agcgtgaagg gcaggttcac catcagcagg gacaacgcca agaacagcct gtacctgcag 300
atgaactctc tgagggccga ggataccgct gtgtactact gcgccaggga gtacttcttt 360
ggcagcggca actacggata ctggggccag ggcaccctgg tgacagtgag ctccgccgga 420
ggaggaggaa gcggaggagg cggaagcgga ggaggcggca gcgaaatcgt gctgacccag 480
agccctgcca ccctgagcct gagccctggc gaaagggcca ccctgagctg cagagccagc 540
cagagcgtga gcagctacct ggcctggtac cagcagaagc ccggacaggc ccccagactg 600
ctgatctacg acgccagcaa cagagccacc ggcattcccg ccagattctc cggcagcggc 660
agcggaaccg acttcacact gaccatcagc tccttagaac ccgaggactt cgccgtgtac 720
tactgtcagc agagaagcaa ctggcctccc accttcggcc agggcacaaa ggtggagatc 780
aaggctagcg tgaaagggaa acacctttgt ccaagtcccc tatttcccgg accttctaag 840
cccttttggg tgctggtggt ggttggtgga gtcctggctt gctatagctt gctagtaaca 900
gtggccttta ttattttctg ggtgaggagt aagaggagca ggctcctgca cagtgactac 960
atgaacatga ctccccgccg ccccgggccc acccgcaagc attaccagcc ctatgcccca 1020
ccacgcgact tcgcagccta tcgctcc 1047

<210> SEQ ID NO 244
<211> LENGTH: 957
<212> TYPE: DNA
<213> ORGANISM: Artificial Sequence
<220> FEATURE:
<223> OTHER INFORMATION: DG05-CD28tm

<400> SEQUENCE: 244
atggaatgga cctgggtgtt tctgttcctc ctgtccgtga ccgccggagt gcactccgaa 60
gtgcagctgg tgcagtccgg cggaggactg gtgaaacccg gaggaagcct cagactgagc 120
tgcgccggca gcggctttac cttctccagc tactccatgc actggctgag acaggcccct 180
ggcaagggcc tggaatgggt cagcgccatc ggcaccgccg gaggcacata ctatgccgac 240
agcgtgaagg gcaggttcac catcagcagg gacaacgcca agaacagcct gtacctgcag 300
atgaactctc tgagggccga ggataccgct gtgtactact gcgccaggga gtacttcttt 360
ggcagcggca actacggata ctggggccag ggcaccctgg tgacagtgag ctccgccgga 420
ggaggaggaa gcggaggagg cggaagcgga ggaggcggca gcgaaatcgt gctgacccag 480
agccctgcca ccctgagcct gagccctggc gaaagggcca ccctgagctg cagagccagc 540

```
cagagcgtga gcagctacct ggcctggtac cagcagaagc ccggacaggc ccccagactg    600

ctgatctacg acgccagcaa cagagccacc ggcattcccg ccagattctc cggcagcggc    660

agcggaaccg acttcacact gaccatcagc tccttagaac ccgaggactt cgccgtgtac    720

tactgtcagc agagaagcaa ctggcctccc accttcggcc agggcacaaa ggtggagatc    780

aaggctagcg tgaaagggaa acacctttgt ccaagtcccc tatttcccgg accttctaag    840

cccttttggg tgctggtggt ggttggtgga gtcctggctt gctatagctt gctagtaaca    900

gtggccttta ttattttctg ggtgaggagt aagaggagca ggctcctgca cagtgac       957
```

<210> SEQ ID NO 245
<211> LENGTH: 1347
<212> TYPE: DNA
<213> ORGANISM: Artificial Sequence
<220> FEATURE:
<223> OTHER INFORMATION: DG03-CD28tm-DAP10-CD3Z

<400> SEQUENCE: 245

```
atggaatgga cctgggtgtt cctgtttctg ctctccgtga ccgccggagt gcacagcgag     60

gtgcagctgg tcgaaagcgg cggaggactg gtgcagcctg gcggcagcct gagactgagc    120

tgtgccgcct ccggcttcac ctttagcagc tacggaatgt cctgggtgag acaggctcct    180

ggcaagggcc tggaactggt ggccagcatc aatagcaacg gcggcagcac ctactaccct    240

gatagcgtga agggcaggtt caccatctcc agggacaacg ccaagaacag cctgtacctg    300

cagatgaaca gcctcagggc cgaggacaca gccgtgtact actgcgccag cggcgactat    360

tggggacagg gaacaaccgt gaccgtcagc agcgccggcg gcggcggcag cggcggcggc    420

ggcagcggcg gcggcggctc cgatatcgtg atgacccaga gccccctgtc cctgcctgtc    480

acacctggcg aacccgccag cattagctgc aggtccagcc agagcctggt gtacagcaat    540

ggcgacacct acctgcactg gtacctgcag aagcctggcc agagccccca gctgctgatc    600

tacaaggtga gcaacaggtt ctccggagtg cctgacaggt tcagcggctc cggcagcgga    660

accgatttca ccctcaagat cagcagagtg gaggccgagg acgtgggcgt ctactattgt    720

agccagagca cccacgtgcc ctggaccttt ggccagggca ccaaggtgga gatcaaagct    780

agcgtgaaag ggaaacacct ttgtccaagt cccctatttc ccggaccttc taagcccttt    840

tgggtgctgg tggtggttgg tggagtcctg gcttgctata gcttgctagt aacagtggcc    900

tttattattt tctgggtgag gagtaagagg agcctgtgcg cacgcccacg ccgcagcccc    960

gcccaagaag atggcaaagt ctacatcaac atgccaggca ggggcaagct tagagtgaag   1020

ttcagcagga gcgcagacgc ccccgcgtac cagcagggcc agaaccagct ctataacgag   1080

ctcaatctag gacgaagaga ggagtacgat gttttggaca agagacgtgg ccgggaccct   1140

gagatggggg gaaagccgag aaggaagaac cctcaggaag gcctgtacaa tgaactgcag   1200

aaagataaga tggcggaggc ctacagtgag attgggatga aaggcgagcg ccggaggggc   1260

aaggggcacg atggccttta ccagggtctc agtacagcca ccaaggacac ctacgacgcc   1320

cttcacatgc aggccctgcc ccctcgc                                       1347
```

<210> SEQ ID NO 246
<211> LENGTH: 1467
<212> TYPE: DNA
<213> ORGANISM: Artificial Sequence
<220> FEATURE:
<223> OTHER INFORMATION: DG03-CD28tm-CD44-CD3Z

<400> SEQUENCE: 246
atggaatgga cctgggtgtt cctgtttctg ctctccgtga ccgccggagt gcacagcgag 60
gtgcagctgg tcgaaagcgg cggaggactg gtgcagcctg gcggcagcct gagactgagc 120
tgtgccgcct ccggcttcac ctttagcagc tacggaatgt cctgggtgag acaggctcct 180
ggcaagggcc tggaactggt ggccagcatc aatagcaacg gcggcagcac ctactaccct 240
gatagcgtga agggcaggtt caccatctcc agggacaacg ccaagaacag cctgtacctg 300
cagatgaaca gcctcagggc cgaggacaca gccgtgtact actgcgccag cggcgactat 360
tggggacagg gaacaaccgt gaccgtcagc agcgccggcg gcggcggcag cggcggcggc 420
ggcagcggcg gcggcggctc cgatatcgtg atgacccaga gccccctgtc cctgcctgtc 480
acacctggcg aacccgccag cattagctgc aggtccagcc agagcctggt gtacagcaat 540
ggcgacacct acctgcactg gtacctgcag aagcctggcc agagccccca gctgctgatc 600
tacaaggtga gcaacaggtt ctccggagtg cctgacaggt tcagcggctc cggcagcgga 660
accgatttca ccctcaagat cagcagagtg gaggccgagg acgtgggcgt ctactattgt 720
agccagagca cccacgtgcc ctggaccttt ggccagggca ccaaggtgga gatcaaagct 780
agcgtgaaag ggaaacacct ttgtccaagt cccctatttc ccggaccttc taagcccttt 840
tgggtgctgg tggtggttgg tggagtcctg gcttgctata gcttgctagt aacagtggcc 900
tttattattt tctgggtgag tcgaagaagg tgtgggcaga agaaaaagct agtgatcaac 960
agtggcaatg gagctgtgga ggacagaaag ccaagtggac tcaacggaga ggccagcaag 1020
tctcaggaaa tggtgcattt ggtgaacaag gagtcgtcag aaactccaga ccagtttatg 1080
acagctgatg agacaaggaa cctgcagaat gtggacatga agattggggt gagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgc 1467

<210> SEQ ID NO 247
<211> LENGTH: 1407
<212> TYPE: DNA
<213> ORGANISM: Artificial Sequence
<220> FEATURE:
<223> OTHER INFORMATION: DG03-CD28tm-4-1-BB-CD3Z

<400> SEQUENCE: 247
atggaatgga cctgggtgtt cctgtttctg ctctccgtga ccgccggagt gcacagcgag 60
gtgcagctgg tcgaaagcgg cggaggactg gtgcagcctg gcggcagcct gagactgagc 120
tgtgccgcct ccggcttcac ctttagcagc tacggaatgt cctgggtgag acaggctcct 180
ggcaagggcc tggaactggt ggccagcatc aatagcaacg gcggcagcac ctactaccct 240
gatagcgtga agggcaggtt caccatctcc agggacaacg ccaagaacag cctgtacctg 300
cagatgaaca gcctcagggc cgaggacaca gccgtgtact actgcgccag cggcgactat 360
tggggacagg gaacaaccgt gaccgtcagc agcgccggcg gcggcggcag cggcggcggc 420
ggcagcggcg gcggcggctc cgatatcgtg atgacccaga gccccctgtc cctgcctgtc 480
acacctggcg aacccgccag cattagctgc aggtccagcc agagcctggt gtacagcaat 540
ggcgacacct acctgcactg gtacctgcag aagcctggcc agagccccca gctgctgatc 600
tacaaggtga gcaacaggtt ctccggagtg cctgacaggt tcagcggctc cggcagcgga 660
accgatttca ccctcaagat cagcagagtg gaggccgagg acgtgggcgt ctactattgt 720
agccagagca cccacgtgcc ctggaccttt ggccagggca ccaaggtgga gatcaaagct 780
agcgtgaaag ggaaacacct ttgtccaagt cccctatttc ccggaccttc taagcccttt 840
tgggtgctgg tggtggttgg tggagtcctg gcttgctata gcttgctagt aacagtggcc 900
tttattattt tctgggtgag gagtaagagg agcctcgaga aacggggcag aaagaaactc 960
ctgtatatat tcaaacaacc atttatgaga ccagtacaaa ctactcaaga ggaagatggc 1020
tgtagctgcc gatttccaga agaagaagaa ggaggatgtg aactgaagct tagagtgaag 1080
ttcagcagga gcgcagacgc ccccgcgtac cagcagggcc agaaccagct ctataacgag 1140
ctcaatctag gacgaagaga ggagtacgat gttttggaca agagacgtgg ccgggaccct 1200
gagatggggg gaaagccgag aaggaagaac cctcaggaag gcctgtacaa tgaactgcag 1260
aaagataaga tggcggaggc ctacagtgag attgggatga aaggcgagcg ccggaggggc 1320
aaggggcacg atggccttta ccagggtctc agtacagcca ccaaggacac ctacgacgcc 1380
cttcacatgc aggccctgcc ccctcgc 1407

<210> SEQ ID NO 248
<211> LENGTH: 1272
<212> TYPE: DNA
<213> ORGANISM: Artificial Sequence
<220> FEATURE:
<223> OTHER INFORMATION: DG03-CD28tm-CD3Z

<400> SEQUENCE: 248
atggaatgga cctgggtgtt cctgtttctg ctctccgtga ccgccggagt gcacagcgag 60
gtgcagctgg tcgaaagcgg cggaggactg gtgcagcctg gcggcagcct gagactgagc 120
tgtgccgcct ccggcttcac ctttagcagc tacggaatgt cctgggtgag acaggctcct 180
ggcaagggcc tggaactggt ggccagcatc aatagcaacg gcggcagcac ctactaccct 240
gatagcgtga agggcaggtt caccatctcc agggacaacg ccaagaacag cctgtacctg 300
cagatgaaca gcctcagggc cgaggacaca gccgtgtact actgcgccag cggcgactat 360
tggggacagg gaacaaccgt gaccgtcagc agcgccggcg gcggcggcag cggcggcggc 420
ggcagcggcg gcggcggctc cgatatcgtg atgacccaga gccccctgtc cctgcctgtc 480
acacctggcg aacccgccag cattagctgc aggtccagcc agagcctggt gtacagcaat 540
ggcgacacct acctgcactg gtacctgcag aagcctggcc agagccccca gctgctgatc 600
tacaaggtga gcaacaggtt ctccggagtg cctgacaggt tcagcggctc cggcagcgga 660
accgatttca ccctcaagat cagcagagtg gaggccgagg acgtgggcgt ctactattgt 720
agccagagca cccacgtgcc ctggaccttt ggccagggca ccaaggtgga gatcaaagct 780
agcgtgaaag ggaaacacct ttgtccaagt cccctatttc ccggaccttc taagcccttt 840
tgggtgctgg tggtggttgg tggagtcctg gcttgctata gcttgctagt aacagtggcc 900
tttattattt tctgggtgag gagtaagagg agcaggagag tgaagttcag caggagcgca 960
gacgcccccg cgtaccagca gggccagaac cagctctata acgagctcaa tctaggacga 1020
agagaggagt acgatgtttt ggacaagaga cgtggccggg accctgagat ggggggaaag 1080
ccgagaagga agaaccctca ggaaggcctg tacaatgaac tgcagaaaga taagatggcg 1140
gaggcctaca gtgagattgg gatgaaaggc gagcgccgga ggggcaaggg gcacgatggc 1200
ctttaccagg gtctcagtac agccaccaag gacacctacg acgcccttca catgcaggcc 1260
ctgccccctc gc 1272

<210> SEQ ID NO 249
<211> LENGTH: 1041
<212> TYPE: DNA
<213> ORGANISM: Artificial Sequence
<220> FEATURE:
<223> OTHER INFORMATION: DG03-CD28

<400> SEQUENCE: 249
atggaatgga cctgggtgtt cctgtttctg ctctccgtga ccgccggagt gcacagcgag 60
gtgcagctgg tcgaaagcgg cggaggactg gtgcagcctg gcggcagcct gagactgagc 120
tgtgccgcct ccggcttcac ctttagcagc tacggaatgt cctgggtgag acaggctcct 180
ggcaagggcc tggaactggt ggccagcatc aatagcaacg gcggcagcac ctactaccct 240
gatagcgtga agggcaggtt caccatctcc agggacaacg ccaagaacag cctgtacctg 300
cagatgaaca gcctcagggc cgaggacaca gccgtgtact actgcgccag cggcgactat 360
tggggacagg gaacaaccgt gaccgtcagc agcgccggcg gcggcggcag cggcggcggc 420
ggcagcggcg gcggcggctc cgatatcgtg atgacccaga gccccctgtc cctgcctgtc 480
acacctggcg aacccgccag cattagctgc aggtccagcc agagcctggt gtacagcaat 540
ggcgacacct acctgcactg gtacctgcag aagcctggcc agagccccca gctgctgatc 600
tacaaggtga gcaacaggtt ctccggagtg cctgacaggt tcagcggctc cggcagcgga 660
accgatttca ccctcaagat cagcagagtg gaggccgagg acgtgggcgt ctactattgt 720
agccagagca cccacgtgcc ctggaccttt ggccagggca ccaaggtgga gatcaaagct 780
agcgtgaaag ggaaacacct ttgtccaagt cccctatttc ccggaccttc taagcccttt 840
tgggtgctgg tggtggttgg tggagtcctg gcttgctata gcttgctagt aacagtggcc 900
tttattattt tctgggtgag gagtaagagg agcaggctcc tgcacagtga ctacatgaac 960
atgactcccc gccgccccgg gcccacccgc aagcattacc agccctatgc cccaccacgc 1020
gacttcgcag cctatcgctc c 1041

<210> SEQ ID NO 250
<211> LENGTH: 918
<212> TYPE: DNA
<213> ORGANISM: Artificial Sequence
<220> FEATURE:
<223> OTHER INFORMATION: DG03-CD28tm

<400> SEQUENCE: 250
atggaatgga cctgggtgtt cctgtttctg ctctccgtga ccgccggagt gcacagcgag 60
gtgcagctgg tcgaaagcgg cggaggactg gtgcagcctg gcggcagcct gagactgagc 120
tgtgccgcct ccggcttcac ctttagcagc tacggaatgt cctgggtgag acaggctcct 180
ggcaagggcc tggaactggt ggccagcatc aatagcaacg gcggcagcac ctactaccct 240
gatagcgtga agggcaggtt caccatctcc agggacaacg ccaagaacag cctgtacctg 300
cagatgaaca gcctcagggc cgaggacaca gccgtgtact actgcgccag cggcgactat 360
tggggacagg gaacaaccgt gaccgtcagc agcgccggcg gcggcggcag cggcggcggc 420
ggcagcggcg gcggcggctc cgatatcgtg atgacccaga gccccctgtc cctgcctgtc 480
acacctggcg aacccgccag cattagctgc aggtccagcc agagcctggt gtacagcaat 540

```
ggcgacacct acctgcactg gtacctgcag aagcctggcc agagccccca gctgctgatc    600

tacaaggtga gcaacaggtt ctccggagtg cctgacaggt tcagcggctc cggcagcgga    660

accgatttca ccctcaagat cagcagagtg gaggccgagg acgtgggcgt ctactattgt    720

agccagagca cccacgtgcc ctggaccttt ggccagggca ccaaggtgga gatcaaagct    780

agcgtgaaag ggaaacacct ttgtccaagt cccctatttc ccggaccttc taagcccttt    840

tgggtgctgg tggtggttgg tggagtcctg gcttgctata gcttgctagt aacagtggcc    900

tttattattt tctgggtg                                                  918
```

<210> SEQ ID NO 251
<211> LENGTH: 270
<212> TYPE: DNA
<213> ORGANISM: Artificial Sequence
<220> FEATURE:
<223> OTHER INFORMATION: Construct for expression of the NDMM Nrf2 (Keap1 inhibitor peptide)

<400> SEQUENCE: 251

```
atgatggatt tggaacttcc ccccccaggg ctcccatccc aacaagacat ggatctcata     60

gacatactgt ggagacagga catcgatctg ggggtcagcc gcgaagtttt cgacttttca    120

caaaggcgga aagaatatga attggaaaag cagaaaaaat tggaaaaaga acgccaggaa    180

cagcttcaga aggagcagga aaaagccttt tttgcccagc ttcagctgga cgaggaaaca    240

ggggaatttc tccccatcca accagcccag                                     270
```

<210> SEQ ID NO 252
<211> LENGTH: 1581
<212> TYPE: DNA
<213> ORGANISM: Artificial Sequence
<220> FEATURE:
<223> OTHER INFORMATION: Construct for expression of the NDMM human catalase

<400> SEQUENCE: 252

```
atggcagaca gtcgagaccc tgctagcgac caaatgcaac attggaaaga gcaacgggcg     60

gcccagaaag ccgacgtttt gaccactggg gcaggtaatc ctgttggaga taagctgaac    120

gtcatcacgg ttggaccccg gggaccgctg ctcgttcaag acgtggtttt tacggatgag    180

atggcccatt ttgatcgaga gaggatacca gaaagggttg tgcacgctaa gggcgcaggt    240

gccttcggat atttcgaggt aactcacgac attactaagt atagcaaggc caaggtattt    300

gaacacattg gcaagaagac gccgatagcg gtccgattca gtacagtggc gggcgagtca    360

ggttcagccg ataccgtgag agatccgaga ggatttgccg tgaaatttta tacagaggac    420

ggcaactggg acttggtagg aaacaatacc ccaatatttt tcataaggga cccaatcctt    480

tttcccagct ttattcattc acagaagcgg aacccacaaa cgcacttgaa agatcctgac    540

atggtgtggg atttttggag cttgaggcca gagagcctgc accaagtgag cttcttgttc    600

agcgacagag gcataccgga cggtcataga cacatgaacg gttacggtag tcacaccttc    660

aaactggtga acgccaacgg agaggctgtc tattgtaagt tccactataa aaccgatcaa    720

ggcatcaaaa acctgagcgt agaggacgca gcccgccttt ctcaagaaga tccagactat    780

gggatccggg atctctttaa cgccatagct acgggtaaat atccctcttg gacgttctat    840

atccaggtaa tgacattcaa tcaagcagag actttcccct ttaacccgtt tgaccttact    900

aaagtatggc cgcataagga ctaccctctg attcccgtcg gcaaactcgt gcttaacagg    960
```

-continued

```
aatccagtca actatttcgc agaagtcgag caaatcgcct ttgacccttc taacatgccg   1020

ccgggaatcg aagcgtcacc ggacaagatg cttcaaggtc ggcttttcgc ataccccgac   1080

actcaccgac acagactggg tccgaattat cttcacatac ctgtcaactg cccatataga   1140

gcacgcgttg cgaactacca gcgcgatggt ccgatgtgca tgcaggacaa ccaggggggg   1200

gcacccaact attatccaaa ttcatttggg gcgccggaac aacaaccgtc agcccttgaa   1260

cactccatcc agtattctgg cgaagtaaga cgcttcaaca cggctaatga tgacaacgtt   1320

acacaggtta gagcgtttta tgtgaacgtc ttgaacgagg aacaacggaa acgactttgc   1380

gaaaacatag cgggtcattt gaaagatgct cagattttta tccaaaaaaa agccgtcaaa   1440

aattttaccg aagtccaccc cgattacggt tcacatattc aggccctgtt ggataagtac   1500

aacgcggaaa agcccaagaa tgcaatacac acgtttgttc agagcgggag ccacctcgct   1560

gctcgagaga aagcaaatct g                                             1581
```

<210> SEQ ID NO 253
<211> LENGTH: 741
<212> TYPE: DNA
<213> ORGANISM: Artificial Sequence
<220> FEATURE:
<223> OTHER INFORMATION: Construct for expression of the NDMM BDNF

<400> SEQUENCE: 253

```
atgacgatcc tgtttctgac aatggtgatt agctatttcg gatgtatgaa agccgccccg     60

atgaaggagg ccaatatcag gggacaaggt gggctggctt atccgggcgt aaggacacac    120

ggcacactgg agagtgtgaa cggcccgaag gccggatcac gaggattgac gagcctcgca    180

gatacgtttg agcatgtaat cgaagagctc ttggatgaag accaaaaggt ccgccccaat    240

gaggagaaca acaaagacgc agacctgtac acatcacgag ttatgctgtc aagtcaagtg    300

ccgctcgaac caccactcct ctttctgctg gaggagtaca aaaactattt ggacgctgct    360

aacatgtcta tgcgagtgcg cagacatagt gaccctgcca gacgcggtga gctttcagtc    420

tgtgattcta taagtgagtg ggtaaccgca gcagataaga agactgccgt agacatgtca    480

gggggaactg tgactgtact tgaaaaggtt cccgtttcta aagggcagct caaacagtat    540

ttctatgaaa caaagtgtaa tccaatgggg tacaccaagg aaggttgcag gggaatcgac    600

aagcgacatt ggaacagtca atgtcggacc actcagagct acgtccgcgc tctcacgatg    660

gatagtaaga aacgcatcgg gtggagattc atcagaatcg acacctcttg cgtctgtact    720

cttacaatta agcgagggcg a                                              741
```

<210> SEQ ID NO 254
<211> LENGTH: 585
<212> TYPE: DNA
<213> ORGANISM: Artificial Sequence
<220> FEATURE:
<223> OTHER INFORMATION: Construct for expression of the NDMM IGF-1

<400> SEQUENCE: 254

```
atggggaaaa tctcctctct ccctacccag ttgttcaagt gttgcttttg tgacttcttg     60

aaggtaaaaa tgcacactat gtcatccagt cacctttttt atttggctct gtgcctcctc    120

acattcacca gttcagctac tgccgggcct gaaacactct gcggcgccga actcgttgat    180

gcgcttcaat tcgtgtgtgg agataggggg ttttacttta acaagccgac gggttatggt    240

agctcaagta gacgagcgcc acagactgga atagtagatg aatgctgttt ccgctcatgc    300

gaccttcgca gattggaaat gtactgcgct cctcttaaac cagcaaagag tgcgcggtcc    360
```

gtgcgagccc aacgacatac cgatatgcca aaaacccaga aatatcagcc gccgtctacc 420
aacaagaaca ccaagagtca gaggagaaag ggttggccca agacgcaccc gggtggcgaa 480
caaaaagaag gtactgaggc aagtttgcaa attcgaggaa agaagaaaga acaacgaaga 540
gagataggtt ctcgcaatgc ggaatgtcga ggcaaaaaag gtaag 585

<210> SEQ ID NO 255
<211> LENGTH: 19
<212> TYPE: DNA
<213> ORGANISM: Artificial Sequence
<220> FEATURE:
<223> OTHER INFORMATION: Forward primer human B-actin

<400> SEQUENCE: 255
ggccgaggac tttgattgc 19

<210> SEQ ID NO 256
<211> LENGTH: 20
<212> TYPE: DNA
<213> ORGANISM: Artificial Sequence
<220> FEATURE:
<223> OTHER INFORMATION: Reverse primer human B-actin

<400> SEQUENCE: 256
tggggtggct tttaggatgg 20

<210> SEQ ID NO 257
<211> LENGTH: 20
<212> TYPE: DNA
<213> ORGANISM: Artificial Sequence
<220> FEATURE:
<223> OTHER INFORMATION: Forward primer human IL-4

<400> SEQUENCE: 257
gcttccccct ctgttcttcc 20

<210> SEQ ID NO 258
<211> LENGTH: 22
<212> TYPE: DNA
<213> ORGANISM: Artificial Sequence
<220> FEATURE:
<223> OTHER INFORMATION: Reverse primer human IL-4

<400> SEQUENCE: 258
gatgtctgtt acggtcaact cg 22

<210> SEQ ID NO 259
<211> LENGTH: 20
<212> TYPE: DNA
<213> ORGANISM: Artificial Sequence
<220> FEATURE:
<223> OTHER INFORMATION: Forward primer human IL-10

<400> SEQUENCE: 259
tcaaggcgca tgtgaactcc 20

-continued

```
<210> SEQ ID NO 260
<211> LENGTH: 22
<212> TYPE: DNA
<213> ORGANISM: Artificial Sequence
<220> FEATURE:
<223> OTHER INFORMATION: Reverse primer human IL-10

<400> SEQUENCE: 260

cagggaagaa atcgatgaca gc                                          22
```

CHIMERIC ANTIGEN RECEPTORS FOR TREATMENT OF NEURODEGENERATIVE DISEASES AND DISORDERS

RELATED APPLICATIONS

This application is a U.S. National Phase Application submitted under 35 U.S.C. 371 based on International Application No. PCT/US2019/017489, filed Feb. 11, 2019 (published as WO2019/157440 on Aug. 15, 2019), which claims the benefit of U.S. Provisional Application No. 62/628,632, filed Feb. 9, 2018, each and all of which are hereby incorporated by reference in their entirety.

GRANTS

The instant application was made with government support under grant no. R21 NS 102556 awarded by the National Institutes of Health ("NIH"). The government has certain rights in the invention.

SEQUENCE DISCLOSURE

The instant application contains a Sequence Listing which has been submitted in ASCII format via EFS-Web and is hereby incorporated by reference in its entirety. Said ASCII copy, created on Aug. 7, 2020, is named "11432520002603.txt" and is 203,578 bytes in size.

FIELD OF THE ART

The present disclosure generally relates to novel chimeric antigen receptors ("CARs"), nucleic acids encoding such CARs and constructs containing same, modified regulatory T cells ("Tregs") expressing such CARs and/or Tregs which are engineered to express neurodegenerative disease modifying molecules, e.g., which prevent oxidative/inflammatory activity, or which promote neuronal growth/survival such as nerve growth factors or non-classical neurotrophic factors. The present disclosure also generally relates to compositions containing such modified Tregs, and methods of use thereof as therapeutics, in particular for treating and preventing neurodegenerative diseases and symptoms associated therewith, and/or for slowing the onset of such neurodegenerative diseases, particularly in persons at risk because of genetic factors or in persons exhibiting early signs of developing such neurodegenerative diseases.

BACKGROUND

Neurodegenerative diseases can generally be characterized by a slow progressive loss of neurons in the central nervous system (CNS), which often leads to deficits in specific brain functions (e.g. memory, movement, cognition) performed by the affected CNS region. These neurodegenerative diseases include, for example, Alzheimer's disease (AD), Parkinson's disease (PD), amyotrophic lateral sclerosis (ALS), multiple sclerosis, Huntington's disease, and multiple system atrophy. Neurodegenerative diseases usually extend over a decade, and the actual onset of neurodegeneration may precede clinical manifestations by many years.

Alzheimer's disease (AD) is a progressive neurodegenerative disease that is one of the primary reasons for memory dysfunction and dementia after 60 years of age. Neuronal dysfunction and death in the frontal cortex and hippocampus, along with microglia-mediated neuroinflammation and formation of aberrant protein aggregates and fibrils are hallmarks of AD. Advancing age increases its prevalence, with an estimated 4.5 million individuals over the age of 65 living with clinical AD in the United States. This number is projected to rise to over 13 million, and to over 130 million worldwide, by 2050 (Hebert et al., Alzheimer disease in the United States (2010-2050) estimated using the 2010 census. *Neurology* 2013, 80:1778-83)

Sporadic and familial forms of AD have an overproduction and/or decreased clearance of extracellular amyloid-beta (Aβ) peptides and intraneuronal tangles of twisted tau protein fibers. The genetic basis for inheritable autosomal dominant, early-onset AD involves mutations in genes that alter Aβ production, aggregation, or clearance: these genes include amyloid precursor protein (APP), presenilin-1 (PS1), and presenilin-2 (PS2). Aβ peptides self-oligomerize into small aggregates that can develop into diffuse plaques. Multiple antibodies that bind Aβ in its monomeric, oligomeric, and plaque forms have been created (Montoliu-Gaya L, Villegas 5: Aβ-Immunotherapeutic strategies: a wide range of approaches for Alzheimer's disease treatment. *Expert reviews in molecular medicine* 2016, 18:e13). Neuroinflammation is known to occur in AD, and when associated near Aβ plaques there is a greater neurodegeneration (Heneka M T, et al.: Neuroinflammation in Alzheimer's disease. *The Lancet Neurology* 2015, 14:388-405; Kreisl W C, et al.: Distinct patterns of increased translocator protein in posterior cortical atrophy and amnestic Alzheimer's disease. *Neurobiol. Aging* 2017, 51:132-40). Data suggest that inflammatory microglia—the resident macrophages of the central nervous system—have a role in neurodegeneration and cognitive decline (Kreisl W C et al.: Distinct patterns of increased translocator protein in posterior cortical atrophy and amnestic Alzheimer's disease. *Neurobiol Aging* 2017, 51:132-40; Paolicelli R C, et al.: TDP-43 Depletion in Microglia Promotes Amyloid Clearance but Also Induces Synapse Loss. *Neuron* 2017, 95:297,308. e6).

There are approximately 7.5 million people with Parkinson's disease worldwide and the disease prevalence increases progressively as age increases (Hebert L E et al.: Alzheimer disease in the United States (2010-2050) estimated using the 2010 census. *Neurology* 2013, 80:1778-83). It is expected that there will be 9 million people living with PD by 2030. Clinical signs of this neurodegenerative disease are resting tremor, muscular rigidity, slowness of movements, and postural instability. These disabilities are caused by the chronic death of dopamine-producing neurons in the substantia nigra pars compacta of the midbrain. Standard treatment generally involves enhancement of the amount of the neurotransmitter dopamine produced by remaining neurons with medicines that are chemical precursors (levodopa) or that block its inherent breakdown (monoamine oxidase B inhibitors). Several dopamine agonists have also been approved for use in treating PD. While these three types of drugs provide transient improvement in symptom relief, there is little impact on the long-term outcome of PD (Montoliu-Gaya L, Villegas S: Aβ-Immunotherapeutic strategies: a wide range of approaches for Alzheimer's disease treatment. *Expert reviews in molecular medicine* 2016, 18:e13). While a possible therapeutic strategy for PD would be to prevent the continual death of dopamine neurons, no such treatment is currently available.

The precise etiology of dopamine neuron loss in PD is not well understood. Aberrantly processed proteins and inflammation mediated by microglia, the resident macrophage of the central nervous system, coincide with the loss of neurons. Lewy bodies that contain the protein α-synuclein are inclusions found in dopamine neurons in sporadic and familial PD. In addition to being found in intracellular inclusion bodies, abnormal α-synuclein is also detected extracellularly (El-Agnaf O M, Salem S A, Paleologou K E, Curran M D, Gibson M J, Court J A, Schlossmacher M G, Allsop D: Detection of oligomeric forms of alpha-synuclein protein in human plasma as a potential biomarker for Parkinson's disease. *FASEB J* 2006, 20:419-25; Alvarez-Erviti L, Couch Y, Richardson J, Cooper J M, Wood M J: Alpha-synuclein release by neurons activates the inflammatory response in a microglial cell line. *Neurosci Res* 2011, 69:337-42; Tokuda T, Qureshi M M, Ardah M T, Varghese S, Shehab S A, Kasai T, Ishigami N, Tamaoka A, Nakagawa M, El-Agnaf O M: Detection of elevated levels of alpha-synuclein oligomers in CSF from patients with Parkinson disease. *Neurology* 2010, 75:1766-72). The physiological role of monomeric α-synuclein is not well understood. The formation of abnormal α-synuclein oligomers, though, is thought to be important in the etiology of PD. This is further supported by a mutation in the α-synuclein gene that results in protein self-aggregation and causes a hereditary form of PD. One hypothesis by which aberrant α-synuclein results in dopamine neuron death is by causing or enhancing toxic neuroinflammation. Oligomeric α-synuclein fibrils activate microglia to produce free radicals and pro-inflammatory cytokines, and leads to neurodegeneration (Reynolds A D, Stone D K, Mosley R L, Gendelman H E: Nitrated {alpha}-synuclein-induced alterations in microglial immunity are regulated by CD4+ T cell subsets. *J Immunol* 2009, 182: 4137-49; Alvarez-Erviti L, Couch Y, Richardson J, Cooper J M, Wood M J: Alpha-synuclein release by neurons activates the inflammatory response in a microglial cell line. *Neurosci Res* 2011, 69:337-42; Theodore S, Cao S, McLean P J, Standaert D G: Targeted overexpression of human alpha-synuclein triggers microglial activation and an adaptive immune response in a mouse model of Parkinson disease. *J Neuropathol Exp Neurol* 2008, 67:1149-58; Zhang W, Wang T, Pei Z, Miller D S, Wu X, Block M L, Wilson B, Zhang W, Zhou Y, Hong J S, Zhang J: Aggregated alpha-synuclein activates microglia: a process leading to disease progression in Parkinson's disease. *FASEB J* 2005, 19:533-42).

Amyotrophic lateral sclerosis (ALS) patients develop fatal paralysis as a result of progressive motor neuron loss in the brain and spinal cord. There are approximately 6,000 new cases of ALS per year in the United States, and the typical age of onset is between 40 and 70 years of age, although onset can occur to people in their twenties. ALS can be either idiopathic or hereditary (~10%), and only about 20% of individuals live more than five years after diagnosis. The absence of an effective therapeutic intervention is especially problematic because the incidence is rising (See e.g., Caller T A et al.: Spatial analysis of amyotrophic lateral sclerosis in Northern New England, USA, 1997-2009. *Muscle Nerve* 2013, 48:235-41). Inhibiting the persistent neuroinflammation, which is driven primarily by the resident macrophages of the brain and spinal cord (the microglia), is considered a promising therapeutic strategy. However, these processes are difficult to regulate with conventional anti-inflammatory drugs.

Cell therapies with genetically engineered T cells have been demonstrated to provide for the effective treatment of various diseases and disease conditions. For example, effector T cells (Teff) are emerging as a "living drug" treatment for cancer (June C H et al.: Adoptive cellular therapy: A race to the finish line. *Sci Transl Med* 2015, 7:280 ps7). In such treatment methods T cells are typically isolated from patients, modified to express chimeric antigen receptors (CARs) against a tumor ligand, and then transferred back into patients for targeted killing of tumors and activation of host immunity.

T regulatory cells (Tregs) are a subset of T cells that have inherent immunosuppressive and anti-inflammatory properties. Tregs are found in the CNS under steady state conditions and have been observed to migrate or traffic in increased numbers to regions of CNS inflammation (Xie L et al.: Cerebral regulatory T cells restrain microglia/macrophage-mediated inflammatory responses via IL-10. *Eur J Immunol* 2015, 45:180-91; Gong N et al.: Brain ingress of regulatory T cells in a murine model of HIV-1 encephalitis. *J Neuroimmunol* 2011, 230:33-41).

BRIEF SUMMARY

The present disclosure generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed at site(s) of neurodegeneration associated with a specific neurodegenerative disease and is associated with the pathology of said specific neurodegenerative disease or condition and/or (ii) a protein which is aberrantly expressed (e.g. overexpressed) at site(s) of neurodegeneration associated with a specific neurodegenerative disease and/or is associated with the pathology of said specific neurodegenerative disease or condition, wherein said CAR cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is associated with the expression of said aberrant or aberrantly expressed protein. In exemplary embodiments, said site(s) of neurodegeneration may be present in the central nervous system, and/or said site(s) of neurodegeneration are present in the peripheral nervous system. In exemplary embodiments, said CAR-expressing cells may comprise immune cells, optionally wherein said CAR-expressing immune cells comprise T cells or T cell progenitors, preferably T regulatory cells (Tregs) such as $FOXP3^+$ Tregs. In exemplary embodiments, the administered cells may comprise a CAR which recognizes at least one aberrant protein expressed at a site of neurodegeneration.

In some embodiments, the CAR comprised on said administered cells may comprise DG01 (SEQ ID NO: 1), DG02 (SEQ ID NO: 2), DG03 (SEQ ID NO: 3), DG04 (SEQ ID NO: 4), DG05 (SEQ ID NO: 5), DG06 (SEQ ID NO: 6), DG07 (SEQ ID NO: 7), DG08 (SEQ ID NO: 8), DG09 (SEQ ID NO: 9), DG10 (SEQ ID NO: 10), DG11 (SEQ ID NO: 11), and/or a construct comprising at least 90%, at least 95%, at least 98%, or at least 99% sequence identity to any one or more of the aforementioned constructs. In some embodiments, said administered cells may be engineered to express one or more of the following constructs: DG05-CD28-CD3ζ (also referred to as DG05-28-3ζ) (SEQ ID NO: 24); DG05-CD28tm-DAP10-CD3ζ (also referred to as DG05-28tm-10-3ζ) (SEQ ID NO: 40); DG05-CD28tm-CD44-CD3ζ (also referred to as DG05-28tm-44-3ζ) (SEQ ID NO: 41); DG05-

CD28tm-CD3ζ (also referred to as DG05-28tm-3ζ) (SEQ ID NO: 42); DG05-CD28 (also referred to as DG05-28) (SEQ ID NO: 43); DG05-CD28tm (also referred to as DG05-28tm) (SEQ ID NO: 44) and/or a construct comprising at least 90%, at least 95%, at least 98%, or at least 99% sequence identity to any one or more of the aforementioned constructs, optionally wherein each of said one or more constructs targets mutSOD1. In some embodiments, said administered cells may be engineered to express one or more of the following: DG03-CD28-CD3ζ (also referred to as DG03-28-3ζ) (SEQ ID NO: 22); DG03-CD28tm-DAP10-CD3ζ (also referred to as DG03-28tm-10-3ζ) (SEQ ID NO: 45); DG03-CD28tm-CD44-CD3ζ (also referred to as DG03-28tm-44-3ζ (SEQ ID NO: 46); D003-CD28tm-4-1-BB-CD3ζ (also referred to as DG03-28tm-BB-3ζ) (SEQ ID NO: 47); DG03-CD28tm-CD3ζ (also referred to as DG03-28tm-3ζ) (SEQ ID NO: 48); DG03-CD28 (also referred to as DG03-28) (SEQ ID NO: 49); DG03-CD28tm (also referred to as DG03-28tm) (SEQ ID NO: 50), and/or a construct comprising at least 90%, at least 95%, at least 98%, or at least 99% sequence identity to any one or more of the aforementioned constructs, optionally wherein each of said one or more constructs targets amyloid beta.

In further exemplary embodiments, the CAR may comprise an scFv or ligand which recognizes at least one aberrant protein expressed at a site of neurodegeneration. In exemplary embodiments, said cells may be further engineered to express at least one pro-neuronal factor or nerve growth factor, optionally wherein said CAR and said NDMM are on the same or are on different cells. In some embodiments, said administered cells may be engineered to express NDMM Nrf2 (Keap1 inhibitor peptide) (SEQ ID NO: 51) and/or a construct comprising at least 90%, at least 95%, at least 98%, or at least 99% sequence identity to the aforementioned construct. In some embodiments, said administered cells may be engineered to express human catalase (SEQ ID NO: 52), and/or a construct comprising at least 90%, at least 95%, at least 98%, or at least 99% sequence identity to the aforementioned construct. In some embodiments, said administered cells may be engineered to express BDNF (SEQ ID NO: 53), and/or a construct comprising at least 90%, at least 95%, at least 98%, or at least 99% sequence identity to the aforementioned construct. In some embodiments, said administered cells are engineered to express IGF-1 (SEQ ID NO: 54), and/or a construct comprising at least 90%, at least 95%, at least 98%, or at least 99% sequence identity to the aforementioned construct. In exemplary embodiments, said cells may be further engineered to express at least one anti-oxidative protein which inhibits or protects neurons from anti-oxidative stress and/or inhibits or prevents the death of neurons at the site of neurodegeneration optionally wherein said CAR and said anti-oxidative protein are on the same or are on different cells, further optionally wherein the anti-oxidant also promotes T cell function or lifespan.

In some embodiments, the administered cells may express increased levels of IL-10 in response to mSOD1 antigen in the treated subject. In some embodiments, the administered cells may express increased levels of cell surface markers including one or more of GITR, PD-1 and/or CTLA-4 in response to mSOD1 antigen in the treated subject. In some embodiments, the administered cells may inhibit superoxide generation in response to mSOD1 antigen and/or anti-CD3 in the treated subject. In some embodiments, the administered cells may inhibit TNF-α production in response to mSOD1 antigen in the treated subject. In some embodiments, the administered cells may be engineered to express a construct comprising DG05 (SEQ ID NO: 5) and/or a construct comprising at least 90%, at least 95%, at least 98%, or at least 99% sequence identity to the aforementioned construct. In some embodiments, the administered cells may be engineered to express one or more of the following constructs: DG05-CD28-CD3ζ (also referred to as DG05-28-3ζ) (SEQ ID NO: 24); DG05-CD28tm-DAP10-CD3ζ (also referred to as DG05-28tm-10-3ζ) (SEQ ID NO: 40); DG05-CD28tm-CD44-CD3ζ (also referred to as DG05-28tm-44-3ζ) (SEQ ID NO: 41); DG05-CD28tm-CD3ζ (also referred to as DG05-28tm-3ζ) (SEQ ID NO: 42); DG05-CD28 (also referred to as DG05-28) (SEQ ID NO: 43); DG05-CD28tm (also referred to as DG05-28tm) (SEQ ID NO: 44), and/or a construct comprising at least 90%, at least 95%, at least 98%, or at least 99% sequence identity to any one or more of the aforementioned constructs. In some embodiments, the administered cells may express increased levels of IL-10 and/or IL-4 in response to amyloid beta antigen in the treated subject. In some embodiments, the administered cells inhibit superoxide generation in response to amyloid beta antigen and/or anti-CD3 in the treated subject. In some embodiments, the administered cells may inhibit IL-6 production in response to amyloid beta antigen and/or anti-CD3 in the treated subject. In some embodiments, the administered cells may protect cells of the treated subject from hydrogen peroxide toxicity. In some embodiments, the administered cells may be engineered to express a construct comprising DG03 (SEQ ID NO: 3), and/or a construct comprising at least 90%, at least 95%, at least 98%, or at least 99% sequence identity to the aforementioned construct. In some embodiments, the administered cells may be engineered to express one or more of the following: DG03-CD28-CD3ζ (also referred to as DG03-28-3ζ) (SEQ ID NO: 22); DG03-CD28tm-DAP10-CD3ζ (also referred to as DG03-28tm-10-3ζ) (SEQ ID NO: 45); DG03-CD28tm-CD44-CD3ζ (also referred to as DG03-28tm-44-3ζ) (SEQ ID NO: 46); DG03-CD28tm-4-1-BB-CD3ζ (also referred to as DG03-28tm-BB-3ζ) (SEQ ID NO: 47); DG03-CD28tm-CD3ζ (also referred to as DG03-28tm-3ζ) (SEQ ID NO: 48); DG03-CD28 (also referred to as DG03-28) (SEQ ID NO: 49); DG03-CD28tm (SEQ ID NO: 50), and/or a construct comprising at least 90%, at least 95%, at least 98%, or at least 99% sequence identity to any one or more of the aforementioned constructs. In some embodiments, the administered cells may protect cells of the treated subject from hydrogen peroxide toxicity, optionally wherein said administered cells are engineered to express one or more of the following constructs: NDMM human catalase construct (SEQ ID NO: 52), NDMM Nrf2 (Keap1 inhibitor peptide) construct (SEQ ID NO: 51), NDMM BDNF construct (SEQ ID NO: 53), and/or NDMM IGF-1 construct (SEQ ID NO: 54), and/or a construct comprising at least 90%, at least 95%, at least 98%, or at least 99% sequence identity to any one or more of the aforementioned constructs.

In further exemplary embodiments, the neurodegenerative disease or condition may comprise at least one of Parkinson's disease, Alzheimer's disease, Prion disease, a Motor neurone disease (MND) such as amyotrophic lateral sclerosis (ALS), Huntington's disease (HD), Spinocerebellar ataxia (SCA), Spinal muscular atrophy (SMA), Friedreich's ataxia, Lewy body disease, epilepsy, encephalitis, hydrocephalus, stroke, chronic traumatic encephalopathy (CTE); a synucleinopathy; a tauopathy, a spongiform encephalopathy; familial amyloidotic polyneuropathy; Dutch hereditary cerebral hemorrhage with amyloidosis; congophilic angiopathy; corticobasal degeneration; Pick's disease; progressive supranuclear palsy; Creutzfeldt-Jacob disease; Gerstmann-Sträussler-Schneiker syndrome; fatal familial insomnia; kuru; bovine spongiform encephalopathy; scrapie; chronic wasting disease; Lewy body variant of Alzheimer's disease; diffuse Lewy body disease; dementia with Lewy bodies; multiple system atrophy; neurodegeneration with brain iron accumulation type I; diffuse Lewy body disease; frontotemporal lobar degeneration; hereditary dentatorubral-pallidoluysian atrophy; Kennedy's disease; Alexander's disease; Cockayne syndrome; and Icelandic hereditary cerebral hemorrhage with amyloidosis. In exemplary embodiments, the neurodegenerative disease may comprise Parkinson's disease. In exemplary embodiments, the neurodegenerative disease may comprise Alzheimer's disease. In exemplary embodiments, the neurodegenerative disease may comprise amyotrophic lateral sclerosis (ALS). IN exemplary embodiments, the CAR may bind to one or more of human amyloid beta, amyloid-beta 1-42, alpha-synuclein, superoxide dismutase-1 (SOD-1), hyperphosphorylated tau protein; TAR DNA-binding protein 43 (TDP-43): chromosome 9 open reading frame 72 (c9orf72); β-Synuclein; γ-Synuclein; RNA-binding protein fused in sarcoma (FUS); ubiquitin; ubiquilin-2, p62; optineurin; ataxin-2; parkin; Serine/threonine-protein kinase PINK1; and Leucine-rich repeat serine/threonine-protein kinase 2 (LRRK2), Huntingtin with tandem glutamine repeats; prion proteins; transthyretin; dentatorubral pallidoluysian atrophy (DRPLA) protein; androgen receptor; an ataxin; P/Q-type calcium channel al A subunit; TATA-box-binding protein; glial fibrillary acidic protein; DNA excision repair protein ERCC-6; survival motor neuron protein; and cystatin C.

In exemplary embodiments, the administered cells may express at least one pro-neuronal factor, neurotrophic factor, or nerve growth factor selected from brain-derived neurotrophic factor (BDNF), ciliary neurotrophic factor (CNTF), glial cell-line derived neurotrophic factor (GDNF), interleukin-1 receptor antagonist (IL-1ra); interleukin-6 (IL-6); activated protein C (APC); thrombomodulin; tissue plasminogen activator (tPA); Protein deglycase DJ-1; a tissue inhibitor of metalloproteinases (TIMP), insulin-like growth factor-1 (IGF-1), vascular endothelial growth factor (VEGF), fibroblast growth factor (FGF), a bone morphogenetic protein (BMP), erythropoietin (EPO), thrombopoietin (TPO), and granulocyte-colony stimulating factor (G-CSF), optionally wherein said at least one pro-neuronal factor, neurotrophic factor, or nerve growth factor are on the same cell as said CAR or on a different cell as said CAR. In exemplary embodiments, the anti-oxidative protein is a protein selected from superoxide dismutases such as human superoxide dismutase, Cu/Zn superoxide dismutase, HO-1, ferritin, glutathione reductase, glutathione peroxidase, ferritin (H), metallothionein I, thioredoxin, thioredoxin reductase, peroxiredoxins (Prxs) such as pereoxiredoxin $MSP_{23}$; activity-dependent neuroprotector homeobox (ADNP); phycocyanin; neuroglobin, catalase, and NRF2, optionally wherein said at least one anti-oxidative protein is on the same cell as said CAR or on a different cell as said CAR. In exemplary embodiments, the administered cells may reduce or stabilize the amount of inflammation present at said site(s) of neurodegeneration. In exemplary embodiments, the administered cells may inhibit or prevent at least one of: (i) microglia cell over-activation wherein over-activation includes microglia which possess at least one activity or increase in an activity characteristic of activated microglia such as (1) a change in morphology, (2) migration to inflammatory sites, (3) production of neurotoxic or inflammatory cytokines such as IL-1, (4) interaction with neural plaques or β amyloid deposits, (5) synthesis of neurotoxic proteins, (6) secretion of proteases and/or reactive oxygen species, (7) induction of amyloid production by neighboring cells, (8) destruction of myelin; (ii) increased numbers of microglia; (iii) the production of inflammatory proteins or inflammatory activities at sites of neurodegeneration; (iv) macrophage activity (v) the expression of inflammatory or neurotoxic moieties by cells within such sites such as cytokines, oxidants, proteases e.g., by macrophages and microglia and/or (vi) neuronal death or impaired neuronal function.

Moreover, the present disclosure generally encompasses a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory domain, the expression of which are optionally controlled by the same or different inducible or constitutive promoters. In exemplary embodiments, the protein associated with a neurodegenerative disease or condition is selected from human amyloid beta, amyloid-beta 1-42, alpha-synuclein, superoxide dismutase-1 (SOD-1), hyperphosphorylated tau protein; TAR DNA-binding protein 43 (TDP-43): chromosome 9 open reading frame 72 (c9orf72); β-Synuclein; γ-Synuclein; RNA-binding protein fused in sarcoma (FUS); ubiquitin; ubiquilin-2, p62; optineurin; ataxin-2; parkin; Serine/threonine-protein kinase PINK1; and Leucine-rich repeat serine/threonine-protein kinase 2 (LRRK2), Huntingtin with tandem glutamine repeats; prion proteins; transthyretin; dentatorubral pallidoluysian atrophy (DRPLA) protein; androgen receptor; an ataxin; P/Q-type calcium channel α1A subunit; TATA-box-binding protein; glial fibrillary acidic protein; DNA excision repair protein ERCC-6; survival motor neuron protein; and cystatin C. Additionally, in exemplary embodiments, the present disclosure generally relates to recombinant or engineered cell which comprises at least one nucleic acid encoding a CAR as described herein.

Furthermore, the present disclosure generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (e.g. overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with Alzheimer's disease. The present disclosure also generally encompasses a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with Alzheimer's disease, and a CAR of said CAR-expressing cells includes DG01 (SEQ ID NO: 1), DG02 (SEQ ID NO: 2), DG03 (SEQ ID NO: 3), and/or D004 (SEQ ID NO: 4), and/or a construct comprising at least 90%, at least 95%, at least 98%, or at least 99% sequence identity to any one or more of the aforementioned constructs. The present disclosure additionally generally encompasses a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with Alzheimer's disease, and a CAR of said CAR-expressing cells includes DG01 (SEQ ID NO: 1), DG02 (SEQ ID NO: 2), DG03 (SEQ ID NO: 3), and/or DG04 (SEQ ID NO: 4), and/or a construct comprising at least 90%, at least 95%, at least 98%, or at least 99% sequence identity to any one or more of the aforementioned constructs, and further wherein said cells are engineered to express one or more neurodegenerative disease modifying molecules (NDMMs).

The present disclosure also generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with ALS. The present disclosure additionally generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with ALS, and a CAR of said CAR-expressing cells includes DG05 (SEQ ID NO: 5), DG06 (SEQ ID NO: 6), and/or DG07 (SEQ ID NO: 7), and/or a construct comprising at least 90%, at least 95%, at least 98%, or at least 99% sequence identity to any one or more of the aforementioned constructs. The present disclosure also generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with ALS, and a CAR of said CAR-expressing cells includes DG05 (SEQ ID NO: 5), DG06 (SEQ ID NO: 6), and/or DG07 (SEQ ID NO: 7), and/or a construct comprising at least 90%, at least 95%, at least 98%, or at least 99% sequence identity to any one or more of the aforementioned constructs, and further wherein said cells are engineered to express one or more neurodegenerative disease modifying molecules (NDMMs).

Furthermore, the present disclosure generally encompasses a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with Parkinson's disease. The present disclosure additionally generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with Parkinson's disease, and a CAR of said CAR-expressing cells includes DG08 (SEQ ID NO: 8), DG09 (SEQ ID NO: 9), DG10 (SEQ ID NO: 10), and/or DG11 (SEQ ID NO: 11), and/or a construct comprising at least 90%, at least 95%, at least 98%, or at least 99% sequence identity to any one or more of the aforementioned constructs. The present disclosure also generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with Parkinson's disease, and a CAR of said CAR-expressing cells includes DG08 (SEQ ID NO: 8), DG09 (SEQ ID NO: 9), DG10 (SEQ ID NO: 10), and/or DG11 (SEQ ID NO: 11), and/or a construct comprising at least 90%, at least 95%, at least 98%, or at least 99% sequence identity to any one or more of the aforementioned constructs, and further wherein said cells are engineered to express one or more neurodegenerative disease modifying molecules (NDMMs).

The present disclosure also generally relates to a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said protein is a protein associated with Alzheimer's disease. Additionally, the present disclosure generally encompasses a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said protein is a form of amyloid beta associated with Alzheimer's disease. The present disclosure also generally relates to a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said protein is a protein associated with ALS disease. The instant disclosure additionally generally encompasses a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said protein is mutated or aberrantly expressed SOD1. Also, the present disclosure generally relates to a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said protein is a protein associated with Parkinson's disease.

Furthermore, the present disclosure generally encompasses a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said protein is a form of alpha-synuclein associated with Parkinson's disease. The present disclosure also generally relates to a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said nucleic acid encodes DG01 (SEQ ID NO: 1), DG02 (SEQ ID NO: 2), D003 (SEQ ID NO: 3), and/or DG04 (SEQ ID NO: 4), and/or a construct comprising at least 90%, at least 95%, at least 98%, or at least 99% sequence identity to any one or more of the aforementioned constructs. The present disclosure additionally generally relates to a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said nucleic acid encodes DG05 (SEQ ID NO: 5), DG06 (SEQ ID NO: 6), and/or DG07 (SEQ ID NO: 7), and/or a construct comprising at least 90%, at least 95%, at least 98%, or at least 99% sequence identity to any one or more of the aforementioned constructs. Additionally, the present disclosure generally encompasses a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, the expression of which are optionally controlled by the same or different inducible or constitutive promoters, wherein said nucleic acid encodes DG08 (SEQ ID NO: 8), DG09 (SEQ ID NO: 9), DG10 (SEQ ID NO: 10), and/or DG11 (SEQ ID NO: 11), and/or a construct comprising at least 90%, at least 95%, at least 98%, or at least 99% sequence identity to any one or more of the aforementioned constructs.

Furthermore, the present disclosure generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") or an NDMM, wherein the CAR and the NDMM may be expressed by the same or different cells, which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with Alzheimer's disease, and said cells are engineered to express any one or more of the following: DG03 (SEQ ID NO: 3); DG03-CD28-CD3ζ (also referred to as DG03-28-3ζ) (SEQ ID NO: 22); DG03-CD28tm-DAP10-CD3ζ (also referred to as DG03-28tm-10-3ζ) (SEQ ID NO: 45); DG03-CD28tm-CD44-CD3ζ (also referred to as DG03-28tm-44-3ζ) (SEQ ID NO: 46); DG03-CD28tm-4-1-BB-CD3ζ (also referred to as DG03-28tm-BB-3ζ) (SEQ ID NO: 47); DG03-CD28tm-CD3ζ (also referred to as DG03-28tm-3ζ) (SEQ ID NO: 48); DG03-CD28 (also referred to as DG03-28) (SEQ ID NO: 49); DG03-CD28tm (SEQ ID NO: 50), and/or a construct comprising at least 90%, at least 95%, at least 98%, or at least 99% sequence identity to any one or more of the aforementioned constructs. Moreover, the present disclosure generally relates to a method of treating a subject comprising a neurodegenerative disease or condition, exhibiting one or more risk factors associated with the development of a neurodegenerative disease or condition, and/or exhibiting one or more signs or symptoms associated with the diagnosis of a neurodegenerative disease or condition, comprising administering an effective amount of cells which are engineered to express a chimeric antigen receptor ("CAR") or an NDMM, wherein the CAR and the NDMM may be expressed by the same or different cells, which targets at least one (i) aberrant protein which is expressed in the central nervous system at site(s) of neurodegeneration associated with a specific neurodegenerative disease and is associated with the pathology of said specific neurodegenerative disease or condition and/or (ii) a protein which is aberrantly expressed (overexpressed) in the central nervous system at site(s) of neurodegeneration associated with a specific neurodegenerative disease and is associated with the pathology of said specific neurodegenerative disease or condition, wherein said cells are administered under conditions whereby they are in contact with said site(s) of neurodegeneration comprising said targeted protein and thereby prevent, inhibit or treat the neurodegenerative disease or condition and/or one or more symptoms associated with the neurodegenerative disease or condition which is characterized by the expression of said aberrant or aberrantly expressed protein, wherein said targeted protein is a protein associated with ALS, and said cells are engineered to express any one or more of the following: DG05 (SEQ ID NO: 5); DG05-CD28-CD3ζ (also referred to as DG05-28-3ζ) (SEQ ID NO: 24); DG05-CD28tm-DAP10-CD3ζ (also referred to as DG05-28tm-10-3ζ) (SEQ ID NO: 40); DG05-CD28tm-CD44-CD3ζ (also referred to as DG05-28tm-44-3ζ) (SEQ ID NO: 41); DG05-CD28tm-CD3ζ (also referred to as DG05-28tm-3ζ) (SEQ ID NO: 42); DG05-CD28 (also referred to as DG05-28) (SEQ ID NO: 43); DG05-CD28tm (also referred to as DG05-28tm) (SEQ ID NO: 44), and/or a construct comprising at least 90%, at least 95%, at least 98%, or at least 99% sequence identity to any one or more of the aforementioned constructs. Furthermore, the present disclosure generally relates to a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, and (iii) further optionally an NDMM, the expression of which are optionally controlled by the same or different inducible or constitutive promoters, wherein said nucleic acid encodes any one or more of the following: DG03-CD28-CD3ζ (also referred to as DG03-28-3ζ) (SEQ ID NO: 22); DG03-CD28tm-DAP10-CD3ζ (also referred to as DG03-28tm-10-3ζ) (SEQ ID NO: 45); DG03-CD28tm-CD44-CD3ζ (also referred to as DG03-28tm-44-3ζ) (SEQ ID NO: 46); DG03-CD28tm-4-1-BB-CD3ζ (also referred to as DG03-28tm-BB-3ζ) (SEQ ID NO: 47); DG03-CD28tm-CD3ζ (also referred to as DG03-28tm-3ζ) (SEQ ID NO: 48); DG03-CD28 (also referred to as DG03-28) (SEQ ID NO: 49); DG03-CD28tm (SEQ ID NO: 50), and/or a construct comprising at least 90%, at least 95%, at least 98%, or at least 99% sequence identity to any one or more of the aforementioned constructs. Moreover, the present disclosure generally relates to a nucleic acid which encodes a chimeric antigen receptor (CAR) comprising (i) at least one ligand binding moiety which binds to an aberrant protein associated with the pathology of a neurodegenerative disease or a protein which is aberrantly (overexpressed) in the central nervous system at site(s) of neurodegeneration which protein is associated with the pathology of a specific neurodegenerative disease or condition and (ii) optionally at least one signaling domain, e.g., a costimulatory signaling domain, and (iii) further optionally an NDMM, the expression of which are optionally controlled by the same or different inducible or constitutive promoters, wherein said nucleic acid encodes any one or more of the following constructs: DG05-CD28-CD3ζ (also referred to as DG05-28-3ζ) (SEQ ID NO: 24); DG05-CD28tm-DAP10-CD3ζ (also referred to as DG05-28tm-10-3ζ) (SEQ ID NO: 40); DG05-CD28tm-CD44-CD3ζ (also referred to as DG05-28tm-44-3ζ) (SEQ ID NO: 41); DG05-CD28tm-CD3ζ (also referred to as DG05-28tm-3ζ) (SEQ ID NO: 42); DG05-CD28 (also referred to as DG05-28) (SEQ ID NO: 43); and/or DG05-CD28tm (also referred to as DG05-28tm) (SEQ ID NO: 44), and/or a construct comprising at least 90%, at least 95%, at least 98%, or at least 99% sequence identity to any one or more of the aforementioned constructs.

BRIEF DESCRIPTION OF THE SEVERAL VIEWS OF THE DRAWING

FIG. 2A presents data that demonstrated that CD4+CD25hi Tregs (R2 box) represented a small percentage of total T cells in human PBMCs prior to CD4 and CD25 enrichment isolation. FIG. 2B presents data that demonstrated that that CD4+CD25hi isolated Tregs expanded 1760-fold after 17 days in culture using the present Treg expansion protocol. FIG. 2C presents data which demonstrate that Day 17 Tregs expressed intracellular FoxP3. FIG. 2D presents data that demonstrated that FoxP3, truncated CD19 (tCD19), and the CAR scFv were detected on most day 17 Tregs transduced on days 10 and 11.

FIG. 3A presents data related to oligomerization of $A\beta_{1-42}$ peptides, and FIG. 3B presents data related to binding specificity and function of CARs comprised by modified human T cells in accordance with Example 1.

FIG. 21A presents data related to an assay in which inhibition of PMA-stimulated superoxide generation was evaluated in accordance with Example 13. FIG. 21B presents data related to an assay in which inhibition of Zymosan-stimulated superoxide generation was evaluated in accordance with Example 13. FIG. 21C presents data related to an assay in which inhibition of TNF-α generation was evaluated in accordance with Example 13.

FIG. 22A presents data related to an assay in which inhibition of PMA-stimulated superoxide generation was evaluated in accordance with Example 14. FIG. 22B presents data related to an assay in which inhibition of Zymosan-stimulated superoxide generation was evaluated in accordance with Example 14. FIG. 22C presents data related to an assay in which inhibition of IL-6 generation was evaluated in accordance with Example 14.

FIG. 23A presents data related to an assay in which NDMM constructs for Nrf2 (Keap1 inhibitor peptide) and human catalase were evaluated in accordance with Example 15. FIG. 23B presents data related to an assay in which NDMM constructs for brain derived neurotrophic factor (BDNF), and insulin growth factor-1 (IGF-1) were evaluated in accordance with Example 15.

DETAILED DESCRIPTION

Figure 1:
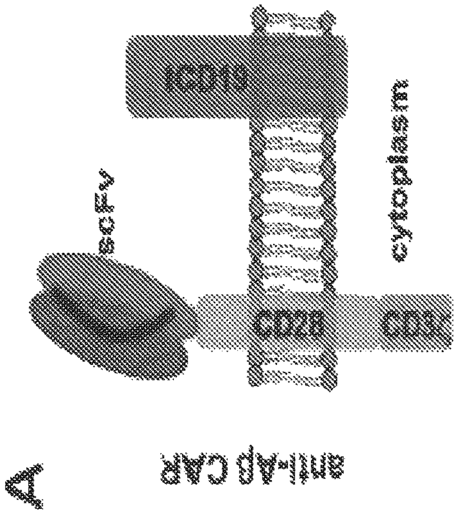
FIG. 1 presents a schematic design of anti-Aβ CARs consisting of an extracellular scFv fused to a CD28 transmembrane and CD3 intracellular signaling domains, and with a co-expressed non-functional truncated CD19 (tCD19) for enriching and tracking transduced cells, in accordance with Example 1.

The present disclosure generally relates to the construction of nucleic acid constructs which encode CARs, especially those which target a protein that is aberrantly expressed in the CNS of a subject with a neurodegenerative disease or condition and/or which encode specific molecules that prevent or inhibit oxidative/inflammatory activity at CNS sites and/or which encode molecules which promote neuronal growth/survival or which promote T cell function. The present disclosure further generally relates to the use of these nucleic acid constructs in the preparation of recombinant or modified cells, in particular recombinant or modified Tregs, preferably human Tregs which are engineered to express such CARs and/or other molecules expressed by such constructs. In exemplary embodiments, these recombinant or modified Tregs may be engineered to express one or more CARs, wherein said one or more CARs may target different proteins and/or molecular markers associated with the pathology of particular neurodegenerative diseases and conditions. These CARs optionally may further comprise a costimulation signaling or T cell signaling moiety such as CD28-CD3ζ, DAP10-CD3ζ, CD44-CD3ζ, CD28 or CD3ζ or another costimulatory signaling or T cell signaling moiety. Modified Tregs according to the invention may further optionally be engineered to express one or more neurodegenerative disease modifying molecules (NDMMs) which may be on the same or different nucleic acid construct as the CAR or may be expressed on modified Tregs which do not comprise a CAR. The present disclosure specifically contemplates modified Tregs expressing one or more specific CARs targeting a neurodegenerative disease and/or neurodegenerative disease modifying molecules (NDMMs), pharmaceutical compositions comprising said modified Tregs, and methods of making and using these modified Tregs. The present disclosure also provides methods for treating a neurodegenerative disease, disorder, or condition, a subject, such as but not limited to Alzheimer's disease, Parkinson's disease, Amyotrophic lateral sclerosis (ALS), and neuroinflammation using these modified Tregs.

Another specific aspect of the present disclosure relates to the construction and use of modified Tregs comprising exogenously introduced polynucleotides encoding specific types of neurodegenerative disease modifying molecules ("NDMMs") such as an anti-oxidants, nerve growth factors and/or non-classical neurotrophic factors. The disclosure also provides vectors for generating such modified Tregs, pharmaceutical compositions comprising such modified Tregs which express one or more CARs and/or one or more NDMMs, and methods of making and using modified Tregs expressing a combination of one or more CARs and one or more NDMMs in the treatment of specific neurodegenerative diseases.

Definitions

As used herein, the terms "neurodegenerative disease", "neurodegenerative disorder", and "neurodegenerative condition" generally refer to any disease, disorder, and/or condition that affects the neurons (sometimes referred to as "nerve cells"), such as neurons of a brain and/or neurons of a nervous system which is associated with the degeneration or loss of neural cells. Often, neurodegenerative diseases may result in progressive degeneration and/or death of nerve cells. In general neurodegeneration is the progressive loss of structure or function of neurons, including the death of neurons. Neurodegenerative diseases may cause problems with movement (called ataxias), or mental or cognitive functioning (called dementias). Frequently neurodegeneration is associated with neuroinflammation and indeed the onset, progression or cause of many debilitating neurodegenerative diseases is thought to involve neuroinflammation. Therefore, it is to be understood that the terms neurodegenerative disease and neurodegenerative disorder and the like encompass neural diseases which are characterized by neuroinflammation. Sometimes in such diseases activated microglia may produce inflammatory cytokines that contribute to widespread inflammation and may lead to and/or result in a neurodegenerative condition and/or disease. Furthermore, some neurodegenerative diseases and/or conditions are associated with microglia cell over-activation, increased numbers of microglia cells, production of inflammatory proteins and/or inflammatory activities, and/or neuronal death. Examples of such neurodegenerative diseases include by way of example Alzheimer's disease and other dementias, Parkinson's disease and other Parkinson's disease related disorders, prion disease, motor neuron diseases other than ALS, Huntington's disease, Spinocerebellar ataxia (SCA), Spinal muscular atrophy (SMA), Friedreich's ataxia, Lewy body disease, epilepsy, multiple sclerosis, encephalitis, hydrocephalus, stroke, chronic traumatic encephalopathy (CTE); synucleinopathies; tauopathies; spongiform encephalopathies; familial amyloidotic polyneuropathy; Dutch hereditary cerebral hemorrhage with amyloidosis; congophilic angiopathy; corticobasal degeneration; Pick's disease; progressive supranuclear palsy; Creutzfeld-Jacob disease; Gerstmann-Sträussler-Schneiker syndrome; fatal familial insomnia; kuru; bovine spongiform encephalopathy; scrapie; chronic wasting disease; Lewy body variant of Alzheimer's disease; diffuse Lewy body disease; dementia with Lewy bodies; multiple system atrophy; neurodegeneration with brain iron accumulation type I; diffuse Lewy body disease; frontotemporal lobar degeneration; hereditary dentatorubral-pallidoluysian atrophy; Kennedy's disease; Alexander's disease; Cockayne syndrome; Icelandic hereditary cerebral hemorrhage with amyloidosis. In exemplary embodiments, a neurodegenerative disease may comprise Alzheimer's disease, Parkinson's disease, and/or ALS. In exemplary embodiments, modified Tregs cells as described herein may be used in a method of treating these and other neurodegenerative diseases.

As used herein, the term "neuroinflammation" generally refers to inflammation of the nervous tissue. Sometimes, activated microglia may produce inflammatory cytokines that contribute to widespread inflammation and may lead to and/or result in a neurodegenerative condition and/or disease. In some instances, neuroinflammation may be initiated in response to a variety of cues, including infection, traumatic brain injury, toxic metabolites, and/or autoimmunity. In the central nervous system (CNS), including the brain and spinal cord, microglia are the resident innate immune cells that are activated in response to these cues, and generally generate reactive oxygen species and release signals to recruit peripheral immune cells for an inflammatory response. Cytokines may also be present at the sites of and/or may cause neuroinflammation, and in some instances they may be produced by microglia or macrophages. In exemplary embodiments, neuroinflammation may be associated with and/or may arise during a neurodegenerative disease, e.g., Alzheimer's disease, ALS, and Parkinson's disease.

The term "inflammation" refers to a broad physiological response mediated by various cell types, proteins, humoral factors, and tissues. While inflammation can send signals within a body to help the immune system eliminate pathogens or undesired conditions, inappropriate levels or altered types of inflammation can cause numerous physiological or immunological problems within the body. Such inflammation can be directly responsible for the pathology of various diseases including autoimmune diseases, fibrotic diseases, chronic infections, and allergies (Laria, A. et al., "The macrophages in rheumatic diseases", *J Inflamm Res.* 2016 Feb. 9; 9: p. 1-11; Wynn, T. A., and Ramalingam, T. R., "Mechanisms of fibrosis: fibrotic translation for fibrotic diseases", *Nat Med,* 2012 Jul. 6; 18(7): p. 1028-40; Yang, Z. P., Kuo, C. C., and Grayston, J. T, "Systemic dissemination of *Chlamidia pneumoniae* following intranasal inoculation in mice", *J Infect Dis.* 1995 March; 171(3): p. 736-8; Jian, Z., and Zhu, L., "Update on the role of alternatively activated macrophages in asthma", *J Asthma Allergy,* 2016 Jun. 3; 9: p. 101-7). Inflammation can also indirectly exacerbate the symptoms of many diseases, or play an assisting role in the pathogenesis, for example in cancers, obesity, metabolic diseases, and cardiovascular diseases, such as atherosclerosis (Coussens, L. M., and Werb, Z., "Inflammation and Cancer". *Nature.* 2002 Dec. 19-26; 420(6917): p. 860-7; Monteiro, R., and Azevedo, I., "Chronic inflammation in obesity and the metabolic syndrome", *Mediators Inflamm.* 2010; 2010; Libby, P., "Inflammation and cardiovascular disease mechanisms", *Am J Clin Nutr.* 2006 February; 83(2): p. 4565-460S).

The term "neurodegenerative disease-modifying molecule" or "NDMM" as used herein generally refers to a molecule capable of altering (reducing, ameliorating or preventing) the symptoms, progression or onset of a neurodegenerative disease, disorder, or condition. Representative neurodegenerative conditions include by way of example Alzheimer's disease, ALS, Parkinson's disease, and other neuroinflammatory conditions. Examples of such NDMM molecules include, but are not limited to including, IL-37, IL-12, TNF-α, IFN-γ, CCL2, TNFAIP3, and other molecules capable of altering the expression level, activation status, or function of a disease-associated protein. In exemplary embodiments, an NDMM may comprise one or more cytokines. In other exemplary embodiments, an NDMM may comprise molecules that prevent oxidative/inflammatory activity. In other exemplary embodiments, an NDMM may comprise molecules that promote neuronal growth and/or survival. In exemplary embodiments, an NDMM may be expressed by modified Tregs according to the invention, e.g., modified Tregs comprising one or more CARs, as discussed in further detail herein. Furthermore, an NDMM may comprise one or more pro-neuronal factors, one or more anti-oxidants, one or more nerve growth factors, and/or one or more non-classical neurotrophic factors. Examples of pro-neuronal factors include, but are not limited to including, interleukin-1 receptor antagonist (IL-1 ra); interleukin-6 (IL-6); activated protein C (APC); thrombomodulin; tissue plasminogen activator (tPA); Protein deglycase DJ-1; tissue inhibitor of metalloproteinases (TIMPs). Examples of antioxidants include, but are not limited to including, HO-1, Ferritin, Glutathione reductase, Glutathione peroxidase, Ferritin (H), Metallothionein I, Thioredoxin, Thioredoxin reductase, Peroxiredoxin MSP23, Cu/Zn superoxide dismutase, Catalase, NRF2 activity, peroxiredoxins (Prxs); activity-dependent neuroprotector homeobox (ADNP); phycocyanin; neuroglobin. Examples of nerve growth factors include, but are not limited to, classic neurotrophins such as brain-derived neurotrophic factor (BDNF), ciliary neurotrophic factor (CNTF), and glial cell-line derived neurotrophic factor (GDNF). Non-limiting examples of non-classical neurotrophic factors include insulin-like growth factor-1 (IGF-1), vascular endothelial growth factor (VEGF), Fibroblast Growth Factors (FGF), Hepatocyte Growth Factor (HGF), Bone Morphogenetic Proteins (BMPs), Erythropoietin (EPO), Thrombopoietin (TPO), and Granulocyte-colony stimulating factor (G-CSF). In some embodiments, NDMM expression may be controlled by an inducible promoter system, e.g., using one known in the art, and/or expression of the NDMM may be regulated by CAR-triggered transcriptional control.

As used herein, a "5' cap" (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi step biochemical reaction. The capping moiety can be modified to modulate functionality of mRNA such as its stability or efficiency of translation.

The term "allogeneic" or "donor-derived" generally refers to any material derived from a different animal of the same species as the individual to whom the material is to be introduced or transplanted. Two or more individuals are said to be allogeneic to one another when the genes at one or more loci are not identical. In some aspects, allogeneic material from individuals of the same species may be sufficiently dissimilar genetically to interact antigenically.

The term "antibody" or "Ab," as used herein, refers to an immunoglobulin molecule which specifically binds with an antigen. In some embodiments, the antigen may be a molecule expressed or aberrantly expressed by neurons in subjects comprising a neurodegenerative disease and/or condition. Examples of such diseases and conditions include, but are not limited to including, Alzheimer's disease, Parkinson's disease, and ALS. Further non-limiting examples include prion disease, motor neuron diseases other than ALS, Huntington's disease, Spinocerebellar ataxia (SCA), Spinal muscular atrophy (SMA), Friedreich's ataxia, Lewy body disease, epilepsy, multiple sclerosis, encephalitis, hydrocephalus, stroke, chronic traumatic encephalopathy (CTE); synucleinopathies; tauopathies; spongiform encephalopathies; familial amyloidotic polyneuropathy; Dutch hereditary cerebral hemorrhage with amyloidosis; congophilic angiopathy; corticobasal degeneration; Pick's disease; progressive supranuclear palsy; Creutzfeld-Jacob disease; Gerstmann-Sträussler-Schneiker syndrome; fatal familial insomnia; kuru; bovine spongiform encephalopathy; scrapie; chronic wasting disease; Lewy body variant of Alzheimer's disease; diffuse Lewy body disease; dementia with Lewy bodies; multiple system atrophy; neurodegeneration with brain iron accumulation type I; diffuse Lewy body disease; frontotemporal lobar degeneration; hereditary dentatorubral-pallidoluysian atrophy; Kennedy's disease; Alexander's disease; Cockayne syndrome; Icelandic hereditary cerebral hemorrhage with amyloidosis. Antibodies can be intact immunoglobulins derived from natural sources or from recombinant sources and can be immunoreactive portions of intact immunoglobulins. The term is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, single chain antibody fragments, including single chain variable fragments (scFv), diabodies, and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The term "antibody fragment" or "Ab fragment" refers to a portion of an intact antibody and refers to the antigenic determining variable regions of an intact antibody. Examples of antibody fragments include, but are not limited to, fragment antigen binding (Fab) fragments, $F(ab')_2$ fragments, Fab' fragments, Fv fragments, recombinant IgG (rIgG) fragments, single chain antibody fragments, including single chain variable fragments (scFv), single domain antibodies (e.g., sdAb, sdFv, nanobody) fragments, diabodies, and multispecific antibodies formed from antibody fragments. In exemplary embodiments, the antibody fragment may be an scFv.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired response. Moreover, a skilled artisan will understand that an antigen need not be encoded by a "gene" at all. It is readily apparent that an antigen can be generated, synthesized, or can be derived from a biological sample, or might be a macromolecule besides a polypeptide. Such a biological sample can include, but is not limited to a tissue sample, a neurological tissue sample, an inflamed tissue sample, a cell, or a fluid with other biological components. In some embodiments, the antigen is a molecule expressed in a neurodegenerative disease or condition, e.g., Alzheimer's disease, Parkinson's disease, and ALS. In exemplary embodiments, an antigen may be a form of any one or more of the following that may be associated with a neurodegenerative disease or condition: amyloid-beta 1-42, alpha-synuclein, superoxide dismutase-1 (SOD-1), hyperphosphorylated tau protein; TAR DNA-binding protein 43 (TDP-43): chromosome 9 open reading frame 72 (c9orf72); β-Synuclein; γ-Synuclein; RNA-binding protein fused in sarcoma (FUS); ubiquitin; ubiquilin-2, p62; optineurin; ataxin-2; parkin; Serine/threonine-protein kinase PINK1; Leucine-rich repeat serine/threonine-protein kinase 2 (LRRK2). In some embodiments, an antigen may be a form of any one or more of the following that may be associated with a neurodegenerative disease or condition: Huntington with tandem glutamine repeats; priori proteins; transthyretin; dentatorubral pallidoluysian atrophy (DRPLA) protein; androgen receptor; ataxins; P/Q-type calcium channel α1A subunit; TATA-box-binding protein; glial fibrillary acidic protein; DNA excision repair protein ERCC-6; survival motor neuron protein; cystatin C.

The term "antigen binding domain" or "AB domain" refers to one or more extracellular domains of a chimeric antigen receptor (CAR) which have specificity for a particular antigen.

The term "apheresis" as used herein refers to the art-recognized extracorporeal process by which the blood of a donor or patient is removed from the donor or patient and passed through an apparatus that separates out selected particular constituent(s) and returns the remainder to the circulation of the donor or patient, e.g., by retransfusion. Thus, in the context of "an apheresis sample" refers to a sample obtained using apheresis.

The term "autologous" or refers to any material derived from the same individual to whom it is later to be re-introduced.

The term "bind" refers to an attractive interaction between two molecules that results in a stable association in which the molecules are in close proximity to each other. The result of molecular binding is sometimes the formation of a molecular complex in which the attractive forces holding the components together are generally non-covalent, and thus are normally energetically weaker than covalent bonds.

The term "CD28" refers to the protein Cluster of Differentiation 28, one of the proteins expressed on T cells that provide co-stimulatory signals required for T cell activation and survival. Mouse CD28 protein may have at least 85, 90, 95, 96, 97, 98, 99 or 100% identity to NCBI Reference No: NP_031668.3 or a fragment thereof that has stimulatory activity. Human CD28 protein may have at least 85, 90, 95, 96, 97, 98, 99 or 100% identity to NCBI Reference No: NP 006130 or a fragment thereof that has stimulatory activity.

The term “CD3 zeta,” or alternatively, “zeta,” “ζ,” “zeta chain,” “CD3-zeta,” “CD3z,” “TCR-zeta,” “CD247,” or “CD3ζ” is a protein encoded by the CD247 gene on chromosome 1, with gene location 1 H2.3; 1 73.14 cM, in mice, and by the CD247 gene on chromosome 1, with gene location 1q24.2, in humans. CD3ζ, together with T cell receptor (TCR) and CD3 (a protein complex composed of a CD3 γ, a CD3 δ and two CD3 ε), forms the TCR complex. Mouse CD3 ζ may have an amino acid sequence provided as NP_001106864.1, NP_001106863.1, NP_001106862.1, or NP_112439.1, or the equivalent residues from a non-mouse species, e.g., human, rodent, monkey, ape and the like. Human CD3 ζ may have an amino acid sequence provided as NP_000725 or NP_932170, or the equivalent residues from a non-human species, e.g., mouse, rodent, monkey, ape and the like.

The term “CD3 zeta intracellular signaling domain,” or alternatively “CD3 zeta ICS domain” or a “CD3zICS,” is defined as the amino acid residues from the cytoplasmic domain of the CD3 zeta chain, or functional derivatives thereof, that are sufficient to functionally transmit an initial signal necessary for T cell activation.

The term “4-1BB” or “BB” refers to a member of the TNFR superfamily with an amino acid sequence provided as GenBank Acc. No. AAA53133.1, or the equivalent residues from a non-human species, e.g., mouse, rodent, monkey, ape and the like. In one aspect, the “4-1BB costimulatory domain” is the sequence provided as SEQ ID NO: 12 or the equivalent residues from a non-human species, e.g., mouse, rodent, monkey, ape and the like and/or the sequence may be encoded by the nucleic acid of SEQ ID NO: 212.

The term “Chimeric Antigen Receptor” or alternatively a “CAR” refers to a set of polypeptides, typically two in the simplest embodiments, which when expressed in an immune effector and/or regulatory cell, provides the cell with specificity for a target cell, and optionally promotes intracellular signal generation. CARs according to the invention will in general comprise a receptor or ligand binding moiety, e.g., one which targets a protein aberrantly expressed in subjects comprising a neurodegenerative disorder and optionally may comprise one or more costimulatory signaling or T cell signaling domains such as CD28, 4-1BB, CD3ζ, DAP10-CD3ζ CD44-CD3ζ, CD28-CD3ζ, or 4-1BB-CD3ζ. In some embodiments, a CAR comprises at least an extracellular antigen binding domain (AB domain), a transmembrane domain (TM domain) and a cytoplasmic signaling domain (also referred to herein as “an intracellular signaling domain (ICS domain) comprising a functional signaling domain derived from a stimulatory molecule and/or costimulatory molecule as defined below. In some aspects, the set of polypeptides are contiguous with each other. In some embodiments, the set of polypeptides include a dimerization switch that, upon the presence of a dimerization molecule, can couple the polypeptides to one another, e.g., can couple an AB domain to an ICS domain. In some aspects, the stimulatory molecule is the zeta chain associated with the T cell receptor complex. In some aspects, the cytoplasmic portion of a CAR further comprises a costimulatory domain (CS domain) comprising one or more functional signaling domains derived from at least one costimulatory molecule as defined below. In some aspects, the costimulatory molecule is chosen from the costimulatory molecules described herein, e.g., 4-1BB (i.e., CD137), CD44, DAP10 and/or CD28. In some aspects, the CAR comprises a chimeric fusion protein comprising an extracellular AB domain, a TM domain and an ICS domain comprising a functional signaling domain derived from a stimulatory molecule. In some aspects, the CAR comprises a chimeric fusion protein comprising an extracellular AB domain, a TM domain, an ICS domain comprising a functional signaling domain derived from a stimulatory molecule, and a CS domain comprising a functional signaling domain derived from a costimulatory molecule. In some aspects, the CAR comprises a chimeric fusion protein comprising an extracellular AB domain, a TM domain, an ICS domain comprising a functional signaling domain derived from a stimulatory molecule, and two CS domains each of the two comprising a functional signaling domain derived from a costimulatory molecule(s) that is/are same with or different from each other. In some aspects, the CAR comprises a chimeric fusion protein comprising an extracellular AB domain, a TM domain, an ICS domain comprising a functional signaling domain derived from a stimulatory molecule, and at least two CS domains each comprising a functional signaling domain derived from a costimulatory molecule(s) that is/are same with or different from each other. In some aspects, the CAR comprises an optional leader sequence at the amino-terminus (N-ter) of the CAR fusion protein. In some aspects, the CAR further comprises a leader sequence at the N-terminus of the extracellular antigen binding domain, wherein the leader sequence is optionally cleaved from the antigen binding domain (e.g., an scFv) during cellular processing and localization of the CAR to the cellular membrane.

The term “compete”, as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to “cross-compete” with each other for binding of their respective epitope(s). Both competing and cross-competing antibodies are encompassed by the invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

The terms “complementarity determining region,” and “CDR,” synonymous with “hypervariable region” or “HVR,” are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). “Framework regions” and “FR” are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The term "costimulatory molecule" or "T cell signaling moiety" herein refers to a cognate binding partner on a T cell that specifically binds with a costimulatory ligand, thereby mediating a costimulatory response by the T cell, such as, but not limited to, proliferation or the expression of specific cytokines. Costimulatory molecules are cell surface molecules other than antigen receptors or their ligands that contribute to an efficient immune response. Costimulatory molecules include, but are not limited to a protein selected from the group consisting of an MHC class I molecule, TNF receptor proteins, Immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CDB8α, CD8β, CD11a, LFA-1 (CD11a/CD18), CD11b, CD11c, CD11d, CD18, CD19, CD19a, CD27, CD28, CD29, CD30, CD40, CD49a, CD49D, CD49f, CD69, CD84, CD96 (Tactile), CD100 (SEMA4D), CD103, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R β, IL2R γ, IL7R α, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, and a ligand that specifically binds with CD83. In embodiments wherein a CAR comprises one or more CS domains, wherein each CS domain comprises a functional signaling domain derived from a costimulatory molecule. In some embodiments, the encoded CS domain is that of 4-1BB, CD28, or DAP10.

The term "cytokines" refers to a broad category of small proteins that are involved in cell signaling. Generally, their release has some effect on the behavior of cells around them. Cytokines may be involved in autocrine signaling, paracrine signaling and/or endocrine signaling as immunomodulating agents. Cytokines include chemokines, interferons, interleukins, lymphokines, and tumor necrosis factors. Cytokines are produced by a broad range of cells, including immune cells like macrophages, B lymphocytes, T lymphocytes and mast cells, as well as endothelial cells, fibroblasts, epithelial cells, and various stromal cells. "Chemokines" are a family of cytokines generally involved in mediating chemotaxis.

An "effective amount" or "an amount effective to treat" refers to a dose that is adequate to prevent or treat a disease, condition, or disorder in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side effects that might accompany the administration of a particular active, and the desired physiological effect. It will be appreciated by one of skill in the art that various diseases or disorders could require prolonged treatment involving multiple administrations, perhaps using one or more modified Tregs in each or various rounds of administration.

The term "hinge", "spacer", or "linker" refers to an amino acid sequence of variable length typically encoded between two or more domains or portions of a polypeptide construct to confer flexibility, improved spatial organization, proximity, etc.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., *Nature Biotechnology,* 14:309-314, 1996; Sheets et al., *Proc. Natl. Acad. Sci.* (USA) 95:6157-6162, 1998; Hogeboom and Winter, *J. Mol. Biol.,* 227:381, 1991; Marks et al., J. *Mol. Biol.,* 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al., "Monoclonal Antibodies and Cancer Therapy", Alan R. Liss, p. 77, 1985; Boerner et al., *J. Immunol.,* 147 (1):86-95, 1991; and U.S. Pat. No. 5,750,373.

An "iCAR" is a chimeric antigen receptor which contains inhibitory receptor signaling domains. These domains may be based, for example, on protectin D1 (PD1) or CTLA-4 (CD152). In some embodiments, the modified Tregs as discussed herein may be further transduced to express an iCAR. As used herein, "immune cell" refers to a cell of hematopoietic origin functionally involved in the initiation and/or execution of innate and/or adaptive immune response.

The term "internal ribosome entry site" or "IRES" refers to a cis-acting RNA sequence that mediates internal entry of the 40S ribosomal subunit on some eukaryotic and viral messenger RNAs. IRES allows for translation initiation in a 5' cap independent manner during protein synthesis, thus enabling co-expression of two proteins from a single mRNA. Further details and variations of IRES sequences may be found in Bonnal et al., *Nucleic Acids Res.* 2003 Jan. 1; 31(1): 427-428.

An "intracellular signaling domain" or "ICS domain" as the term is used herein, refers to an intracellular portion of a molecule. The intracellular signaling domain generates a signal that promotes an immune regulatory and/or effector function of the cell transduced with a nucleic acid sequence comprising a CAR, e.g., a modified Treg comprising one or more CARs. Examples of immune effector function include cytolytic activity and helper activity, including the secretion of cytokines. Example of immune regulatory function, e.g., in a modified Treg, include, but are not limited to including, ICS domains include, but are not limited to including, CD28-CD3zeta; 4-1BB-CD3 zeta; Dap10-CD3zeta; CD44-

CD3zeta; CTLA-4-CD3zeta; CD28; Dap10; 4-1BB; 3-zeta. Further examples include an ICS domain of a TCR/CD3 complex protein, an Fc receptor subunit, an IL-2 receptor subunit, CD3 zeta, FcR γ, FcR β, CD3 γ, CD3 δ, CD3 ε, CD5, CD22, CD79a, CD79b, CD66d, CD278 (ICOS), Fe ε RI, DAP10, or DAP12.

The term "DAP10" refers to a protein, which in humans is encoded by the HSCT gene. It may also be referred to as HCST, KAP10, PIK3AP, or hematopoietic cell signal transducer. In some embodiments, DAP10 may have the sequence provided in Genbank Accession No.: Q9UBK5.1.

An "isolated" biological component (such as an isolated chimeric antigen receptor or cell or vector or protein or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis. An isolated nucleic acid or protein can exist in substantially purified form, or can exist in a non-native environment such as, for example, a host cell.

The term "linker" as used in the context of an scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises one or more repeats of the amino acid sequence unit Gly-Gly-Gly-Gly-Ser (SEQ ID NO: 13). In one embodiment, the flexible polypeptide linker includes, but is not limited to, $(Gly_4Ser)_3$, which is also referred to as G4S X3 (SEQ ID NO: 13). Such a linker may be encoded for example, by the nucleic acid sequence (SEQ ID NO: 213).

The term "nucleic acid" and "polynucleotide" refer to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

A "pharmaceutically acceptable carrier" or "excipient" refers to compounds or materials conventionally used in immunogenic compositions during formulation and/or to permit storage.

The term "promoter", as used herein, is defined as a DNA sequence recognized by the synthetic machinery of the cell, or introduced synthetic machinery, required to initiate the specific transcription of a polynucleotide sequence.

The term "recombinant" means a moiety, e.g., a polynucleotide with semi-synthetic or synthetic origin which either does not occur in nature or is linked to another polynucleotide in an arrangement not found in nature or it may refer to a cell which is modified to express or not express a polynucleotide normally not expressed or expressed by a corresponding unmodified cell.

The term "scFv," "single-chain Fv," or "single-chain variable fragment" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$. The linker may comprise portions of the framework sequences.

The term "sequence identity" or "sequence homology" are used interchangeably herein and both refer to the sequence similarity of different polypeptides or nucleic acids. In general the invention contemplates polypeptide or nucleic acids or constructs containing same having at least 90% or greater sequence homology or identity to any one or more of the polypeptide or nucleic acid sequences disclosed herein, more typically polypeptide or nucleic acid sequences having at least 95% or greater sequence homology to any one or more of the polypeptide or nucleic acid sequences disclosed herein or possessing at least 98% or greater sequence homology or sequence identity, or at least 99% or greater sequence homology or identity to any one or more of the polypeptide or nucleic acid sequences set forth herein. Methods for determining homology between nucleic acid and amino acid sequences are well known to those of ordinary skill in the art. Generally such homologous nucleic acids or polypeptides will be selected or designed so as to improve or so as to not adversely impact the desired properties of the specific polypeptide or nucleic acid or construct containing same.

A "signal peptide" (also referred to as a signal sequence, targeting signal, localization signal, localization sequence, transit peptide, leader sequence or leader peptide) is a short peptide present at the N-terminus of the majority of newly synthesized proteins that are destined towards the secretory pathway. The core of the signal peptide may contain a long stretch of hydrophobic amino acids. The signal peptide may or may not be cleaved from the mature polypeptide.

A "leader sequence" as used herein, also referred to as "signal peptide," "signal sequence," "targeting signal," "localization signal," "localization sequence," "transit peptide," or "leader peptide" in the art, is a short peptide present at the N-terminus of the majority of newly synthesized proteins that are destined towards the secretary pathway. The core of the signal peptide may contain a long stretch of hydrophobic amino acids. The signal peptide may or may not be cleaved from the mature polypeptide.

The "ribosome skip sequence" refers to an amino acid sequence that, when translated, causes cleavage of a nascent polyprotein on the ribosome, allowing for co-expression of multiple genes. In one aspect, the ribosome skip sequence may be the T2A sequence and comprises the amino acid sequence of SEQ ID NO: 14 or nucleotide sequence encoding such, such as SEQ ID NO: 214. Alternatively, any other 2A sequences may be used. Examples of other 2A sequences may be found elsewhere in the literature of the relevant art (for example, see Kim, J. H., et al., "High cleavage efficiency of a 2A peptide derived from porcine teschovirus-1 in human cell lines, zebrafish and mice" *PLoS One.* 2011; 6(4)).

The term "signaling domain" refers to the functional portion of a protein which acts by transmitting information within the cell to regulate cellular activity via defined signaling pathways by generating second messengers or functioning as effectors by responding to such messengers. Examples of signaling domains include, but are not limited to including, CD28-CD3ζ; 4-1BB-CD3ζ; Dap10-CD3ζ; CD44-CD3ζ; CTLA-4-CD3ζ; CD28; Dap10; 4-1BB; and CD3-ζ.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with antigenic peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as an immunoreceptor tyrosine-based activation motif or ITAM. Examples of an ITAM containing cytoplasmic signaling sequence include, but are not limited to, those derived from CD4 (amino acid sequence of SEQ ID NO: 16, which may be encoded by SEQ ID NO: 216), common FcRγ (FCER1G), FcγRIIa, FcR β (Fc ε R1b), CD3γ, CD3δ, CD3ε, CD79a, CD79b, DAP10, and DAP12. In exemplary embodiments, the intracellular signaling domain in any one or more CARs comprised by a modified Treg may comprise an intracellular signaling sequence, e.g., a primary signaling sequence of CD3ζ. Alternatively, equivalent residues from a non-human or mouse species, e.g., rodent, monkey, ape and the like, may be utilized.

The term "subject" is intended to include living organisms in which an immune response can be elicited (e.g., mammals, human). The subject may have a disease or may be healthy. The subject may also be referred to as "patient" in the art.

The term "suicide mechanism" or "suicide gene" as used herein refers to a mechanism by which CAR-expressing cells of present invention may be eradicated from a subject administered with CAR-expressing cells. The suicide mechanism may be driven by, for example, inducible caspase 9 (Budde et al., *PLoS One* 2013 8(12):82742), codon-optimized CD20 (Marin et al., *Hum. Gene Ther. Meth.* 2012 23(6)376-86), CD34, a truncated EGFR (Wang X, Chang W-C, Wong C W, et al. A transgene-encoded cell surface polypeptide for selection, in vivo tracking, and ablation of engineered cells. Blood. 2011; 118(5):1255-1263. doi:10.1182/blood-2011-02-337360), a truncated CD19, or polypeptide RQR8 (Philip et al, and WO2013153391A, which is hereby incorporated herein by reference). In some embodiments, the suicide mechanism may be included and utilized in modified Tregs discussed herein to optimize the length for the modified Tregs to stay in the system of a subject or the amount of the modified Tregs, to reduce or minimize the toxicity and/or to maximize the benefit of said modified Tregs.

The term "target cell" as used herein refers to a cell expressing the target molecule of a CAR comprised by a modified Treg on the cell surface. In some embodiments, the target cell is a microglia cell. In some embodiments, the target cell is a neuron. In some embodiments, the target cell is a cell type that has a particular role in the pathology of a neurodegenerative disease and/or condition and/or neuroinflammation. In some embodiments, the target cell is a cell type that has a particular role in the pathology of a disease such as but not limited to Alzheimer's disease, Parkinson's disease, ALS, and any of the other neurodegenerative diseases and conditions discussed herein.

The term "target molecule" as used herein refers to a molecule that is targeted by a CAR or a cell which expresses same such as a modified Treg, e.g., a modified Treg comprising one or more CARs, of the present disclosure. The AB domain of a CAR comprised by a modified Treg of the present disclosure may have a binding affinity for the target molecule. In some embodiments, the target molecule is a form of amyloid-beta 1-42 associated with a neurodegenerative disease or condition. In some embodiments, the target molecule is a form of alpha-synuclein associated with a neurodegenerative disease or condition. In some embodiments, the target molecule is a form of superoxide dismutase-1 (SOD-1) associated with a neurodegenerative disease or condition, In some embodiments, the target molecule may be, but is not limited to being, forms of any of the following associated with a neurodegenerative disease and/or condition: hyperphosphorylated tau protein; TAR DNA-binding protein 43 (TDP-43): chromosome 9 open reading frame 72 (c9orf72); β-Synuclein; γ-Synuclein; RNA-binding protein fused in sarcoma (FUS); ubiquitin; ubiquilin-2, p62; optineurin; ataxin-2; parkin; Serine/threonine-protein kinase PINK1; Leucine-rich repeat serine/threonine-protein kinase 2 (LRRK2), Huntington with tandem glutamine repeats; prion proteins; transthyretin; dentatorubral pallidoluysian atrophy (DRPLA) protein; androgen receptor; ataxins; P/Q-type calcium channel α1A subunit; TATA-box-binding protein; glial fibrillary acidic protein; DNA excision repair protein ERCC-6; survival motor neuron protein; and cystatin C. In some embodiments, the target molecule may be a molecule associated with any of the following non-limiting list of neurodegenerative diseases: Alzheimer's disease, Parkinson's disease, ALS, prion disease, motor neuron diseases other than ALS, Huntington's disease, Spinocerebellar ataxia (SCA), Spinal muscular atrophy (SMA), Friedreich's ataxia, Lewy body disease, epilepsy, multiple sclerosis, encephalitis, hydrocephalus, stroke, chronic traumatic encephalopathy (CTE); synucleinopathies; tauopathies; spongiform encephalopathies; familial amyloidotic polyneuropathy; Dutch hereditary cerebral hemorrhage with amyloidosis; congophilic angiopathy; corticobasal degeneration; Pick's disease; progressive supranuclear palsy; Creutzfeld-Jacob disease; Gerstmann-Sträussler-Schneiker syndrome; fatal familial insomnia; kuru; bovine spongiform encephalopathy; scrapie; chronic wasting disease; Lewy body variant of Alzheimer's disease; diffuse Lewy body disease; dementia with Lewy bodies; multiple system atrophy; neurodegeneration with brain iron accumulation type I; diffuse Lewy body disease; frontotemporal lobar degeneration; hereditary dentatorubral-pallidoluysian atrophy; Kennedy's disease; Alexander's disease; Cockayne syndrome; Icelandic hereditary cerebral hemorrhage with amyloidosis.

The term "transfected," "transformed," or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

By the term "transmembrane domain" or "TM domain", what is implied is any three-dimensional protein structure which is thermodynamically stable in a membrane. This may be a single a helix, a transmembrane β barrel, a β-helix of gramicidin A, or any other structure. Transmembrane helices are usually about 20 amino acids in length. Typically, the transmembrane domain denotes a single transmembrane α helix of a transmembrane protein, also known as an integral protein.

As used herein, the terms "treat," "treatment," or "treating" generally refers to a clinical procedure for reducing or ameliorating the onset, progression, severity, and/or duration of a disease and/or condition, or for ameliorating one or more symptoms (preferably, one or more discernible symptoms) of a disease and/or condition. The disease may be, for example, a neurodegenerative disease or condition. In some embodiments, the effect of the "treatment" may be evaluated by the amelioration of at least one measurable physical parameter of a disease, resulting from the administration of one or more therapies (e.g., one or more therapeutic agents such as a modified Treg as described herein). The parameter may be, for example, gene expression profiles, the mass of disease-affected tissues, inflammation-associated markers, neurodegenerative disease-associated markers, the presence or absence of certain cytokines or chemokines or other disease-associated molecules, and may not necessarily discernible by the patient. In other embodiments "treat", "treatment," or "treating" may result in the inhibition of the progression of a disease and/or condition, either physically by, e.g., stabilization of a discernible symptom, physiologically by, e.g., stabilization of a physical parameter, or both. Additionally, the terms "treat," and "prevent" as well as words stemming therefrom, as used herein, do not necessarily imply 100% or complete cure or prevention. Rather, there are varying degrees of treatment effects or prevention effects of which one of ordinary skill in the art recognizes as having a potential benefit or therapeutic effect. In this respect, the inventive methods can provide any amount of any level of treatment or prevention effects of a disease and/or condition in a mammal. Furthermore, the treatment or prevention provided by the methods described herein can include treatment or prevention of one or more conditions or symptoms of the disease being treated or prevented. Also, for purposes herein, "prevention" can encompass delaying the onset of the disease, or a symptom or condition thereof.

The term "xenogeneic" refers to a graft derived from an animal of a different species.

As used herein, the term "recombinant Tregs" or "modified Tregs" generally refers to a regulatory T cell that has been altered relative to its native state, e.g., genetically modified. For example, in exemplary embodiments, a modified Treg may be engineered to express one or more CARs. Additionally, exemplary modified Tregs may be engineered to express one or more NDMMs. Modified Tregs according to the invention may be used to treat various diseases in exemplary embodiments. For example, modified Tregs may be used in methods of treating specific neurodegenerative diseases, conditions, or disorders. Exemplary neurodegenerative diseases, conditions, and/or disorders that may be treated with modified Tregs as disclosed herein include by way of example ALS, Alzheimer's disease, and Parkinson's disease. Furthermore, in exemplary embodiments the modified Tregs of the present disclosure may be used to treat neuroinflammation in the CNS. In some embodiments, the modified Tregs of the present disclosure may be used to treat any of the following non-limiting list of neurodegenerative diseases and/or conditions: Alzheimer's disease, Parkinson's disease, ALS, prion disease, motor neuron diseases other than ALS, Huntington's disease, Spinocerebellar ataxia (SCA), Spinal muscular atrophy (SMA), Friedreich's ataxia, Lewy body disease, epilepsy, multiple sclerosis, encephalitis, hydrocephalus, stroke, chronic traumatic encephalopathy (CTE); synucleinopathies; tauopathies; spongiform encephalopathies; familial amyloidotic polyneuropathy; Dutch hereditary cerebral hemorrhage with amyloidosis; congophilic angiopathy; corticobasal degeneration; Pick's disease; progressive supranuclear palsy; Creutzfeld-Jacob disease; Gerstmann-Sträussler-Schneiker syndrome; fatal familial insomnia; kuru; bovine spongiform encephalopathy; scrapie; chronic wasting disease; Lewy body variant of Alzheimer's disease; diffuse Lewy body disease; dementia with Lewy bodies; multiple system atrophy; neurodegeneration with brain iron accumulation type I; diffuse Lewy body disease; frontotemporal lobar degeneration; hereditary dentatorubral-pallidoluysian atrophy; Kennedy's disease; Alexander's disease; Cockayne syndrome; Icelandic hereditary cerebral hemorrhage with amyloidosis.

Modified Tregs, and Compositions and Methods of Use Thereof

The present disclosure generally relates to modified Tregs, e.g., Tregs engineered to express one or more chimeric antigen receptors ("CARs") and/or one or more neurodegenerative disease modifying molecules, compositions comprising said modified Tregs and methods of using said modified Tregs and compositions containing, in particular for treating a disease, disorder, or condition, e.g., neurodegenerative diseases, disorders, or conditions. In exemplary embodiments, these modified Tregs are engineered to express on their surface at least one moiety, e.g., an antibody and typically an scFv which recognizes a protein the expression of which is associated with a specific neurodegenerative condition, e.g., specific molecular markers of a particular neurodegenerative disease or condition, such as, for example, proteins and/or molecular markers associated with neuroinflammation, ALS, Alzheimer's disease, and/or Parkinson's disease. In other exemplary embodiments, modified Tregs are engineered to express or further express specific molecules that prevent oxidative/inflammatory activity and/or which promote neuronal growth, function and/or survival such as anti-oxidants, nerve growth factors and non-classical neurotrophic growth factors. In exemplary embodiments, modified Tregs according to the invention will maintain Treg phenotype and/or maintain at least one Treg effector function, and ideally will retain substantially all effector functions possessed by unmodified Tregs. In some exemplary embodiments modified Tregs according to the invention may migrate or traffic to the site of neurodegeneration and/or neuroinflammation. In further exemplary embodiments, modified Tregs according to the invention may lead to an anti-inflammatory activity at a site of neurodegeneration and/or neuroinflammation. Said activities may comprise any activities which are associated with neurodegeneration and/or neuroinflammation, such as, for example, (1) microglia cell over-activation, (2) production of inflammatory proteins/activities, and (3) neuronal death. Exemplary methods of treatment comprising modified Tregs may result in reduced disease progression and/or may repair and/or improve function in a patient in need thereof. In some embodiments, Tregs may be isolated from donor PBMCs and expanded for use, e.g., clinical use. In some exemplary embodiments the donor cells may be allogeneic. In other exemplary embodiments the donor PBMCs used to derive Tregs may be isolated from the same subject who is to be treated. In some exemplary embodiments the isolated Tregs may be modified to reduce or eliminate the expression or functionality of the endogenous TCR. In some exemplary embodiments the isolated Tregs may be combined with Tregs isolated from different donors which donors may be MHC compatible or incompatible. In some embodiments, Tregs may be expanded by up to a 550-fold increase in number, in some instances in a two week period of culturing. In other exemplary embodiments, said Tregs will comprise a purity of 90% or greater. In other exemplary embodiments, modified Tregs may cross the blood-brain barrier (BBB).

In some embodiments, Tregs may be isolated, expanded, and transduced as follows: cells may be isolated from human PBMCs via a two-step negative and positive selection protocol, First, $CD4^+$ cells are isolated using negative selection, followed by a positive selection of $CD25hi^+$ cells to isolate $CD4^+CD25hi^+$ Treg cells. The isolated $CD4^+CD25hi^+$ Tregs may be activated with anti-CD3, anti-CD28, anti-CD2 multimers or anti-CD3, anti-CD28 multimers (STEMCELL ImmunoCult) with human IL-2 (300 U/ml to 500 U/ml) over two weeks in culture in Treg growth medium. On day 9, Treg cells can be cryopreserved for use at a later date, so we can test the same donor and preparation on multiple occasions to assess assay variability.

CARs

In further exemplary aspects, modified Tregs may be modified to express one or more CARs, preferably expressed on their cell surface. Exemplary CARs according to the invention may comprise a ligand binding moiety such as a receptor or an antibody, e.g., an scFv which recognizes proteins and/or other molecular markers associated with diseases and/or conditions which are to be treated using the Tregs, for example, particular neurodegenerative diseases and/or neuroinflammation. In some embodiments of the invention these CARs may further comprise one or more costimulatory signaling or T cell signaling moieties or domains such as are identified herein and exemplified in the working examples or others which are generally known in the art. Exemplary neurodegenerative diseases characterized by the expression of aberrant proteins or aberrantly expressed proteins which are associated with disease pathology that may be recognized by CARs expressed by modified Tregs according to the invention include by way of example ALS, Alzheimer's disease, and Parkinson's disease. When expressed in modified Tregs, one or more CARs as described herein may trigger effector responses, such as, for example, cytokine expression. In exemplary embodiments, the CAR may trigger effector responses in the presence of one or more specific antigens. Moreover, in some aspects, modified Tregs may comprise one or more CARs, and said one or more CARs may trigger IL-10 production upon stimulation, e.g., stimulation by a specific antigen. In further exemplary embodiments, modified Tregs may comprise one or more CARs, and said modified Tregs may retain their ability to suppress other T cells. In some embodiments, modified Tregs may comprise one or more CARs, and said modified Tregs may be in subsets of T cells with known regulatory and/or anti-inflammatory activity, such as, for example, $FOXP3^+$ Tregs. In exemplary embodiments, modified Tregs may comprise one or more CARs, wherein said one or more CARs comprise single chain variable fragments (scFv) that may be targeted to a protein and/or molecular marker of a disease, transmembrane signaling domain, and cytoplasmic signaling domain. In exemplary embodiments, modified Tregs comprising one or more CARs targeted to a disease of interest may result in greater inhibition of inflammatory cytokine production, higher expression of anti-inflammatory cytokines, greater protection against neuroinflarnrnation-mediated motor neuron death, and improve survival as compared to control treatments.

In some embodiments, a modified Treg may comprise one or more CARs as described herein, wherein the sequence that encodes said CARs may comprise a signal sequence. It is to be understood that said signal sequence may or may not be cleaved during expression of said CAR. In some embodiments, a modified Treg may comprise one or more CARs that comprise a sequence of SEQ ID NO: 1 (DG01), which may optionally be encoded by the nucleic acid sequence of SEQ ID NO: 201), and/or a construct comprising at least 90%, at least 95%, at least 98%, or at least 99% sequence identity to the aforementioned construct. In some embodiments, DG01 may target a form of amyloid-beta associated with a neurodegenerative disease or condition. In some embodiments, a modified Treg may comprise one or more CARs that comprise a sequence of SEQ ID NO: 2 (DG02), which may optionally be encoded by the nucleic acid sequence of SEQ ID NO: 202, and/or a construct comprising at least 90%, at least 95%, at least 98%, or at least 99% sequence identity to the aforementioned construct. In some embodiments, DG02 may target a form of amyloid-beta associated with a neurodegenerative disease or condition In some embodiments, a modified Treg may comprise one or more CARs that comprise a sequence of SEQ ID NO: 3 (DG03), which may optionally be encoded by the nucleic acid sequence of SEQ ID NO: 203, and/or a construct comprising at least 90%, at least 95%, at least 98%, or at least 99% sequence identity to the aforementioned construct. In some embodiments, DG03 may target a form of amyloid-beta associated with a neurodegenerative disease or condition. In some embodiments, a modified Treg may comprise one or more CARs that comprise a sequence of SEQ ID NO: 4 (DG04), which may optionally be encoded by the nucleic acid sequence of SEQ ID NO: 204, and/or a construct comprising at least 90%, at least 95%, at least 98%, or at least 99% sequence identity to the aforementioned construct. In some embodiments, DG04 may target a form of amyloid-beta associated with a neurodegenerative disease or condition. In some embodiments, a modified Treg may comprise one or more CARs that comprise a sequence of SEQ ID NO: 5 (DG05), which may optionally be encoded by the nucleic acid sequence of SEQ ID NO: 205, and/or a construct comprising at least 90%, at least 95%, at least 98%, or at least 99% sequence identity to the aforementioned construct. In some embodiments, DUOS may target a form of human superoxide mutase associated with a neurodegenerative disease or condition. In some embodiments, a modified Treg may comprise one or more CARs that comprise a sequence of SEQ ID NO: 6 (DG06), which may optionally be encoded by the nucleic acid sequence of SEQ ID NO: 206, and/or a construct comprising at least 90%, at least 95%, at least 98%, or at least 99% sequence identity to the aforementioned construct. In some embodiments, DG06 may target a form of superoxide mutase associated with a neurodegenerative disease or condition. In some embodiments, a modified Treg may comprise one or more CARs that comprise a sequence of SEQ ID NO: 7 (DG07), which may optionally be encoded by the nucleic acid sequence of SEQ ID NO: 207, and/or a construct comprising at least 90%, at least 95%, at least 98%, or at least 99% sequence identity to the aforementioned construct. In some embodiments, DG07 may target a form of superoxide mutase associated with a neurodegenerative disease or condition. In some embodiments, a modified Treg may comprise one or more CARs that comprise a sequence of SEQ ID NO: 8 (DG08), which may optionally be encoded by the nucleic acid sequence of SEQ ID NO: 208, and/or a construct comprising at least 90%, at least 95%, at least 98%, or at least 99% sequence identity to the aforementioned construct. In some embodiments, D008 may target a form of alpha-synuclein associated with a neurodegenerative disease or condition. In some embodiments, a modified Treg may comprise one or more CARs that comprise a sequence of SEQ ID NO: 9 (DG09), which may optionally be encoded by the nucleic acid sequence of SEQ ID NO: 209, and/or a construct comprising at least 90%, at least 95%, at least 98%, or at least 99% sequence identity to the aforementioned construct. In some embodiments, DG09 may target a form of alpha-synuclein associated with a neurodegenerative disease or condition. In some embodiments, a modified Treg may comprise one or more CARs that comprise a sequence of SEQ ID NO: 10 (DG010), which may optionally be encoded by the nucleic acid sequence of SEQ ID NO: 210, and/or a construct comprising at least 90%, at least 95%, at least 98%, or at least 99% sequence identity to the aforementioned construct. In some embodiments, DG10 may target a form of alpha-synuclein associated with a neurodegenerative disease or condition. In some embodiments, a modified Treg may comprise one or more CARs that comprise a sequence of SEQ ID NO: 11 (DG11), which may optionally be encoded by the nucleic acid sequence of SEQ ID NO: 211, and/or a construct comprising at least 90%, at least 95%, at least 98%, or at least 99% sequence identity to the aforementioned construct. In some embodiments, DG11 may target a form of alpha-synuclein associated with a neurodegenerative disease or condition.

In exemplary embodiments, a CAR may target a protein or a mutant version of a protein comprising a sequence as set forth in Table 1:

TABLE 1

| TARGET MOLECULE | SEQUENCE |
|---|---|
| Human amyloid beta, isoform APP770 (identifier: P05067-1) | SEQ ID NO: 17 |
| human superoxide dismutase (human superoxide dismutase, identifier: P00441-1, wild type sequence) | SEQ ID NO: 18 |
| human alpha-synuclein, Isoform 1 (identifier: P37840-1) | SEQ ID NO: 19 |

In some embodiments, a CAR may target a molecular marker, e.g., a protein, associated with any one or more of the following neurodegenerative diseases: Alzheimer's disease, Parkinson's disease, ALS, prion disease, motor neuron diseases other than ALS, Huntington's disease, Spinocerebellar ataxia (SCA), Spinal muscular atrophy (SMA), Friedreich's ataxia, Lewy body disease, epilepsy, multiple sclerosis, encephalitis, hydrocephalus, stroke, chronic traumatic encephalopathy (GTE); synucleinopathies; tauopathies; spongiform encephalopathies; familial amyloidotic polyneuropathy; Dutch hereditary cerebral hemorrhage with amyloidosis; congophilic angiopathy; corticobasal degeneration; Pick's disease; progressive supranuclear palsy; Creutzfeld-Jacob disease; Gerstmann-Sträussler-Schneiker syndrome; fatal familial insomnia; kuru; bovine spongiform encephalopathy; scrapie; chronic wasting disease; Lewy body variant of Alzheimer's disease; diffuse Lewy body disease; dementia with Lewy bodies; multiple system atrophy; neurodegeneration with brain iron accumulation type I; diffuse Lewy body disease; frontotemporal lobar degeneration; hereditary dentatorubral-pallidoluysian atrophy; Kennedy's disease; Alexander's disease; Cockayne syndrome; Icelandic hereditary cerebral hemorrhage with amyloidosis.

In some exemplary embodiments, a CAR comprised by a modified Treg may target amyloid beta 1-42, In other exemplary embodiments, a CAR comprised by a modified Treg may target superoxide dismutase-1 (SOD-1). In other exemplary embodiments, a CAR comprised by a modified Treg may target alpha-synuclein. In other exemplary embodiments, a CAR comprised by a modified Treg may target any of the following non-limiting list: hyperphosphorylated tau protein; TAR DNA-binding protein 43 (TDP-43): chromosome 9 open reading frame 72 (c9orf72); β-Synuclein; γ-Synuclein; RNA-binding protein fused in sarcoma (FUS); ubiquitin; ubiquilin-2, p62; optineurin; ataxin-2; parkin; Serine/threonine-protein kinase PINK1; Leucine-rich repeat serine/threonine-protein kinase 2 (LRRK2). In some embodiments, a CAR comprised by a modified Treg may target any one or more of the following: Huntington with tandem glutamine repeats; prion proteins; transthyretin; dentatorubral pallidoluysian atrophy (DRPLA) protein; androgen receptor; ataxins; P/Q-type calcium channel α1A subunit; TATA-box-binding protein; glial fibrillary acidic protein; DNA excision repair protein ERCC-6; survival motor neuron protein; cystatin C.

In other exemplary embodiments, modified Tregs may comprise one or more CARs and may further comprise one or more signaling domains which may be encoded by nucleic acids which are comprised on the same or different nucleic acid construct as the nucleic acids encoding the one or more CARs. Said signaling domains may activate different effector pathways and/or survival pathways in said modified Tregs and optionally may affect cytokine expression, e.g., trigger. IL-10 expression in the presence of a target antigen such as an aberrantly expressed protein expressed in the CNS at a site of neurodegeneration.

In some exemplary embodiments, modified Tregs may have no signaling, or T cell signaling may be used (i.e. an antigen tether as CAR, e.g., CD28 transmembrane only). In other exemplary embodiments, one or more CARs expressed by the modified Tregs may comprise signaling domain combinations (costimulation signaling domains) including by way of example: CD28-CD3ζ; 4-1BB-CD3ζ; Dap10-CD3ζ; CD44-CD3ζ; CTLA-4-CD3ζ; CD28; Dap10; 4-1BB; CD3-ζ. In further exemplary embodiments, a costimulation signaling domain expressed by the modified Tregs may comprise CD28-CD3ζ; DAP10-CD3ζ; CD44-CD3ζ; 4-1BB-CD3ζ; CD28; or CD3-ζ.

Moreover, specific exemplary embodiments of the present invention relate to modified Tregs that comprise one or CARs which comprise single chain variable fragments that were derived from antibodies specific to proteins and/or other molecular markers associated with diseases and/or conditions associated with diseases, such as, for example, neurodegenerative diseases and/or neuroinflammation including but not limited to specific scFv antibody sequences which are disclosed herein.

In some embodiments, a modified Treg may comprise CAR DG05-28Z (SEQ ID NO: 24, which may optionally be encoded by SEQ ID NO: 224), and/or a construct comprising at least 90%, at least 95%, at least 98%, or at least 99% sequence identity to the aforementioned construct. In some embodiments, a modified Treg may comprise CAR DG06-28Z (SEQ ID NO: 25, which may optionally be encoded by SEQ ID NO: 225)), and/or a construct comprising at least 90%, at least 95%, at least 98%, or at least 99% sequence identity to the aforementioned construct. In some embodiments, a modified Treg may comprise CAR DG07-28Z (SEQ ID NO: 26, which may optionally be encoded by SEQ ID NO: 226), and/or a construct comprising at least 90%, at least 95%, at least 98%, or at least 99% sequence identity to the aforementioned construct. In some embodiments, a modified Treg may comprise CAR DG10-28Z (SEQ ID NO: 29, which may optionally be encoded by SEQ ID NO: 229), and/or a construct comprising at least 90%, at least 95%, at least 98%, or at least 99% sequence identity to the aforementioned construct. In some embodiments, a modified Treg may comprise DG01-CD28-CD3ζ (SEQ ID NO: 20, which may optionally be encoded by SEQ ID NO: 220), DG02-CD28-CD3ζ (SEQ ID NO: 21, which may optionally be encoded by SEQ ID NO: 221), DG03-CD28-CD3ζ (SEQ ID NO: 22, which may optionally be encoded by SEQ ID NO: 222), DG04-CD28-CD3ζ (SEQ ID NO: 23, which may optionally be encoded by SEQ ID NO: 223), and/or a construct comprising at least 90%, at least 95%, at least 98%, or at least 99% sequence identity to any one or more of the aforementioned constructs. In some embodiments, a modified Treg may comprise DG05-CD28-CD3ζ (SEQ ID NO: 24, which may optionally be encoded by SEQ ID NO: 224), DG06-CD28-CD3ζ (SEQ ID NO: 25, which may optionally be encoded by SEQ ID NO: 225), DG07-CD28-CD3ζ (SEQ ID NO: 26, which may optionally be encoded by SEQ ID NO: 226), and/or a construct comprising at least 90%, at least 95%, at least 98%, or at least 99% sequence identity to any one or more of the aforementioned constructs. In some embodiments, a modified Treg may comprise DG08-CD28-CD3ζ (SEQ ID NO: 27, which may optionally be encoded by SEQ ID NO: 227), DG09-CD28-CD3ζ (SEQ ID NO: 28, which may optionally be encoded by SEQ ID NO: 228), DG10-CD28-CD3ζ (SEQ ID NO: 29, which may optionally be encoded by SEQ ID NO: 229), DG11-CD28-CD3ζ (SEQ ID NO: 30, which may optionally be encoded by SEQ ID NO: 230), and/or a construct comprising at least 90%, at least 95%, at least 98%, or at least 99% sequence identity to any one or more of the aforementioned constructs. In some embodiments, a modified Treg may comprise DG05-CD28-CD3ζ (also referred to as DG05-28-3ζ) (SEQ ID NO: 24, which may optionally be encoded by SEQ ID NO: 224), and/or a construct comprising at least 90%, at least 95%, at least 98%, or at least 99% sequence identity to the aforementioned construct. In some embodiments, a modified Treg may comprise DG05-CD28tm-DAP10-CD3ζ (also referred to as DG05-28tm-10-3ζ) (SEQ ID NO: 40, which may optionally be encoded by SEQ ID NO: 240), and/or a construct comprising at least 90%, at least 95%, at least 98%, or at least 99% sequence identity to the aforementioned construct. In some embodiments, a modified Treg may comprise DG05-CD28tm-CD44-CD3ζ (also referred to as DG05-28tm-44-3ζ) (SEQ ID NO: 41, which may optionally be encoded by SEQ ID NO: 241), and/or a construct comprising at least 90%, at least 95%, at least 98%, or at least 99% sequence identity to the aforementioned construct. In some embodiments, a modified Treg may comprise DG05-CD28tm-CD3ζ (also referred to as DG05-28tm-3ζ) (SEQ ID NO: 42, which may optionally be encoded by SEQ ID NO: 242), and/or a construct comprising at least 90%, at least 95%, at least 98%, or at least 99% sequence identity to the aforementioned construct. In some embodiments, a modified Treg may comprise D005-CD28 (also referred to as DG05-28) (SEQ ID NO: 43, which may optionally be encoded by SEQ ID NO: 243), and/or a construct comprising at least 90%, at least 95%, at least 98%, or at least 99% sequence identity to the aforementioned construct. In some embodiments, a modified Treg may comprise DG05-CD28tm (also referred to as DG05-28tm) (SEQ ID NO: 44, which may optionally be encoded by SEQ ID NO: 244), and/or a construct comprising at least 90%, at least 95%, at least 98%, or at least 99% sequence identity to the aforementioned construct. In some embodiments, a modified Treg may comprise DG03-CD28-CD3ζ (also referred to as DG03-28-3ζ) (SEQ ID NO: 22, which may optionally be encoded by SEQ ID NO: 222), and/or a construct comprising at least 90%, at least 95%, at least 98%, or at least 99% sequence identity to the aforementioned construct. In some embodiments, a modified Treg may comprise DG03-CD28tm-DAP10-CD3ζ (also referred to as DG03-28tm-10-3ζ) (SEQ ID NO: 45, which may optionally be encoded by SEQ ID NO: 245), and/or a construct comprising at least 90%, at least 95%, at least 98%, or at least 99% sequence identity to the aforementioned construct. In some embodiments, a modified Treg may comprise DG03-CD28tm-CD44-CD3ζ (also referred to as DG03-28tm-44-3ζ) (SEQ ID NO: 46, which may optionally be encoded by SEQ ID NO: 246), and/or a construct comprising at least 90%, at least 95%, at least 98%, or at least 99% sequence identity to the aforementioned construct. In some embodiments, a modified Treg may comprise DG03-CD28tm-4-1-BB-CD3ζ (also referred to as DG03-28tm-BB-3ζ) (SEQ ID NO: 47, which may optionally be encoded by SEQ ID NO: 247), and/or a construct comprising at least 90%, at least 95%, at least 98%, or at least 99% sequence identity to the aforementioned construct. In some embodiments, a modified Treg may comprise DG03-CD28tm-CD3ζ (also referred to as DG03-28tm-3ζ) (SEQ ID NO: 48, which may optionally be encoded by SEQ ID NO: 248), and/or a construct comprising at least 90%, at least 95%, at least 98%, or at least 99% sequence identity to the aforementioned construct. In some embodiments, a modified Treg may comprise DG03-CD28 (also referred to as DG03-28) (SEQ ID NO: 49, which may optionally be encoded by SEQ ID NO: 249), and/or a construct comprising at least 90%, at least 95%, at least 98%, or at least 99% sequence identity to the aforementioned construct. In some embodiments, a modified Treg may comprise DG03-CD28tm (also referred to as DG03-28tm) (SEQ ID NO: 50, which may optionally be encoded by SEQ ID NO: 250), and/or a construct comprising at least 90%, at least 95%, at least 98%, or at least 99% sequence identity to the aforementioned construct.

In further exemplary embodiments, modified Tregs according to the invention may express one or more CARs, e.g., which target proteins aberrantly expressed at a site of CNS neurodegeneration and may further be modified to express one or more NDMMs. Alternatively modified Tregs may be generated which express one or more NDMMs which do not express a CAR. These modified NDMM expressing Tregs optionally may be combined with modified Tregs which express one or more CARs. Said NDMMs may comprise molecules that prevent oxidative and/or inflammatory activity. In further exemplary embodiments, said NDMMs when expressed in Tregs may activate neuronal growth and/or survival. Exemplary NDMMs may comprise pro-neuronal factors, anti-oxidants, nerve growth factors, and/or non-classical neurotrophic factors. Exemplary anti-oxidants include, but are not limited to including, HO-1, Ferritin, Glutathione reductase, Glutathione peroxidase, Ferritin (H), Metallothionein I, Thioredoxin, Thioredoxin reductase, Peroxiredoxin MSP23, Cu/Zn superoxide dismutase, Catalase, NRF2 activity, peroxiredoxins (Prxs); activity-dependent neuroprotector homeobox (ADNP); phycocyanin; neuroglobin. Exemplary pro-neuronal factors include, but are not limited to including: interleukin-1 receptor antagonist (IL-1ra); interleukin-6 (IL-6); activated protein C (APC); thrombomodulin; tissue plasminogen activator (tPA); Protein deglycase DJ-1; tissue inhibitor of metalloproteinases (TIMPs). Exemplary nerve growth factors include, but are not limited to including, classic neurotrophins: Brain-derived neurotrophic factor (BDNF), Ciliary neurotrophic factor (CNTF), Glial cell-line derived neurotrophic factor (GDNF). Exemplary non-classical neurotrophic factors include, but are not limited to including, Insulin-like growth factor-1 (IGF-1), Vascular endothelial growth factor, VEGF), Fibroblast Growth Factors (FGF), Hepatocyte Growth Factor (HGF), Bone Morphogenetic Proteins (BMPs), Erythropoietin (EPO), Thrombopoietin (TPO), Granulocyte-colony stimulating factor (G-CSF). In some exemplary embodiments, NDMMs which are expressed by modified Tregs according to the invention may be controlled by a constitutive promoter. In other exemplary embodiments, NDMMs which are expressed by modified Tregs according to the invention may be controlled by an inducible promoter system. The selection of suitable constitutive and inducible promoters is well within the skill in the art and many such promoters are known and readily available. Furthermore, expression of said NDMMs by said modified Tregs may be regulated by CAR-triggered transcriptional control. In some embodiments of the present invention, CAR-expressing modified Tregs as described herein may further comprise exogenously introduced polynucleotides encoding one or more NDMMs. In some embodiments, the exogenously introduced polynucleotides encoding an NDMM and the CAR construct may be introduced into the cell using a single vector. When one vector is used for both a CAR and an NDMM, the CAR and the NDMM may be encoded in the vector under the same promoter in cis. In such cases, the CAR and NDMM constructs may be separated by a sequence that allows generation of two separate translation products, for example the IRES sequence or T2A sequence (encoded by SEQ ID NO: 214).

In some embodiments, a CAR-expressing modified Treg may express an NDMM which may be human catalase. In some embodiments, a CAR-expressing modified Treg may express an NDMM which may be Neh2 domain of human Nrf2. In some embodiments, a CAR-expressing modified Treg may express an NDMM which may be human BDNF. In some embodiments, a CAR-expressing modified Treg may express an NDMM which may be human IGF-1. In some embodiments, a modified Treg may comprise a construct for expression of the NDMM Nrf2 (Keap1 inhibitor peptide) (SEQ ID NO: 51, which may optionally be encoded by SEQ ID NO: 251), and/or a construct comprising at least 90%, at least 95%, at least 98%, or at least 99% sequence identity to the aforementioned construct. In some embodiments, a modified Treg may comprise a construct for expression of the NDMM human catalase (SEQ ID NO: 52, which may optionally be encoded by SEQ ID NO: 252), and/or a construct comprising at least 90%, at least 95%, at least 98%, or at least 99% sequence identity to the aforementioned construct. In some embodiments, a modified Treg may comprise a construct for expression of the NDMM BDNF (SEQ ID NO: 53, which may optionally be encoded by SEQ ID NO: 253), and/or a construct comprising at least 90%, at least 95%, at least 98%, or at least 99% sequence identity to the aforementioned construct. In some embodiments, a modified Treg may comprise a construct for expression of the NDMM IGF-1 (SEQ ID NO: 54, which may optionally be encoded by SEQ ID NO: 254), and/or a construct comprising at least 90%, at least 95%, at least 98%, or at least 99% sequence identity to the aforementioned construct.

Alternatively, a CAR construct and NDMM construct may be contained in separate vectors for transfecting or transducing cells using two or more different vectors.

Exemplary modified Tregs may comprise modified Tregs targeting proteins and/or molecular markers of Parkinson's disease. In exemplary embodiments, modified Tregs targeted to Parkinson's disease may comprise one or more CARs, wherein said one or more CARs may target α-synuclein fibrils. In some embodiments, a CAR targeted to alpha-synuclein may comprise a sequence of DG08 (SEQ ID NO: 8), and/or a construct comprising at least 90%, at least 95%, at least 98%, or at least 99% sequence identity to the aforementioned construct. In some embodiments, a CAR targeted to alpha-synuclein may comprise a sequence of DG09 (SEQ ID NO: 9), and/or a construct comprising at least 90%, at least 95%, at least 98%, or at least 99% sequence identity to the aforementioned construct. In some embodiments, a CAR targeted to alpha-synuclein may comprise a sequence of DG10 (SEQ ID NO: 10), and/or a construct comprising at least 90%, at least 95%, at least 98%, or at least 99% sequence identity to the aforementioned construct. In some embodiments, a CAR targeted to alpha-synuclein may comprise a sequence of DG11 (SEQ ID NO: 11), and/or a construct comprising at least 90%, at least 95%, at least 98%, or at least 99% sequence identity to the aforementioned construct. In some embodiments, a modified Treg may comprise DG08-CD28-CD3ζ (SEQ ID NO: 27), DG09-CD28-CD3ζ (SEQ ID NO: 28), DG10-CD28-CD3ζ (SEQ ID NO: 29), DG11-CD28-CD3ζ (SEQ ID NO: 30), and/or a construct comprising at least 90%, at least 95%, at least 98%, or at least 99% sequence identity to any one or more of the aforementioned constructs, wherein each of the constructs is targeted to alpha-synuclein. In further exemplary embodiments, modified Tregs, such as modified Tregs comprising one or more CARs, may target one or more neurotoxic inflammatory mediators, e.g., neurotoxic inflammatory mediations produced by activated microglia. Said modified Tregs may decrease and/or inhibit microglia activation. In exemplary embodiments, modified Tregs comprise targeted anti-inflammatory and neuroprotective therapeutic activity at the disease site of dopamine neuron degeneration in PD. In some embodiments, modified Tregs may mediate their function only at the site where α-synuclein fibrils are present.

In exemplary embodiments, modified Tregs may comprise one or more CARs and/or one or more NDMMs targeted to Parkinson's disease, wherein said one or more CARs comprise single chain variable fragments such as $V_H$ and $V_L$ amino acid sequences of human and mouse monoclonal antibodies against human α-synuclein fibrils (such as, for example, amino acid sequences derived from clones NI 202.3G12, NI 202.12F4, NI 202.21D11, and mAb49/G). In exemplary embodiments, modified Tregs may comprise said scFV and further comprise a construct comprising CD28-CD3ζ CAR, i.e., scFv-CD28-CD3ζ CAR, wherein said scFv is specific for human α-synuclein fibrils. Constructs comprising said scFv may comprise $V_H$+$V_L$ and $V_L$+$V_H$ arrangements. In exemplary embodiments, a vector may comprise said scFv-CD28-CD3ζ CAR construct, and may further comprise a separate truncated (non-signaling) human CD19 (tCD19). Said tCD19 may be used as a transduction marker, such as for cell monitoring and/or cell purification purposes. In exemplary embodiments, a vector comprising any of the sequences described herein may comprise a retroviral expression vector, e.g., pSFG.

Furthermore, in exemplary embodiments, modified Tregs may comprise one or more CARs and/or one or more NDMMs targeted to ALS. Said modified Tregs may target mutSOD1, e.g., said modified Tregs may comprise one or more CARs targeted to mutSOD1. In some embodiments, a CAR targeted to mutSOD1 may comprise a sequence of DG05 (SEQ ID NO: 5), and/or a construct comprising at least 90%, at least 95%, at least 98%, or at least 99% sequence identity to the aforementioned construct. In some embodiments, a CAR targeted to mutSOD1 may comprise a sequence of DG06 (SEQ ID NO: 6), and/or a construct comprising at least 90%, at least 95%, at least 98%, or at least 99% sequence identity to the aforementioned construct. In some embodiments, a CAR targeted to mutSOD1 may comprise a sequence of DG07 (SEQ ID NO: 7), and/or a construct comprising at least 90%, at least 95%, at least 98%, or at least 99% sequence identity to the aforementioned construct. In some embodiments, a modified Treg may comprise DG05-CD28-CD3ζ (SEQ ID NO: 24), DG06-CD28-CD3ζ (SEQ ID NO: 25), DG07-CD28-CD3ζ (SEQ ID NO: 26), and/or a construct comprising at least 90%, at least 95%, at least 98%, or at least 99% sequence identity to any one or more of the aforementioned constructs, wherein each of the constructs is targeted to mutSOD1. In some embodiments, a modified Treg may comprise DG05-CD28-CD3ζ (also referred to as DG05-28-3ζ) (SEQ ID NO: 24); DG05-CD28tm-DAP10-CD3ζ (also referred to as DG05-28tm-10-3ζ) (SEQ ID NO: 40); DG05-CD28tm-CD44-CD3ζ (also referred to as DG05-28tm-44-3ζ) (SEQ ID NO: 41); DG05-CD28tm-CD3ζ (also referred to as DG05-28tm-3ζ) (SEQ ID NO: 42); DG05-CD28 (also referred to as DG05-28) (SEQ ID NO: 43); DG05-CD28tm (also referred to as DG05-28tm) (SEQ ID NO: 44), and/or a construct comprising at least 90%, at least 95%, at least 98%, or at least 99% sequence identity to any one or more of the aforementioned constructs, wherein each of the constructs is targeted to mutSOD1.

In some embodiments, modified Tregs may comprise CARs targeted to mutSOD1, and in some exemplary embodiments an scFv of said CARs may be expressed extracellularly with the C-terminus of the $V_L$ fused to human CD28 hinge, transmembrane, and cytoplasmic domain, followed by a human CD3ζ cytoplasmic domain to create an anti-mutSOD1-CD28-CD3ζ CAR. In some embodiments, an scFv of a CAR comprised by a modified Treg may be constructed by linking heavy chain variable region and light chain variable region with a linker, such as, for example, a $(G_4S)_3$ linker. In some embodiments, the C-terminus of a $V_L$ of a CAR of a modified Treg may be fused with human CD28 hinge, transmembrane, and cytoplasmic domain, and may be followed by a human CD3ζ cytoplasmic domain. Said CAR of said modified Treg may be an anti-mutSOD1 CAR. Said CARs may trigger both primary and costimulation signaling upon antigen binding, e.g., binding of mutSOD1. In some embodiments, a CAR costimulating domain may comprise, but not limited to one comprising, CD3ζ alone, 4-1BB, or CD28 or it may comprise CD28-CD3ζ, DAP10-CD3ζ or CD44-CD3ζ. In some embodiments a truncated (non-signaling) human CD19 (tCD19) may also expressed in the same vector as said CARS, such as by using a 2A co-expression system, said tCD19 may serve as a way to track and purify transduced T cells. In some embodiments, modified Tregs targeted to ALS may enter the spinal cord when administered to a patient in need of treatment. In exemplary embodiments, modified Tregs may comprise markers such as, for example, VLA4, LFA-1, CCR6, or CXCR3. In some exemplary embodiments, modified CARs targeted to ALS, e.g., modified Tregs comprising one or more anti-mutSOD1 CARs, and optionally will retain a Treg phenotype and/or elicit at least some Treg effector functions when expressing one or more CARs and/or one or more NDMMs. In exemplary embodiments, modified Tregs may express IL-10 in response to an ALS protein and/or molecular marker of disease.

In some exemplary embodiments, modified Tregs according to the invention may secrete anti-inflammatory cytokines, which may result in inhibition of activated microglia and/or macrophages. Said secretion may occur as a result of stimulation of one or more CARs comprised by said modified Tregs by an ALS protein and/or disease associated marker, such as mutSOD1. In some embodiments, said cytokines may comprise IL-10, IL-4, or TGF-β. In some exemplary embodiments, modified Tregs may reduce and/or prevent production of neurotoxic free radicals and inflammatory cytokines by microglia. In some exemplary embodiments, modified Tregs may be used in methods of treating ALS, and said methods may result in one or more of the following as compared to a control treatment: less macrophage mediated motor neuron death; less IL-1β, TNF-α, nitric oxide and/or free radicals (superoxide anion); and greater amounts of IL-10, IL-4, and TGF-β.

In some exemplary embodiments, modified Tregs may comprise CARs targeted to the short isoform of C9orf72 (sC9orf72), which, like mutSOD1, may be expressed on or near motor neurons in ALS. In exemplary embodiments, modified Tregs may comprise CARs targeted to sC9orf72, wherein said CAR may comprise a human scFV against sC9orf72. In some specific exemplary embodiments, CARs targeted to sC9orf27 may comprise anti-sC9orf72 CARs using $V_H$ and $V_L$ sequences from a unique human αsC9orf72. In some embodiments, said $V_L$ c-terminus of each αsC9orf72 scFv may be fused with human CD28 hinge, transmembrane, and cytoplasmic domain, followed by a human CD3ζ cytoplasmic domain to create an anti-sC9orf72 CAR that may be comprised by a modified Treg. In some embodiments, a non-signaling, truncated human CD19 (tCD19) can serve as a transduction marker on a vector comprising said CARs. In exemplary embodiments, modified Tregs targeted to sC9orf72 may inhibit microglia mediated motor neuron degeneration; decrease IL-1β, TNF-α, nitric oxide; and/or increase IL-10. IL-4, and TGF-β, such as when administered to a patient in need of treatment.

In some exemplary embodiments, modified Tregs may comprise modified Tregs targeted to ALS, such as modified Tregs comprising anti-mutSOD1 CARs, and said modified Tregs may enter the spinal cord parenchyma, recognize accumulated spinal mutSOD1 protein, and react by producing anti-inflammatory mediators. Said modified Tregs may decrease expression of inflammatory mediators (e.g. CCL2, CCL3, CCL4, TNF-α, IL1β, NOX2) and increase expression of anti-inflammatory mediators (e.g. IL-10, IL-4, and TGF-β) when administered to a patient in need of treatment. Furthermore, modified Tregs targeted to ALS, such as modified Tregs comprising anti-mutSOD1 CARs, may inhibit persistent and/or neurotoxic inflammation around motor neurons when used in methods of treatment of ALS.

Furthermore, in other exemplary embodiments, modified Tregs may be targeted to proteins and/or molecular markers associated with Alzheimer's disease. In some exemplary embodiments, said modified Tregs may comprise one or more CARs targeted to said proteins and/or markers. In some embodiments, said protein and/or marker may comprise amyloid-beta (Aβ), in particular oligomeric Aβ, and/or intraneuronal tangles of twisted tau protein fibers. In some embodiments, a CAR targeted to amyloid beta may comprise a sequence of DG01 (SEQ ID NO: 1), and/or a construct comprising at least 90%, at least 95%, at least 98%, or at least 99% sequence identity to the aforementioned construct. In some embodiments, a CAR targeted to amyloid beta may comprise a sequence of DG02 (SEQ ID NO: 2), and/or a construct comprising at least 90%, at least 95%, at least 98%, or at least 99% sequence identity to the aforementioned construct. In some embodiments, a CAR targeted to amyloid beta may comprise a sequence of DG03 (SEQ ID NO: 3), and/or a construct comprising at least 90%, at least 95%, at least 98%, or at least 99% sequence identity to the aforementioned construct. In some embodiments, a CAR targeted to amyloid beta may comprise a sequence of DG04 (SEQ ID NO: 4), and/or a construct comprising at least 90%, at least 95%, at least 98%, or at least 99% sequence identity to the aforementioned construct. In some embodiments, a modified Treg may comprise DG01-CD28-CD3ζ (SEQ ID NO: 20), DG02-CD28-CD3ζ (SEQ ID NO: 21), DG03-CD28-CD3ζ (SEQ ID NO: 22), DG04-CD28-CD3ζ (SEQ ID NO: 23), and/or a construct comprising at least 90%, at least 95%, at least 98%, or at least 99% sequence identity to any one or more of the aforementioned constructs, wherein each of the constructs is targeted to amyloid-beta. In some embodiments, a modified Treg may comprise DG03-CD28-CD3ζ (also referred to as DG03-28-3ζ) (SEQ ID NO: 22); DG03-CD28tm-DAP10-CD3ζ (also referred to as DG03-28tm-10-3ζ) (SEQ ID NO: 45); DG03-CD28tm-CD44-CD3ζ (also referred to as DG03-28tm-44-3ζ) (SEQ ID NO: 46); DG03-CD28tm-4-1-BB-CD3ζ (also referred to as DG03-28tm-BB-3ζ) (SEQ ID NO: 47); DG03-CD28tm-CD3ζ (also referred to as DG03-28tm-3ζ) (SEQ ID NO: 48); DG03-CD28 (also referred to as DG03-28) (SEQ ID NO: 49); and/or DG03-CD28tm (also referred to as DG03-28tm) (SEQ ID NO: 50), and/or a construct comprising at least 90%, at least 95%, at least 98%, or at least 99% sequence identity to any one or more of the aforementioned constructs, wherein each of the constructs is targeted to amyloid-beta.

In exemplary embodiments, CARs comprised by modified Tregs may be targeted to Aβ peptides, and may comprise anti-Aβ CARs using single chain variable fragment (scFv) sequences from antibodies, e.g., human and/or humanized antibodies, with different binding specificities to Aβ, e.g., oligomeric Aβ. In exemplary embodiments, said scFvs may be fused to human CD28 hinge, transmembrane, and cytoplasmic domains, followed by a human CD3ζ cytoplasmic domain. Said CARs may trigger both primary (CD3ζ) and co-stimulatory (CD28) signaling upon antigen binding and cross-linking. In some embodiments, a truncated (non-signaling) CD19 (tCD19) may also expressed in the same vector comprising said CARs, such as by using a T2A co-expression system, and it may serve as a means to track and purify transduced T cells. Modified Tregs comprising anti-Aβ CARs may suppress proliferation of CD3-activated allogeneic $CD8^+$ T cells in some embodiments. Furthermore, in some embodiments, when activated with oligomeric Aβ, modified Tregs comprising anti-Aβ CARs may produce anti-inflammatory cytokines, e.g., IL-10. Furthermore, said modified Tregs may inhibit production of pro-inflammatory mediators and may enhance phagocytic capacity of activated microglia or macrophages, such as by secreting IL-10, TGF-β, and IL-4 anti-inflammatory cytokines for example. In some exemplary embodiments, modified Tregs according to the invention which express a CAR specific for oligomeric Aβ may have targeted anti-inflammatory activity and neuroprotective effects in regions where oligomeric Aβ may accumulate. In some exemplary embodiments, e.g., modified Tregs which express a CAR specific for oligomeric Aβ may migrate to the hippocampus, wherein oligomeric Aβ may accumulate.

Moreover, in some exemplary embodiments, modified Tregs comprising anti-Aβ CARs may traffic and accumulate to brain regions of Aβ deposits and neuroinflammation, wherein such regions may include sites of Aβ deposits in the hippocampus and frontal cortex. In some embodiments, modified Tregs comprising CARs targeting Alzheimer's may accumulate in said brain regions and may lead to increased expression of human anti-inflammatory cytokines IL-10, TGF-β, and IL4 in said regions. These anti-inflammatory cytokines may lead to decreased expression of pro-inflammatory mediators and the numbers of microglia. In some exemplary embodiments, modified Tregs comprising CARs targeting Alzheimer's disease may improve memory function in a patient treated with said modified Tregs.

Specific features of and/or that may be comprised by modified Tregs and/or specific features that may be comprised by targets of modified Tregs are discussed in greater detail below.

CARs

In exemplary embodiments, modified Tregs may comprise one or more CARs targeted to a neurodegenerative disease or condition, as discussed above and below. In some exemplary embodiments, one or more CARs may comprise an AB domain that binds to a target molecule which is associated with a neurodegenerative disease or condition. AB domains are discussed further below.

Antigen Binding (AB) Domain

The AB domain may be derived from a polypeptide that binds to a target molecule. In some embodiments, the polypeptide may be a receptor or a portion of a receptor that binds to a target molecule. In another embodiment, the AB domain may be derived from a ligand that binds to the target molecule.

In another embodiment, the AB domain may be derived from an antibody (Ab) or antigen-binding fragment thereof that binds to a target molecule. Examples of an Ab or antigen-binding fragment thereof include, but are not limited to, a monoclonal Ab, a monospecific Ab, a polyspecific Ab, a humanized Ab, a tetrameric Ab, a tetravalent Ab, a multispecific Ab, a single chain Ab, a domain-specific Ab, a single-domain Ab (dAb), a domain-deleted Ab, an scFc fusion protein, a chimeric Ab, a synthetic Ab, a recombinant Ab, a hybrid Ab, a mutated Ab, CDR-grafted Ab, an Ab fragment comprising a fragment antigen-binding (Fab), an $F(ab')_2$, an Fab' fragment, an variable fragment (Fv), a single-chain antibody fragment, a single-chain Fv (scFv) fragment, an Fd fragment, a dAb fragment, a diabody, a nanobody, a bivalent nanobody, a shark variable IgNAR domain, a VHH Ab, a camelid Ab, and a minibody. In a particular embodiment, the AB domain comprises a single-chain antibody fragments comprising a variable heavy chain region and/or a variable light chain region, such as scFv. In another particular embodiment, the AB domain comprises a nanobody.

Single-domain Abs are Ab fragments comprising all or a portion of the heavy chain variable domain or all or a portion of the light chain variable domain of an antibody. In certain embodiments, a single-domain antibody is a human single-domain antibody Antibody fragments can be made by various techniques, including but not limited to proteolytic digestion of an intact Ab as well as production by recombinant host cells. In some embodiments, the antibodies are recombinantly produced fragments, such as fragments comprising arrangements that do not naturally occur, such as those with two or more Ab regions or chains joined by synthetic linkers, such as peptide linkers, and/or that may not be produced by enzyme digestion of a naturally occurring intact Ab. In some aspects, the Ab fragments are scFvs. In some aspects, the Ab fragments are nanobodies.

In some aspects, the AB domain may be derived from an Ab or an antigen-binding fragment thereof that has one or more specified functional features, such as binding properties, including binding to particular epitopes, such as epitopes that are similar to or overlap with those of other Abs.

In some embodiments, the AB comprises an scFv comprising CDR sequences of an Ab specific to the target molecule. CDRs may be determined using conventional methods. The precise amino acid sequence boundaries of a given CDR or FR can be readily determined using any of a number of well-known schemes, including those described by Kabat et al. (1991), "Sequences of Proteins of Immunological Interest," $5^{th}$ Ed. Public Health Service, National Institutes of Health, Bethesda, Md. ("Kabat" numbering scheme), Al-Lazikani et al., "(1997) *J. Mol. Biol.* 273, 927-948 ("Chothia" numbering scheme), MacCallum et al., *J. Mol. Biol.* 262:732-745 (1996), "Antibody-antigen interactions: Contact analysis and binding site topography," *J. Mol. Biol.* 262, 732-745 ("Contact" numbering scheme), Lefranc M P et al., "IMGT unique numbering for immunoglobulin and T cell receptor variable domains and Ig superfamily V-like domains," *Dev Comp Immunol,* 2003 January; 27(1):55-77 ("IMGT" numbering scheme), and Honegger A and Pluckthun A, "Yet another numbering scheme for immunoglobulin variable domains: an automatic modeling and analysis tool," *J Mol Biol,* 2001 Jun. 8; 309(3):657-70, ("Aho" numbering scheme).

In some embodiments, the sequence comprising the AB domain further comprises a leader sequence or signal sequence. In some embodiments where the AB domain comprises an scFv, the leader sequence may be positioned at the amino terminus of the scFv. In some embodiments where the heavy chain variable region is N-terminal, the leader sequence may be positioned at the amino terminus of the heavy chain variable region. In some embodiments where the light chain variable region is N-terminal, the leader sequence may be positioned at the amino terminus of the light chain variable region. The leader sequence may comprise any suitable leader sequence. In some embodiments of the invention, the amino acid sequence of the leader sequence may comprise a sequence as set forth in SEQ ID NO: 31, or a sequence encoded by the nucleic acid sequence as set forth in SEQ ID NO: 231. In the mature form of the isolated cells of the invention, the leader sequence may not be present.

Hinge

In some embodiments, a modified Treg may comprise one or more CARs, and said CARs may comprise a hinge sequence between the AB domain and a TM domain. One of the ordinary skill in the art will appreciate that a hinge sequence is a short sequence of amino acids that facilitates flexibility (see, e.g. Woof et al., *Nat. Rev. Immunol.,* 4(2): 89-99 (2004)). The hinge sequence can be any suitable sequence derived or obtained from any suitable molecule. In some embodiments, the length of the hinge sequence may be optimized based on the desired length of the extracellular portion of a CAR, which may be based on the location of the epitope within the target molecule. For example, if the epitope is in the membrane proximal region within the target molecule, longer hinges may be optimal.

In some embodiments, the hinge may be derived from or include at least a portion of an immunoglobulin Fc region, for example, an IgG1 Fc region, an IgG2 Fe region, an IgG3 Fc region, an IgG4 Fc region, an IgE Fc region, an IgM Fc region, or an IgA Fe region. In some embodiments, the hinge includes at least a portion of an IgG1, an IgG2, an IgG3, an IgG4, an IgE, an IgM, or an IgA immunoglobulin Fc region that falls within its CH2 and CH3 domains. In some embodiments, the hinge may also include at least a portion of a corresponding immunoglobulin hinge region. In some embodiments, the hinge is derived from or includes at least a portion of a modified immunoglobulin Fc region, for example, a modified IgG1 Fc region, a modified IgG2 Fc region, a modified IgG3 Fc region, a modified IgG4 Fc region, a modified IgE Fc region, a modified IgM Fc region, or a modified IgA Fc region. The modified immunoglobulin Fc region may have one or more mutations (e.g., point mutations, insertions, deletions, duplications) resulting in one or more amino acid substitutions, modifications, or deletions that cause impaired binding of the hinge to an Fe receptor (FcR). In some aspects, the modified immunoglobulin Fe region may be designed with one or more mutations which result in one ore more amino acid substitutions, modifications, or deletions that cause impaired binding of the hinge to one or more FcR including, but not limited to, FcγRI, FcγR2A, FcγR2B1, Fcγ2B2, Fcγ 3A, Fcγ 3B, FcεRI, FcεR2, FcαRI, Fcα/μR, or FcRn.

In some aspects, a portion of the immunoglobulin constant region serves as a hinge between the AB domain, for example scFv or nanobody, and the TM domain. The hinge can be of a length that provides for increased responsiveness of the CAR-expressing cell following antigen binding, as compared to in the absence of the hinge. In some examples, the hinge is at or about 12 amino acids in length or is no more than 12 amino acids in length. Exemplary hinges include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a hinge has about 12 amino acids or less, about 119 amino acids or less, or about 229 amino acids or less. Exemplary hinges include a CD28 hinge, IgG4 hinge alone, IgG4 hinge linked to $CH_2$ and $CH_3$ domains, or IgG4 hinge linked to the CH3 domain. Exemplary hinges include, but are not limited to, those described in Hudecek et al.

(2013) *Clin. Cancer Res.,* 19:3153, international patent application publication number WO2014031687, U.S. Pat. No. 8,822,647 or published App. No. US2014/0271635.

In some embodiments, the hinge sequence is derived from CD8a molecule, a DAP10 molecule, a CD8a molecule, or a CD28 molecule. In a preferred embodiment, the hinge sequence is derived from CD28. In one embodiment, the hinge comprises the amino acid sequence of human CD28 hinge (SEQ ID NO: 32) or the sequence encoded by SEQ ID NO: 232. In some embodiments, the hinge has an amino acid sequence at least 85%, 86%, 87%, 88%, 89%, 90%, 91%, 92%, 93%, 94%, 95%, 96%, 97%, 98%, 99%, or 100% identical to SEQ ID NO: 32. In some embodiments, the hinge comprises the amino acid sequence of mouse CD28 hinge (SEQ ID NO: 33) or the sequence encoded by SEQ ID NO: 233. In some embodiments, the hinge has an amino acid sequence at least 85%, 86%, 87%, 88%, 89%, 90%, 91%, 92%, 93%, 94%, 95%, 96%, 97%, 98%, 99%, or 100% identical to SEQ ID NO: 33. In one embodiment, the hinge comprises the amino acid sequence of human CD8A hinge (SEQ ID NO: 34) or the sequence encoded by SEQ ID NO: 234. In some embodiments, the hinge has an amino acid sequence at least 85%, 86%, 87%, 88%, 89%, 90%, 91%, 92%, 93%, 94%, 95%, 96%, 97%, 98%, 99%, or 100% identical to SEQ ID NO: 34. In one embodiment, the hinge comprises the amino acid sequence of human DAP10 hinge (SEQ ID NO: 35) or the sequence encoded by SEQ ID NO: 235. In some embodiments, the hinge has an amino acid sequence at least 85%, 86%, 87%, 88%, 89%, 90%, 91%, 92%, 93%, 94%, 95%, 96%, 97%, 98%, 99%, or 100% identical to SEQ ID NO: 35.

Transmembrane (TM) Domain

In some embodiments, a modified Treg may comprise one or more CARs, and said CARs may comprise a TM domain. With respect to the TM domain, a CAR can be designed to comprise a TM domain that is fused to the AB domain of the CAR. A hinge sequence may be inserted between the AB domain and the TM domain. In some embodiments, a TM domain that naturally is associated with one of the domains in the CAR is used. In some instances, the TM domain can be selected or modified by amino acid substitution to avoid binding of such domains to the transmembrane domains of the same or different surface membrane proteins to minimize interactions with other members of the receptor complex.

A TM domain may be derived either from a natural or from a synthetic source. Where the source is natural, the domain may be derived from any membrane-bound or transmembrane protein. Typically, the TM domain denotes a single transmembrane α helix of a transmembrane protein, also known as an integral protein. TM domains of particular use in this invention may be derived from (i.e. comprise at least the transmembrane region(s) of) CD28, CD3 ε, CD4, CD8, CD8, CD9, CD16, CD22, CD33, CD3ζ, CD45, CD64, CD80, CD86, CD134, CD137, CD154, Dap10, CD44, CTLA-4, TCR α, TCR β, or CD3 zeta (SEQ ID NO: 16, which may be encoded by SEQ ID NO: 216) and/or TM domains containing functional variants thereof such as those retaining a substantial portion of the structural, e.g., transmembrane, properties thereof.

Alternatively the TM domain may be synthetic, in which case the TM domain will comprise predominantly hydrophobic residues such as leucine and valine. Preferably a triplet of phenylalanine, tryptophan and valine will be found at each end of a synthetic TM domain. A TM domain of the invention is thermodynamically stable in a membrane. It may be a single a helix, a transmembrane β barrel, a β-helix of gramicidin A, or any other structure. Transmembrane helices are usually about 20 amino acids in length.

In some preferred embodiments, the TM domain in a CAR may be derived from the TM region of CD28. In one embodiment, the TM domain comprises the amino acid sequence of human CD28 TM (SEQ ID NO: 36) or the sequence encoded by SEQ ID NO: 236. In some embodiments, the TM domain comprises an amino acid sequence at least 85%, 86%, 87%, 88%, 89%, 90%, 91%, 92%, 93%, 94%, 95%, 96%, 97%, 98%, 99%, or 100% identical to SEQ ID NO: 36. In one embodiment, the TM domain comprises the amino acid sequence of mouse CD28 TM (SEQ ID NO: 37) or the sequence encoded by SEQ ID NO: 237. In some embodiments, the TM domain comprises an amino acid sequence at least 85%, 86%, 87%, 88%, 89%, 90%, 91%, 92%, 93%, 94%, 95%, 96%, 97%, 98%, 99%, or 100% identical to SEQ ID NO: 37. In one embodiment, the TM domain comprises the amino acid sequence of human CD8A TM (SEQ ID NO: 38) or the sequence encoded by SEQ ID NO: 238. In some embodiments, the TM domain comprises an amino acid sequence at least 85%, 86%, 87%, 88%, 89%, 90%, 91%, 92%, 93%, 94%, 95%, 96%, 97%, 98%, 99%, or 100% identical to SEQ ID NO: 38. In one embodiment, the TM domain comprises the amino acid sequence of human DAP10 TM (SEQ ID NO: 39) or the sequence encoded by SEQ ID NO: 239. In some embodiments, the TM domain comprises an amino acid sequence at least 85%, 86%, 87%, 88%, 89%, 90%, 91%, 92%, 93%, 94%, 95%, 96%, 97%, 98%, 99%, or 100% identical to SEQ ID NO: 39.

Optionally, a short oligo- or polypeptide spacer, preferably between 2 and 10 amino acids in length may form the linkage between the TM domain and the ICS domain(s) of a CAR. A glycine-serine doublet may provide a suitable spacer.

Intracellular Signaling (ICS) Domain and Costimulatory (CS) Domain

In some embodiments, a modified Treg may comprise one or more CARs, and said CARs may comprise a ICS and/or CS domain. The ICS domain or otherwise the cytoplasmic domain of a CAR may trigger or elicit activation of at least one of the normal functions of the cell in which the CAR has been placed, for example, the secretion of cytokines. Thus, the term "intracellular signaling domain" or "ICS domain" refers to the portion of a protein which transduces a functional signal and directs the cell to perform a specialized function. While usually the entire ICS domain may be employed, in many cases it is not necessary to use the entire chain. To the extent that a truncated portion of the intracellular signaling domain is used, such truncated portion may be used in place of the intact chain as long as it transduces the function signal. The term "intracellular signaling domain" or "ICS domain" is thus meant to include any truncated portion of the ICS domain sufficient to transduce a function signal.

Signals generated through one ICS domain alone may be insufficient for full activation of a cell, and a secondary or costimulatory signal may also be required. In such cases, a costimulatory domain (CS domain) may be included in the cytoplasmic portion of a CAR. A CS domain is a domain that transduces such a secondary or costimulatory signal. Optionally, a CAR may comprise two or more CS domains. The CS domain(s) may be placed upstream of the ICS domain or downstream of the ICS domain.

For example, T cell activation can be said to be mediated by two distinct classes of cytoplasmic signaling sequence: those that initiate antigen-dependent primary activation through the T cell receptor (TCR) (primary cytoplasmic signaling sequences) and those that act in an antigen-independent manner to provide a secondary or costimulatory signal (secondary cytoplasmic signaling sequences). Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Such a cytoplasmic signaling sequence may be contained in the ICS or the CS domain of a CAR.

Examples of ITAM-containing primary cytoplasmic signaling sequences that are of particular use may include those derived from an ICS domain of a lymphocyte receptor chain, a TCR/CD3 complex protein, an Fc receptor subunit, an IL-2 receptor subunit, CD3 ζ, FcR γ, FcR β, CD3 γ, CD3 δ, CD3 ε, CD5, CD22, CD66d, CD79a, CD79b, CD278 (ICOS), Fc ε RI, DAP10, and DAP12.

In some embodiments, an ICS domain in a CAR may comprise a cytoplasmic signaling sequence derived from CD3 zeta. In some embodiments, the ICS domain comprises the amino acid sequence of SEQ ID NO: 16), or the sequence encoded by SEQ ID NO: 216. In some embodiments, the ICS domain comprises an amino acid sequence at least 85%, 86%, 87%, 88%, 89%, 90%, 91%, 92%, 93%, 94%, 95%, 96%, 97%, 98%, 99%, or 100% identical to SEQ ID NO: 16.

Various CS domains have been reported to confer differing properties (Gacerez et al. J. Cell. Physiol. 231: 2590-2598, 2016). For example, the 4-1BB CS domain has been reported to exhibit enhanced persistence in some in vivo xenograph models (Milone et al. *Mol Ther* 2009; 17:1453-1464; Song et al. *Cancer Res* 2011; 71:4617-4627). Additionally, these different CS domains produce different cytokine profiles, which in turn, may produce different effects on target cell-mediated cytotoxicity and the disease microenvironment.

Examples of co-stimulatory molecules include MHC class I molecules, TNF receptor proteins, immunoglobulin-like proteins, cytokine receptors, integrins, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8 α, CD8 β, CD11a, LFA-1 (CD11a/CD18), CD11b, CD11c, CD1 Id, CD18, CD19, CD19a, CD27, CD28, CD29, CD30, CD40, CD49a, CD49D, CD49f, CD69, CD84, CD96 (Tactile), CD100 (SEMA4D), CD103, CRTAM, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2R β, IL2R γ, IL7R α, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGL1, SLAMF6 (NTB-A, Ly108), SLAMF7, SLP-76, TNFR2, TRANCE/RANKL, VLA1, VLA-6, a ligand that specifically binds with CD83, and the like.

The ICS domain and the CS domain(s) of a CAR may be linked to each other in a random or specified order. Optionally, a short oligo- or polypeptide linker, preferably between 2 and 10 amino acids in length may form the linkage. A glycine-serine doublet provides a particularly suitable linker.

Further Modifications

In some embodiments, a modified Treg may comprise one or more CARs, and said CARs may comprise further modifications. In some embodiments, one or more CARs, nucleotide sequences encoding the same, vectors encoding the same, and cells comprising nucleotide sequences encoding said CARs may be further modified, engineered, optimized, or appended in order to provide or select for various features. These features may include, but are not limited to, efficacy, persistence, target specificity, reduced immunogenicity, multi-targeting, enhanced immune response, expansion, growth, reduced off-target effects, reduced subject toxicity, detection, selection, targeting, and the like. For example, the cells may be engineered to express another CAR, or to have a suicide mechanism, and may be modified to remove or modify expression of an endogenous receptor or molecule such as a TCR and/or MHC molecule.

In some embodiments, a vector or nucleic acid sequence encoding a CAR further encodes other genes. The vector or nucleic acid sequence may be constructed to allow for the co-expression of multiple genes using a multitude of techniques including co-transfection of two or more plasmids, the use of multiple or bidirectional promoters, or the creation of bicistronic or multicistronic vectors. The construction of multicistronic vectors may include the encoding of IRES elements or 2A peptides, such as T2A, P2A (which amino acid sequence may comprise SEQ ID NO: 15, which may be encoded by SEQ ID NO: 215), E2A, or F2A (for example, see Kim, J. H., et al., "High cleavage efficiency of a 2A peptide derived from porcine teschovirus-1 in human cell lines, zebrafish and mice", *PLoS One.* 2011; 6(4)). In some embodiments, the nucleic acid sequence or vector encoding a CAR further encodes tCD19 with the use of a T2A ribosomal skip sequence. In one embodiment, the T2A ribosomal skip sequence comprises the nucleic acid sequence as set forth in SEQ ID NO: 214. In one embodiment, the T2A ribosomal skip sequence encodes the amino acid sequence of SEQ ID NO: 14.

CARs comprised by modified Tregs according to the invention optionally may be further modified to improve efficacy against cells expressing the target molecule. In some embodiments, the improved efficacy may be measured by a decrease in microglial cell activation, a decrease in inflammatory response, and/or a decrease in neuronal death. In some embodiments, modified Tregs comprising one or more CARs may further comprise more than a CAR. Additional CARs may or may not be specific for the target molecule of the first CAR. In some embodiments, the one or more additional CARs may act as inhibitory or activating CARs. In some aspects, a CAR of some embodiments is the stimulatory or activating CAR; in other aspects, it is the costimulatory CAR. In some embodiments, modified Tregs may further include inhibitory CARs (iCARs, see Fedorov et al., *Sci. Transl. Medicine,* 2013 December; 5(215): 215ra172), such as a CAR recognizing an antigen other than the target molecule of the first CAR, whereby an activating signal delivered through the first CAR is modified or altered by binding of the inhibitory CAR to its ligand, e.g., to reduce off target effects.

Vectors or Constructs

The present disclosure also provides vectors or constructs such as plasmids or retroviral constructs in which a DNA may be inserted such as one encoding a CAR. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs may typically achieved by operably linking a nucleic acid encoding a CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, γ-retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Various promoter sequences may be used, including, but not limited to the immediate early cytomegalovirus (CMV) promoter, the CMV-actin-globin hybrid (CAG) promotor, Elongation Growth Factor-1α (EF-1α), simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Inducible promoters are also contemplated for use. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

In some embodiments, the selectable marker gene comprises a nucleic acid sequence encoding truncated CD19 (trCD19).

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tei et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Transduction of Tregs

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means Treg Cells Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and disease sites. In some embodiments, any number of T cell lines available and known to those skilled in the art, may be used. In some embodiments, cells can be derived from a healthy donor or from a patient diagnosed with a neurodegenerative disease or condition.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom In some aspects, the sample from which the cells are derived or isolated is blood or a blood-derived sample, or is or is derived from an apheresis product. Exemplary samples include whole blood, peripheral blood mononuclear cells (PBMCs), leukocytes, bone marrow, thymus, tissue biopsy, neural tissue, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

Cell Purification

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, the surface maker is trCD19. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population In some embodiments, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level ($marker^{high}$) on the positively or negatively selected cells, respectively.

In some embodiments, Tregs may be isolated, expanded, and transduced as follows: cells may be isolated from human PBMCs via a two-step negative and positive selection protocol. First, $CD4^+$ cells are isolated using negative selection, followed by a positive selection of $CD25hi^+$ cells to isolate $CD4^+CD25hi^+$ Treg cells. The isolated $CD4^+CD25hi^+$ Tregs may be activated with anti-CD3, anti-CD28, anti-CD2 multimers or anti-CD3, anti-CD28 multimers (STEMCELL ImmunoCult) with human IL-2 (300 U/ml to 500 U/ml) over two weeks in culture in Treg growth medium. On day 9, Treg cells can be cryopreserved for use at a later date, so we can test the same donor and preparation on multiple occasions to assess assay variability.

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 disclose other examples of such particles.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the magnetically responsive particles are coated in primary antibodies or other binding partners, secondary antibodies, lectins, enzymes, or streptavidin. In some embodiments, the magnetic particles are attached to cells via a coating of primary antibodies specific for one or more markers. In some embodiments, the cells, rather than the beads, are labeled with a primary antibody or binding partner, and then cell-type specific secondary antibody- or other binding partner (e.g., streptavidin)-coated magnetic particles, are added. In some embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In some embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) *J Biophoton.* 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (PACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the methods include density-based cell separation methods, such as the preparation of white blood cells from peripheral blood by lysing the red blood cells and centrifugation through a Percoll or Ficoll gradient.

In any of the aforementioned separation steps, the separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

Cell Preparation and Expansion

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation.

In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The cells discussed herein can be activated and expanded, either prior to or after genetic modification of the cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318;

7,172,869; 7,232,566; 7,175,843; 5,883,223; 6,905,874; 6,797,514; 6,867,041; and U.S. Patent Application Publication No. 20060121005. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

Tregs can be expanded in vitro or in vivo. In some embodiments, the isolated cells of the invention can be expanded by co-culturing with tissue or cells. The cells can also be expanded in vivo, for example in the subject's blood after administrating the cell into the subject.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° Celsius at a rate of 1 degree per minute and stored in the vapor phase of a liquid nitrogen storage tank.

Methods Using Modified TREGS According to the Invention

In exemplary embodiments, treatment of neurodegenerative diseases, conditions, and/or disorders may comprise administration of an effective amount of one or more modified Tregs as disclosed herein. In exemplary embodiments, treatment of a neurodegenerative disease by administering one or more types of modified Tregs according to the invention (e.g., wherein such Tregs may include those which express different CARS and/or NDDMs) may result in a decrease in inflammation, modulation of microglial cell activity, and/or decreased neuronal damage at the sites where the protein and/or molecular marker is expressed (i.e. diseased tissue). In exemplary embodiments, modified Tregs according to the invention may be administered to a patient in need of treatment, wherein said modified Tregs may be administered by intravenous injection, subcutaneous injection, intracavitary injection, intraventricular injection, intracranial injection, or intrathecally injection. Exemplary treatment methods generally comprise the administration of an effective amount of one or more modified Tregs, wherein such treatment comprising said modified Tregs may modulate local inflammation or neuronal survival. Said modulation may occur, in some embodiments, by expression of specific molecules, e.g., NDMMs, e.g., anti-oxidants, e.g., neuronal growth and/or survival factors.

In exemplary embodiments, modified Tregs according to the invention, e.g., modified Tregs comprising one or more CARs, may be used in a method of treating Parkinson's disease. Said modified Tregs targeted to Parkinson's disease may comprise one or more CARs, wherein said one or more CARs may target α-synuclein fibrils. In some embodiments, a CAR targeted to alpha-synuclein may comprise a sequence of DG08 (SEQ ID NO: 8). In some embodiments, a CAR targeted to alpha-synuclein may comprise a sequence of DG09 (SEQ ID NO: 9). In some embodiments, a CAR targeted to alpha-synuclein may comprise a sequence of DG10 (SEQ ID NO: 10). In some embodiments, a CAR targeted to alpha-synuclein may comprise a sequence of DG11 (SEQ ID NO: 11). In some embodiments, a modified Treg may comprise DG08-CD28-CD3ζ (SEQ ID NO: 27), DG09-CD28-CD3ζ (SEQ ID NO: 28), DG10-CD28-CD3ζ (SEQ ID NO: 29), and/or DG11-CD28-CD3ζ (SEQ ID NO: 30), wherein each construct is targeted to alpha-synuclein. In further exemplary embodiments, modified Tregs, such as modified Tregs comprising one or more CARs, may be used to treat Parkinson's disease and may target one or more neurotoxic inflammatory mediators, e.g., neurotoxic inflammatory mediations produced by activated microglia. Said modified Tregs may decrease and/or inhibit microglia activation. In exemplary embodiments, modified Tregs targeting Parkinson's disease may comprise targeted anti-inflammatory and neuroprotective therapeutic activity at the disease site of dopamine neuron degeneration in PD. In some embodiments, modified Tregs targeting Parkinson's may mediate their function only at the site where α-synuclein fibrils are present.

Furthermore, modified Tregs targeting Parkinson's disease may be used in methods of treating Parkinson's disease, wherein said modified Tregs may comprise one or more CARs and/or one or more NDMMs targeted to Parkinson's disease, and further wherein said one or more CARs comprise single chain variable fragments such as $V_H$ and $V_L$ amino acid sequences of human and mouse monoclonal antibodies against human α-synuclein fibrils (such as, for example, amino acid sequences derived from clones NI 202.3G12, NI 202.12F4, NI 202.21D11, and mAb49/G). In exemplary embodiments, modified Tregs targeting Parkinson's disease may comprise said scFV and further comprise a construct comprising CD28-CD3ζ CAR, i.e., scFv-CD28-CD3ζ CAR, wherein said scFv is specific for human α-synuclein fibrils. Constructs comprising said scFv may comprise $V_H$+$V_L$ and $V_L$+$V_H$ arrangements.

In exemplary embodiments, modified Tregs according to the invention, e.g., modified Tregs comprising one or more CARs, may be used in a method of treating ALS. Said modified Tregs targeted to Parkinson's disease may comprise one or more CARs and/or one or more NDMMs targeted to ALS. Said modified Tregs may target mutSOD1, e.g., said modified Tregs may comprise one or more CARs targeted to mutSOD1. In some embodiments, a CAR targeted to mutSOD1 may comprise a sequence of DG05 (SEQ ID NO: 5). In some embodiments, a CAR targeted to mutSOD1 may comprise a sequence of DG06 (SEQ ID NO: 6). In some embodiments, a CAR targeted to mutSOD1 may comprise a sequence of DG07 (SEQ ID NO: 7). In some embodiments, a modified Treg may comprise DG05-CD28-CD3ζ (SEQ ID NO: 24), DG06-CD28-CD3ζ (SEQ ID NO: 25), and/or DG07-CD28-CD3ζ (SEQ ID NO: 26), wherein each construct is targeted to mutSOD1. In some embodiments, a modified Treg may comprise DG05-CD28-CD3ζ (also referred to as DG05-28-3ζ) (SEQ ID NO: 24); DG05-CD28tm-DAP10-CD3ζ (also referred to as DG05-28tm-10-3ζ) (SEQ ID NO: 40); DG05-CD28tm-CD44-CD3ζ (also referred to as DG05-28tm-44-3ζ) (SEQ ID NO: 41); DG05-CD28tm-CD3ζ (also referred to as DG05-28tm-3ζ) (SEQ ID NO: 42); DG05-CD28 (also referred to as DG05-28) (SEQ ID NO: 43); and/or DG05-CD28tm (also referred to as DG05-28tm) (SEQ ID NO: 44), wherein each of the constructs is targeted to mutSOD1. In some embodiments, modified Tregs may become activated at sites of mutSOD1-producing motor neurons and/or sites of inflammation thereby resulting in reduced inflammation at the disease site in methods comprising treatment of ALS comprising use of modified Tregs.

In some embodiments, one or more modified Tregs may comprise any one or more of DG05-28-3ζ; DG05-28tm-10-3ζ; DG05-28tm-44-3ζ; DG05-28tm-3ζ; and/or DUOS-28, and said modified Tregs may produce IL-10 in response to mSOD1 antigen. In some embodiments, one or more modified Tregs may comprise any one or more of DG05-28-3ζ; DG05-28tm-10-3ζ; DG05-28tm-44-3ζ; DG05-28tm-3ζ; and/or DG05-28, and said modified Tregs may produce increased levels of IL-10 in response to mSOD1 antigen as compared to modified Tregs not exposed to mSOD1. In some embodiments, one or more modified Tregs may comprise DG05-CD28-CD3ζ, and said modified Tregs may comprise increased expression of cell surface markers such as GITR, PD-1, and/or CTLA-4 in response to mSOD1 as compared to modified Tregs not exposed to mSOD1. In some embodiments, one or more modified Tregs may comprise DG05-CD28-CD3ζ, and said modified Tregs may produce IL-10 in response to mSOD1 antigen, e.g., mSOD1 antigen that may be found in spinal cord tissue, as compared to modified Tregs not exposed to mSOD1 antigen. In some embodiments, one or more modified Tregs may comprise DG05-CD28-CD3ζ, and said modified Tregs, when stimulated with mSOD1 antigen and/or anti-CD3 antibody, may inhibit superoxide generation as compared to modified Tregs that were not stimulated with mSOD1 antigen or anti-CD3 antibody. In some embodiments, one or more modified Tregs may comprise DG05-CD28-CD3ζ, and said modified Tregs, when stimulated with mSOD1 antigen, may inhibit TNF-α production as compared to modified Tregs not stimulated with mSOD1 antigen.

In some embodiments, modified Tregs targeting ALS may be used in methods of treating ALS and may comprise CARs targeted to mutSOD1, and in some exemplary embodiments an scFv of one or more of said CARs may be expressed extracellularly with the C-terminus of the $V_L$ fused to human CD28 hinge, transmembrane, and cytoplasmic domain, followed by a human CD3ζ t cytoplasmic domain to create an anti-mutSOD1-CD28-CD3ζ CAR. In some embodiments, an scFv of a CAR comprised by a modified Treg according to the invention targeting ALS may be constructed by linking heavy chain variable region and light chain variable region with a linker, such as, for example, a $(G_4S)_3$ linker. In some embodiments, the C-terminus of a $V_L$ of a CAR of a modified Treg targeting ALS may be fused with human CD28 hinge, transmembrane, and cytoplasmic domain, and may be followed by a human CD3ζ cytoplasmic domain. Said CAR of said modified Treg targeting ALS may e.g., be an anti-mutSOD1 CAR. Said CARs may trigger both primary and costimulation signaling upon antigen binding, e.g., binding of mutSOD1. In some embodiments, a CAR expressed by the Treg may comprise a costimulating domain including but not limited to comprising, CD3ζ alone, 4-1BB, or CD28. In some embodiments a truncated (non-signaling) human CD19 (tCD19) may also expressed in the same vector as said CARs, such as by using a 2A co-expression system, said tCD19 may serve as a way to track and purify transduced T cells. In some embodiments, methods of treating ALS may comprise use of modified Tregs targeted to ALS that may enter the spinal cord when administered to a patient in need of treatment. In some exemplary embodiments, modified Tregs targeted to ALS may comprise markers such as, for example, VLA4, LFA-1, CCR6, CXCR3 or other proteins which promote neuron survival and/or functionality and/or prolong T cell function. In exemplary embodiments, modified CARs targeted to ALS, e.g., modified Tregs comprising one or more anti-mutSOD1 CARs, may preserve a Treg phenotype when expressing one or more CARs and/or one or more NDMMs. In exemplary embodiments, modified Tregs may express IL-10 in response to an ALS protein and/or molecular marker of disease when used in methods of treating ALS.

Furthermore, methods of treating ALS according to the invention may comprise use of modified Tregs which secrete anti-inflammatory cytokines, thereby resulting in an inhibition of activated microglia and/or macrophages. Said secretion may occur as a result of stimulation of one or more CARs expressed by said modified Tregs for an ALS protein and/or disease associated marker, such as mutSOD1. In some embodiments, said cytokines may comprise IL-10, IL-4, TGF-β. In exemplary embodiments, modified Tregs may reduce and/or prevent production of neurotoxic free radicals and inflammatory cytokines by microglia when used in methods of treating ALS. In some exemplary embodiments, modified Tregs may be used in methods of treating ALS, and said methods may result in one or more of the following as compared to a control treatment less macrophage mediated motor neuron death; less IL-1β, TNF-α, and nitric oxide; and greater amounts of IL-10, IL-4, and TGF-β. In some embodiments, a method of treating ALS may comprise use of modified Tregs targeting C9orf72 (sC9orf72), and may achieve similar results and may be used in a similar manner as to modified Tregs targeting mutSOD1.

Moreover, some methods of treating ALS according to the invention may comprise use of modified Tregs, wherein said modified Tregs may comprise anti-mutSOD1 CARs, and said modified Tregs may enter the spinal cord parenchyma, recognize accumulated spinal mutSOD1 protein, and react by producing anti-inflammatory mediators. Said modified Tregs may decrease expression of inflammatory mediators (e.g. CCL2, CCL3, CCL4, TNF-α, IL1β, NOX2) and increase expression of anti-inflammatory mediators (e.g. IL-10, IL-4, and TGF-β) when administered to a patient in need of treatment. Furthermore, modified Tregs targeted to ALS, such as modified Tregs comprising anti-mutSOD1 CARs, may inhibit persistent and/or neurotoxic inflammation around motor neurons when used in methods of treating ALS.

In some exemplary embodiments, modified Tregs, e.g., modified Tregs comprising one or more CARs, may be used in methods of treating Alzheimer's disease. Said modified Tregs may be targeted to proteins and/or molecular markers associated with Alzheimer's disease. In exemplary embodiments, said modified Tregs may comprise one or more CARs targeted to said proteins and/or markers. In some embodiments, said protein and/or marker may comprise amyloid-beta (Aβ), in particular oligomeric Aβ, and/or intraneuronal tangles of twisted tau protein fibers. In some embodiments, a CAR targeted to amyloid beta may comprise a sequence of DG01 (SEQ ID NO: 1). In some embodiments, a CAR targeted to amyloid beta may comprise a sequence of D002 (SEQ ID NO: 2). In some embodiments, a CAR targeted to amyloid beta may comprise a sequence of DG03 (SEQ ID NO: 3). In some embodiments, a CAR targeted to amyloid beta may comprise a sequence of DG04 (SEQ ID NO: 4). In some embodiments, a modified Treg may comprise DG01-CD28-CD3ζ (SEQ ID NO: 20), DG02-CD28-CD3ζ (SEQ ID NO: 21), DG03-CD28-CD3ζ (SEQ ID NO: 22), and/or DG04-CD28-CD3ζ (SEQ ID NO: 23), wherein each construct is targeted to amyloid-beta. In some embodiments, a modified Treg may comprise DG03-CD28-CD3ζ (also referred to as DG03-28-3ζ) (SEQ ID NO: 22); DG03-CD28tm-DAP10-CD3ζ (also referred to as DG03-28tm-10-3ζ) (SEQ ID NO: 45); D003-CD28tm-CD44-CD3ζ (also referred to as DG03-28tm-44-3ζ) (SEQ ID NO: 46); D003-CD28tm-4-1-BB-CD3ζ (also referred to as DG03-28tm-BB-3ζ) (SEQ ID NO: 47); DG03-CD28tm-CD3ζ (also referred to as DG03-28tm-3ζ) (SEQ ID NO: 48); DG03-CD28 (also referred to as DG03-28) (SEQ ID NO: 49); and/or DG03-CD28tm (also referred to as D003-28tm) (SEQ ID NO: 50), wherein each of the constructs is targeted to amyloid-beta. In exemplary embodiments, CARs comprised by modified Tregs may be targeted to Aβ peptides, and may comprise anti-AβCARs using single chain variable fragment (scFv) sequences from antibodies, e.g., human and/or humanized antibodies, with different binding specificities to Aβ, e.g., oligomeric Aβ. In some exemplary embodiments, said scFvs may fused to human CD28 hinge, transmembrane, and cytoplasmic domains, followed by a human CDR3ζ cytoplasmic domain. Said CARs may trigger both primary (CD3ζ) and co-stimulatory (CD28) signaling upon antigen binding and cross-linking. In some embodiments, a truncated (non-signaling) CD19 (tCD19) may also expressed in the same vector comprising said CARs, such as by using a T2A co-expression system, and it may serve as a means to track and purify transduced T cells. Modified Tregs comprising anti-Aβ CARs used in methods of treating Alzheimer's disease may suppress proliferation of CD3-activated allogeneic CD8+ T cells in some embodiments. Furthermore, in some embodiments, when activated with oligomeric Aβ, modified Tregs comprising anti-Aβ CARs may produce anti-inflammatory cytokines, e.g., IL-10 when used in methods of treating Alzheimer's disease. Furthermore, said modified Tregs may inhibit production of pro-inflammatory mediators and may enhance phagocytic capacity of activated microglia or macrophages such as by secreting IL-10, TGF-β, and IL-4 anti-inflammatory cytokines for example when used in methods of treating Alzheimer's disease. In some exemplary embodiments, modified Tregs comprising expression of a CAR specific for oligomeric Aβ may have targeted anti-inflammatory activity and neuroprotective effects in regions where oligomeric Aβ may accumulate when used in methods of treating Alzheimer's disease. In some exemplary embodiments, modified Tregs according to the invention may migrate to the hippocampus, wherein oligomeric Aβ may accumulate, when used in methods of treating Alzheimer's disease.

In some embodiments, one or more modified Tregs may comprise any one or more of DG03-28-3ζ; DG03-28tm-10-3ζ; DG03-28tm-44-3ζ; and/or DG03-28tm-CD3ζ, and said modified Tregs may produce IL-10 in response to Aβ antigen, as compared to modified Tregs that were not exposed to said Aβ antigen. In some embodiments, one or more modified Tregs may comprise DG03-CD28-CD3ζ, and said modified Tregs may produce increased levels of IL-10 and/or IL-4 in response to Aβ antigen, which may, for example, be measured by mRNA levels of IL-10 and/or IL-4, and/or be measured by and ELISA assay, as compared to modified Tregs that were not exposed to said Aβ antigen. In some embodiments, one or more modified Tregs may comprise DG03-CD28-CD3ζ, and said modified Tregs may, when stimulated with Aβ antigen and/or anti-CD3 antibody, may inhibit superoxide generation as compared to modified Tregs that were not stimulated with Aβ antigen or anti-CD3 antibody. In some embodiments, one or more modified Tregs may comprise DG03-CD28-CD3ζ, and said modified Tregs, when stimulated with Aβ antigen and/or anti-CD3 antibody, may inhibit IL-6 production as compared to modified Tregs that were not stimulated with Aβ antigen or anti-CD3 antibody.

Moreover, in some exemplary embodiments, modified Tregs that may be used in methods of treating Alzheimer's disease may comprise anti-Aβ CARs and may traffic and accumulate to brain regions of Aβ deposits and neuroinflammation, wherein such regions may include sites of Aβ deposits in the hippocampus and frontal cortex. In some embodiments, modified Tregs comprising CARs targeting Alzheimer's may accumulate in said brain regions and may lead to increased expression of human anti-inflammatory cytokines IL-10, TGF-1β, and IL4 in said regions when used in methods of treating Alzheimer's disease. These anti-inflammatory cytokines may lead to a decrease expression of pro-inflammatory mediators and the numbers of microglia. In exemplary embodiments, modified Tregs comprising CARs targeting Alzheimer's disease may improve memory function in a patient treated with said modified Tregs.

In some embodiments, modified Tregs may comprise a construct for expression of the NDMM Nrf2 (Keap1 inhibitor peptide), and said modified Tregs may demonstrate cytoprotective activity, such as, for example, protection of cells from hydrogen peroxide toxicity as compared to methods of treatment that do not comprise use of said modified Tregs. In some embodiments, a modified Treg may comprise a construct for expression of the NDMM human catalase and said modified Tregs may demonstrate cytoprotective activity, such as, for example, protection of cells from hydrogen peroxide toxicity as compared to methods of treatment that do not comprise use of said modified Tregs. In some embodiments, a modified Treg may comprise a construct for expression of the NDMM BDNF and said modified Tregs may demonstrate cytoprotective activity, such as, for example, protection of cells from hydrogen peroxide toxicity as compared to methods of treatment that do not comprise use of said modified Tregs. In some embodiments, a modified Treg may comprise a construct for expression of the NDMM IGF-1 and said modified Tregs may demonstrate cytoprotective activity, such as, for example, protection of cells from hydrogen peroxide toxicity as compared to methods of treatment that do not comprise use of said modified Tregs.

Further therapeutic applications of modified Tregs according to the invention are discussed in detail below.

Therapeutic Applications

Isolated cells obtained by the methods described above, or cell lines derived from such isolated cells, can be used as a medicament in the treatment of a disease, disorder, or condition in a subject. In some embodiments, such a medicament can be used for treating a neurodegenerative disease or condition. In some embodiments, said neurodegenerative disease or condition may be Parkinson's disease, Alzheimer's disease, or ALS.

Cell Origin

For purposes of the inventive methods, wherein host cells or populations of cells are administered, the cells can be cells that are xenogeneic, allogeneic or autologous to the subject. Generally, the cells are autologous or allogeneic compared to the treated subject. In instances wherein the cells are allogeneic, preferably the cells are MHC or HLA histocompatible relative to the subject to be treated and/or are modified to impair or eliminate expression or functionality of the cells' endogenous TCRs and/or MHCs. In some instances, allogeneic Tregs may be preferred, especially if the Tregs of the subject to be treated are diseased and/or possess some property that renders them less than ideal for therapeutic use. In some instances, allogeneic Tregs may be preferred, especially if the Tregs are obtained from healthy donors as they may better migrate or traffic to desired sites, i.e., sites of neurodegeneration or neuroinflammation within the CNS.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

Subject

The subject referred to herein may be any living subject. In a preferred embodiment, the subject is a mammal. The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes).

In some embodiments, the subject, to whom the cells, cell populations, or compositions are administered is a primate, preferably a human. In some embodiments, the primate is a monkey or an ape. The subject can be male or female and can be any suitable age, including infant, juvenile, adolescent, adult, and geriatric subjects. In some examples, the patient or subject is a validated animal model for disease, adoptive cell therapy, and/or for assessing toxic outcomes, such as cytokine release syndrome (CRS).

In some embodiments, the subject has persistent or relapsed disease, e.g., following treatment with another immunotherapy and/or other therapy. In some embodiments, the administration effectively treats the subject despite the subject having become resistant to another therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the methods include administration of modified Tregs comprising one or more CARs and/or one or more NDMMs or a composition containing the cells to a subject, tissue, or cell, such as one having, at risk for, or suspected of having a neurodegenerative disease or condition. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by reducing, inhibiting, or inactivating microglia cells, reducing inflammation and/or neuroinflammation, and/or decreasing neuronal death.

Functional Activity

In some embodiments, the present disclosure includes a type of cellular therapy wherein isolated cells, e.g., Tregs, are genetically modified to express one or more CARs and/or one or more NDMMs against a target molecule which is expressed in a neurodegenerative disease or condition, and a modified Treg cell is infused into a subject in need thereof. Examples of such target molecules include amyloid beta 1-42, superoxide dismutase-1 (SOD-1), alpha-synuclein, hyperphosphorylated tau protein; TAR DNA-binding protein 43 (TDP-43): chromosome 9 open reading frame 72 (c9orf72); β-Synuclein; γ-Synuclein; RNA-binding protein fused in sarcoma (FUS); ubiquitin; ubiquilin-2, p62; optineurin; ataxin-2; parkin; Serine/threonine-protein kinase PINK I; Leucine-rich repeat serine/threonine-protein kinase 2 (LRRK2), Huntington with tandem glutamine repeats; prion proteins; transthyretin; dentatorubral pallidoluysian atrophy (DRPLA) protein; androgen receptor; ataxins; P/Q-type calcium channel α1A subunit; TATA-box-binding protein; glial fibrillary acidic protein; DNA excision repair protein ERCC-6; survival motor neuron protein; cystatin C. Such administration can decrease neurodegeneration and/or neuroinflammation in a target molecule specific manner.

In some embodiments, the modified Tregs can undergo in vivo expansion and can persist for an extended amount of time.

Once the cells (modified Tregs) are administered to a subject (e.g., a human), the biological activity of the engineered cell populations in some aspects is measured by any of a number of known methods. Parameters to assess include specific binding of an engineered or natural Treg cell or other immune cell to antigen, in vivo, e.g., by imaging, or ex vivo, e.g., by ELISA or flow cytometry.

In some aspects the biological activity is measured by assessing clinical outcome, such as the reduction in disease symptoms, such as symptoms associated a neurodegenerative disease or condition, e.g., Alzheimer's disease, ALS and Parkinson's disease.

Targets

The Tregs of the present disclosure, which may comprise one or more CARs and/or one or more NDMMs, may be used to treat, prevent, or diagnose any conditions, disorders, or diseases involving the expression of target molecules described herein (e.g., alpha-synuclein, amyloid beta, or mutSOD1). For example, the invention also contemplates a method of treating or preventing neurodegenerative diseases or conditions that may include: Alzheimer's disease, Parkinson's disease, ALS, prion disease, motor neuron diseases other than ALS, Huntington's disease, Spinocerebellar ataxia (SCA), Spinal muscular atrophy (SMA), Friedreich's ataxia, Lewy body disease, epilepsy, multiple sclerosis, encephalitis, hydrocephalus, stroke, chronic traumatic encephalopathy (CTE); synucleinopathies; tauopathies; spongiform encephalopathies; familial amyloidotic polyneuropathy; Dutch hereditary cerebral hemorrhage with amyloidosis; congophilic angiopathy; corticobasal degeneration; Pick's disease; progressive supranuclear palsy; Creutzfeld-Jacob disease; Gerstmann-Sträussler-Schneiker syndrome; fatal familial insomnia; kuru; bovine spongiform encephalopathy; scrapie; chronic wasting disease; Lewy body variant of Alzheimer's disease; diffuse Lewy body disease; dementia with Lewy bodies; multiple system atrophy; neurodegeneration with brain iron accumulation type I; diffuse Lewy body disease; frontotemporal lobar degeneration; hereditary dentatorubral-pallidoluysian atrophy; Kennedy's disease; Alexander's disease; Cockayne syndrome; Icelandic hereditary cerebral hemorrhage with amyloidosis. The contemplated method comprises administering modified Tregs that optionally may comprise one or more CARs and/or one or more NDMMs according to the present disclosure.

Modes of Administration

The compositions of the present invention may be administered in a number of ways depending upon whether local or systemic treatment is desired. In the case of adoptive cell therapy, methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

Such administration may be topical, parenteral, or enteral. The compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. In some embodiments, parenteral administration of the compositions of the present invention comprises subcutaneous or intraperitoneal administration.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In some embodiments of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a composition from the mouth, administration of a composition through a nasojejunal or gastrostomy tube, intraduodenal administration of a composition, and rectal administration, e.g., using suppositories for the lower intestinal tract of the alimentary canal. Preferably, the formulated composition comprising modified Tregs is suitable for administration via injection.

Pharmaceutical compositions and formulations for topical administration may include transdermal patches, ointments, lotions, creams, gels, drops, suppositories, sprays, liquids, semi-solids, monophasic compositions, multiphasic compositions (e.g., oil-in-water, water-in-oil), foams, microsponges, liposomes, nanoemulsions, aerosol foams, polymers, fullerenes, and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical compositions of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, aerosols, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In some embodiments of the present disclosure the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Formulations comprising populations of modified Tregs of the present disclosure may include pharmaceutically acceptable excipient(s). Excipients included in the formulations will have different purposes depending, for example, on the modified Treg, the subpopulation of modified Tregs used, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising populations of the modified Tregs of the present disclosure may typically have been prepared and cultured in the absence of any non human components, such as animal serum (e.g., bovine serum albumin).

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

Dosing

The pharmaceutical composition in some embodiments contains modified Tregs of the present disclosure, e.g., Tregs comprising one or more CARs and/or one or more NDMMs, in amounts effective to treat or prevent the disease or condition, e.g., a neurodegenerative disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of modified Tregs, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject. For example, in some embodiments the administration of the cells or population of cells can comprise administration of about $10^3$ to about $10^9$ cells per kg body weight including all integer values of cell numbers within those ranges.

The cells or population of cells can be administrated in one or more doses. In some embodiments, said effective amount of cells can be administrated as a single dose. In some embodiments, said effective amount of cells can be administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of cells or composition comprising those cells are administrated parenterally. In some embodiments, administration can be an intravenous administration. In some embodiments, administration can be directly done by injection into the disease site.

For purposes of the present disclosure, the amount or dose of modified Tregs administered should be sufficient to effect a therapeutic or prophylactic response in the subject or animal over a reasonable time frame. For example, the dose of modified Tregs should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular modified Treg and the condition of the animal (e.g., human), as well as the body weight of the animal (e.g., human) to be treated.

In some embodiments, modified Tregs according to the invention are administered as part of a combination treatment, such as simultaneously with or sequentially with, in any order, another therapeutic intervention known in the art. For example modified Treg cells according to the invention in some embodiments are co-administered with one or more additional therapeutic agents such as an antibody, nucleic acid or small molecule or in combination with another therapeutic intervention, either simultaneously or sequentially in any order. In some contexts, the cells are co-administered with another moiety which promotes the ability of the cells to cross the BBB. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after to the one or more additional therapeutic agents.

EXAMPLES

Example 1: Treg Isolation, Expansion and CAR Transduction for Modified Tregs Targeting Alzheimer's Disease In the present Example, modified Tregs targeting Alzheimer's disease comprised extracellular scFvs fused to human CD28 hinge, transmembrane, and cytoplasmic domains, followed by a human CD3ζ cytoplasmic domain (FIG. 1). CARs targeting Alzheimer's disease include DG01 (SEQ ID NO: 1), DG02 (SEQ ID NO: 2), DG03 (SEQ ID NO: 3), and DG04 (SEQ ID NO: 4), DG01-CD28-CD3ζ (SEQ ID NO: 20), DG02-CD28-CD3ζ (SEQ ID NO: 21), DG03-CD28-CD3ζ (SEQ ID NO: 22), and DG04-CD28-CD3ζ (SEQ ID NO: 23). Modified Tregs targeting Alzheimer's disease were prepared as follows.

CD4+CD25+ Tregs were isolated from human PBMCs in a two-step cell isolation process. First, human CD4+ cells were isolated by negative-selection using MOJOSORT™ Human CD4 T Cell Isolation Kit (Biolegend) and a EASYSEP™ Magnet (StemCell) according to manufacturer's instructions. Second, CD25hi cells were enriched from the CD4+-isolated cells by positive-selection using anti-human CD25 MicroBeads II (Miltenyi) and MS Columns with MiniMACS™ Separator magnet (Miltenyi). The CD4+ CD25hi cells were cultured in 24-well non-tissue culture plates at $1\times10^6$ cells/mL in Treg growth medium supplemented with 10% heat-inactivated human AB serum (Sigma). Treg growth media was either (1) X-Vivo-15 or (2) RPMI supplemented with 10 mM HEPES, 0.1 mM non-essential amino acids, 1 mM sodium pyruvate, 100 U/mL penicillin, 100 μg/mL streptomycin and 5011M 2-ME. Cell incubation condition was humidified 37° C. and 5% $CO_2$. Cells were stimulated with 25 μL/$1\times10^6$ cells of ImmunoCult™ Human CD3/CD28 T Cell Activator (StemCell) on days 0 and 9 in culture. In some instances, it is possible to use the CD3/CD28/CD2 T cell activator instead. Treg growth media was supplemented with 300 to 500 U/mL human IL-2 (Tecin from Roche, kindly provided by the NIH) starting on culture day 2. Cultured cells were transferred to 25 $cm^2$ tissue culture-treated flasks on day 5. Cells were transduced over two days with retroviral CAR constructs on day 10 and 11 in culture. 24-well non-tissue culture plate wells were pre-coated with RetroNectin® (Takara Bio USA, Inc.) according to manufacturer's instructions and then day 10 cultured cells were added at $0.3\times10^6$ cells/well in 0.3 mL of Treg growth media. Retroviral supernatant was added at 0.7 mL/well and plates were centrifuged at 1500 rcf at 30° C.; for 1 h, and then incubated overnight. On the next day, 0.5 mL culture supernatant was replaced with 0.5 mL retroviral supernatant with 500 U/mL IL-2 and cells were re-centrifuged and then incubated overnight. The next day cells were transferred to 25 $cm^2$ tissue culture-treated flasks at $1\times10^6$ cells/mL. On day 13 of culture, a sample of cells was evaluated for transduction efficiency by measuring the percentage of the co-transduced truncated CD19 on cells by flow cytometry. If cells were less than 30% transduced, then cells can be enriched using anti-CD19-PE and EasySep™ Release PE Positive Selection Kit (StemCell) according to manufacturer's instructions. Cells were cultured with fresh Treg growth media added every two days until day 17.

The flow cytometry step proceeded as follows.

Cell phenotyping was determined by staining with specific antibodies: FITC-conjugated anti-human CD3 (clone OKT3; Biolegend), FITC anti-human CD4 (clone OKT4; Biolegend), PE anti-human CD127 (clone A019DS; Biolegend), PE anti-human CD25 (clone (clone M-A251; Biolegend), PE anti-human CD19 (clone SJ25C1; Biolegend), or PE anti-mouse CD19 (clone 6D5; Biolegend). For intracellular staining, eBioscience™ Foxp3/Transcription Factor Staining Buffer Set was used with APC anti-human Fox3 (clone PCH101; Invitrogen) or APC rat IgG2a isotype control (clone eBR2a; Invitrogen). For direct labeling of the CAR scFv, biotinylated protein L (1 μg/mL; GenScript) followed by streptavidin-PE (Biolegend) was used. Other reagents to label scFv-based CARs can include FITC anti-human IgG, F(ab')2-specific (Jackson ImmunoResearch), PE AffiniPure F(ab')2 Fragment anti-human IgG (Jackson ImmunoResearch), or PE AffiniPure $F(ab')_2$ Fragment anti-mouse IgG (Jackson ImmunoResearch). Cells were analyzed using an ACCURI™ C6 flow cytometer (BD Biosciences, Ann Arbor, MI, USA).

Figures 2A, 2B, 2C, 2D:
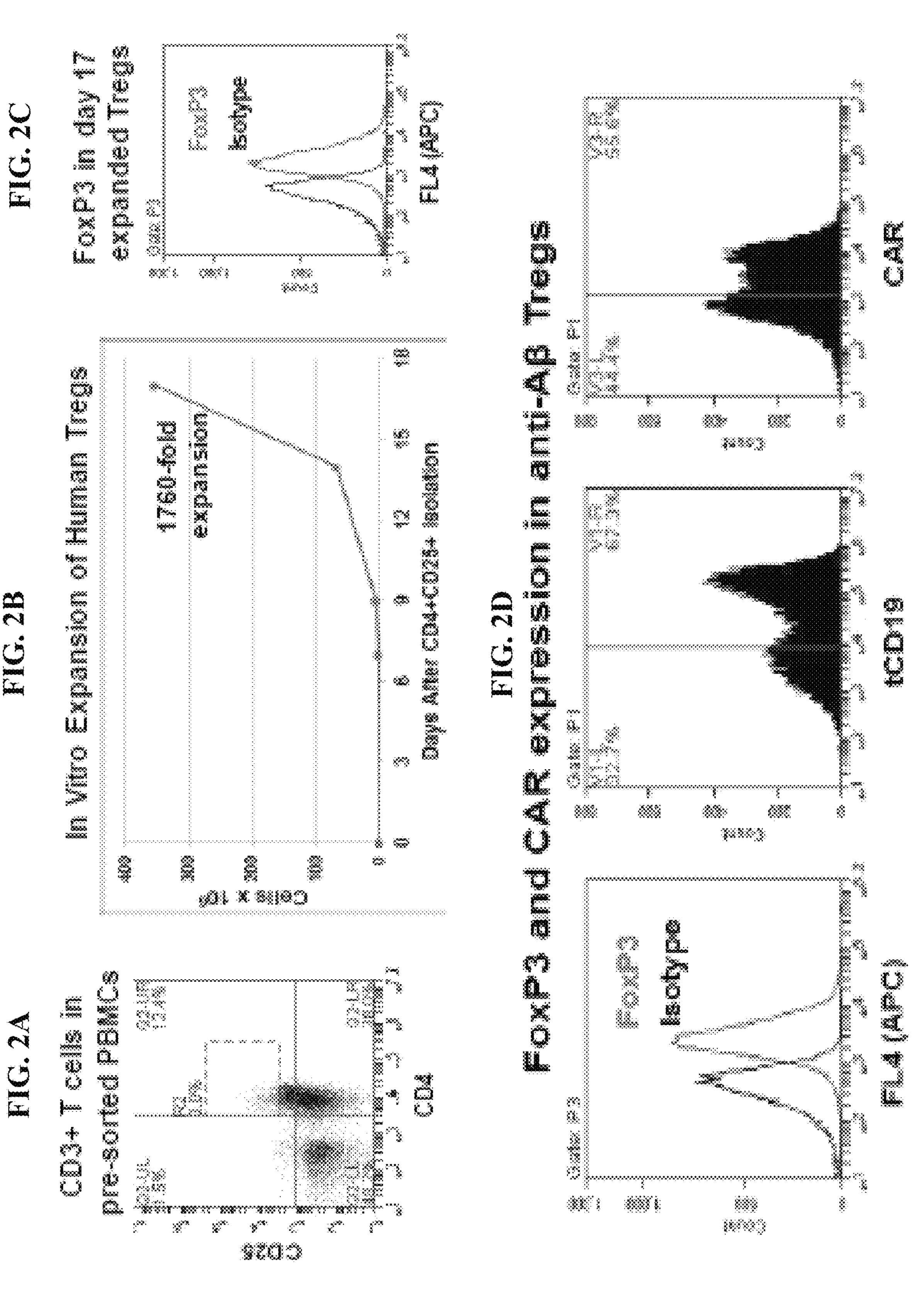
FIG. 2A-FIG. 2D present data related to in vitro expansion and phenotype validation of Tregs isolated from human PBMCs in accordance with Example 1.

FIG. 2A-FIG. 2D presents data related to the in vitro expansion and phenotype validation of Tregs isolated from human PBMCs as discussed above. FIG. 2A demonstrates that $CD4^+CD25hi$ Tregs (R2 box) represented a small percentage of total T cells in human PBMCs prior to CD4 and CD25 enrichment isolation. FIG. 2B demonstrates that $CD4^+CD25hi$ isolated Tregs expanded 1760-fold after 17 days in culture using the present Treg expansion protocol. FIG. 2C demonstrates that Day 17 Tregs expressed intracellular FoxP3. FIG. 2D demonstrates that FoxP3, truncated CD19 (tCD19), and the CAR scFv were detected on most day 17 Tregs transduced on days 10 and 11.

Figure 3B:
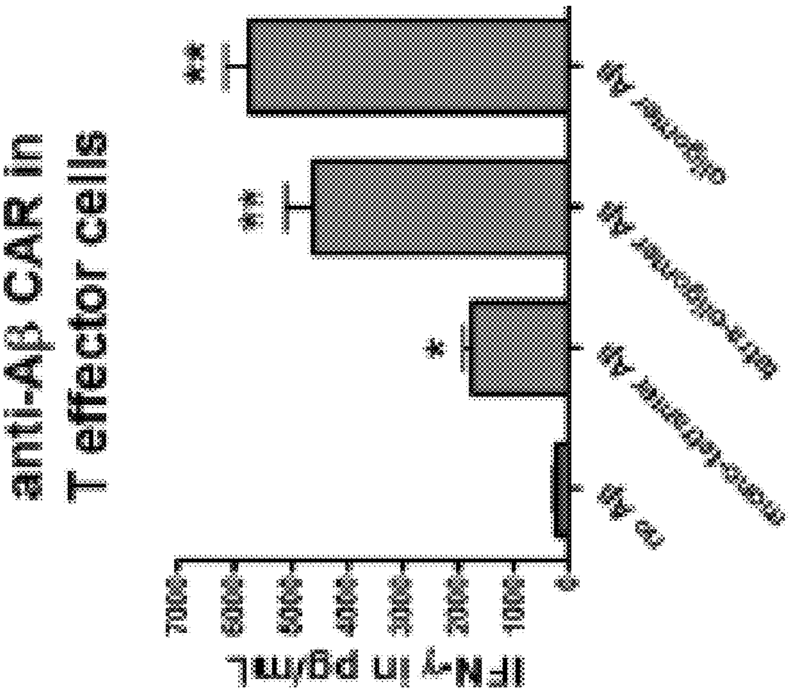
FIG. 3A-FIG. 3B presents data related to functional validation of the exemplary modified CARs in accordance with Example 1.
Figure 3A:
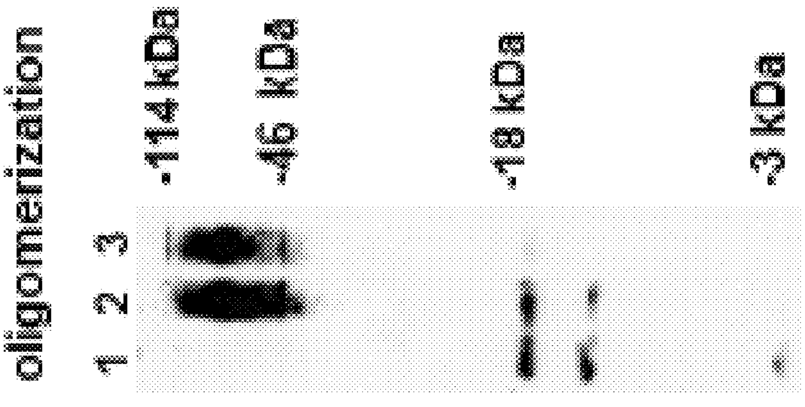

CARs targeting amyloid beta were functionally validated as follows. Oligomerization of $A\beta_{1-42}$ peptides can occur over the course of seven days incubation in PBS, and in the present example resulted in increasing ratios of larger oligomers as a function of time, as demonstrated by FIG. 3A. To test CAR antigen-specific activity, total effector T cells ($CD4^+$ and $CD8^+$ Teff cells) transduced to express DG03-28ζ anti-Aβ CAR (SEQ ID NO: 22) were used. Higher secretion of IFN-γ was found when these CAR T cells were exposed to Aβ oligomers with a higher ratio of larger aggregates, whereas little response occurs without antigen (FIG. 3B). This demonstrated that the CAR retains binding specificity to Aβ and that the oligomerized antigen activated CAR T cells (FIG. 3B).

Example 2: Treg Suppression Assay Using Exemplary Modified Tregs Targeting Alzheimer's Disease Modified Tregs comprising CARs, as described in Example 1, were plated in a 96-well V bottom plate in Treg growth medium at serial dilutions between 12,500 and 400,000 cells/0.1 mL/well. Allogeneic PBMCs were pre-labeled using CellTrace™ CFSE Cell Proliferation Kit (Invitrogen) according to manufacturer's instructions. CSFE-labeled PBMCs were stimulated with or without anti-CD3 (1 ug/mL; clone HIT3a; Biolegend) and added to plated Tregs or to wells with no Tregs. After 72 h, cells were blocked using human Cohns fraction (1 mg/mL; Sigma), and then stained with APC anti-CD8 (clone RTA-T8; Biolegend) for flow cytometer analysis of $CD8^+$ cells expression of CSFE. The CFSE can be reduced with each cell division, so dividing cells can have a lower CFSE value. The % suppression of $CD8^+$ T cell proliferation was determined compared to control wells of stimulated PBMCs with anti-CD3 mAbs.

Figure 4:
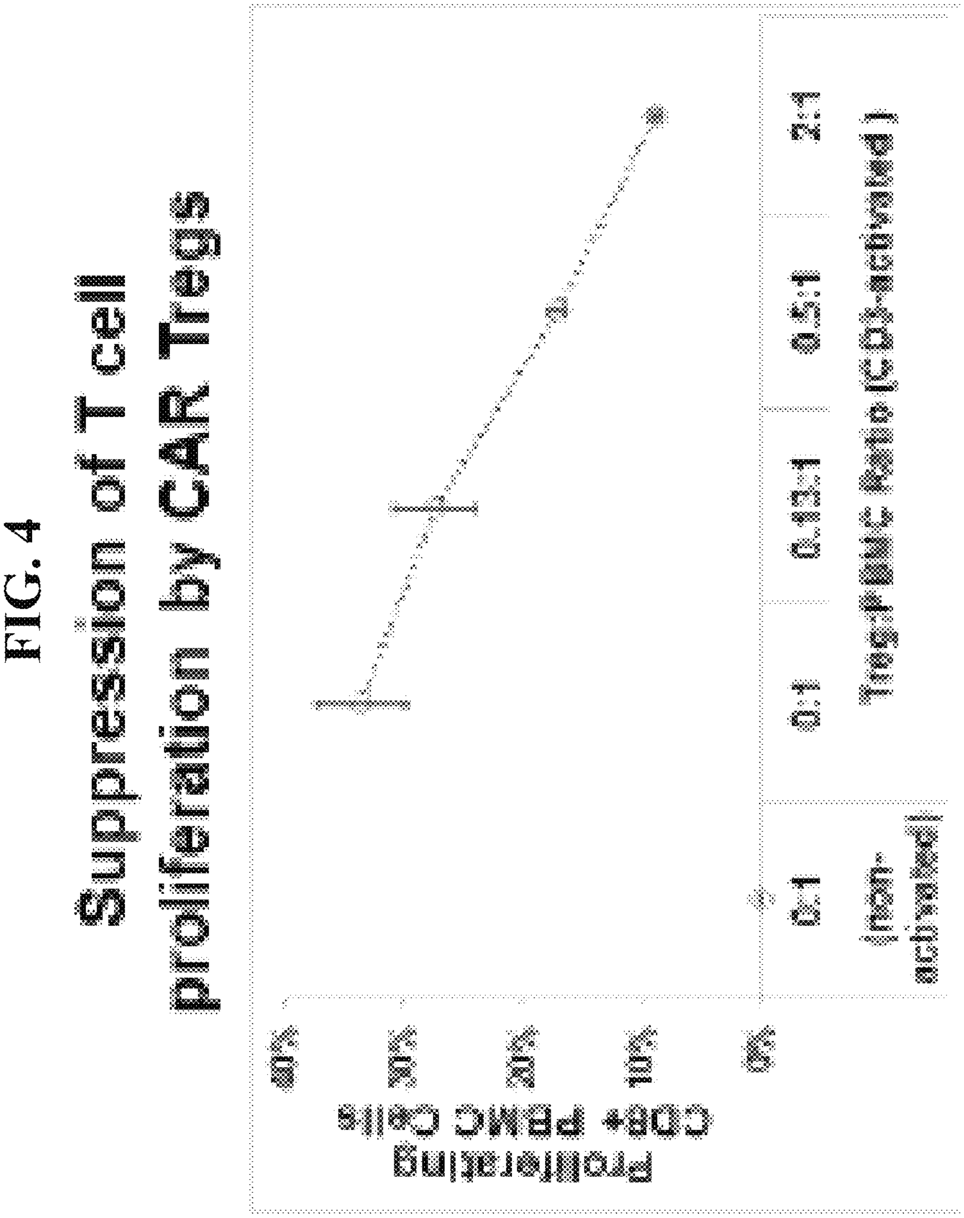
FIG. 4 presents data related to DG03-28z anti-Aβ CAR modified Treg-mediated suppression of T cell proliferation in accordance with Example 2.

Results of the above Treg suppression assay are presented in FIG. 4. FIG. 4 demonstrates that increasing ratios of day 17 anti-Aβ CAR Tregs comprising DG03-28z suppressed the proliferation of CSFE-labeled $CD8^+$ cells in co-cultured CD3-stimulated allogeneic PBMCs.

Example 3: Antigen-Stimulation Modified Tregs Targeting Alzheimer's Disease

For stimulation with soluble antigen, day 17 CAR Tregs were plated in non-coated 96-well tissue culture plates at 50,000 cell/well in Treg growth media without IL-2. $A\beta_{1-42}$ or α-synuclein was pre-oligomerized by incubating at 40 μM in PBS at 37° C.; for 1 week with daily agitation. Oligomerized $A\beta_{1-42}$ was added to Tregs in 0.1 mL Treg growth media and cell free supernatant was collected for human IL-10 ELISA (Biolegend) at 24 h and 72 h. For stimulation with plate-bound antigens, 96-well ELISA plates were coated with $A\beta_{1-42}$, wtSOD1, mutSOD1, or α-synuclein in PBS overnight at 4° C. Plates were rinsed three times with PBS and day 17 CAR Tregs were added to the antigen-coated 96-well ELISA plates at 50,000 cell/well in Treg growth media without IL-2. Cell free supernatant was collected for human IL-10 ELISA (Biolegend) at 24 h and 72 h. Alternatively, streptavidin in PBS was coated on 96-well ELISA plates overnight at 4° C.; and biotinylated antigens were applied after rinsing unbound streptavidin. Another alternative method for antigen stimulation can be to use nanometer- or micrometer-sized polystyrene beads coated with the antigen e.g. biotinylated antigen linked to streptavidin-conjugated beads.

Figure 5:
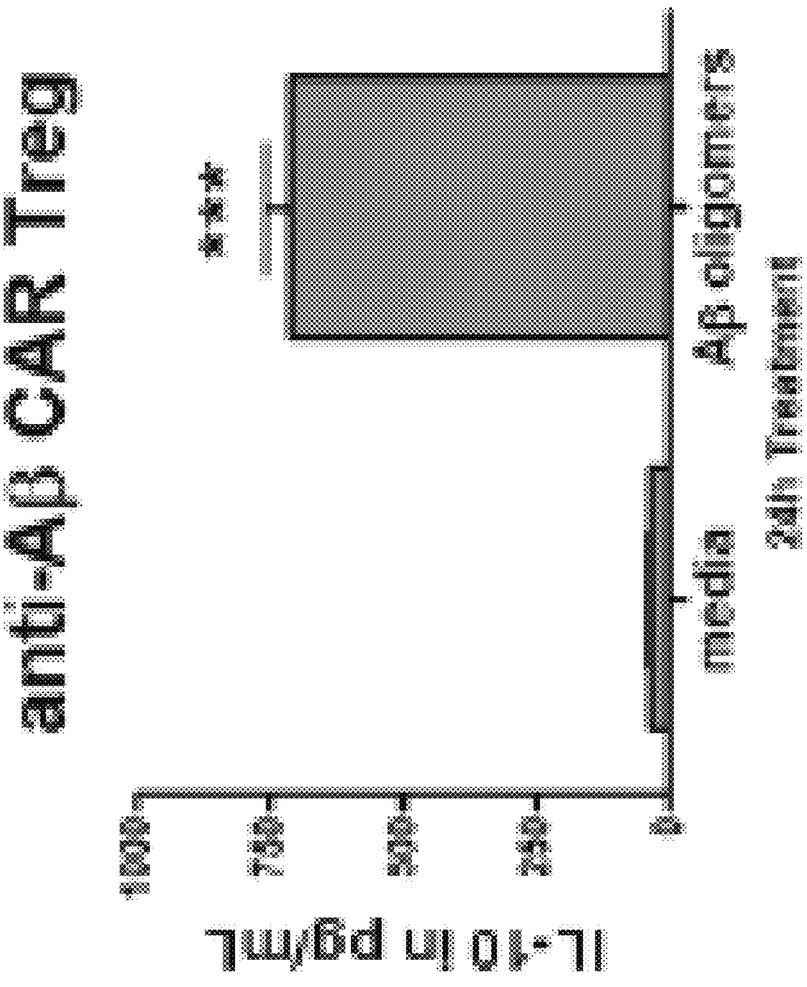
FIG. 5 presents data related to Aβ CAR Tregs stimulated with oligomeric Aβ in vitro for 24 hours and the production of IL-10 in accordance with Example 3.

FIG. 5 demonstrates that anti-Aβ CAR Tregs comprising DG03-28z stimulated with oligomeric Aβ in vitro for 24 hours produced IL-10. $P<0.001$ by Student's t-test.

Figure 6:
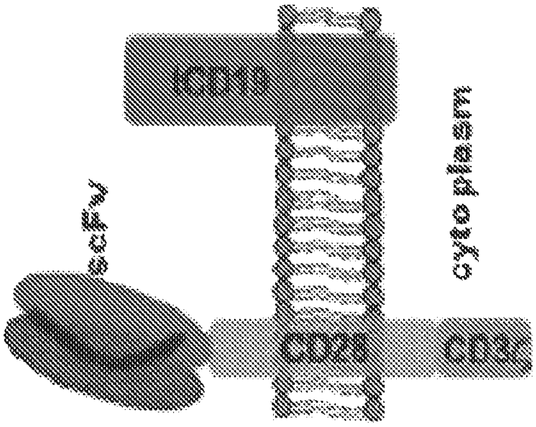
FIG. 6 presents a schematic design of an anti-mutSOD1-CD28-CD3ζ CAR in accordance with Example 4.

Example 4: Treg Isolation, Expansion and CAR Transduction for Modified Tregs Targeting ALS In the present example, modified Tregs targeting ALS comprised anti-mutSOD1 CARs using human variable heavy ($V_H$) and light ($V_L$) chain sequences. The anti-mutSOD1 scFv were expressed extracellularly with the C-terminus of the $V_L$ fused to human CD28 hinge, transmembrane, and cytoplasmic domain, followed by a human CD3ζ cytoplasmic domain to create an anti-mutSOD1-CD28-CD3ζ CAR (FIG. 6). This CAR will trigger both primary and costimulation signaling upon antigen binding. A truncated (non-signaling) human or mouse CD19 (tCD19) is also expressed in the same vector using a 2A co-expression system and it serves as a way to track and purify transduced T cells. Modified Tregs targeting ALS are prepared as follows. CARs targeting ALS include DG05 (SEQ ID NO: 5), DG06 (SEQ ID NO: 6), DG07 (SEQ ID NO: 7), DG05-CD28-CD3ζ (SEQ ID NO: 24), DG06-CD28-CD3ζ (SEQ ID NO: 25), and DG07-CD28-CD3ζ (SEQ ID NO: 26).

CD4+CD25+ Tregs were isolated from human PBMCs in a two-step cell isolation process. First, human CD4+ cells were isolated by negative-selection using MOJOSORT™ Human CD4 T Cell Isolation Kit (Biolegend) and a EASYSEP™ Magnet (StemCell) according to manufacturer's instructions. Second, CD25hi cells were enriched from the CD4+-isolated cells by positive-selection using anti-human CD25 MicroBeads II (Miltenyi) and MS Columns with MiniMACS™ Separator magnet (Miltenyi). The CD4+ CD25hi cells were cultured in 24-well non-tissue culture plates at $1\times10^6$ cells/mL in Treg growth medium supplemented with 10% heat-inactivated human AB serum (Sigma). Treg growth media was either (1) X-Vivo-15 or (2) RPMI supplemented with 10 mM HEPES, 0.1 mM non-essential amino acids, 1 mM sodium pyruvate, 100 U/mL penicillin, 100 μg/mL streptomycin and 50 μM 2-ME. Cell incubation condition was humidified 37° C.; and 5% $CO_2$. Cells were stimulated with 25 $\mu L/1\times10^6$ cells of ImmunoCult™ Human CD3/CD28 T Cell Activator (StemCell) on days 0 and 9 in culture. In some instances, it is possible to use the CD3/CD28/CD2 T cell activator instead. Treg growth media was supplemented with 300 to 500 U/mL human IL-2 (Tecin from Roche, kindly provided by the NIH) starting on culture day 2. Cultured cells were transferred to 25 $cm^2$ tissue culture-treated flasks on day 5. Cells were transduced over two days with retroviral CAR constructs on day 10 and 11 in culture. 24-well non-tissue culture plate wells were pre-coated with RetroNectin® (Takara Bio USA, Inc.) according to manufacturer's instructions and then day 10 cultured cells were added at $0.3\times10^6$ cells/well in 0.3 mL of Treg growth media. Retroviral supernatant was added at 0.7 mL/well and plates were centrifuged at 1500 ref at 30° C.; for 1 h, and then incubated overnight. On the next day, 0.5 mL culture supernatant was replaced with 0.5 mL retroviral supernatant with 500 U/mL IL-2 and cells were re-centrifuged and then incubated overnight. The next day cells were transferred to 25 $cm^2$ tissue culture-treated flasks at $1\times10^6$ cells/mL. On day 13 of culture, a sample of cells was evaluated for transduction efficiency by measuring the percentage of the co-transduced truncated CD19 on cells by flow cytometry. If cells were less than 30% transduced, then cells can be enriched using anti-CD19-PE and EasySep™ Release PE Positive Selection Kit (StemCell) according to manufacturer's instructions. Cells were cultured with fresh Treg growth media added every two days until day 17.

The flow cytometry step proceeded as follows.

Cell phenotyping was determined by staining with specific antibodies: FITC-conjugated anti-human CD3 (clone OKT3; Biolegend), FITC anti-human CD4 (clone OKT4; Biolegend), PE anti-human CD127 (clone A019DS; Biolegend), PE anti-human CD25 (clone (clone M-A251; Biolegend), PE anti-human CD19 (clone SJ25C1; Biolegend), or PE anti-mouse CD19 (clone 6D5; Biolegend). For intracellular staining, eBioscience™ Foxp3/Transcription Factor Staining Buffer Set was used with APC anti-human Fox3 (clone PCH101; Invitrogen) or APC rat IgG2a isotype control (clone eBR2a; Invitrogen). For direct labeling of the CAR scFv, biotinylated protein L (1 μg/mL; GenScript) followed by streptavidin-PE (Biolegend) was used. Other reagents to label scFv-based CARs can include FITC anti-human IgG, $F(ab')_2$-specific (Jackson ImmunoResearch), PE AffiniPure F(ab')2 Fragment anti-human IgG (Jackson ImmunoResearch), or PE AffiniPure $F(ab')_2$ Fragment anti-mouse IgG (Jackson ImmunoResearch). Cells were analyzed using an ACCURI™ C6 flow cytometer (BD Biosciences, Ann Arbor, MI, USA).

Alternatively, for control CAR TZ47-28z CAR, transduction proceeded as follows. Cells were isolated from human PBMCs via a two-step negative and positive selection protocol. First, $CD4^+CD127^-$ T cells were isolated using negative selection, followed by a positive selection of $CD25^+$ cells to isolate $CD4^+CD127^-CD25^+$ Treg cells. The isolated $CD4^+CD25^+CD127^-$ Tregs were activated with anti-CD3, anti-CD28, anti-CD2 coated beads (STEMCELL ImmunoCult) with human IL-2 over two weeks in culture. On day 9, Treg cells were cryopreserved for use at a later date, so the same donor and preparation can be tested on multiple occasions to assess assay variability. Using this protocol, it was possible to generate $5\times10^8$ Treg cells ($CD4^+$, $CD127^-$, $CD25^+$, $FoxP3^+$) from an initial $1\times10^8$ whole PBMCs.

Figure 7A:
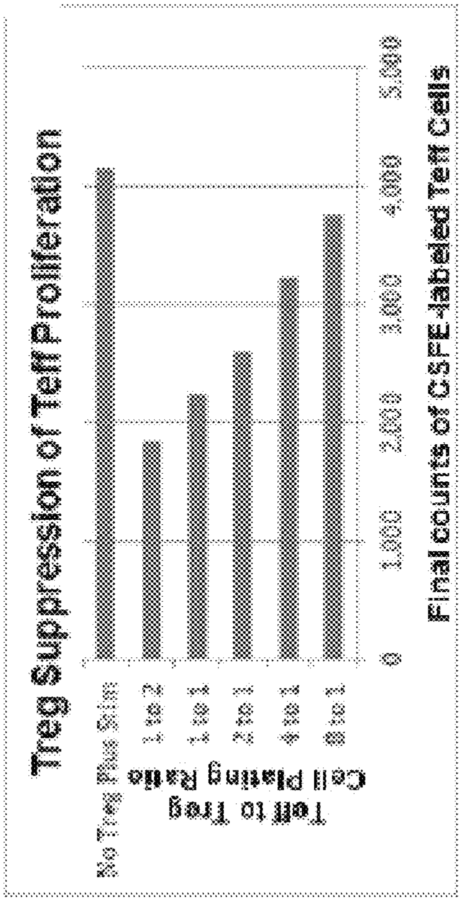
FIG. 7A-FIG. 7D presents data demonstrating suppression of effector T cell proliferation (FIG. 7A); expression of intracellular FoxP3 (FIG. 7B); and purification for $tCD19^+$ cells (FIG. 7C-FIG. D) in accordance with an alternative Treg isolation method consisting of $CD4^+CD127^-$ T cells isolated using negative selection, followed by a positive selection of $CD25^{hi}$ cells to isolate $CD4^+CD127^-CD25^{hi}$ Treg cells, and stimulation with anti-CD3, anti-CD28, anti-CD2 multimers as described in Example 4.
Figure 7B:
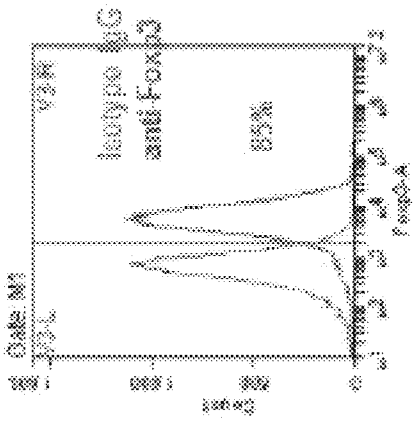
Figure 7C:
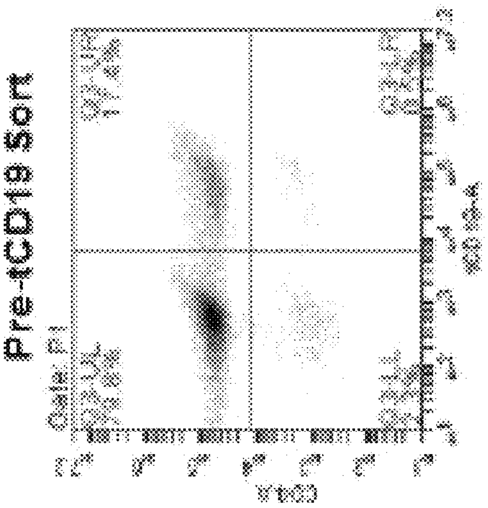
Figure 7D:
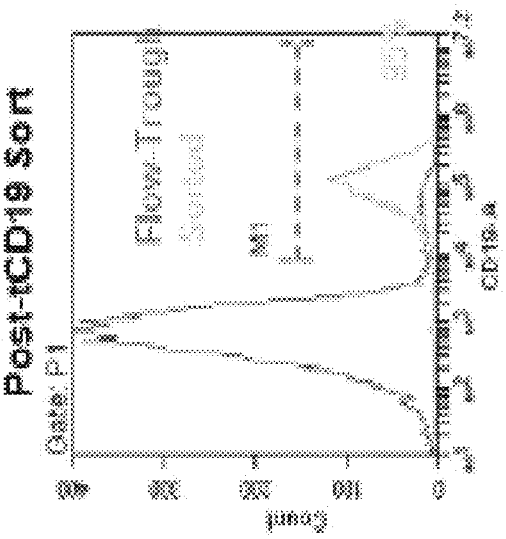

For CAR transduction, thawed 9-day-expanded Treg cells were stimulated for 48 hours with Immunocult activator beads. Tregs were transduced by spin inoculation with anti-mutSOD1 CARs or a negative control CAR and tCD19 or tCD19 vector alone in Rectronection-coated plates (Clontech Laboratories, Inc.). Transduced $tCD19^+$ cells were purified using magnetic bead selection (StemCell) three days after transduction. With this method it was shown that expanded Tregs transduced with an anti-B7H6 CAR and tCD19 retained a Treg phenotype: suppression of effector T cell proliferation (FIG. 7A), and the majority of cells expressed intracellular FoxP3 (FIG. 7B). Purification for $tCD19^+$ cells resulted in a purity of up to 95% (FIG. 7C-FIG. 7D). Regarding FIG. 7A, $CD4^+CD127^-$ $CD25^+$ cells isolated from human PBMCs and expanded in vitro had Treg-like function as shown by suppression of CD3-stimulated proliferation of CSFE-labeled T effector cells (Teff). Regarding FIG. 7B, $CD4^+CD127^-CD25^+$ isolated and expanded cells were positive for intracellular Treg marker FoxP3. Regarding FIG. 7C-FIG. 7D, following transduction of isolated Tregs with truncated CD19 (tCD19) retrovirus, 17% of $CD4^+$ cells expressed tCD19 (FIG. 7C), and after tCD19 purification 95% of sorted cells were $tCD19^+$ (FIG. 7D).

Figure 8:
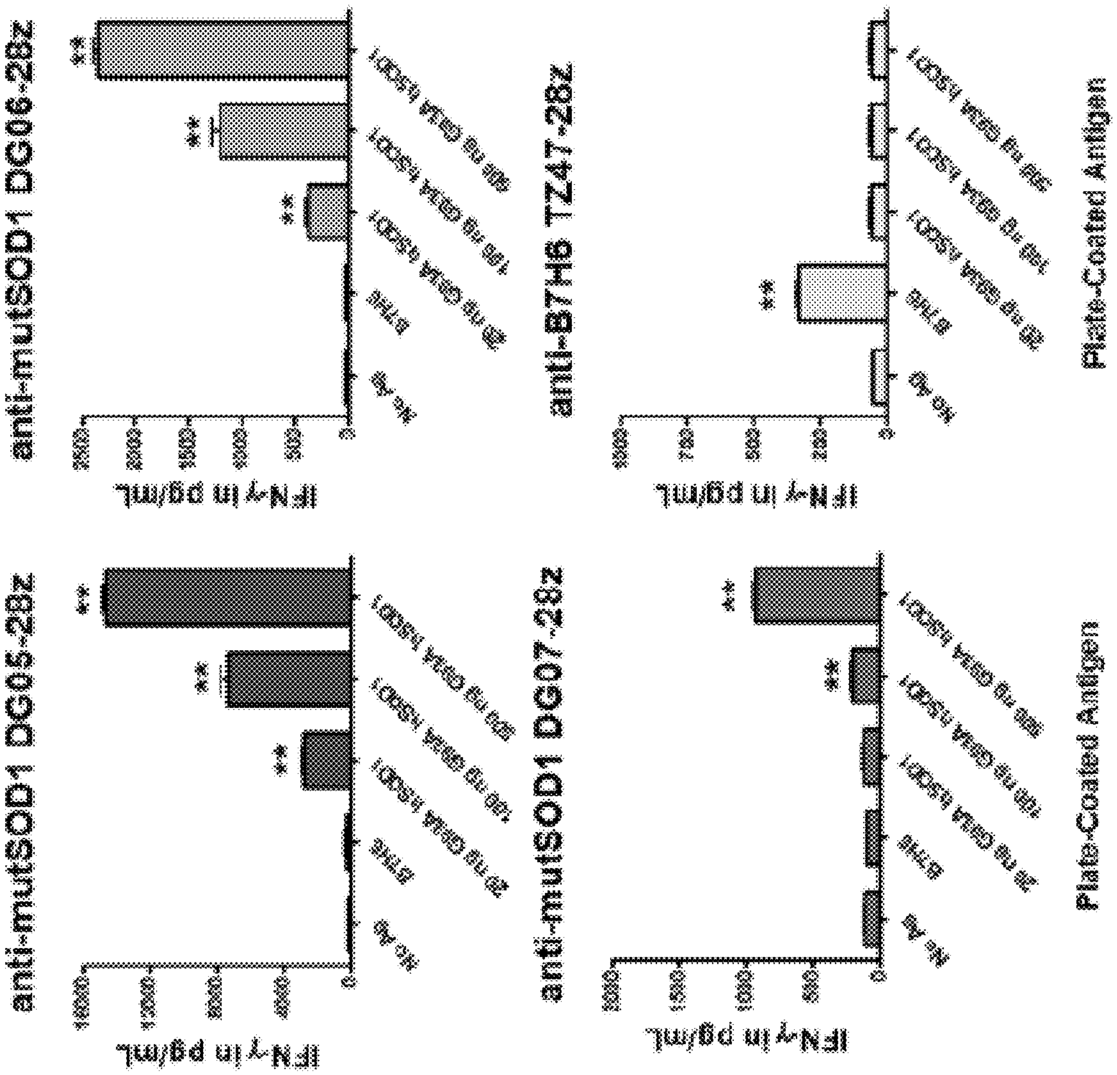
FIG. 8 presents data related to three exemplary anti-mutSOD1 CARs (named DG05, DG06, and DG07) and their antigen specific activity against the G93A mutated form of SOD1 in accordance with Example 4. A negative control anti-B7H6 CAR does not respond to mutated SOD1.

Using total effector T cells ($CD4^+$ and $CD8^+$ T cells)—derived from human PBMCs stimulated with 40 ng/mL soluble OKT3 and 100 u/mL IL-2, spin transduced on Retronectin-coated wells on days 2 and 3 in culture, and used on day 8 in culture—three anti-mutSOD1 CARs (named DUOS, DG06, and DG07) showed antigen specific activity against the G93A mutated form of SOD1, which was similar to anti-B7H6 (TZ47) CAR T cells targeting B7H6 (FIG. 8). The two human antibodies from which anti-mutSOD1 CARs DG05 and DG06 were developed were selective for human SOD1 with ALS mutations.

Figure 9:
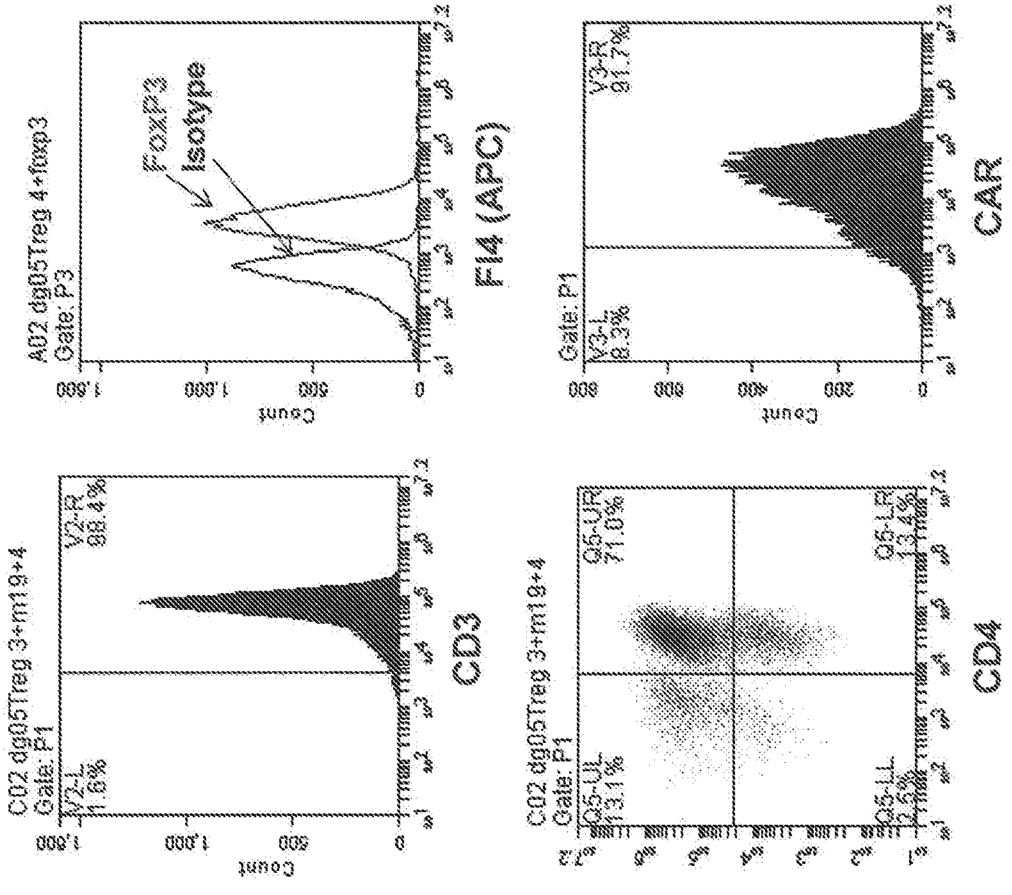
FIG. 9 presents data related to the phenotype validation of Tregs isolated from human PBMCs in accordance with Example 4. CD3, FoxP3, CD4, truncated CD19 (tCD19), and the CAR scFv with protein L labeling were detected on most day 17 Tregs transduced on days 10 and 11 with an anti-mutSOD1 CAR (DG05-28z).
Figure 10:
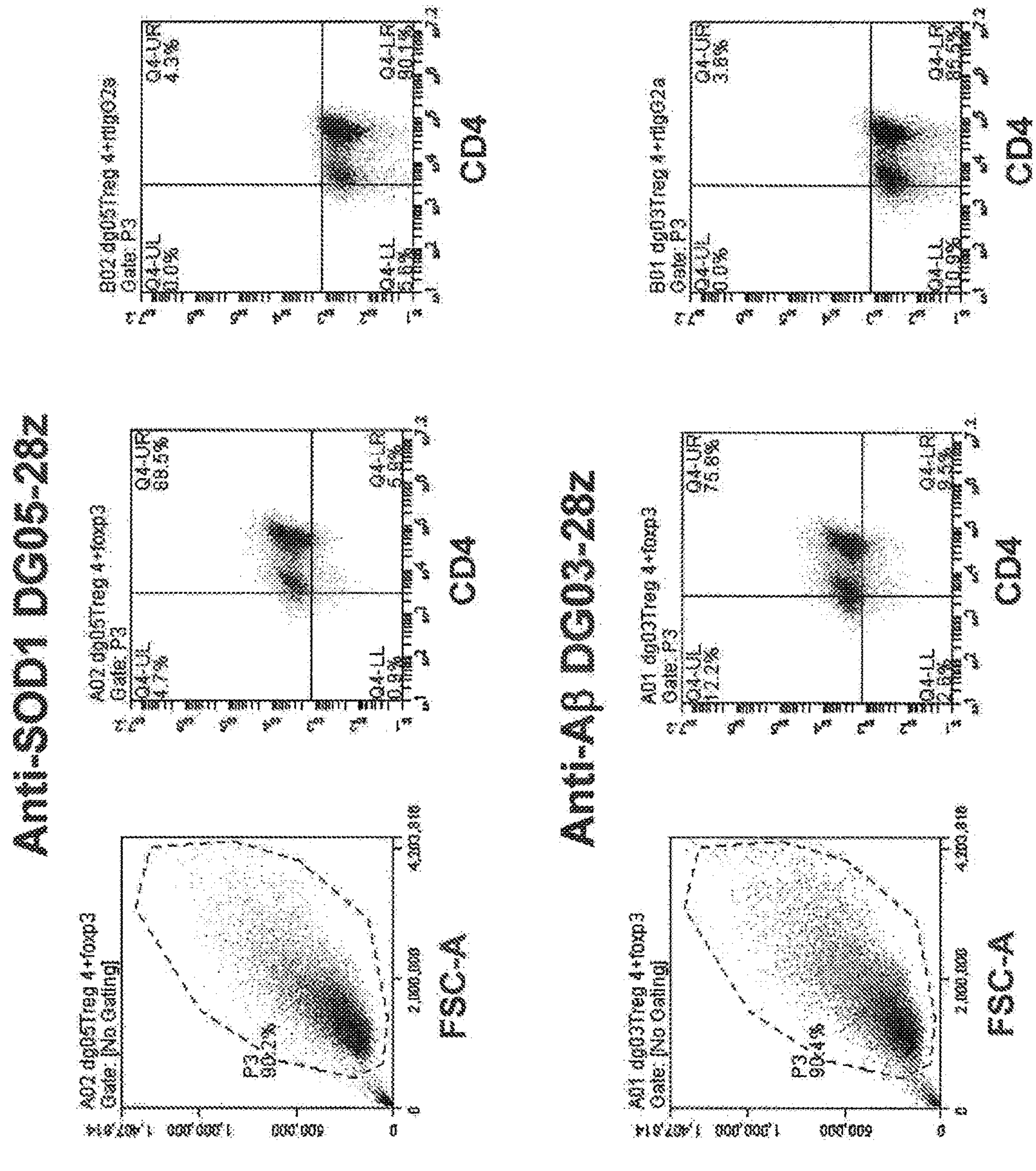
FIG. 10 presents data related to the phenotype validation of Tregs isolated from human PBMCs in accordance with Example 4. Scatter plot, CD4 and FoxP3 on most day 17 Tregs transduced on days 10 and 11 with an anti-mutSOD1 CAR (DG05-28z) or anti-AβCAR (DG03-28z).

FIG. 9 presents data related to the phenotype validation of Tregs isolated from human PBMCs as discussed above. FIG. 9 demonstrates that DG05-28Z (SEQ ID NO: 24) expressed in human Tregs tested positive for the following markers using a flow cytometry-based assay: FoxP3; CD4; CD3; transduction marker truncated CD19 (tCD19); and CAR by labeling with biotinylated protein L and streptavidin-PE. Furthermore, modified Tregs expressing anti-mutSOD1 CAR DG05-28z had a similar phenotype to Tregs expressing CAR targeting a different target (DG03-28z (SEQ ID NO: 22)) (FIG. 10).

Example 5: Functional Activity of Modified Tregs Targeting ALS

Figure 11:
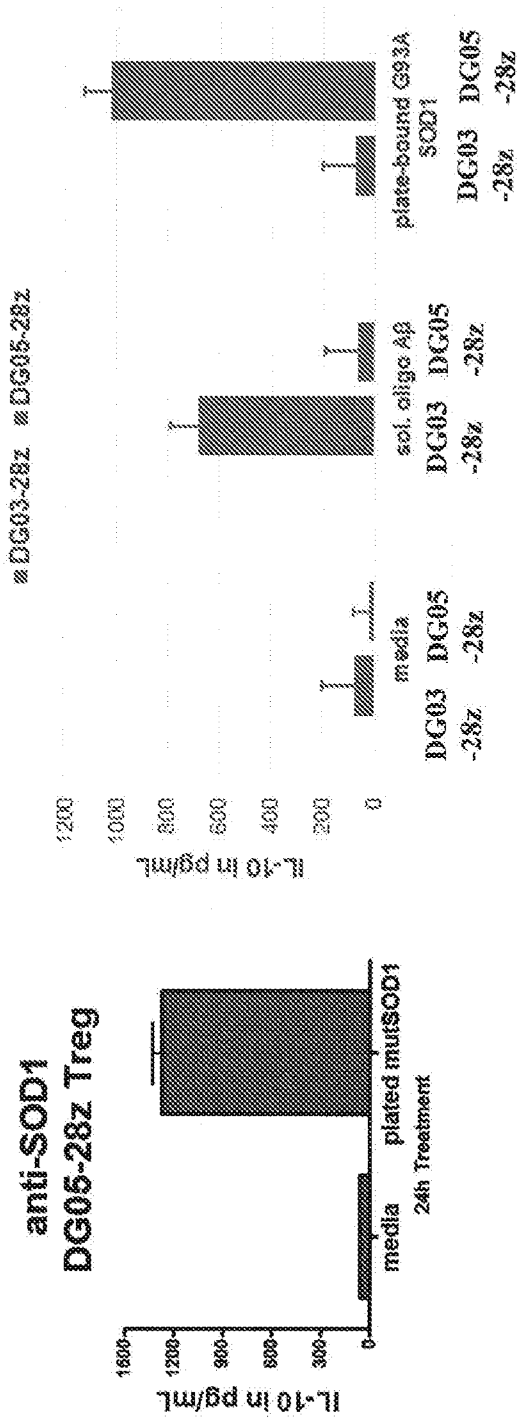
FIG. 11 presents data demonstrating antigen-specific activity of exemplary anti-mutSOD1 CARs in accordance with Example 5. IL-10 production in response to plate-bound mutSOD1 or soluble oligomerized $A\beta_{1-42}$ by day 17 Tregs transduced on days 10 and 11 with an anti-mutSOD1 CAR (DG05-28z) or anti-Aβ CAR (DG03-28z).

IL-10 ELISA data using anti-mutSOD1 CAR DG05-28z (SEQ ID NO: 24) expressed in human Tregs are presented below. FIG. 11 demonstrates that anti-mutSOD1 CAR Tregs DG05-28z produced IL-10 when cultured in wells with mutSOD1 coated on the well surface (plate-bound) versus media alone. Furthermore, FIG. 11 demonstrates that anti-mutSOD1 CAR Tregs did not produce IL-10 in response to soluble oligomerized $A\beta_{1-42}$, whereas anti-Aβ CAR Tregs did produce IL-10 in response to soluble oligomerized $A\beta_{1-42}$.

Figure 12:
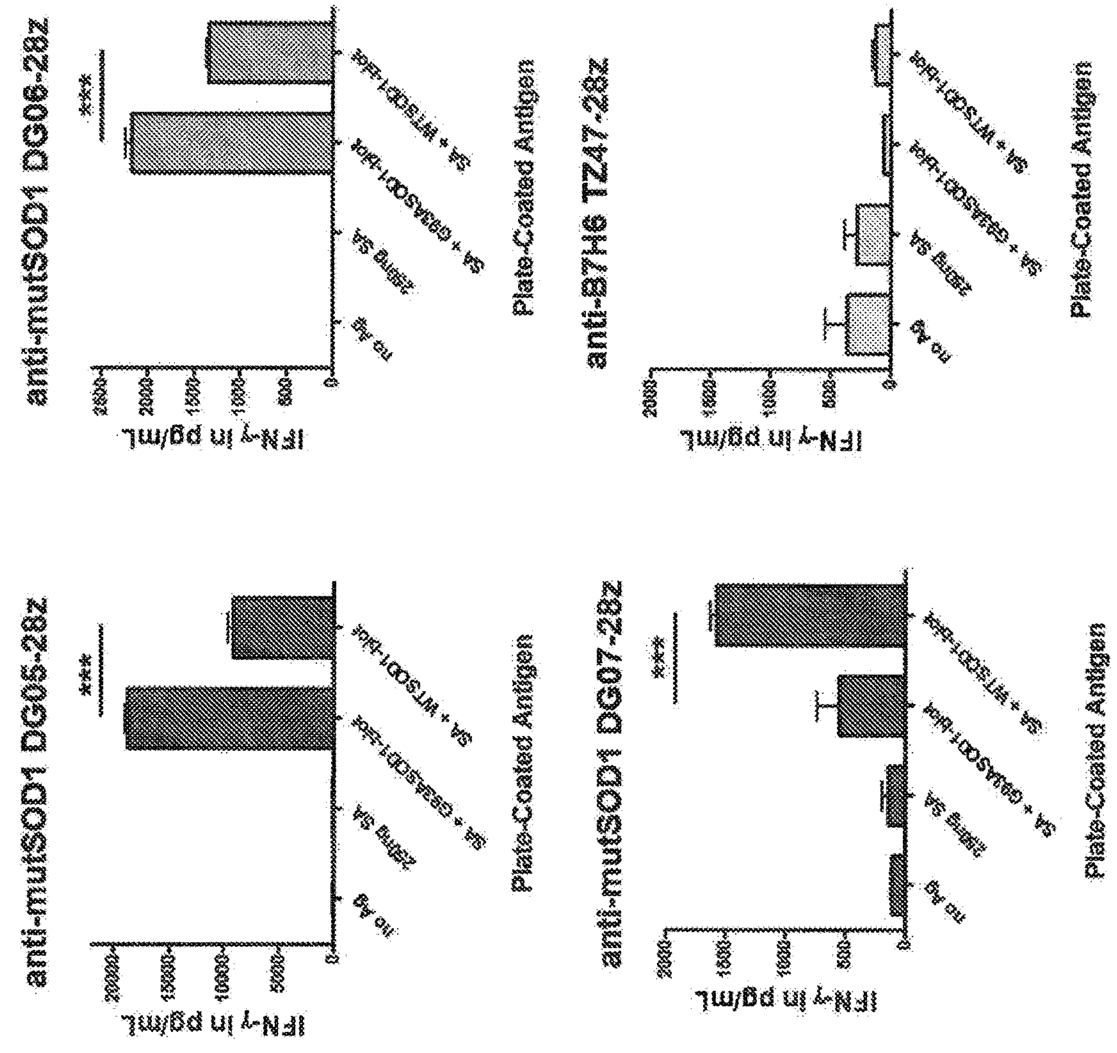
FIG. 12 presents data demonstrating antigen-specific activity of exemplary anti-mutSOD1 CARs in accordance with Example 5. IFN-γ production in response to biotinylated wt or mut SOD1 linked to plate-bound streptavidin (SA) by human T effector cells transduced to express anti-mutSOD1 CARs (named D005, DG06, and DG07) or negative control anti-B7H6 CAR.

FIG. 12 demonstrates that DG05-28z (SEQ ID NO: 24) and D006-28z (SEQ ID NO: 25) anti-mutSOD1 CARs expressed in human effector T cells produced IFN-gamma in response to biotinylated mutSOD1 relative to wtSOD1 that was linked to plate-bound streptavidin as described above. A third anti-mutSOD1 CAR called DG07-28z (SEQ ID NO: 26) produced a higher amount of IFN-γ in response to wtSOD1 as compared to mutSOD1 when expressed in human T effector cells.

The IL-10 production assays involving modified Tregs expressing anti-mutSOD1 CAR DG05-28z demonstrated that it is reasonable to expect that anti-SOD1 CAR Tregs can respond to mutant and wild-type forms of SOD1, but only when they were aggregated or bound on a surface (e.g. tissue culture plate). Based on data of DG05-28z and DG06-28z anti-mutSOD1 CARs expressed in human T effector cells as described above, it is reasonable to expect that CARs can be more selective to aggregated or plate-bound mutSOD1 relative to wtSOD1.

Figure 13:
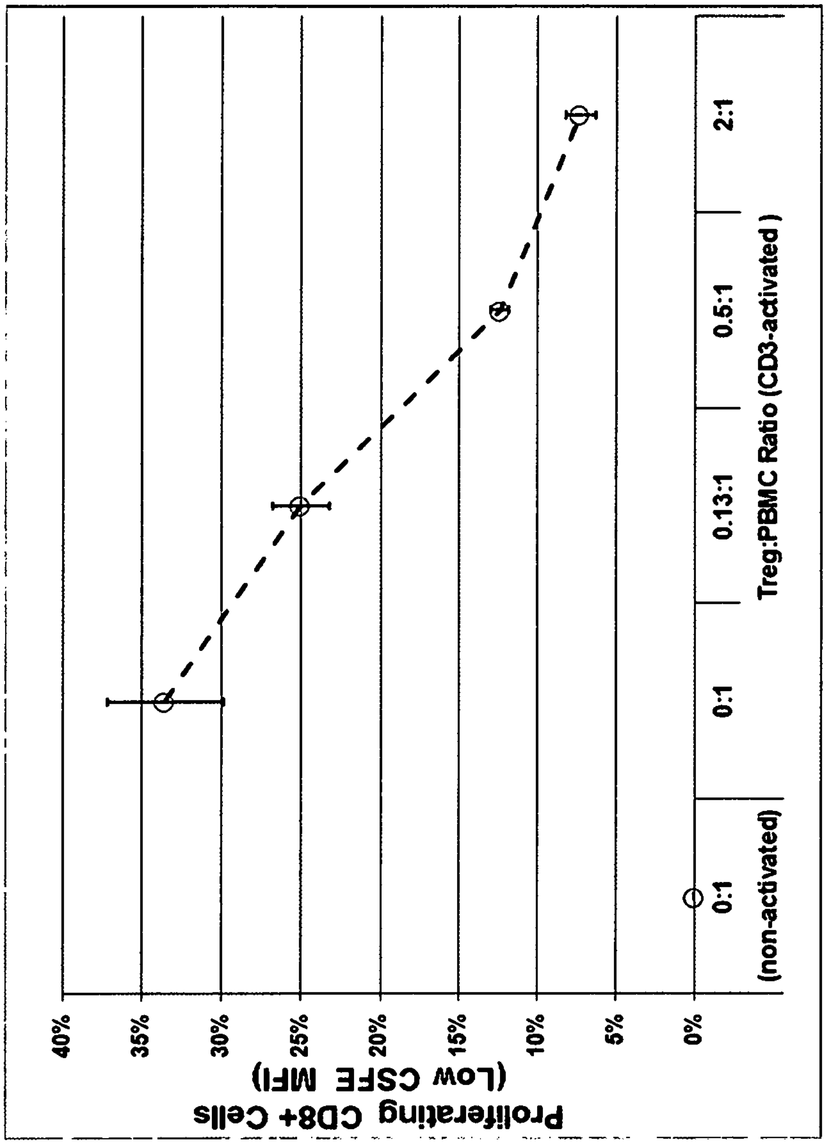
FIG. 13 presents data demonstrating D005-28z anti-mutSOD1 CAR modified Treg-mediated suppression of T cell proliferation in accordance with Example 5.

Modified Treg regulator function was evaluated by in vitro proliferation inhibition of T effector cells. The source of Teff was allogeneic PBMCs that were CSFE-labeled. Modified Tregs comprising CARs were plated in a 96-well V bottom plate in Treg growth medium at serial dilutions between 12,500 and 400,000 cells/0.1 mL/well. Allogeneic PBMCs were pre-labeled using CellTrace™ CFSE Cell Proliferation Kit (Invitrogen) according to manufacturer's instructions. CSFE-labeled PBMCs were stimulated with or without anti-CD3 (1 ug/mL; clone HIT3a; Biolegend) and added to plated Tregs or to wells with no Tregs. After 72 h, cells were blocked using human Cohns fraction (1 mg/mL;

Sigma), and then stained with APC anti-CD8 (clone RTA-T8; Biolegend) for flow cytometer analysis of $CD8^+$ cells expression of CSFE. The CFSE can be reduced with each cell division, so dividing cells can have a lower CFSE value. The % suppression of $CD8^+$ T cell proliferation was determined compared to control wells of stimulated PBMCs with anti-CD3 mAbs. Proliferation of the CD8 subset of Teff in the CSFE-labeled PBMCs was measured after 72 h or co-cultured with anti-mutSOD1 CAR Tregs. The CAR Tregs were co-cultured with PBMCs at Treg:PBMC ratios of 0.13:1, 0.5:1, and at 2:1 (FIG. 13).

Figure 14:
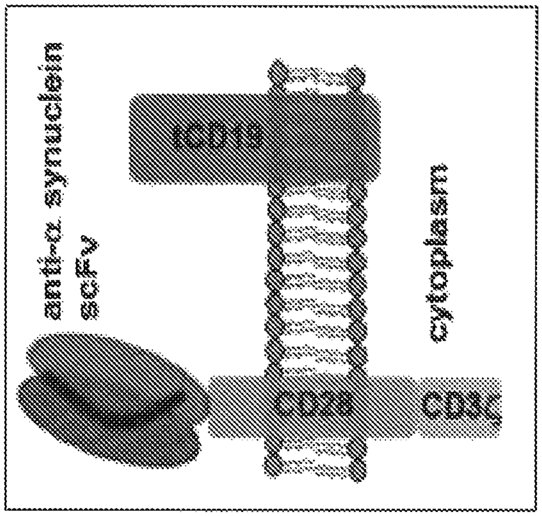
FIG. 14 presents a schematic design of an anti-α-synuclein-CD28-CD3ζ CAR in accordance with Example 6.

Example 6: Treg Isolation, Expansion and CAR Transduction for Modified Tregs Targeting Parkinson's Disease In the present example, modified Tregs targeting Parkinson's disease comprised anti-α-synuclein CARs using human variable heavy ($V_H$) and light ($V_L$) chain sequences. The anti-α-synuclein scFv was expressed extracellularly with the C-terminus of the $V_L$ fused to human CD28 hinge, transmembrane, and cytoplasmic domain, followed by a human CD3ζ cytoplasmic domain to create an anti-α-synuclein-CD28-CD3ζ CAR (FIG. 14). This CAR will trigger both primary and costimulation signaling upon antigen binding. A truncated (non-signaling) human CD19 (tCD19) is also expressed in the same vector using a 2A co-expression system and it serves as a way to track and purify transduced T cells. CARs targeting Parkinson's disease include DG08 (SEQ ID NO: 8), DG09 (SEQ ID NO: 9), DG10 (SEQ ID NO: 10), DG11 (SEQ ID NO: 11), DG08-CD28-CD3ζ (SEQ ID NO: 27), DG09-CD28-CD3ζ (SEQ ID NO: 28), DG10-CD28-CD3ζ (SEQ ID NO: 29), and DG11-CD28-CD3ζ (SEQ ID NO: 30). Modified Tregs targeting Parkinson's disease were prepared as follows.

CD4+CD25+ Tregs were isolated from human PBMCs in a two-step cell isolation process. First, human CD4+ cells were isolated by negative-selection using MOJOSORT™ Human CD4 T Cell Isolation Kit (Biolegend) and a EASYSEP™ Magnet (StemCell) according to manufacturer's instructions. Second, CD25hi cells were enriched from the CD4+-isolated cells by positive-selection using anti-human CD25 MicroBeads II (Miltenyi) and MS Columns with MiniMACS™ Separator magnet (Miltenyi). The CD4+ CD25hi cells were cultured in 24-well non-tissue culture plates at $1\times10^6$ cells/mL in Treg growth medium supplemented with 10% heat-inactivated human AB serum (Sigma). Treg growth media was either (1) X-Vivo-15 or (2) RPMI supplemented with 10 mM HEPES, 0.1 mM non-essential amino acids, 1 mM sodium pyruvate, 100 U/mL penicillin, 100 μg/mL streptomycin and 50 μM 2-ME. Cell incubation condition was humidified 37° C.; and 5% $CO_2$. Cells were stimulated with 25 $\mu L/1\times10^6$ cells of ImmunoCult™ Human CD3/CD28 T Cell Activator (StemCell) on days 0 and 9 in culture. In some instances, it is possible to use the CD3/CD28/CD2 T cell activator instead. Treg growth media was supplemented with 300 to 500 U/mL human IL-2 (Tecin from Roche, kindly provided by the NIH) starting on culture day 2. Cultured cells were transferred to 25 $cm^2$ tissue culture-treated flasks on day 5. Cells were transduced over two days with retroviral CAR constructs on day 10 and 11 in culture. 24-well non-tissue culture plate wells were pre-coated with RetroNectin® (Takara Bio USA, Inc.) according to manufacturer's instructions and then day 10 cultured cells were added at $0.3\times10^6$ cells/well in 0.3 mL of Treg growth media. Retroviral supernatant was added at 0.7 mL/well and plates were centrifuged at 1500 ref at 30° C.; for 1 h, and then incubated overnight. On the next day, 0.5 mL culture supernatant was replaced with 0.5 mL retroviral supernatant with 500 U/mL IL-2 and cells were re-centrifuged and then incubated overnight. The next day cells were transferred to 25 $cm^2$ tissue culture-treated flasks at $1\times10^6$ cells/mL. On day 13 of culture, a sample of cells was evaluated for transduction efficiency by measuring the percentage of the co-transduced truncated CD19 on cells by flow cytometry. If cells were less than 30% transduced, then cells can be enriched using anti-CD19-PE and EasySep™ Release PE Positive Selection Kit (StemCell) according to manufacturer's instructions. Cells were cultured with fresh Treg growth media added every two days until day 17.

Figure 15:
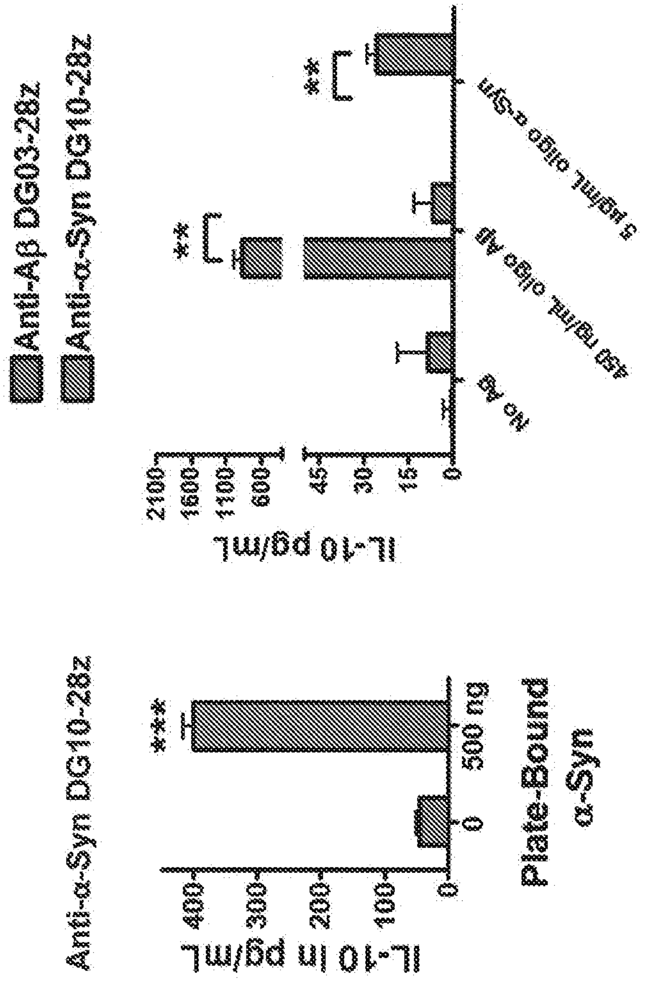
FIG. 15 presents data demonstrating the functional activity of exemplary modified Tregs in accordance with Example 7. IL-10 production in response to plate-bound α-synuclein, or to soluble oligomerized α-synuclein or $A\beta_{1-42}$ by day 17 Tregs transduced on days 10 and 11 with an anti-α-synuclein CAR (DG10-28z) or anti-Aβ CAR (DG03-28z).

Example 7: Functional Activity of Modified Tregs Targeting Parkinson's Disease The functional activity of modified Tregs targeting Parkinson's disease was evaluated by culturing modified Tregs in wells with α-synuclein coated on the well surface (plate-bound) and with soluble oligomerized α-synuclein versus media alone For stimulation with soluble antigen, day 17 CAR Tregs were plated in non-coated 96-well tissue culture plates at 50,000 cell/well in Treg growth media without IL-2. $A\beta_{1-42}$ or α-synuclein was pre-oligomerized by incubating at 40 μM in PBS at 37° C.; for 1 week with daily agitation. Oligomerized α-synuclein was added to Tregs in 0.1 mL Treg growth media and cell free supernatant was collected for human IL-10 ELISA (Biolegend) at 24 h and 72 h. For stimulation with plate-bound antigens, 96-well ELISA plates were coated with Aβ1-42, wtSOD1, mutSOD1, or α-synuclein in PBS overnight at 4° C. Plates were rinsed three times with PBS and day 17 CAR Tregs were added to the antigen-coated 96-well ELISA plates at 50,000 cell/well in Treg growth media without IL-2. Cell free supernatant was collected for human IL-10 ELISA (Biolegend) at 24 h and 72 h. Alternatively, streptavidin in PBS was coated on 96-well ELISA plates overnight at 4° C.; and biotinylated antigens were applied after rinsing unbound streptavidin. Another alternative method for antigen stimulation can be to use nanometer- or micrometer-sized polystyrene beads coated with the antigen e.g. biotinylated antigen linked to streptavidin-conjugated beads. FIG. 15 presents data that demonstrated anti-α-synuclein CAR Tregs produced IL-10 when cultured in wells with α-synuclein coated on the well surface (plate-bound) and with soluble oligomerized α-synuclein versus media alone. Additionally, as presented in FIG. 15, anti-α-synuclein CAR Tregs did not produce IL-10 in response to soluble oligomerized $A\beta_{1-42}$, whereas anti-Aβ CAR Tregs did produce IL-10 in response to soluble oligomerized $A\beta_{1-42}$, thus, demonstrating antigen specificity for the CARs on Tregs.

Example 8: Expression and Functional Activity of Modified Tregs Targeting ALS In the present example, expression and function of anti-mSOD1 CARs with different costimulatory signaling domains, and also with or without the CD3-zeta ("CD3ζ") stimulatory domain, were evaluated in ex vivo expanded and CAR transduced human Tregs. The anti-mSOD1 scFv DG05 and CD28 transmembrane domain ("28tm") were in all constructs, and mouse truncated CD19 was in the vector with the CAR on the same construct. The CD3-zeta ("CD3ζ") domain was joined to co-stimulatory domains CD28 ("28"), DAP10 ("10"), or CD44 ("44") to produce the following anti-mSOD1 CARs: DG05-28-3ζ (SEQ ID NO: 24); DG05-28tm-10-3ζ (SEQ ID NO: 40), and DG05-28tm-44-3ζ (SEQ ID NO: 41). Additionally, an anti-mSOD1 CAR comprising CD28 transmembrane domain ("CD28tm") with no stimulatory or co-stimulatory domain was produced (DG05-28tm, SEQ ID NO: 44); an anti-mSOD1 CAR comprising CD28 transmembrane domain with a 3ζ domain and without a CD28 co-stimulatory domain was produced (DG05-28tm-3ζ, SEQ ID NO: 42); and an anti-mSOD1 CAR comprising a CD28 co-stimulatory domain with no 3ζ domain was produced (DG05-28, SEQ ID NO: 43).

The modified Tregs of the present example were isolated, expanded, and transduced as generally described in Example 4. More specifically, Day 17 CAR Tregs were prepared from human PBMCs as described in Example 4). PG13 retrovirus with the following anti-mSOD1 CARs was used: DG05-28-3ζ (SEQ ID NO: 24); DG05-28tm-10-g (SEQ ID NO: 40); DG05-28tm-44-3ζ (SEQ ID NO: 41), DG05-28tm-3ζ (SEQ ID NO: 42), DG05-28 (SEQ ID NO: 43), and DG05-28tm (SEQ ID NO: 44).

The flow cytometry assays of the present example proceeded as follows. The percentage of CAR-transduced Tregs was measured by direct labeling of the CAR scFv with biotinylated protein L (1 μg/mL; GenScript, Piscataway, NJ, USA) followed by streptavidin-PE (BioLegend, San Diego, CA, USA). Cells were analyzed using an ACCURI™ C6 flow cytometer (BD Biosciences, Ann Arbor, MI, USA). Cells stained with streptavidin-PE only were used to threshold for non-specific background signal (see FIG. 16A, red vertical line of the six flow cytometry panels).

Assays of the present example that comprised CAR Treg activation by plate-bound antigen were performed as follows. 96-well ELISA plates were coated with 50 μL/well of 10 μg/mL of purified mutSOD1 protein in PBS overnight at 4° C. Plates were rinsed three times with PBS and then blocked with 0.1 mL/well of X-VIVO™-15+10% human sera. Media was added to control wells that were not coated with mSOD1 protein. CAR Tregs were added at 50,000 cells/0.2 mL/well and incubated for 6 h. Cells were transferred to 96 well cell culture plate wells and incubated for another 18 h. Cell-free media was collected for human IL-10 ELISA (BioLegend, San Diego, CA, USA).

Figure 16A:
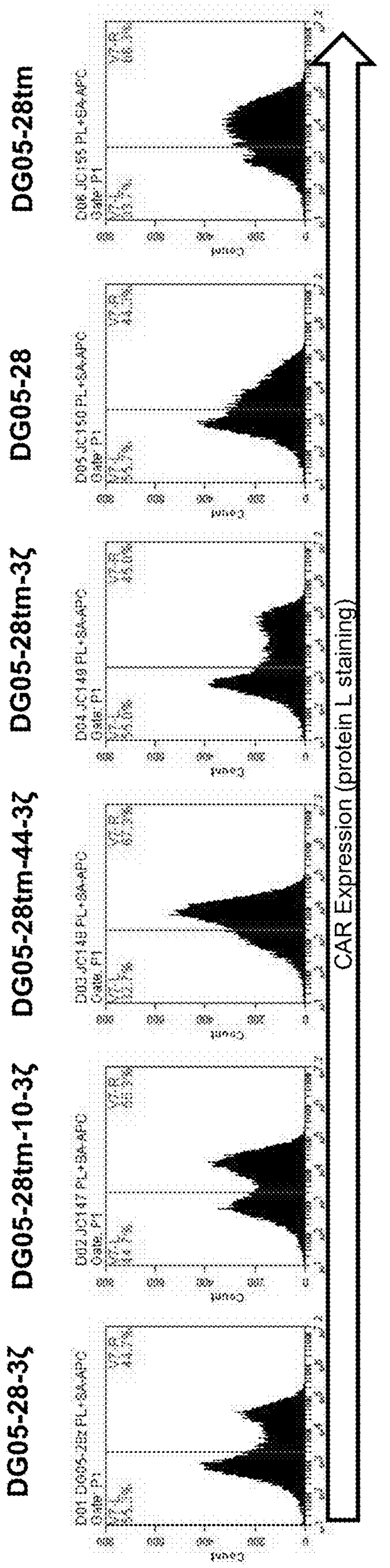
FIG. 16A-FIG. 16B present data demonstrating expression (FIG. 16A) and function (FIG. 16B) of anti-mSOD1 CARs with different co-stimulatory signaling domains and with or without the CD3zeta (3ζ) stimulatory domain in ex vivo expanded and CAR transduced human Tregs in accordance with Example 8.

Referring now to FIG. 16A, the flow cytometry results, which utilized protein L staining, demonstrated expression of each of the CAR constructs DG05-28-3ζ; DG05-28tm-10-3ζ DG05-28tm-44-3ζ; DG05-28tm-3ζ; DG05-28; and DG05-28tm on human Tregs.

Figure 16B:
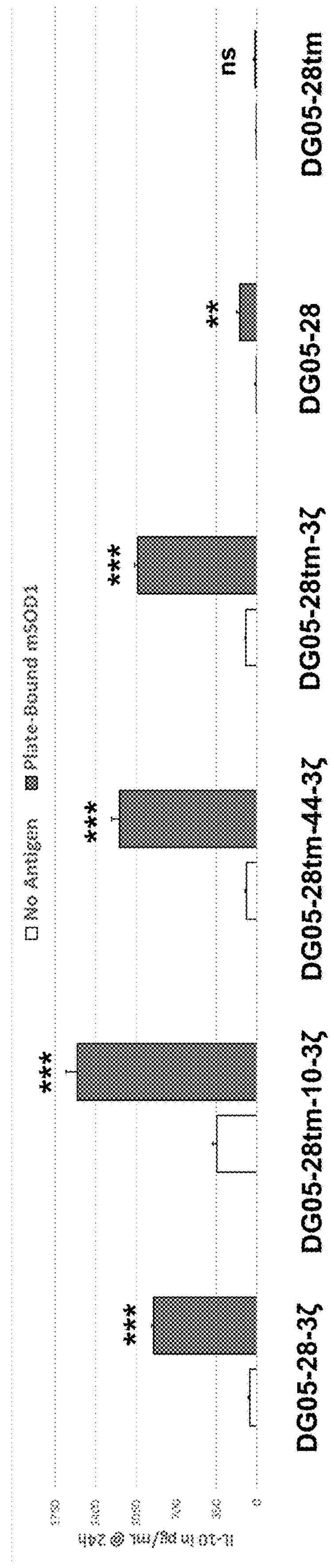

Referring now to FIG. 16B, DG05-28-3ζ; DG05-28tm-10-3ζ; DG05-28tm-44-3ζ; DG05-28tm-3ζ; DG05-28, but not DG05-28tm, produced IL-10 in response to mSOD1 antigen (ELISA). Regarding FIG. 16B, ns=not significant; =p<0.01; *=p<0.001 by student t-test (n=3).

Example 9: Functional Activity of Modified Tregs Targeting Alzheimer's Disease In the present example, expression and function of anti-Aβ CARs with different costimulatory signaling domains, and with or without the CD3-zeta (3ζ) stimulatory domain, were evaluated in ex vivo expanded and CAR transduced human Tregs. The anti-Aβ scFv DG03 and CD28 transmembrane ("28tm") domain were in all constructs, and mouse truncated CD19 was also expressed with the CAR on the same construct. The CD3zeta ("3ζ") was joined to co-stimulatory domains from CD28 ("28"), DAP10 ("10"), CD44 ("44"), 4-1BB ("BB") to produce the following anti-Aβ CARs: DG03-28-3ζ (SEQ ID NO: 22); D003-28tm-10-3ζ (SEQ ID NO: 45); DG03-28tm-44-3ζ (SEQ ID NO: 46); and DG03-28tm-BB-3 ((SEQ ID NO: 47). Additionally, an anti-Aβ CAR comprising a CD28 transmembrane domain with no stimulatory or co-stimulatory domains was produced (DG03-28tm (SEQ ID NO: 50)); an anti-Aβ CAR comprising a CD28 transmembrane domain with a CD3ζ domain and without a costimulatory domain was produced (DG03-28tm-3ζ (SEQ ID NO: 48)); and an anti-Aβ CAR comprising a CD28 transmembrane domain and a CD28 costimulatory domain but without a CD3ζ domain was produced (DG03-28 (SEQ ID NO: 49)).

The modified Tregs of the present example were isolated, expanded, and transduced as generally described in Example 1. More specifically, Day 17 CAR Tregs were prepared from human PBMCs as described in Example 1. PG13 retrovirus with the following anti-Aβ CARs was used: DG03-28-3ζ (SEQ ID NO: 22), DG03-28tm-10-3ζ (SEQ ID NO: 45), DG03-28tm-44-3ζ; (SEQ ID NO: 46), DG03-28tm-BB-3ζ (SEQ ID NO: 47), DG03-28tm-3ζ (SEQ ID NO: 48), DG03-28 (SEQ ID NO: 49), and DG03-28tm (SEQ ID NO: 50).

The flow cytometry assays of the present example proceeded as follows. The percentage of CAR-transduced Tregs was measured by indirect labeling of the co-expressed mouse truncated CD19 with PE anti-mouse CD19 (BioLegend, San Diego, CA, USA). Cells were analyzed using an ACCURI™ C6 flow cytometer (BD Biosciences, Ann Arbor, MI, USA). Non-stained cells were used to set the threshold for non-specific background signal (see FIG. 17A, red vertical line of the seven flow cytometry panels).

The oligomerized Aβ of the present example was prepared as follows. Aβ1-42 peptide in PBS at 2001.1114 was incubated for seven days at 37° C. in PBS. Oligomerized Aβ was diluted to 40 μM, aliquoted, and stored at −20° C.

Assays of the present example that comprised CAR Treg activation by plate-bound oligomerized Aβ proceeded as follows. CAR Tregs were plated in tissue culture-treated 96-well plates at 50,000 cells/0.2 mL/well in X-VIVO™-15+10% human sera with or without 100 nM Aβ and incubated for 24 h. Cell-free media was collected for human IL-10 ELISA (BioLegend, San Diego, CA, USA).

Figure 17A:
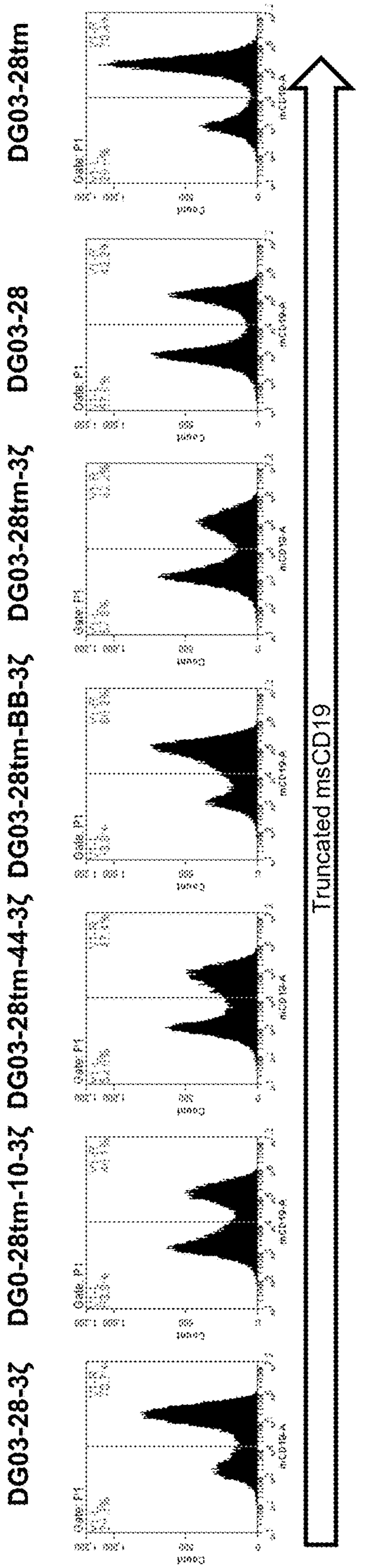
FIG. 17A-FIG. 17B present data demonstrating expression (FIG. 17A) and function (FIG. 17B) of anti-Aβ CARs with different co-stimulatory signaling domains and with or without the CD3zeta (3ζ) stimulatory domain in ex vivo expanded and CAR transduced human Tregs in accordance with Example 9.

Referring now to FIG. 17A, the flow cytometry results, which utilized msCD19 staining, demonstrated expression of each of the CAR constructs DG03-28-3ζ, DG03-28tm-10-3ζ, DG03-28tm-44-3ζ, DG03-28tm-BB-3ζ, DG03-28tm-3ζ, DG03-28, and DG03-28tm on human Tregs.

Figure 17B:
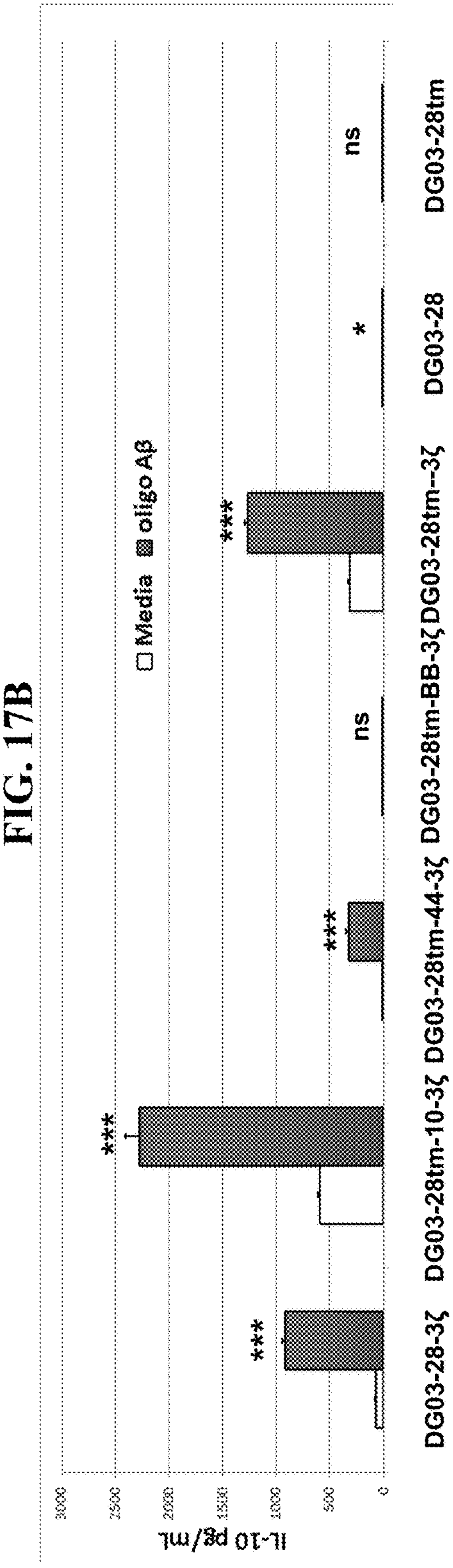

Referring now to FIG. 17B, DG03-28-3ζ; DG03-28tm-10-3ζ; DG03-28tm-44-3ζ; and DG03-28tm-CD3ζ, but not DG03-28tm-BB-3ζ; DG03-28; and DG03-28tm; produced IL-10 in response to plate-bound oligomerized Aβ antigen (ELISA). Regarding FIG. 17B, ns=not significant; *=p<0.05; ***=p<0.001 by student t-test (n=3).

Example 10: Functional Activity of Modified Tregs Targeting ALS

In the present example, the antigen-specific activity of anti-mutSOD1 CARs were evaluated in general accordance with the procedures described in Example 5. Ex viva expanded and CAR transduced human Tregs engineered to express the anti-mSOD1 CAR DG05-28-3ζ; (SEQ ID NO: 24) were co-cultured with 6.0-μm or 0.6-μm diameter polystyrene beads (used to mimic aggregates of mSOD1 that develop in CNS of ALS patients) pre-coated with mSOD1, and the effects on cell surface expression of GITR, PD-1, and CTLA-4 were monitored (see FIG. 18). Additionally, production of IL-10 was evaluated by performing an ELISA assay (see FIG. 18). The anti-mSOD1 CAR targeting ALS included modified Tregs comprising DG05-28-CD3ζ (SEQ ID NO: 24).

Modified Treg isolation, expansion, and CAR transduction proceeded as generally described in Example 4. More specifically, CAR Tregs were prepared from human PBMCs as described in Example 4, and PG13 retrovirus with the anti-mSOD1 CAR DG05-28-3ζ was used for transduction on Days 10 and 11.

CAR Treg cryopreservation and recovery after thawing proceeded as follows for the present example. Day 16 CAR Tregs were cryopreserved in cryovials at $20\times10^6$ cells/mL in solution of 90% heat-inactivated FBS and 10% DMSO in MR. FROSTY™ Freezing Container at −80° C. for 24 h and then transferred to liquid nitrogen. Cells were thawed and rinsed in PBS, resuspended to $2\times10^6$ cells/mL in X-VIVO™-15+10% human sera+500 u/mL IL-2, and incubated for 24 h. Cells were centrifuged to pellet cells, resuspended in 4 mL X-VIVO™-15 media and centrifuged over 4 mL of LYMPHOPREP™ separation media at 800×g for 20 min. Cells at the interphase were collected and rinsed in X-VIVO™-15 and pelleted. Cells were resuspended to $1\times10^6$ cells/mL in X-VIVO™-15+10% human sera (no IL-2).

Preparation of antigen-coated polystyrene beads for use with the bead-based assays of the present example proceeded as follows. Purified biotinylated, His-tagged human mutant G93A SOD1 protein (mSOD1) was provided as a gift by Dr. Roos (University of Chicago Medical Center, Chicago, IL, USA). SPHERO™ Streptavidin Coated Particles 6 gm-diameter polystyrene (Spherotech cat. # SVP-60-5, Lake Forest, IL, USA) and SPHERO™ Rabbit anti-6×His Coated Particles 0.6 μm-diameter polystyrene (Spherotech cat. # HISP-05-2, Lake Forest, IL, USA) were rinsed in PBS with sterile 1% heat-inactivated FBS. Beads were pelleted by microcentrifugation at 12,000×g for 2 min. Beads were resuspended in 1% FBS with or without 2 μg/mL mSOD1 and incubated at RT for 1.5 h. Cells were pelleted, rinsed in 1% FBS, and resuspended in X-VIVO™-15+10% human sera.

The bead-based assays of the present example that comprised CAR Treg activation by bead-bound antigen proceeded as follows. CAR Tregs were plated in tissue culture-treated 12-well plates at $1.6\times10^6$ cells/0.8 mL/well in X-VIVO™-15+10% human sera. The non-coated and mSOD1-coated 6 μm-diameter polystyrene beads were added at bead:cell ratio of 4:1. The non-coated and mSOD1-coated 0.6 μm-diameter polystyrene beads were added at a bead:cell ratio of 100:1. No beads were added to some wells as media-only controls. After 24 h incubation cell-free media was collected for human IL-10 ELISA (BioLegend, San Diego, CA, USA). Cells were collected for flow cytometry to assess cell surface markers. Cells were labeled with APC anti-human GITR (clone 621; BioLegend, San Diego, CA, USA), APC anti-human PD-1 (clone EH12.2H7; BioLegend, San Diego, CA, USA), and PE anti-human CTLA-4 (clone BNI3; BioLegend, San Diego, CA, USA). Mean fluorescence intensity (MFI) was measured and histograms prepared using an ACCURI™ C6 flow cytometer (BD Biosciences, Ann Arbor, MI, USA). Non-stained cells were used to set the threshold for non-specific background signal (see FIG. 18, vertical line of each of the six flow cytometry plots).

Figure 18:
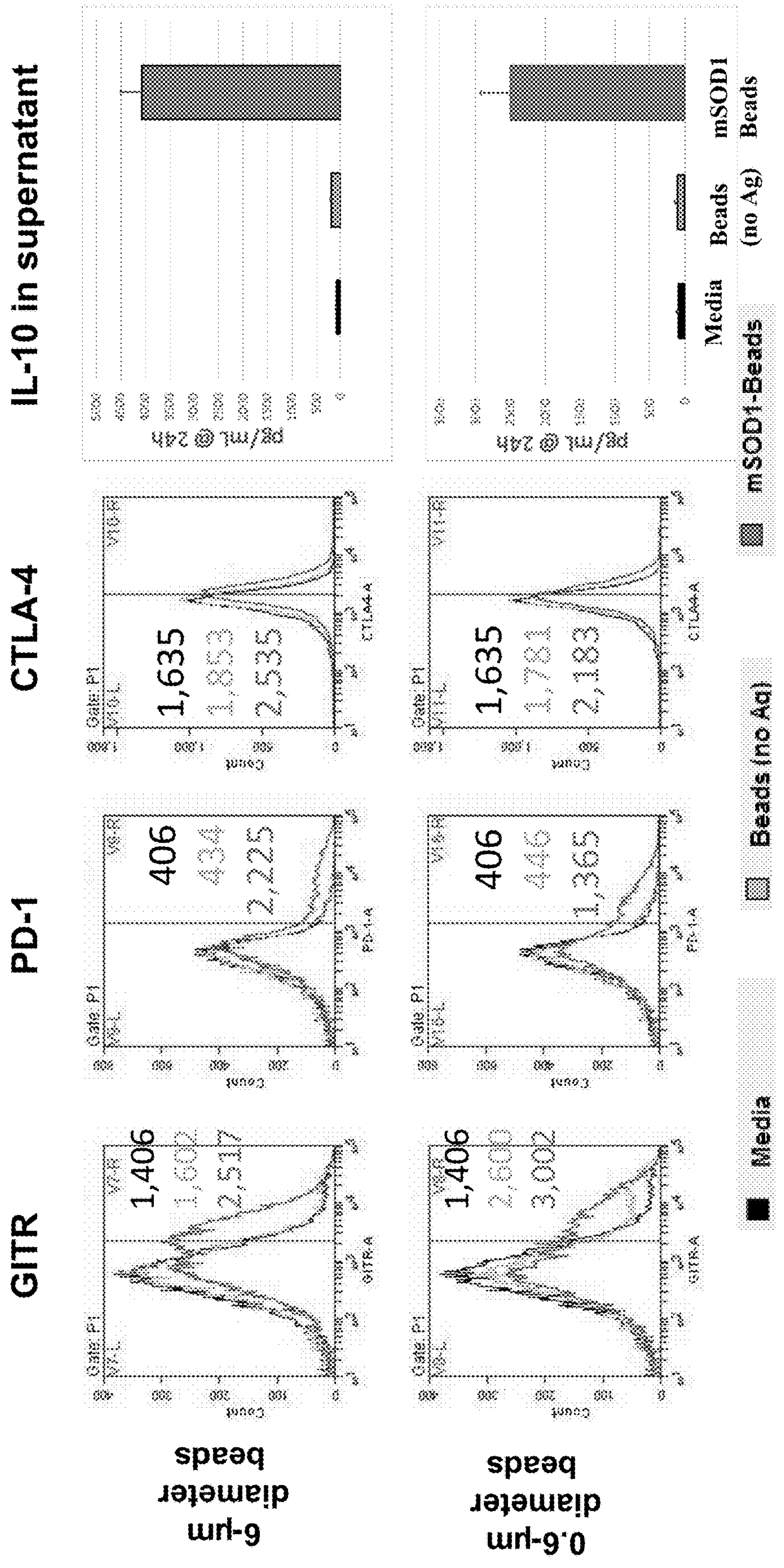
FIG. 18 presents data demonstrating the antigen-specific activity of anti-mutSOD1 CARs as demonstrated by assays evaluating the cell surface expression of GITR, PD-1, and CTLA-4 and the production of IL-10 in accordance with Example 10. With regard to each of the six plots related to cell surface expression markers: the numerical values reported for each correspond to, from top to bottom: media; beads (no Ag); and mSOD1 Beads.

Referring now to FIG. 18, the results demonstrated that the modified Tregs co-cultured with 6.0 um or 0.6 um beads pre-coated with mSOD1 increased cell surface expression of GITR, PD-1, and CTLA-4 (flow cytometry after 24 h; mean MFI shown) (see FIG. 18, six flow cytometry plots).

Moreover, the IL-10 ELISA assay of the present example further demonstrated the responsiveness of the modified human Tregs to mSOD1, as the modified human Tregs responded to the mSOD1 coated beads as demonstrated by the increase in IL-10 production relative to beads not coated with antigen or to media alone (see FIG. 18, two IL-10 in supernatant graphs).

Example 11: Functional Activity of Modified Tregs Targeting ALS

In the present example, the functional activity of modified Tregs targeting ALS was evaluated by co-culturing modified Tregs with spinal cord tissue explants derived from transgenic mice expressing human mSOD1. Additionally, the functional activity of modified Tregs targeting ALS was evaluated by co-culturing modified Tregs with spinal, liver, or lung tissue explants derived from transgenic mice expressing human mSOD1. The modified Tregs included modified Tregs comprising DG05-CD28-CD3ζ (referred to as DG05-28z in FIG. 19A and FIG. 1913) (SEQ ID NO: 24), and, as a negative control, modified Tregs comprising an anti-Aβ CAR (referred to as DG03-28z in FIG. 19A and FIG. 19B) (DG03-CD28-CD3ζ (SEQ ID NO: 22)).

Modified Treg isolation, expansion, and CAR transduction proceeded as generally described in Example 4. More specifically, CAR Tregs were prepared from human PBMCs as described in Example 4. PG13 retrovirus with the anti-mSOD1 CAR DG05-CD28-CD3ζ or anti-Aβ CAR DG03-CD28-CD3ζ was used for transductions on Days 10 and 11.

CAR Treg cryopreservation and recovery after thaw proceeded as follows. Day 16 CAR Tregs were cryopreserved in cryovials at $20\times10^6$ cells/mL in solution of 90% heat-inactivated FBS and 10% DMSO in Mr. FROSTY™ Freezing Container at −80° C. for 24 h and then transferred to liquid nitrogen. Cells were thawed and rinsed in PBS, resuspended to $2\times10^6$ cells/mL in X-VIVO™-15+10% human sera+500 u/mL IL-2, and incubated for 24 h. Cells were centrifuged to pellet cells, resuspended in 4 mL X-VIVO™-15 media and centrifuged over 4 mL of LYMPHOPREP™ separation media at 800×g for 20 min. Cells at the interphase were collected and rinsed in X-VIVO™-15 and pelleted. Cells were resuspended to $1\times10^6$ cells/mL in X-VIVO™-15+10% human sera (no IL-2).

CAR Treg activation by mouse tissue explants proceeded as follows for the present example. B6SJL.SOD1-G93A (stock #002726, The Jackson Laboratory, Bar Harbor, ME, USA) and non-transgenic littermates were used in the present example. The mSOD1 transgenic mice were monitored for weight loss and limb paralysis. Spinal cord tissues were collected from non-transgenic mice or mSOD1 transgenic mice at different stages of disease development: 13 weeks (pre-paralysis), 14 weeks (clinical onset), 16 weeks (paralysis), or 18 weeks (disease end-stage weeks defined as 15% weight loss and hind-limb paralysis). Liver and lung were also collected from mSOD1 transgenic mice at disease end-stage. Tissues were transferred to ice-cold X-VIVO™-15 media, cut into 2 mm×2 mm pieces, placed in wells of 96-well ELISA plate without media for 5 min., then CAR Tregs were added at 50,000 cells/well in 0.2 mL of X-VIVO™-15+10% human sera (no IL-2). After 24 h incubation cell-free media was collected for human IL-10 ELISA (BioLegend, San Diego, CA, USA).

Figure 19A:
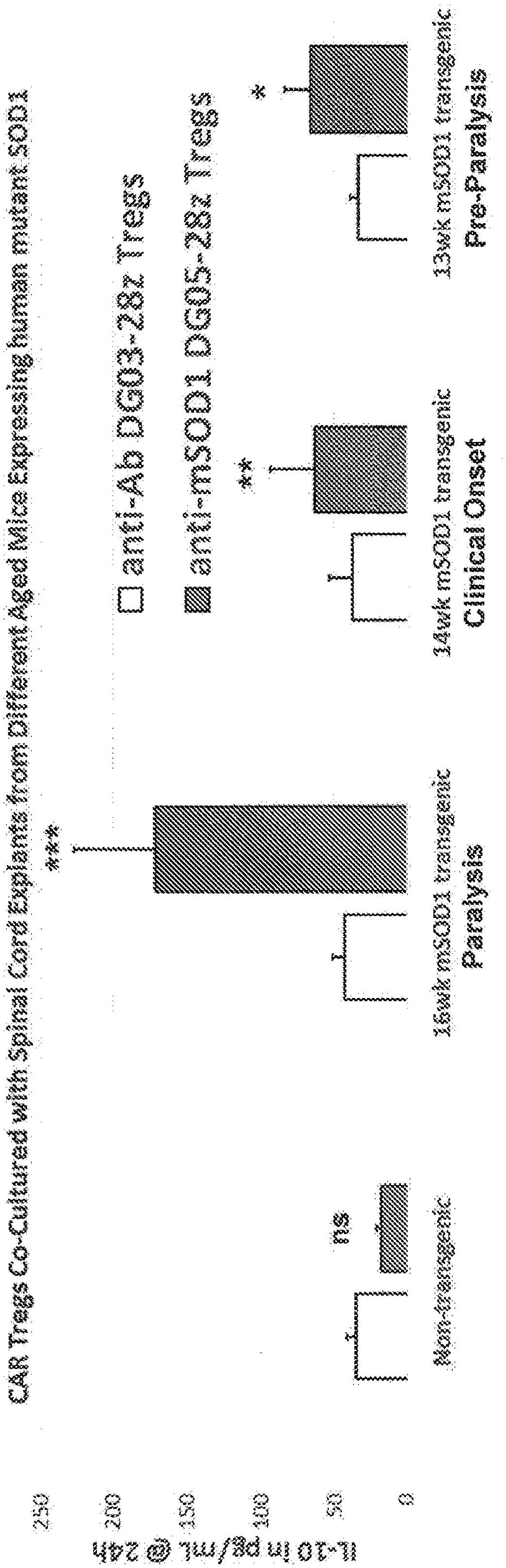
FIG. 19A-FIG. 19B present data demonstrating the functional activity of modified Tregs targeting ALS by assays comprising co-culturing said modified Tregs with spinal cord tissue explants derived from transgenic mice expressing human mSOD1 (FIG. 19A), and co-culturing modified Tregs with spinal, liver, or lung tissue explants derived from transgenic mice expressing human mSOD1 (FIG. 19B) in accordance with Example 11. Spinal cord tissues were collected from non-transgenic mice or mSOD1 transgenic mice at different stages of disease development: 13 weeks (see FIG. 19A: pre-paralysis), 14 weeks (see FIG. 19A: clinical onset), 16 weeks (see FIG. 19A: paralysis), or 18 weeks (disease end-stage weeks defined as 15% weight loss and hind-limb paralysis; see FIG. 19B). Liver and lung were also collected from mSOD1 transgenic mice at disease end-stage (see FIG. 19B).
Figure 19B:
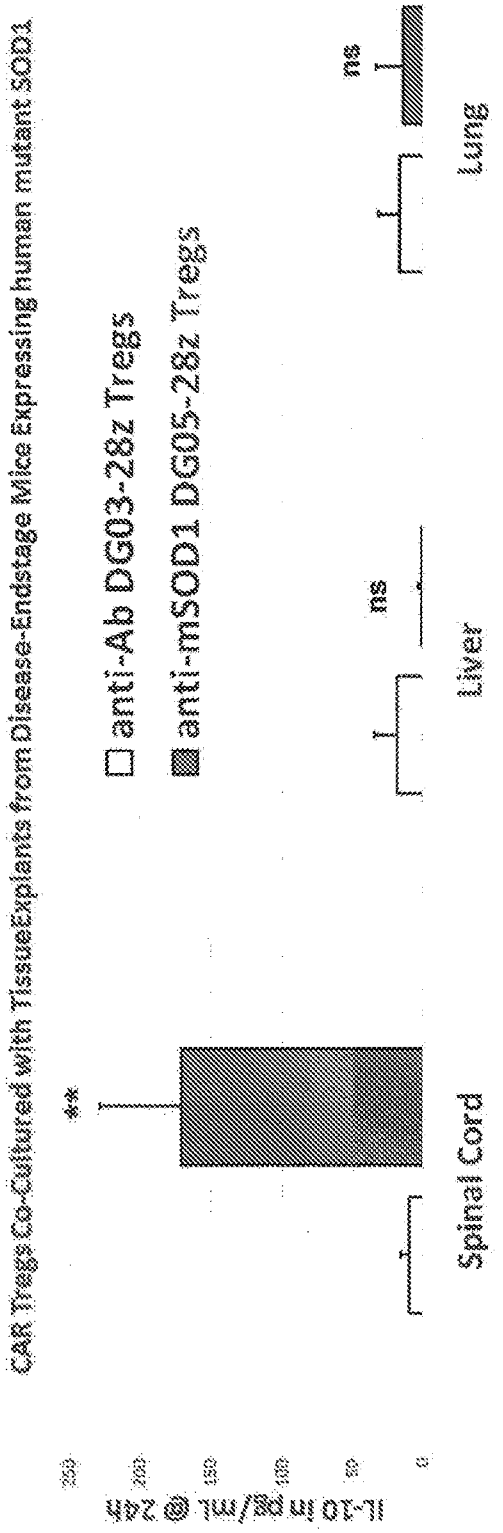

Referring now to FIG. 19A, DG05-CD28-CD3ζ, which targeted mSOD1, stimulated production of IL10, whereas Tregs expressing the negative control CAR (DG03-CD28-CD3ζ) did not stimulate production of IL-10 when co-cultured with spinal cord explants (ns=not significant; *=p<0.05; =p<0.01; *=p<0.001 by student t-test (n=8 for FIG. 19A)).

Referring now to FIG. 1913, DG05-CD28-CD3ζ, which targeted mSOD1, stimulated production of IL10 when co-cultured with spinal cord tissue, but not when co-cultured with liver or lung tissue, whereas Tregs expressing the negative control CAR (DG03-CD28-CD3ζ) did not stimulate production of IL-10 when co-cultured with any of spinal cord, liver, or lung tissue (ns=not significant; *=p<0.05; =p<0.01; *=p<0.001 by student t-test (n=3 for FIG. 19B)).

Example 12: Functional Activity of Modified Tregs Targeting Alzheimer's Disease In the present example, the functional activity of modified Tregs targeting Alzheimer's disease was evaluated by exposing said modified Tregs to oligomerized Aβ and monitoring mRNA and protein secretion levels of IL-10 and IL-4. The modified Tregs included modified Tregs comprising the anti-Aβ CAR DG03-CD28-CD3ζ (SEQ ID NO: 22).

Modified Treg isolation, expansion, and CAR transduction proceeded as generally described in Example 1. More specifically, Day 17 CAR Tregs were prepared from human PBMCs as described in Example 1. PG13 retrovirus with the anti-Aβ CAR DG03-CD28-CD3ζ was used for transductions on Days 10 and 11.

Preparation of oligomerized Aβ for use with the present example proceeded as follows. Aβ1-42 peptide in PBS at 200 μM was incubated for seven days at 37° C. in PBS. Oligomerized Aβ was diluted to 40 μM, aliquoted, and stored at −20° C.

CAR Treg activation by oligomerized Aβ proceeded as follows for the present example. CAR Tregs were plated in tissue culture-treated 96-well plates at 50,000 cells/0.2 mL/well in X-VIVO™-15+10% human sera with or without 100 nM Aβ and incubated for 24 h. Cell-free media was collected for human IL-4 and human IL-10 ELISAs (BioLegend, San Diego, CA, USA).

Qualitative RT-PCR proceeded as follows for the present example. CAR Tregs were plated in tissue culture-treated 12-well plates at $1.0\times10^6$ cells/1.0 mL/well in X-VIVO™-15+10% human sera and incubated overnight. Oligomerized Aβ (100 nM) was added the next day with some wells left untreated (no antigen). Cells were collected 7.5 h after addition of oligomerized Aβ to the cells, which were then pelleted, and then the RNA extracted using TRIzol Reagent (Invitrogen, ThermoFisher Scientific, Waltham, MA, USA). Eluted RNA was quantified by spectrophotometry and 1 ug was reverse-transcribed using QSCRIPT™ cDNA SuperMix (Quanta Biosciences, Beverly, MA, USA). Reaction mixtures contained 2 ng cDNA, 200 nM dNTPs, 400 nM primers, 1× Standard Taq Buffer (New England BioLabs), and 0.625 U of TAQ polymerase (BioLabs) in a total reaction volume of 25 μl. The sequences of the primer used were as follows: human β-actin (101-bp product): forward, 5'-GGC CGA GGA CTT TGA TTG C-3' (SEQ ID NO: 255); reverse, 5'-TGG GGT GGC TTT TAG GAT GG-3' (SEQ ID NO: 256); human IL-4 (148-bp product): forward, 5'-GCT TCC CCC TCT GTT CTT CC-3' (SEQ ID NO: 257); reverse, 5'-GAT GTC TGT TAC GGT CAA CTC G-3' (SEQ ID NO: 258); and human IL-10 (82-bp product): forward, 5'-TCA AGG CGC ATG TGA ACT CC-3' (SEQ ID NO: 259); reverse, 5'-CAG GGA AGA AAT CGA TGA CAG C-3' (SEQ ID NO: 260). Samples were placed in a 2720 Thermal Cycler (Applied BioSystems, Foster City, CA, USA) at 95° C. for 2 min followed sequentially by a cyclic phase at 95° C. for 30 s, 60° C. for 30 s, and then 68° C. for 35 s for 35 cycles. Amplification products were electrophoresed on a 1.5% agarose gel containing 1×SYBR™ Safe DNA Gel Stain (Invitrogen, Thermo Fisher Scientific, Waltham, MA, USA) at 105 V for 35 min. Bands were visualized and imaged at 302 nm using Alpha Imager EP gel documentation system (Alpha Innotech, San Leandro, CA, USA).

Figure 20B:
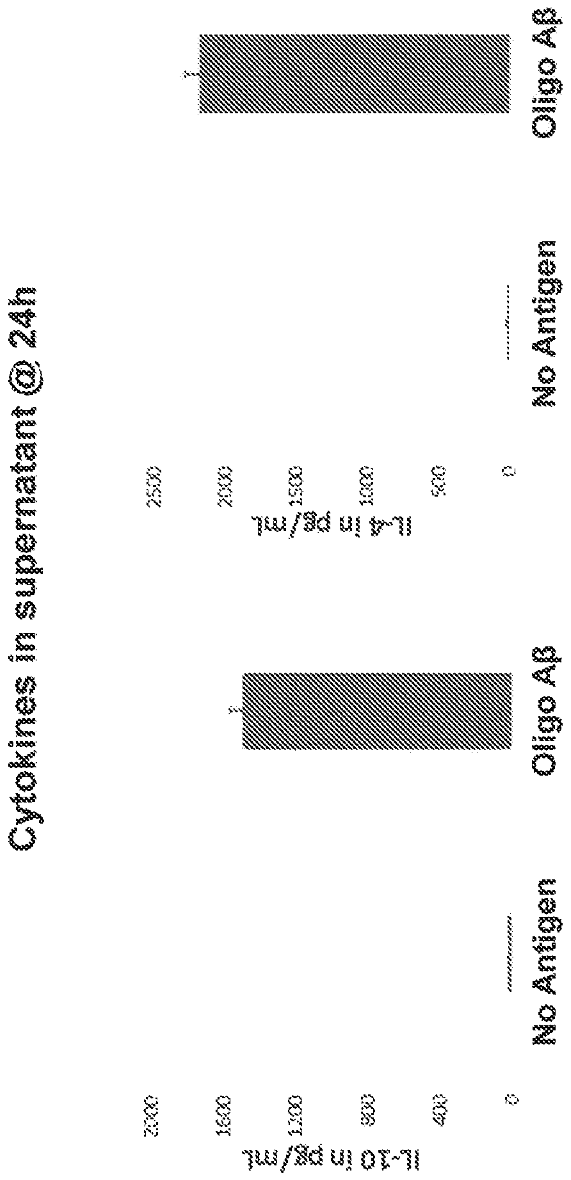
FIG. 20A-FIG. 20B present data demonstrating the functional activity of modified Tregs targeting Alzheimer's disease, wherein said modified Tregs were exposed to oligomerized Aβ and then the mRNA levels of IL-10 and IL-4 (FIG. 20A) and protein secretion levels of IL-10 and IL-4 (FIG. 20B) were monitored in accordance with Example 12.
Figure 20A:
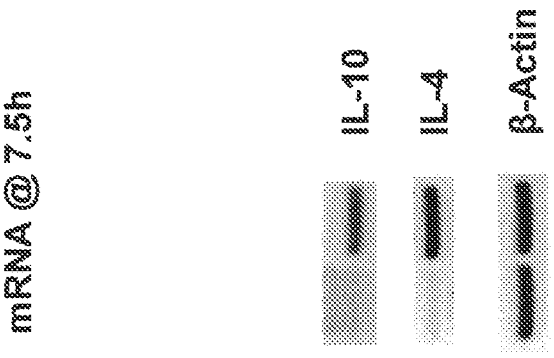

Referring now to FIG. 20A, the modified Tregs exposed to oligomerized Aβ demonstrated an increase in IL-10 and IL-4 mRNA levels as compared to the modified Tregs which were not exposed to oligomerized Aβ as monitored by RT-PCR gel staining. β-actin staining served as a control (see FIG. 20A).

Referring now to FIG. 20B, the modified Tregs exposed to oligomerized Aβ demonstrated an increase in IL-10 and IL-4 production as compared to modified Tregs which were not exposed to oligomerized Aβ as monitored by ELISA.

Example 13: Functional Activity of Modified Tregs Targeting ALS

In the present example, the antigen-specific anti-inflammatory activity of anti-mutSOD1 CARs was evaluated in the assays described below. The modified Tregs included modified Tregs comprising anti-mSOD1 CAR DG05-CD28-CD3ζ (SEQ ID NO: 24).

Modified Treg isolation, expansion, and CAR transduction proceeded as generally described in Example 4. More specifically, CAR Tregs were prepared from human PBMCs as described in Example 4. PG13 retrovirus with the anti-mSOD1 CAR DG05-CD28-CD3ζ was used for transduction on Days 10 and 11.

CAR Treg cryopreservation and recovery after thaw proceeded as follows for the present example. Day 16 CAR Tregs were cryopreserved in a cryovials at $20\times10^6$ cells/mL in solution of 90% heat-inactivated FBS and 10% DMSO in Mr. FROSTY™ Freezing Container at −80° C. for 24 h and then transferred to liquid nitrogen. Cells were thawed and rinsed in PBS, resuspended to $2\times10^6$ cells/mL in X-VIVO™-15+10% human sera+500 u/mL IL-2, and incubated for 24 h. Cells were centrifuged to pellet cells, resuspended in 4 mL X-VIVO™-15 media and centrifuged over 4 mL of LYMPHOPREP™ separation media at 800×g for 20 min. Cells at the interphase were collected and rinsed in X-VIVO™-15 and pelleted. Cells were resuspended to $1\times10^6$ cells/mL in X-VIVO™-15+10% human sera (no IL-2).

Pre-activation of the CAR Tregs of the present example proceeded as follows. 96-well ELISA plates were coated with 50 μL/well of 10 μg/mL of purified mutSOD1 protein or 5 ug/mL OKT3 antibody (anti-CD3) in PBS overnight at 4° C. Control wells for non-activated CAR Tregs were left uncoated. Plates were rinsed three times with PBS and then blocked with 0.1 mL/well of X-VIVO™-15+10% human sera. CAR Tregs were added at 100,000 cells/0.2 mL/well and incubated for 6 h. Cells were then collected and diluted to 500,000 CAR Tregs/mL in X-VIVO™-15+10% human sera.

Co-culture of the pre-activated CAR Tregs and monocyte/macrophages of the present example proceeded as follows. Monocytes were isolated by CD14-negative selection (StemCell 19359) from human PBMCs (different donor from CAR Tregs) and incubated for 6 h at 50,000 cells/0.1 mL/well in a 96-well tissue culture-treated white luminometer plate (CORNING® COSTAR® 3719). Non-Activated, mSOD1 pre-activated, or anti-CD3 pre-activated CAR Tregs were added at 40,000 cells/0.1 mL/well. Co-cultured cells were incubated in a final volume of 0.2 mL/well for 2 days.

Stimulation of the CAR Treg/macrophage co-cultures of the present example proceeded as follows. After 2 days of incubation, CAR Treg/macrophage co-cultures were stimulated by adding either phorbol myristate acetate (PMA; 40 nM), zymosan particles (20 μg/mL), or lipopolysaccharide (LPS; 20 ng/mL). To measure superoxide generation, lucigenin (5 μM) was added with PMA or zymosan and lucigenin-mediated bioluminescence was measured on a Centro LB 960 Microplate Luminometer (2 s exposure) at 7 timepoints over 6 h. To measure TNF-α by ELISA (BioLegend, San Diego, CA, USA), cell-free media was collected 6 h after adding LPS.

Figure 21A:
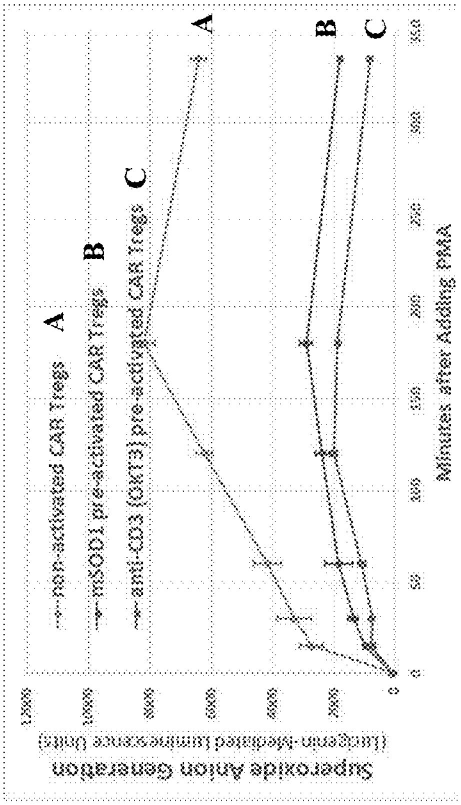
FIG. 21A-FIG. 21C present data demonstrating the antigen-specific anti-inflammatory activity of anti-mutSOD1 CARs in accordance with Example 13.

Referring now to FIG. 21A, modified Tregs comprising DG05-CD28-CD3ζ which were pre-stimulated with either mSOD1 or anti-CD3 antibody demonstrated inhibition of PMA-stimulated superoxide generation (as measured by Lucigenin-mediated luminescence). Regarding FIG. 21A, ns=not significant; **=p<0.01 relative to non-activated CAR Tregs by Dunnett's multiple comparison test (n=3).

Figure 21B:
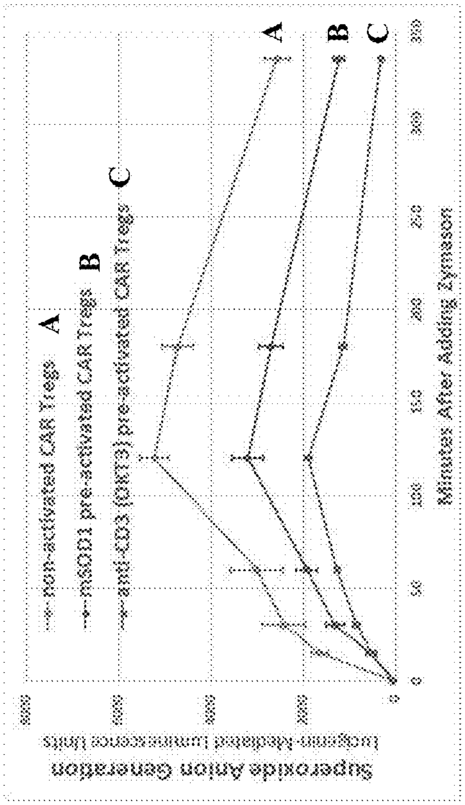

Referring now to FIG. 21B, modified Tregs comprising DG05-CD28-CD3ζ which were pre-stimulated with either mSOD1 or anti-CD3 antibody demonstrated inhibition of zymason-stimulated superoxide generation (as measured by Lucigenin-mediated luminescence). Regarding FIG. 21B, ns=not significant; **=p<0.01 relative to non-activated CAR Tregs by Dunnett's multiple comparison test (n=3).

Figure 21C:
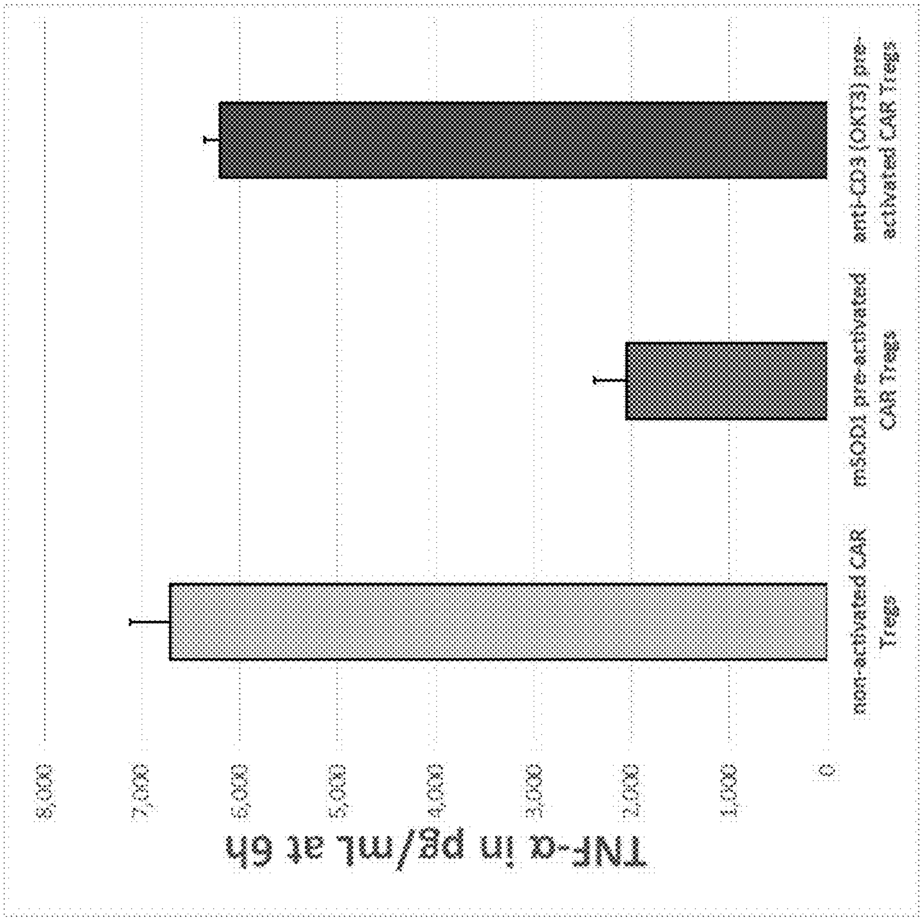

Referring now to FIG. 21C, modified Tregs comprising DG05-CD28-CD3ζ which were pre-stimulated with mSOD1 demonstrated inhibition of LPS-stimulated TNF-α production as measured by ELISA at 24 h, whereas modified Tregs comprising D005-CD28-CD3ζ which were pre-stimulated with anti-CD3 antibody did not demonstrate inhibition of LPS-stimulated TNF-α production. Regarding FIG. 21C, ns=not significant; **=p<0.01 relative to non-activated CAR Tregs by Dunnett's multiple comparison test (n=3).

Example 14: Functional Activity of Modified Tregs Targeting Alzheimer's Disease In the present example, the antigen-specific anti-inflammatory activity of anti-Aβ CARs was evaluated in the assays described below. The modified Tregs included modified Tregs comprising anti-Aβ CAR DG03-CD28-CD3ζ (SEQ ID NO: 22).

Modified Treg isolation, expansion, and CAR transduction proceeded as generally described in Example 1. More specifically, CAR Tregs were prepared from human PBMCs as described in Example 1. PG13 retrovirus with the anti-Aβ CAR DG03-CD28-CD3ζ was used for transduction on Days 10 and 11.

Modified CAR Treg cryopreservation and recovery after thaw proceeded as follows for the present example. Day 16 CAR Tregs were cryopreserved in a cryovials at $20\times10^6$ cells/mL in solution of 90% heat-inactivated FBS and 10% DMSO in Mr. FROSTY™ Freezing Container at −80° C. for 24 h and then transferred to liquid nitrogen. Cells were thawed and rinsed in PBS, resuspended to $2\times10^6$ cells/mL in X-VIVO™-15+10% human sera+500 u/mL IL-2, and incubated for 24 h. Cells were centrifuged to pellet cells, resuspended in 4 mL X-VIVO™-15 media and centrifuged over 4 mL of LYMPHOPREP™ separation media at 800×g for 20 min. Cells at the interphase were collected and rinsed in X-VIVO™-15 and pelleted. Cells were resuspended to $1\times10^6$ cells/mL in X-VIVO™-15+10% human sera (no IL-2).

Pre-activation of the modified CAR Tregs of the present example proceeded as follows. 96-well ELISA plates were coated with 50 μL/well of 3 μg/mL of Aβ1-42 peptide or 5 ug/mL OKT3 antibody (anti-CD3) in PBS overnight at 4° C. Control wells for non-activated CAR Tregs were left uncoated. Plates were rinsed three times with PBS and then blocked with 0.1 mL/well of X-VIVO™-15+10% human sera. CAR Tregs were added at 100,000 cells/0.2 mL/well and incubated for 6 h. Cells were then collected and diluted to 500,000 CAR Tregs/mL in X-VIVO™-15+10% human sera.

Co-culture of the pre-activated modified CAR Tregs and monocytes/macrophages of the present example proceeded as follows. Monocytes were isolated by CD14-negative selection (BioLegend 480060, San Diego, CA, USA) from human PBMCs (different donor from CAR Tregs) and incubated for 6 h at 50,000 cells/0.1 mL/well in a 96-well tissue culture-treated white luminometer plate (CORNING® COSTAR® 3719). Non-activated, Aβ pre-activated, or anti-CD3 pre-activated CAR Tregs were added at 50,000 cells/0.1 mL/well. Co-cultured cells were incubated in a final volume of 0.2 mL/well for 2 days.

Stimulation of the modified CAR Treg/macrophage co-cultures of the present example proceeded as follows. After 2 days of incubation, CAR Treg/macrophage co-cultures were stimulated by adding either phorbol myristate acetate (PMA; 40 nM), zymosan particles (20 μg/mL), or lipopolysaccharide (LPS; 20 ng/mL). To measure superoxide generation, lucigenin (5 μM) was added with PMA or zymosan and lucigenin-mediated bioluminescence was measured on a Centro LB 960 Microplate Luminometer (2 s exposure) at 6 timepoints over 6 h. To measure IL-6 by ELISA (BioLegend, San Diego, CA, USA), cell-free media was collected 24 h after adding LPS.

Figure 22C:
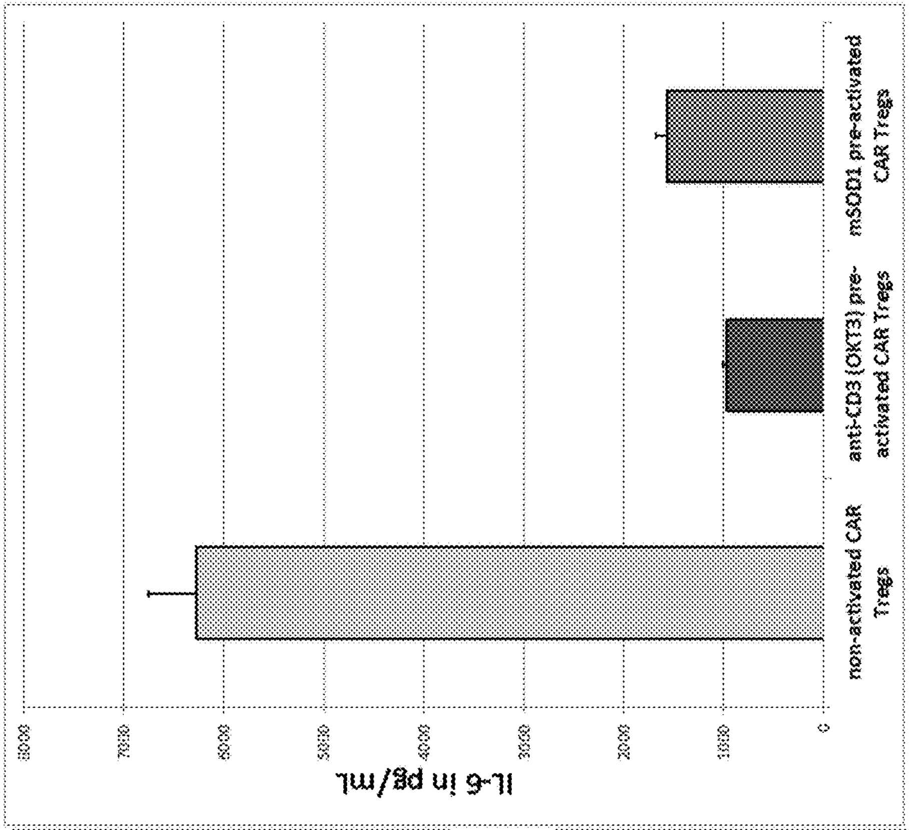
FIG. 22A-FIG. 22C present data demonstrating the antigen-specific anti-inflammatory activity of anti-Aβ CARs in accordance with Example 14.
Figure 22A:
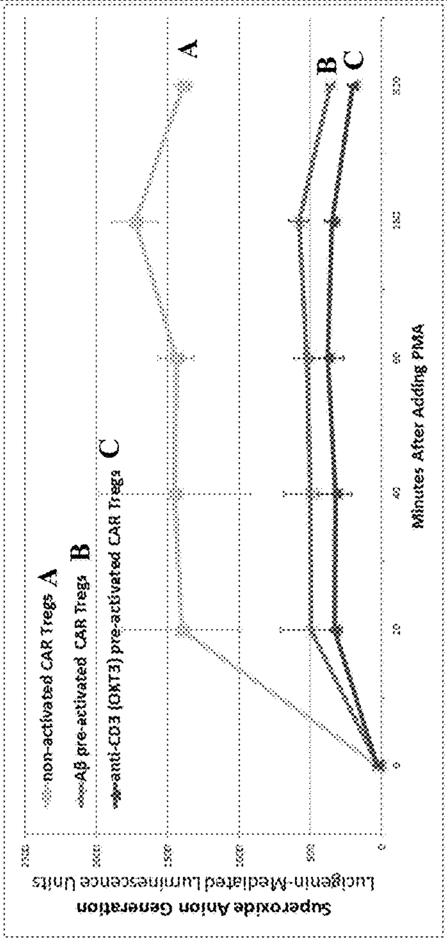

Referring now to FIG. 22A, modified Tregs comprising DG03-CD28-CD3ζ which were pre-stimulated with either plate bound Aβ antigen or with anti-CD3 antibody inhibited PMA stimulated superoxide generation (as measured by Lucigenin-mediated luminescence). Regarding FIG. 22A, **=p<0.01 relative to non-activated CAR Tregs by Dunnett's multiple comparison test (n=3).

Figure 22B:
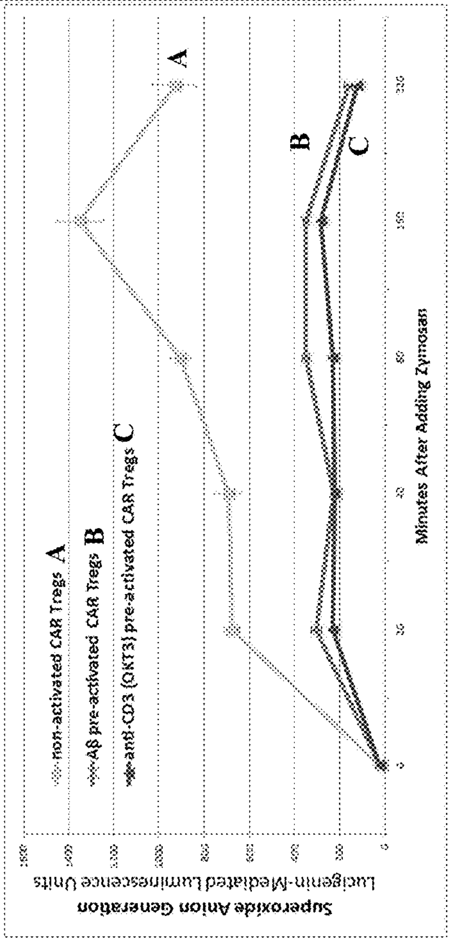

Referring now to FIG. 22B, modified Tregs comprising DG03-CD28-CD3ζ which were pre-stimulated with either plate-bound Aβ antigen or with anti-CD3 antibody inhibited Zymosan-stimulated superoxide generation (as measured by Lucigenin-mediated luminescence). Regarding FIG. 22B, **=p<0.01 relative to non-activated CAR Tregs by Dunnett's multiple comparison test (n=3).

Referring now to FIG. 22C, modified Tregs comprising DG03-CD28-CD3ζ which were pre-stimulated with either plate-bound Aβ antigen or with anti-CD3 antibody inhibited LPS-stimulated IL-6 production as measured by ELISA at 24 h. Regarding FIG. 22C, **=p<0.01 relative to non-activated CAR Tregs by Dunnett's multiple comparison test (n=3).

Example 15: Functional Activity of Neurodegenerative Disease Modifying Molecule (NDMM) Tregs Engineered to Express Anti-Oxidants or Growth Factors In the present example, the cytoprotective activity of neurodegenerative disease-modifying molecules (NDMMs) expressed in human Tregs was evaluated.

Isolation, expansion, and transduction of the NDMM-Tregs of the present example proceeded as follows. NDMM-engineered Tregs were prepared from human PBMCs as described in Example 1; Example 4; and Example 6. Instead of CAR constructs, the PG13 retrovirus used for Treg transduction on Days 10 and 11 were with NDMM constructs for Nrf2 (Keap1 inhibitor peptide) (SEQ ID NO: 51), human catalase (SEQ ID NO: 52), brain derived neurotrophic factor (BDNF) (SEQ ID NO: 53), and insulin growth factor-1 (IGF-1) (SEQ ID NO: 54). The NDMM constructs co-expressed truncated mouse CD19 to monitor transduction efficiency. Mock-transduced Tregs (no PG13 retrovirus) were used as controls.

Flow cytometry of the NDMM Tregs of the present example proceeded as follows. The percentage of NDMM-transduced Tregs was measured by indirect labeling of the co-expressed mouse truncated CD19 with PE anti-mouse CD19 (BioLegend, San Diego, CA, USA). Cells were analyzed using an ACCURI™ C6 flow cytometer (BD Biosciences, Ann Arbor, MI, USA). Non-stained cells were used to set the threshold for non-specific background signal.

Cryopreservation and recovery after thaw of the NDMM Tregs of the present example proceeded as follows. Day 17 CAR Tregs were cryopreserved in a cryovials at $20\times10^6$ cells/mL in solution of 90% heat-inactivated FBS and 10% DMSO in Mr. FROSTY™ Freezing Container at −80° C. for 24 h and then transferred to liquid nitrogen. Cells were thawed and rinsed in PBS, resuspended to $2\times10^6$ cells/mL in X-VIVO™-15+10% human sera+500 u/mL IL-2, and incubated for 24 h. Cells were centrifuged to pellet cells, resuspended in 4 mL X-VIVO™-15 media and centrifuged over 4 mL of LYMPHOPREP separation media at 800×g for 20 min. Cells at the interphase were collected and rinsed in X-VIVO™-15 and pelleted. Cells were resuspended to $2\times10^6$ cells/mL in incomplete Dulbecco's High Glucose Modified Eagles Medium (DMEM; Hyclone 30022) supplemented with 10% heat-inactivated FBS, MEM nonessential amino acid solution, HEPES (10 mM), and penicillin/streptomycin solution.

Co-culture of NDMM-Tregs and luciferase-expressing SH-SY5Y neuronal cells of the present example proceed as follows. The human neurobalstoma cell line SH-SY5Y, previously transduced to express luciferase (Luc), was grown to 60%-90% confluency in complete DMEM supplemented with 10% heat-inactivated FBS, MEM nonessential amino acid solution, HEPES (10 mM), sodium pyruvate (1 mM), 2-merceptoethanol (50 μM), and penicillin/streptomycin solution. Luc-SH-SY5Y cells were collected by trypsinization, pelleted by centrifugation at 500×g for 5 min, resuspended in incomplete DMEM (without sodium pyruvate and 2-merceptoethanol), and plated at 10,000 cells/0.1 mL/well in 96-well tissue culture-treated white luminometer plate (CORNING® COSTAR® 3719). After 3 h incubation, NDMM- or mock-Tregs in incomplete DMEM media were added to Luc-SH-SY5Y cells at 100,000 Tregs/0.05 mL/well (final volume of 0.15 mL/well). Co-cultured cells were incubated for 24 h.

The hydrogen peroxide toxicity assay of the present example was performed as follows. After 24 h of incubation of NDMM-Treg/luc-SH-SY5Y co-cultures, 50 μL of incomplete DMEM media with final concentrations of hydrogen peroxide ($H_2O_2$) at 0, 20, 40, 60, 80, and 320 μM was added. $H_2O_2$-exposed co-cultures were incubated for 24 h and then the relative number of surviving luc-SH-SY5Y neuronal cells was measured by bioluminescence. Luciferin (50 μg/mL) was added to each well, incubated for 30 min, and bioluminescence was measured on a Centro LB 960 Microplate Luminometer (2 s exposure).

Figure 23A:
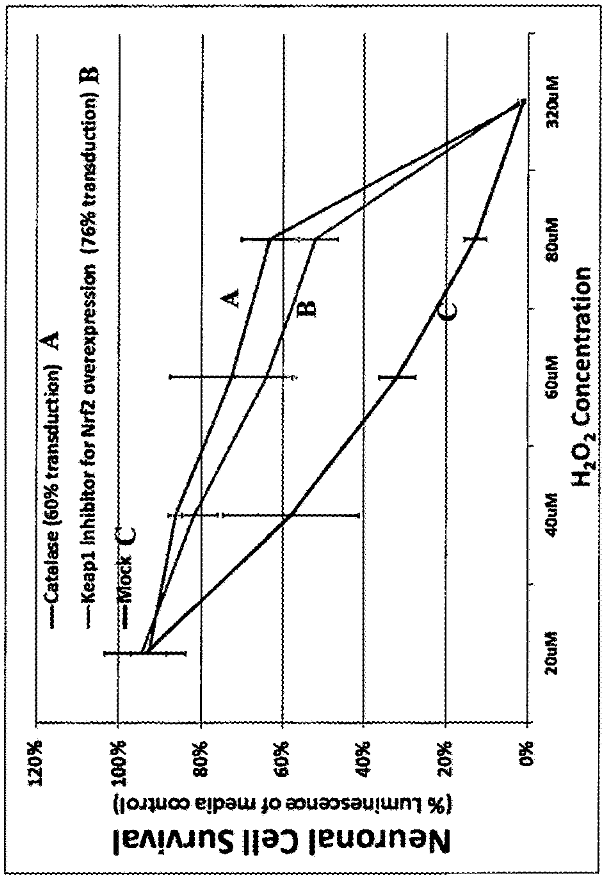
FIG. 23A-FIG. 23B present data demonstrating the cytoprotective activity of neurodegenerative disease-modifying molecule (NDMM) expressed in human Tregs in accordance with Example 15.

Referring now to FIG. 23A, ex vivo expanded and transduced human Tregs engineered to express antioxidants (Keap1 inhibitor peptide or Catalase) protected human SH-SY5Y neuronal cells (luciferase-expressing) from hydrogen peroxide toxicity. Regarding FIG. 23A, ns=not significant; *=p<0.05; **=p<0.01 relative to mock-transduced Tregs by Dunnett's multiple comparison test (n=3).

Figure 23B:
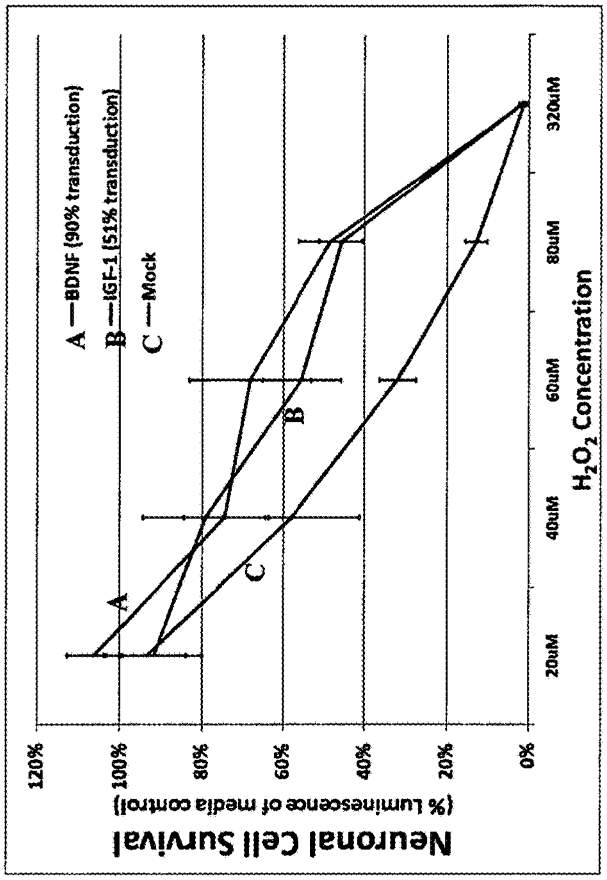

Referring now to FIG. 23B, ex vivo expanded and transduced human Tregs engineered to express growth factors (BDNF or IGF-1) protected human SH-SY5Y neuronal cells (luciferase-expressing) from hydrogen peroxide toxicity. Regarding FIG. 23B, ns=not significant; *=p<0.05; **=p<0.01 relative to mock-transduced Tregs by Dunnett's multiple comparison test (n=3).

In the preceding procedures, various steps have been described. It will, however, be evident that various modifications and changes may be made thereto, and additional procedures may be implemented, without departing from the broader scope of the exemplary procedures as set forth in the claims that follow.

APPENDIX A-AMINO ACID AND NUCLEIC ACID SEQUENCES

DG01 SCFV (SEQ ID NO: 1)
MEWTWVFLFLLSVTAGVHSQVQLVESGGGVVQPGRSLRLSCAASGFAFSSYGMHWVRQAPGKGLEWVAVIWFDGTKKYYTDSVKGRF
TISRDNSKNTLYLQMNTLRAEDTAVYYCARDRGIGARRGPYYMDVWGKGTTVTVSSAGGGGSGGGGSGGGGSDIQMTQSPSSLSASV
GDRVTITCRASQSISSYLNWYQQKPGKAPKLLIYAASSLQSGVPSRFSGSGSGTDFTLTISSLQPEDFATYYCQQSYSTPLTFGGGT
KVEIK

DG02 SCFV (SEQ ID NO: 2)
MEWTWVFLFLLSVTAGVHSEVQLLESGGGLVQPGGSLRLSCAASGFTFSNYGMSWVRQAPGKGLEWVASIRSGGGRTYYSDNVKGRF
TISRDNSKNTLYLQMNSLRAEDTAVYYCVRYDHYSGSSDYWGQGTLVTVSSAGGGGSGGGGSGGGGSDVVMTQSPLSLPVTPGEPAS
ISCKSSQSLLDSDGKTYLNWLLQKPGQSPQRLIYLVSKLDSGVPDRFSGSGSGTDFTLKISRVEAEDVGVYYCWQGTHFPRTFGQGT
KVEIK

DG03 SCFV (SEQ ID NO: 3)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIK

DG04 SCFV (SEQ ID NO: 4)
MEWTWVFLFLLSVTAGVHSQVELVESGGGLVQPGGSLRLSCAASGFTFSSYAMSWVRQAPGKGLEWVSAINASGTRTYYADSVKGRF
TISRDNSKNTLYLQMNSLRAEDTAVYYCARGKGNTHKPYGYVRYFDVWGQGTLVTVSSAGGGGSGGGGSGGGGSDIVLTQSPATLSL
SPGERATLSCRASQSVSSSYLAWYQQKPGQAPRLLIYGASSRATGVPARFSGSGSGTDFTLTISSLEPEDFATYYCLQIYNMPITFG
QGTKVEIK

-continued

APPENDIX A-AMINO ACID AND NUCLEIC ACID SEQUENCES

DG05 SCFV (SEQ ID NO: 5)
MEWTWVFLFLLSVTAGVHSEVQLVQSGGGLVKPGGSLRLSCAGSGFTFSSYSMHWLRQAPGKGLEWVSAIGTAGGTYYADSVKGRFT
ISRDNAKNSLYLQMNSLRAEDTAVYYCAREYFFGSGNYGYWGQGTLVTVSSAGGGGSGGGGSGGGGSEIVLTQSPATLSLSPGERAT
LSCRASQSVSSSYLAWYQQKPGQAPRLLIYDASNRATGIPARFSGSGSGTDFTLTISSLEPEDFAVYYCQQRSNWPPTFGQGTKVEIK

DG06 SCFV (SEQ ID NO: 6)
MEWTWVFLFLLSVTAGVHSQVQLVESGGGVVQPGRSLRLSCAASGFTFSNYGIHWVRQAPGKGLEWVAIIWHDGSNSYYVDSVKGRF
TISRDNSKNTLYLQMNSLRAEDTAVYFCARTIGGAFDIWGQGTMVTVSSAGGGGSGGGGSGGGGSDIQMTQSPSSLSASVGDRVTIT
CRASQGISSWLAWYQQKPEKAPKSLIYAASSLQSGVPSRFSGSGSGTDFTLTISSLQPEDFATYYCQQYNSYPITFGQGTRLEIK

DG07 SCFV (SEQ ID NO: 7)
MEWTWVFLFLLSVTAGVHSEVQLVESGGGLVQPGGSLRLSCAASGFSISGYWMSWVRQAPGKGLEWVANIKQDGGEKYYGDSVKGRF
TISRDNAKNSLYLQMNSLRAEDTAVYYCVMAGGLDYWGQGTLVTVSSAGGGGSGGGGSGGGGSEIVLTQSPATLSLSPGERATLSCR
ASQSVSSSYLAWYQQKPGQAPRLLIYDASNRATGIPARFSGSGSGTDFTLTISSLEPEDFAVYYCQQRSNWYTFGQGTKLEIK

DG08 SCFV (SEQ ID NO: 8)
MEWTWVFLFLLSVTAGVHSQVQLVQSGAEVKKPGASVRLSCRASGYNFIDFHIHWVRQAPGEGLEWMGWSNPQSGNSSSAQRFQGRV
TMTTDTSMSAAYMDLNWLTLDDTAVYYCTRPHDGAGNYRFDTWGQGTLVTVSSAGGGGSGGGGSGGGGSSYELTQPPSVSVAPGQTA
RITCSGDALPKHYAHWYQQKPGQVPIVVIYKDTERPSGIPERFSGSTSGTTVTLTISGVQAEDEAHYYCQSADVSSTYVVFGGGTKL
TVL

DG09 SCFV (SEQ ID NO: 9)
MEWTWVFLFLLSVTAGVHSEVQLVESGGGLVEPGGSLRLSCAVSGFDFEKAWMSWVRQAPGQGLQWVARIKSTADGGTTSYAAPVEG
RFIISRDDSRNMLYLQMNSLKTEDTAVYYCTSAHWGQGTLVTVSSAGGGGSGGGGSGGGGSSYELTQPPSVSVSPGQTARITCSGEA
LPMQFAHWYQQRPGKAPVIVVYKDSERPSGVPERFSGSSSGTTATLTITGVQAEDEADYYCQSPDSTNTYEVFGGGTKLTVL

DG10 SCFV (SEQ ID NO: 10)
MEWTWVFLFLLSVTAGVHSQVQLVQSGAEVKKPGASVKVSCKASGYTFTNYAMHWVRQAPGQRLEWMGWINAGNGKRKYSQKFQDRV
TINRDTSASTIYMELSSLGSEDTAVYYCAREEDHAGSGSYLSMDVWGQGSTVTVSSAGGGGSGGGGSGGGGSDIVMTQSPDSLAVSL
GERATINCKSSQNVLYSSNNKNYLAWYQQKPGHPPKLLIYWASTRESGVPDRFSGSGSGTDFTLTITSLQTEDVAVYYCQQYYSSPL
TFGGGTKVEIK

DG11 SCFV (SEQ ID NO: 11)
MEWTWVFLFLLSVTAGVHSEVQLVETGGGLVQPKGSLKLSCATSGFTFNTYAMNWVRQAPGKGLEWVARIRTKSNDYATYYADSVKG
RITISRDDSQSMLYLQMNNLKTEDTAMYYCVRVGYRPYAMDYWGQGTSVTVSSAGGGGSGGGGSGGGGSDVLMTQTPLSLPVSLGDQ
ASISCRSSQNIVHSNGNTYLEWYLQKPGQSPTLLIYKVSNRFSGVPDRFSGSGSGTDFTLKISRVEAEDLGVYYCFQGSHVPLTFGA
GTKLELK 4-1BB CO-STIMULATORY DOMAIN (SEQ ID NO: 12)
KRGRKKLLYIFKQPFMRPVQTTQEEDGCSCRFPEEEEGGCEL (G4S)3 LINKER (SEQ ID NO: 13)
GGGGSGGGGSGGGGS

T2A (SEQ ID NO: 14)
RAKRSGSGEGRGSLITCGDVEENPGP

P2A (SEQ ID NO: 15)
RAKRSGSGATNFSLLKQAGDVEENPGP

CD3Z (SEQ ID NO: 16)
RVKFSRSADAPAYQQGQNQLYNELNLGRREEYDVLDKRRGRDPEMGGKPRRKNPQEGLYNELQKDKMAEAYSEIGMKGERRRGKGHD
GLYQGLSTATKDTYDALHMQALPPR

HUMAN AMYLOID BETA, ISOFORM APP770 (IDENTIFIER: P05067-1) (SEQ ID NO: 17)
MLPGLALLLLAAWTARALEVPTDGNAGLLAEPQIAMFCGRLNMHMNVQNGKWDSDPSGTKTCIDTKEGILQYCQEVYPELQITNVVE
ANQPVTIQNWCKRGRKQCKTHPHFVIPYRCLVGEFVSDALLVPDKCKFLHQERMDVCETHLHWHTVAKETCSEKSTNLHDYGMLLPC
GIDKFRGVEFVCCPLAEESDNVDSADAEEDDSDVWWGGADTDYADGSEDKVVEVAEEEEVAEVEEEEADDDEDDEDGDEVEEEAEEP
YEEATERTTSIATTTTTTTESVEEVVREVCSEQAETGPCRAMISRWYFDVTEGKCAPFFYGGCGGNRNNFDTEEYCMAVCGSAMSQS
LLKTTQEPLARDPVKLPTTAASTPDAVDKYLETPGDENEHAHFQKAKERLEAKHRERMSQVMREWEEAERQAKNLPKADKKAVIQHF
QEKVESLEQEAANERQQLVETHMARVEAMLNDRRRLALENYITALQAVPPRPRHVFNMLKKYVRAEQKDRQHTLKHFEHVRMVDPKK
AAQIRSQVMTHLRVIYERMNQSLSLLYNVPAVAEEIQDEVDELLQKEQNYSDDVLANMISEPRISYGNDALMPSLTETKTTVELLPV
NGEFSLDDLQPWHSFGADSVPANTENEVEPVDARPAADRGLTTRPGSGLTNIKTEEISEVKMDAEFRHDSGYEVHHQKLVFFAEDVQ
SNKGAIIGLMVGGVVIATVIVITLVMLKKKQYTSIHHGVVEVDAAVTPEERHLSKMQQNGYENPTYKFFEQMQN

HUMAN SUPEROXIDE DISMUTASE, IDENTIFIER: P00441-1 (SEQ ID NO: 18)
MATKAVCVLKGDGPVQGIINFEQKESNGPVKVWGSIKGLTEGLHGFHVHEFGDNTAGCTSAGPHFNPLSRKHGGPKDEERHVGDLGN
VTADKDGVADVSIEDSVISLSGDHCIIGRTLVVHEKADDLGKGGNEESTKTGNAGSRLACGVIGIAQ

HUMAN ALPHA-SYNUCLEIN, ISOFORM 1 (IDENTIFIER: P37840-1) (SEQ ID NO: 19)
MDVFMKGLSKAKEGVVAAAEKTKQGVAEAAGKTKEGVLYVGSKTKEGVVHGVATVAEKTKEQVTNVGGAVVTGVTAVAQKTVEGAGS
IAAATGFVKKDQLGKNEEGAPQEGILEDMPVDPDNEAYEMPSEEGYQDYEPEA

DG01.28.Z CAR (SEQ ID NO: 20)
MEWTWVFLFLLSVTAGVHSQVQLVESGGGVVQPGRSLRLSCAASGFAFSSYGMHWVRQAPGKGLEWVAVIWFDGTKKYYTDSVKGRF
TISRDNSKNTLYLQMNTLRAEDTAVYYCARDRGIGARRGPYYMDVWGKGTTVTVSSAGGGGSGGGGSGGGGSDIQMTQSPSSLSASV
GDRVTITCRASQSISSYLNWYQQKPGKAPKLLIYAASSLQSGVPSRFSGSGSGTDFTLTISSLQPEDFATYYCQQSYSTPLTFGGGT

-continued

APPENDIX A-AMINO ACID AND NUCLEIC ACID SEQUENCES

KVEIKASVKGKHLCPSPLFPGPSKPFWVLVVVGGVLACYSLLVTVAFIIFWVRSKRSRLLHSDYMNMTPRRPGPTRKHYQPYAPPRD
FAAYRSKLRVKFSRSADAPAYQQGQNQLYNELNLGRREEYDVLDKRRGRDPEMGGKPRRKNPQEGLYNELQKDKMAEAYSEIGMKGE
RRRGKGHDGLYQGLSTATKDTYDALHMQALPP

DG02.28.Z CAR (SEQ ID NO: 21)
MEWTWVFLFLLSVTAGVHSEVQLLESGGGLVQPGGSLRLSCAASGFTFSNYGMSWVRQAPGKGLEWVASIRSGGGRTYYSDNVKGRF
TISRDNSKNTLYLQMNSLRAEDTAVYYCVRYDHYSGSSDYWGQGTLVTVSSAGGGGSGGGGSGGGGSDVVMTQSPLSLPVTPGEPAS
ISCKSSQSLLDSDGKTYLNWLLQKPGQSPQRLIYLVSKLDSGVPDRFSGSGSGTDFTLKISRVEAEDVGVYYCWQGTHFPRTFGQGT
KVEIKASVKGKHLCPSPLFPGPSKPFWVLVVVGGVLACYSLLVTVAFIIFWVRSKRSRLLHSDYMNMTPRRPGPTRKHYQPYAPPRD
FAAYRSKLRVKFSRSADAPAYQQGQNQLYNELNLGRREEYDVLDKRRGRDPEMGGKPRRKNPQEGLYNELQKDKMAEAYSEIGMKGE
RRRGKGHDGLYQGLSTATKDTYDALHMQALPP

DG03.28.Z CAR (SEQ ID NO: 22)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIKAS
VKGICHLCPSPLFPGPSKPFWVLVVVGGVLACYSLLVTVAFIIFWVRSKRSRLLHSDYMNMTPRRPGPTRKHYQPYAPPRDFAAYRS
KLRVKFSRSADAPAYQQGQNQLYNELNLGRREEYDVLDKRRGRDPEMGGKPRRKNPQEGLYNELQKDKMAEAYSEIGMKGERRRGKG
HDGLYQGLSTATKDTYDALHMQALPP

DG04.28.Z CAR (SEQ ID NO: 23)
MEWTWVFLFLLSVTAGVHSQVELVESGGGLVQPGGSLRLSCAASGFTFSSYAMSWVRQAPGKGLEWVSAINASGTRTYYADSVKGRF
TISRDNSKNTLYLQMNSLRAEDTAVYYCARGKGNTHKPYGYVRYFDVWGQGTLVTVSSAGGGGSGGGGSGGGGSDIVLTQSPATLSL
SPGERATLSCRASQSYSSSYLAWYQQKPGQAPRLLIYGASSRATGVPARFSGSGSGTDFTLTISSLEPEDFATYYCLQIYNMPITFG
QGTKVEIKASVKGKHLCPSPLFPGPSKPFWVLVVVGGVLACYSLLVTVAFIIFWVRSKRSRLLHSDYMNMTPRRPGPTRKHYQPYAP
PRDFAAYRSKLRVKFSRSADAPAYQQGQNQINNELNLGRREEYDVLDKRRGRDPEMGGKPRRKNPQEGLYNELQKDKMAEAYSEIGM
KGERRRGKGHDGLYQGLSTATKDTYDALHMQALPP

DG05.28.Z CAR (SEQ ID NO: 24)
MEWTWVFLFLLSVTAGVHSEVQLVQSGGGLVKPGGSLRLSCAGSGFTFSSYSMHWLRQAPGKGLEWVSAIGTAGGTYYADSVKGRFT
ISRDNAKNSLYLQMNSLRAEDTAVYYCAREYFFGSGNYGYWGQGTLVTVSSAGGGGSGGGGSGGGGSEIVLTQSPATLSLSPGERAT
LSCRASQSVSSYLAWYQQKPGQAPRLLIYDASNRATGIPARFSGSGSGTDFTLTISSLEPEDFAVYYCQQRSNWPPTFGQGTKVEIK
ASVKGKHLCPSPLFPGPSKPFWVLVVVGGVLACYSLLVTVAFIIFWVRSKRSIZLLHSDYMNMTPRRPGPTRKHYQPYAPPRDFAAY
RSKLRVKFSRSADAPAYQQGQNQLYNELNLGRREEYDVLDKRRGRDPEMGGKPRRKNPQEGLYNELQKDKMAEAYSEIGMKGERRRG
KGHDGLYQGLSTATKDTYDALHMQALPP

DG06.28.Z CAR (SEQ ID NO: 25)
MEWTWVFLFLLSVTAGVHSQVQLVESGGGVVQPGRSLRLSCAASGFTFSNYGIHWVRQAPGKGLEWVAIIWHDGSNSYYVDSVKGRF
TISRDNSKNTLYLQMNSLRAEDTAVYFCARIIGGAFDIWGQGTMVTVSSAGGGGSGGGGSGGGGSDIQMTQSPSSLSASVGDRVTIT
CRASQGISSWLAWYQQKPEKAPKSLIYAASSLQSGVPSRFSGSGSGTDFTLTISSLQPEDFATYYCQQYNSYPITFGQGTRLEIKAS
VKGKHLCPSPLFPGPSKPFWVLVVVGGVLACYSLLVTVAFIIFWVRSKRSRLLHSDYMNMTPRRPGPTRKHYQPYAPPRDFAAYRSK
LRVKFSRSADAPAYQQGQNQLYNELNLGRREEYDVLDKRRGRDPEMGGKPRRKNPQEGLYNELQKDKMAEAYSEIGMKGERRRGKGH
DGLYQGLSTATKDTYDALHMQALPP

DG07.28.Z CAR (SEQ ID NO: 26)
MEWTWVFLFLLSVTAGVHSEVQLVESGGGLVQPGGSLRLSCAASGFSISGYWMSWVRQAPGKGLEWVANIKQDGGEKYYGDSVKGRF
TISRDNAKNSLYLQMNSLRAEDTAVYYCVMAGGLDYWGQGTLVTVSSAGGGGSGGGGSGGGGSEIVLTQSPATLSLSPGERATLSCR
ASQSVSSYLAWYQQKPGQAPRLLIYDASNRATGIPARFSGSGSGTDFTLTISSLEPEDFAVYYCQQRSNWYTFGQGTKLEIKASVKG
KHLCPSPLFPGPSKPFWVLVVVGGVLACYSLLVTVAFIIFWVRSKRSRLLHSDYMNMTPRRPGPTRKHYQPYAPPRDFAAYRSKLRV
KFSRSADAPAYQQGQNQLYNELNLGRREEYDVLDKRRGRDPEMGGKPRRKNPQEGLYNELQKDKMAEAYSEIGMKGERRRGKGHDGL
YQGLSTATKDTYDALHMQALPP

DG08.28.Z CAR (SEQ ID NO: 27)
MEWTWVFLFLLSVTAGVHSQVQLVQSGAEVICKPGASVRLSCRASGYNFIDFHIHWVRQAPGEGLEWMGWSNPQSGNSSSAQRFQGR
VTMTTDTSMSAAYMDLNWLTLDDTAVYYCTRPHDGAGNYRFDTWGQGTLVTVSSAGGGGSGGGGSGGGGSSYELTQPPSVSVAPGQT
ARITCSGDALPKHYAHWYQQKPGQVPIVVIYKDTERPSGIPERFSGSTSGTTVTLTISGVQAEDEAHYYCQSADVSSTYVVFGGGTK
LTVLASVKGKHLCPSPLFPGPSKPFWVLVVVGGVLACYSLLVTVAFTIFWVRSKRSRLLHSDYMNMTPRRPGPTRKHYQPYAPPRDF
AAYRSKLRVKFSRSADAPAYQQGQNQLYNELNLGRREEYDVLDKRRGRDPEMGGKPRRKNPQEGLYNELQKDKMAEAYSEIGMKGER
RRGKGHDGLYQGLSTATKDTYDALHMQALPP

DG09.28.Z CAR (SEQ ID NO: 28)
MEWTWVFLFLLSVTAGVHSEVQLVESGGGLVEPGGSLRLSCAVSGFDFEKAWMSWVRQAPGQGLQWVARIKSTADGGTTSYAAPVEG
RFIISRDDSRNMLYLQMNSLKTEDTAVYYCTSAHWGQGTLVTVSSAGGGGSGGGGSGGGGSSYELTQPPSVSVSPGQTARITCSGEA
LPMQFAHWYQQRPGKAPVIVVYKDSERPSGVPERFSGSSSGTTATLTITGVQAEDEADYYCQSPDSTNTYEVFGGGTKLTVLASVKG
KHLCPSPLFPGPSKPFWVLVVVGGVLACYSLLVTVAFIIFWVRSKRSRLLHSDYMNMTPRRPGPTRKHYQPYAPPRDFAAYRSKLRV
KFSRSADAPAYQQGQNQLYNELNLGRREEYDVLDKRRGRDPEMGGKPRRKNPQEGLYNELQKDKMAEAYSEIGMKGERRRGKGHDGL
YQGLSTATKDTYDALHMQALPP

DG10.28.Z CAR (SEQ ID NO: 29)
MEWTWVFLFLLSVTAGVHSQVQLVQSGAEVKKPGASVKVSCKASGYTFTNYAMHWVRQAPGQRLEWMGWINAGNGKRKYSQKFQDRV
TINRDTSASTIYMELSSLGSEDTAVYYCAREEDHAGSGSYLSMDVWGQGSTVTVSSAGGGGSGGGGSGGGGSDIVMTQSPDSLAVSL
GERATINCKSSQNVLYSSNNKNYLAWYQQKPGHPPKLLIYWASTRESGVPDRFSGSGSGTDFTLTITSLQTEDVAVYYCQQYYSSPL
TFGGGTKVEIKASVKGKHLCPSPLFPGPSKPFWVLVVVGGVLACYSLLVTVAFIIFWVRSKRSRLLHSDYMNMTPRRPGPTRKHYQP
YAPPRDFAAYRSKLRVKFSRSADAPAYQQGQNQLYNELNLGRREEYDVLDKRRGRDPEMGGKPRRKNPQEGLYNELQKDKMAEAYSE
IGMKGERRRGKGHDGLYQGLSTATKDTYDALHMQALPP

-continued

APPENDIX A-AMINO ACID AND NUCLEIC ACID SEQUENCES

DG11.28.Z CAR (SEQ ID NO: 30)
MEWTWVFLFLLSVTAGVHSEVQLVETGGGLVQPKGSLKLSCATSGFTFNTYAMNWVRQAPGKGLEWVARIRTKSNDYATYYADSVKG
RITISRDDSQSMLYLQMNNLKTEDTAMYYCVRVGYRPYAMDYWGQGTSVTVSSAGGGGSGGGGSGGGGSDVLMTQTPLSLPVSLGDQ
ASISCRSSQNIVHSNGNTYLEWYLQKPGQSPTLLIYKVSNRFSGVPDRFSGSGSGTDFTLKISRVEAEDLGVYYCFQGSHVPLTFGA
GTKLELKASVKGKHLCPSPLFPGPSKPFWVLVVVGGVLACYSLLVTVAFIIFWVRSKRSRLLHSDYMNMTPRRPGPTRKHYQPYAPP
RDFAAYRSKLRVKFSRSADAPAYQQGQNQLYNELNLGRREEYDVLDKRRGRDPEMGGKPRRKNPQEGLYNELQKDKMAEAYSEIGMK
GERRRGKGHDGLYQGLSTATKDTYDALHMQALPP

SIGNAL SEQUENCE (SEQ ID NO: 31)
MEWTWVFLFLLSVTAGVHS

HUMAN CD28 HINGE (SEQ ID NO: 32)
VKGKHLCPSPLFPGPSKP

MOUSE CD28 HINGE (SEQ ID NO: 33)
IKEKHLCHTQSSPKL

HUMAN CD8A HINGE (SEQ ID NO: 34)
TTTPAPRPPTPAPTIASQPLSLRPEACRPAAGGAVHTRGLDFACD

HUMAN DAP10 HINGE (SEQ ID NO: 35)
QTTPGERSSLPAFYPGTSGSCSGCGSLSLP

HUMAN CD28 TM (SEQ ID NO: 36)
FWVLVVVGGVLACYSLLVTVAFIIFWV

MOUSE CD28 TM (SEQ ID NO: 37)
FWALVVVAGVLFCYGLLVTVALCVIWT

HUMAN CD8A TM (SEQ ID NO: 38)
IYIWAPLAGTCGVLLLSLVITLYC

HUMAN DAP 10 TM (SEQ ID NO: 39)
LLAGLVAADAVASLLIVGAVF

DG05-CD28tm-DAP10-CD3ζ (SEQ ID NO: 40)
MEWTWVFLFLLSVTAGVHSEVQLVQSGGGLVKPGGSLRLSCAGSGFTFSSYSMHWLRQAPGKGLEWVSAIGTAGGTYYADSVKGRFT
ISRDNAKNSLYLQMNSLRAEDTAVYYCAREYFFGSGNYGYWGQGTLVTVSSAGGGGSGGGGSGGGGSEIVLTQSPATLSLSPGERAT
LSCRASQSVSSYLAWYQQKPGQAPRLLIYDASNRATGIPARFSGSGSGTDFTLTISSLEPEDFAVYYCQQRSNWPPTFGQGTKVEIK
ASVKGKHLCPSPLFPGPSKPFWVLVVVGGVLACYSLLVTVAFITFWVRSKRSLCARPRRSPAQEDGKVYINMPGRGKLRVKFSRSAD
APAYQQGQNQLYNELNLGRREEYDVLDKRRGRDPEMGGKPRRKNPQEGLYNELQKDKMAEAYSEIGMKGERRRGKGHDGLYQGLSTA
TKDTYDALHMQALPPR

DG05-CD28tm-CD44-CD3ζ (SEQ ID NO: 41)
MEWTWVFLFLLSVTAGVHSEVQLVQSGGGLVKPGGSLRLSCAGSGFTFSSYSMHWLRQAPGKGLEWVSAIGTAGGTYYADSVKGRFT
ISRDNAKNSLYLQMNSLRAEDTAVYYCAREYFFGSGNYGYWGQGTLVTVSSAGGGGSGGGGSGGGGSEIVLTQSPATLSLSPGERAT
LSCRASQSVSSYLAWYQQKPGQAPRLLIYDASNRATGIPARFSGSGSGTDFTLTISSLEPEDFAVYYCQQRSNWPPTFGQGTKVEIK
ASVKGKHLCPSPLFPGPSKPFWVLVVVGGVLACYSLLVTVAFIIFWVSRRRCGQKKKLVINSGNGAVEDRKPSGLNGEASKSQEMVH
LVNKESSETPDQFMTADETRNLQNVDMKIGVRVKFSRSADAPAYQQGQNQLYNELNLGRREEYDVLDKRRGRDPEMGGKPRRKNPQE
GLYNELQKDKMAEAYSEIGMKGERRRGKGHDGLYQGLSTATKDTYDALHMQALPPR

DG05-CD28tm-CD3ζ (SEQ ID NO: 42)
MEWTWVFLFLLSVTAGVHSEVQLVQSGGGLVKPGGSLRLSCAGSGFTFSSYSMHWLRQAPGKGLEWVSAIGTAGGTYYADSVKGRFT
ISRDNAKNSLYLQMNSLRAEDTAVYYCAREYFFGSGNYGYWGQGTLVTVSSAGGGGSGGGGSGGGGSEIVLTQSPATLSLSPGERAT
LSCRASQSVSSYLAWYQQKPGQAPRLLIYDASNRATGIPARFSGSGSGTDFTLTISSLEPEDFAVYYCQQRSNWPPTFGQGTKVEIK
ASVKGKHLCPSPLFPGPSKPFWVLVVVGGVLACYSLLVTVAFIIFWVRSKRSRRVKFSRSADAPAYQQGQNQLYNELNLGRREEYDV
LDKRRGRDPEMGGKPRRKNPQEGLYNELQKDKMAEAYSEIGMKGERRRGKGHDGLYQGLSTATKDTYDALHMQALPPR

DG05-CD28 (SEQ ID NO: 43)
MEWTWVFLFLLSVTAGVHSEVQLVQSGGGLVKPGGSLRLSCAGSGFTFSSYSMHWLRQAPGKGLEWVSAIGTAGGTYYADSVKGRFT
ISRDNAKNSLYLQMNSLRAEDTAVYYCAREYFFGSGNYGYWGQGTLVTVSSAGGGGSGGGGSGGGGSEIVLTQSPATLSLSPGERAT
LSCRASQSVSSYLAWYQQKPGQAPRLLIYDASNRATGIPARFSGSGSGTDFTLTISSLEPEDFAVYYCQQRSNWPPTFGQGTKVEIK
ASVKGKHLCPSPLFPGPSKPFWVLVVVGGVLACYSLLVTVAFIIFWVRSKRSRLLHSDYMNMTPRRPGPTRKHYQPYAPPRDFAAYR
S

DG05-CD28tm (SEQ ID NO: 44)
MEWTWVFLFLLSVTAGVHSEVQLVQSGGGLVKPGGSLRLSCAGSGFTFSSYSMHWLRQAPGKGLEWVSAIGTAGGTYYADSVKGRFT
ISRDNAKNSLYLQMNSLRAEDTAVYYCAREYFFGSGNYGYWGQGTLVTVSSAGGGGSGGGGSGGGGSEIVLTQSPATLSLSPGERAT
LSCRASQSVSSYLAWYQQKPGQAPRLLIYDASNRATGIPARFSGSGSGTDFTLTISSLEPEDFAVYYCQQRSNWPPTFGQGTKVEIK
ASVKGKHLCPSPLFPGPSKPFWVLVVVGGVLACYSLLVTVAFTIFWVRSKRSRLLHSD

DGC13-CD28tm-DAP10-CD3ζ (SEQ ID NO: 45)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIKAS
VKGKHLCPSPLFPGPSKPFWVLVVVGGVLACYSLLVTVAFIIFWVRSKRSLCARPRRSPAQEDGKVYINMPGRGKLRVKFSRSADAP

-continued

APPENDIX A-AMINO ACID AND NUCLEIC ACID SEQUENCES

AYQQGQNQLYNELNLGRREEYDVLDKRRGRDPEMGGKPRRKNPQEGLYNELQKDKMAEAYSEIGMKGERRRGKGHDGLYQGLSTATK
DTYDALHMQALPPR

DG03-CD28tm-CD44-CD3ζ (SEQ ID NO: 46)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIKAS
VKGKHLCPSPLFPGPSKPFWVLVVVGGVLACYSLLVTVAFIIFWVSRRRCGQKKKLVINSGNGAVEDRKPSGLNGEASKSQEMVHLV
NKESSETPDQFMTADETRNLQNVDMKIGVRVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR

DG03-CD28tin-4-1-BB-CD3ζ (SEQ ID NO: 47)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIKAS
VKGKHLCPSPLFPGPSKPFWVLVVVGGVLACYSLLVTVAFIIFWVRSKRSLEKRGRKKLLYIFKQPFMRPVQTTQEEDGCSCRFPEE
EEGGCELKLRVKFSRSADAPAYQQGQNQLYNELNLGRREEYDVLDKRRGRDPEMGGKPRRKNPQEGLYNELQKDKMAEAYSEIGMKG
ERRRGKGHDGLYQGLSTATKDTYDALHMQALPPR DG03-CD28tm-CD3ζ (SEQ ID NO: 48)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIKAS
VKGKHLCPSPLFPGPSKPFWVLVVVGGVLACYSLLVTVAFTIFWVRSKRSRRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQALPPR DG03-CD28 (SEQ ID NO: 49)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIKAS
VKGKHLCPSPLFPGPSKPFWVLVVVGGVLACYSLLVTVAFIIFWVRSKRSRLLHSDYMNMTPRRPGPTRKHYQPYAPPRDFAAYRS DG03-CD28tm (SEQ ID NO: 50)
MEWTWVFLFLLSVTAGVHSEVQLVESGGGLVQPGGSLRLSCAASGFTFSSYGMSWVRQAPGKGLELVASINSNGGSTYYPDSVKGRF
TISRDNAKNSLYLQMNSLRAEDTAVYYCASGDYWGQGTTVTVSSAGGGGSGGGGSGGGGSDIVMTQSPLSLPVTPGEPASISCRSSQ
SLVYSNGDTYLHWYLQKPGQSPQLLIYKVSNRFSGVPDRFSGSGSGTDFTLKISRVEAEDVGVYYCSQSTHVPWTFGQGTKVEIKAS
VKGKHLCPSPLFPGPSKPFWVLVVVGGVLACYSLLVTVAFIIFWV Construct for expression of the NDMM Nrf2 (Keap1 inhibitor peptide) (SEQ ID NO: 51)
MMDLELPPPGLPSQQDMDLIDILWRQDIDLGVSREVFDFSQRRKEYELEKQKKLEKERQEQLQKEQEKAFFAQLQLDEETGEFLPIQ
PAQ Construct for expression of the NDMM human catalase (SEQ ID NO: 52)
MADSRDPASDQMQHWKEQRAAQKADVLTTGAGNPVGDKLNVITVGPRGFELVQDVVFTDEMAHFDRERIPERVVHAKGAGAFGYFEV
THDITKYSKAKVFEHIGKKTPIAVRFSTVAGESGSADTVRDPRGFAVKFYTEDGNWDLVGNNTPIFFIRDPILFPSFIHSQKRNPQT
HLKDADMVWDFWSLRPESLHQVSFLFSDRGIPDGHRHMNGYGSHTFKLVNANGEAVYCKFHYKTDQGIKNLSVEDAARLSQEDPDYG
IRDLFNAIATGKYPSWTFYIQVMTFNQAETFPFNPFDLTKVWPHKDYPLIPVGKLVLNRNPVNYFAEVEQIAFDPSNMPPGIEASPD
KMLQGRLFAYPDTHRHRLGPNYLHIPVNCPYRARVANYQRDGPMCMQDNQGGAPNYYPNSFGAPEQQPSALEHSIQYSGEVRRFNTA
NDDNVTQVRAFYVNVLNEEQRKRLCENIAGHLKDAQIFIQICICAVKNFTEVHPDYGSHIQALLDKYNAEKPKNAIHTFVQSGSHLA
AREKANL Construct for expression of the NDMM BDNF (SEQ ID NO: 53)
MTILFLTMVISYFGCMKAAPMKEANIRGQGGLAYPGVRTHGTLESVNGPKAGSRGLTSLADTFEHVIEELLDEDQKVRPNEENNKDA
DLYTSRVMLSSQVPLEPPLLFLLEEYKNYLDAANMSMRVRRHSDPARRGELSVCDSISEWVTAADKKTAVDMSGGTVTVLEKVPVSK
GQLKQYFYETKCNPMGYTKEGCRGIDKRHWNSQCRTTQSYVRALTMDSKKRIGWRFIRIDTSCVCTLTIKRGR Construct for expression of the NDMM IGF-1 (SEQ ID NO: 54)
MGKISSLPTQLFKCCFCDFLKVICMHTMSSSHLFYLALCLLTFTSSATAGPETLCGAELVDALQFVCGDRGFYFNKPTGYGSSSRRA
PQTGIVDECCFRSCDLRRLEMYCAPLKPAKSARSVRAQRHTDMPKTQKYQPPSTNICNTKSQRRKGWPKTHPGGEQICEGTEASLQI
RGICKKEQRREIGSRNAECRGKKGK DG01 SCFV (SEQ ID NO: 201)
atggaatgga cctgggtgtt cctgtttctg ctgtccgtga ccgctggcgt gcacagccag gtgcagctgg tggaaagcgg
cggaggagtc gtgcagcctg gcagaagcct gaggctgagc tgtgccgcca gcggcttcgc cttcagctcc tacggcatgc
actgggtgag acaggcccct ggcaagggac tggagtgggt ggctgtgatc tggttcgacg gcaccaagaa gtactacacc
gacagcgtca agggcaggtt caccatctcc agggacaata gcaagaatac cctgtacctc caaatgaaca ccctgagggc
cgaggacacc gccgtgtatt actgcgccag ggatagggga atcggcgcca ggagaggccc ctactacatg gacgtgtggg
gcaagggcac aacagtgacc gtttcttctg ctggaggagg aggttctgga ggaggaggaa gcggaggagg aggctccgac
atccagatga cacagtcccc cagctccctg tccgccagcg tgggcgatag agtgaccatc acctgcaggg ccagccagag
catctccagc tacctgaact ggtatcaaca gaagcccggc aaagccccca aactgctgat ctacgctgcc agcagcctgc
agagcggcgt gccttccaga ttcagcggct ccggcagcgg caccgatttc acactgacca tctccagcct gcagcccgag
gacttcgcca cctactactg ccagcagagc tacagcaccc ccctgacctt tggcggaggc accaaggtgg agatcaaa DG02 SCFV (SEQ ID NO: 202)
atggaatgga cctgggtgtt tctgttcctg ctgagcgtga cagccggcgt gcacagcgag gtgcagctgc tggagagcgg
aggaggactg gtgcaacccg gcggaagcct cagactgagc tgtgccgcca gcggcttcac cttcagcaac tatggcatga
gctgggtgag gcaggcccct ggcaaaggcc tcgaatgggt ggcttccatt aggagcggcg gcggcaggac ctattacagc -continued

APPENDIX A-AMINO ACID AND NUCLEIC ACID SEQUENCES gacaacgtga agggcaggtt caccatctcc agggacaata gcaagaacac cctgtacctg cagatgaact ccctgagggc
cgaggatacc gccgtgtact actgcgtgag gtacgaccac tacagcggct ccagcgacta ttggggacag ggcaccctgg
tgacagtgtc cagcgccgga ggaggcggca gcggcggcgg cggcagcggc ggcggcggaa gcgatgtggt gatgacccag
tccccccctga gcctgcctgt gacacctgga gagcccgcca gcatcagctg taagagcagc cagagcctcc tggacagcga
cggcaaaacc tacctgaact ggctcctgca gaagcccgga caaagccccc agaggctgat ctacctggtg agcaaactgg
acagcggcgt gcctgacaga ttctccggct ccggcagcgg caccgacttc acactgaaga tcagcagagt ggaggctgag
gacgtgggcg tctactactg ctggcagggc acccacttcc ccaggacctt cggccaggga accaaggtgg agatcaag DG03 SCFV (SEQ ID NO: 203)
atggaatgga cctgggtgtt cctgtttctg ctctccgtga ccgccggagt gcacagcgag gtgcagctgg tcgaaagcgg
cggaggactg gtgcagcctg gcggcagcct gagactgagc tgtgccgcct ccggcttcac ctttagcagc tacggaatgt
cctgggtgag acaggctcct ggcaagggcc tggaactggt ggccagcatc aatagcaacg gcggcagcac ctactaccct
gatagcgtga agggcaggtt caccatctcc agggacaacg ccaagaacag cctgtacctg cagatgaaca gcctcagggc
cgaggacaca gccgtgtact actgcgccag cggcgactat tggggacagg gaacaaccgt gaccgtcagc agcgccggcg
gcggcggcag cggcggcggc ggcagcggcg gcggcggctc cgatatcgtg atgacccaga gcccccctgtc cctgcctgtc
acacctggcg aacccgccag cattagctgc aggtccagcc agagcctggt gtacagcaat ggcgacacct acctgcactg
gtacctgcag aagcctggcc agagccccca gctgctgatc tacaaggtga gcaacaggtt ctccggagtg cctgacaggt
tcagcggctc cggcagcgga accgatttca ccctcaagat cagcagagtg gaggccgagg acgtgggcgt ctactattgt
agccagagca cccacgtgcc ctggaccttt ggccagggca ccaaggtgga gatcaaa DG04 SCFV (SEQ ID NO: 204)
atggaatgga cctgggtgtt tctgttcctc ctgagcgtga ccgccggagt gcacagccaa gtggagctgg tggagagcgg
aggaggactg gtgcagcctg gaggctccct gaggctgagc tgtgctgcca gcggcttcac cttcagctcc tatgctatga
gctgggtgag acaggcccct ggcaaaggcc tggagtgggt gagcgccatc aacgcctccg gcaccaggac ctactatgcc
gactccgtga agggcaggtt caccatctcc agggacaaca gcaagaacac cctgtacctg cagatgaaca gcctgagggc
tgaagacacc gccgtgtact actgtgccag gggcaagggc aacacacaca agccctatgg ctacgtgaga tacttcgacg
tgtggggaca gggcaccctg gtgacagtga gcagcgccgg aggaggaggt tctggaggag gaggaagcgg cggaggagga
agcgacatcg tgctgacaca atcccccgcc acactgtccc tgtcccctgg cgagagggcc acactgagct gcagggccag
ccagagcgtg tcctcctcct acctggcctg gtaccagcag aaacctggcc aggcccccag gctgctgatc tatggcgcca
gcagcagagc cacaggagtg cctgccagat ttagcggcag cggcagcggc accgacttta ccctgaccat ttccagcctg
gagcccgagg acttcgccac ctactactgc ctgcagatct acaacatgcc tatcaccttc ggccagggca caaaagtgga
aatcaag DG05 SCFV (SEQ ID NO: 205)
atggaatgga cctgggtgtt tctgttcctc ctgtccgtga ccgccggagt gcactccgaa gtgcagctgg tgcagtccgg
cggaggactg gtgaaacccg gaggaagcct cagactgagc tgcgccggca gcggctttac cttctccagc tactccatgc
actggctgag acaggcccct ggcaagggcc tggaatgggt cagcgccatc ggcaccgccg gaggcacata ctatgccgac
agcgtgaagg gcaggttcac catcagcagg gacaacgcca agaacagcct gtacctgcag atgaactctc tgagggccga
ggataccgct gtgtactact gcgccaggga gtacttcttt ggcagcggca actacggata ctgggggccag ggcaccctgg
tgacagtgag ctccgccgga ggaggaggaa gcggaggagg cggaagcgga ggaggcggca gcgaaatcgt gctgacccag
agccctgcca ccctgagcct gagccctggc gaaagggcca ccctgagctg cagagccagc cagagcgtga gcagctacct
ggcctggtac cagcagaagc ccggacaggc ccccagactg ctgatctacg acgccagcaa cagagccacc ggcattcccg
ccagattctc cggcagcggc agcggaaccg acttcacact gaccatcagc tccttagaac ccgaggactt cgccgtgtac
tactgtcagc agagaagcaa ctggcctccc accttcggcc agggcacaaa ggtggagatc aag DG06 SCFV (SEQ ID NO: 206)
atggaatgga cctgggtgtt cctgttcctc ctgagcgtga ccgctggcgt ccacagccag gtgcagctgg tggaaagcgg
aggcggagtg gtgcagcctg gaaggtccct cagactgagc tgcgctgcca gcggcttcac cttcagcaac tacggcatcc
actgggtgag acaagccccc ggcaaaggcc tggagtgggt ggccatcatc tggcacgacg gcagcaactc ctactacgtg
gactccgtga agggcaggtt cacaatcagc agagacaaca gcaagaatac cctgtacctg cagatgaaca gcctcagggc
cgaagatacc gccgtgtact tctgcgccag gatcatcggc ggcgcctttg acatttgggg ccaaggcact atggttaccg
tgagcagcgc tggcggaggc ggcagcggcg gcggcggcag cggcggcggc ggaagcgaca tccagatgac ccagagccct
tccagcctca gcgcctccgt gggagacaga gtgaccatca cctgcagggc cagccagggc atctccagct ggctggcctg
gtaccagcag aagcctgaga aagcccccaa gagcctgatc tacgctgcct ccagcctgca gtccggcgtg ccttccagat
tctccggcag cggcagcggc accgacttta ccctgaccat ttccagcctg caacccgagg acttcgccac ctactactgc
cagcagtaca acagctaccc catcaccttt ggccagggca ccagactgga gatcaag DG07 SCFV (SEQ ID NO: 207)
atggaatgga cctgggtgtt cctgttcctg ctgtccgtga ccgccggagt ccacagcgag gtgcagctgg tggaaagcgg
cggaggactg gtgcagcctg gaggcagcct gaggctgagc tgtgctgcca gcggcttctc catcagcggc tactggatgt
cctgggtgag gcaggcccct ggaaagggct tagaatgggt ggccaacatc aaacaggacg gcggcgagaa gtactacgga
gacagcgtca agggcagatt caccatcagc agggacaacg ccaagaacag cctgtacctg cagatgaaca gcctgagggc
cgaggacacc gctgtgtact actgcgtgat ggccggaggc ctggattatt ggggccaggg cacactggtg acagtgagca
gcgccggcgg cggcggcagc ggcggcggcg gcagcggcgg cggcggcagc gagatcgtgc tgacccagag ccctgccaca
ctgagcctga gccccggcga aagagccacc ctcagctgca gggccagcca gagcgtgagc agctacctgg cctggtacca
gcagaagccc ggacaggccc ctaggctgct gatctacgat gccagcaaca gagccaccgg catccctgct aggttcagcg
gttctggcag cggcaccgac ttcaccctga ccatcagcag cctggagcct gaggacttcg ctgtctacta ctgccagcag
aggagcaact ggtatacctt cggccaggga accaagctgg agatcaag DG08 SCFV (SEQ ID NO: 208)
atggaatgga cctgggtgtt cctgttcctg ctcagcgtga ccgccggagt gcactcccag gtgcagctgg tgcagagcgg
cgccgaagtg aaaaagcccg gcgccagcgt gagactctcc tgtagagcca gcggctacaa cttcatcgac ttccacatcc
actgggtgag acaggcccct ggagagggcc tggagtggat gggctggagc aacccccaga gcggcaatag cagcagcgcc
cagaggttcc agggcagagt gaccatgacc accgatacct ccatgagcgc cgcctacatg gacctgaact ggctgaccct
ggacgacacc gccgtgtact actgcaccag gcctcacgac ggcgctggca actacaggtt cgacacctgg ggacagggaa
ccctggtgac agtcagcagc gcgggaggtg gtggtagcgg tggtggggt tccggtggag gtggcagttc atatgagctt
acacaacccc caagtgtgag cgtggctcct ggccagacag ccaggatcac ctgcagcgga gacgccctgc ccaaacacta -continued

APPENDIX A-AMINO ACID AND NUCLEIC ACID SEQUENCES cgcccactgg tatcagcaga aacccggcca ggtgcccatc gtggtgatct acaaggacac cgagagacct agcggcatcc
ccgagagatt cagcggcagc accagcggca ccacagtcac cctgaccatc tccggcgtgc aggccgagga tgaagcccac
tactactgcc aaagcgccga cgtgtcctcc acctatgtgg tgtlcggcgg cggcaccaag ctgaccgtcc tc DG09 SCFV (SEQ ID NO: 209)
atggagtgga cttgggtatt cctgttttg ttgtccgtaa ctgctggggt acactcagag gtgcagctgg tagagtctgg
agggggctc gtcgaaccag gcggctctct caggctttcc tgtgccgtaa gcgggtttga ttttgagaaa gcatggatgt
cctgggtaag gcaagctcca gggcagggac tccagtgggt agcgcggata aagtcaacag ctgatggcgg aaccacctct
tatgcagcac cggttgaggg aaggttcatc atctcacgag acgattcccg caacatgttg tatctgcaga tgaacagttt
gaaaactgaa gacacagctg tttactactg tacttcagcg cattggggac agggtactct tgtgacggtc tctagcgccg
gggggggagg ctctggaggg gggggttcag ggggtggtgg cagctcctat gagctgactc aaccgccttc agtaagcgta
agccctggtc agaccgctag aataacctgt agtggagagg ccctgccgat gcaattcgcc cactggtatc agcagaggcc
tggaaaagcc ccagtgattg tcgtttacaa agattccgaa cgccctagcg gggttcccga acgctttagc ggtagttcaa
gcgggacaac agcaaccctt acgataaccg gtgtacaagc ggaagacgaa gcggattact attgccaatc acctgatagt
acaaatactt atgaggtatt tggcggggga acgaagttga ctgtactg DG10 SCFV (SEQ ID NO: 210)
atggaatgga cctgggtgtt cctcttcctc ctgtccgtca ccgctggcgt gcacagccag gtgcagctgg tccagagcgg
agccgaggtg aaaaagcccg gcgcctccgt gaaggtcagc tgcaaggcct ccggctacac cttcaccaac tacgccatgc
actgggtgag acaggcccct ggccagagac tggagtggat gggctggatc aacgccggca acggcaagag aaagtacagc
cagaagtttc aggacagggt gaccatcaac agggacacca gcgcctccac catctacatg gagctgtcca gcctgggcag
cgaggatacc gccgtgtact actgtgccag agaggaggat cacgctggca gcggcagcta cctgagcatg gacgtctggg
gacagggcag caccgtgaca gtgagcagcg ctggaggcgg cggctccggc ggcggaggaa gcggaggcgg aggctccgac
atcgtgatga cccagtcccc cgatagcctg gctgtgagcc tgggcgagag ggccacaatc aactgtaaga gcagccagaa
cgtgctgtac tcctccaaca acaagaacta cctggcctgg taccagcaga aacctggcca tccccccaag ctgctgatct
actgggccag caccagggag agcggagtgc ctgacaggtt tagcggcagc ggcagcggca cagactttac cctgaccatc
acctccctgc agaccgagga cgtggccgtg tactattgcc agcagtacta cagctcccct ctgaccttcg gcggcggcac
caaagtggag atcaaa DG11 SCFV (SEQ ID NO: 211)
atggagtgga cttgggtatt ccttttcctc ctctccgtga cagcgggtgt gcactctgaa gtacaacttg tagagaccgg
tgggggattg gtgcaaccca agggttccct gaaactctca tgtgctacct ctggttttac tttcaacacc tatgcaatga
attgggaagg gcaagcaccc ggtaaaggac ttgagtgggt ggcacggata cgcactaaga gtaatgacta tgctacgtac
tacgcagact ccgtaaaagg ccggatcacc atatctcgag acgatagcca gtctatgctg tatcttcaaa tgaacaacct
caaaacggaa gatacggcga tgtattactg cgtgcgagtt ggttataggc cttatgctat ggattactgg ggacagggca
cgtctgtcac ggtaagttct gccggagggg ggggcagcgg aggaggagga tctggcggag gggctccga tgtccttatg
acacagactc ccctcagttt gcccgtgtcc ttgggggacc aggcttctat atcatgccgc agttcccaaa atatcgtcca
ttcaaatggc aatacttacc ttgagtggta tttgcagaag cctggacaga gcccgacgct tctgatctat aaggtaagca
acaggttcag tggtgtaccc gacagattta gtggaagtgg gtccggaact gatttcactc ttaagattag tcgggtagag
gctgaagacc ttggggtgta ttattgcttt caagggagtc acgtccctct tacatttggt gctgggacta agttggagct
gaag 4-1BB CO-STIMULATORY DOMAIN (SEQ ID NO: 212)
aaacggggca gaaagaaact cctgtatata ttcaaacaac catttatgag accagtacaa actactcaag aggaagatgg
ctgtagctgc cgatttccag aagaagaaga aggaggatgt gaactg (G4S)3 LINKER (SEQ ID NO: 213)
ggcggaggcg gatcaggagg aggaggatca ggcggaggag gatca T2A (SEQ ID NO: 214)
agagccaaaa ggtctggctc cggtgagggc agaggaagtc ttataacatg cggtgacgtg gaggagaatc ccggccct P2A (SEQ ID NO: 215)
agagccaaaa ggtccggaag cggcgccacc aacttcagcc tgctgaagca ggccggcgac gtggaagaga atcctggccc
c CD3Z (SEQ ID NO: 216)
agagtgaagt tcagcaggag cgcagacgcc cccgcgtacc agcagggcca gaaccagctc tataacgagc tcaatctagg
acgaagagag gagtacgatg ttttggacaa gagacgtggc cgggaccctg agatgggggg aaagccgaga aggaagaacc
ctcaggaagg cctgtacaat gaactgcaga aagataagat ggcggaggcc tacagtgaga ttgggatgaa aggcgagcgc
cggaggggca aggggcacga tggcctttac cagggtctca gtacagccac caaggacacc tacgacgccc ttcacatgca
ggccctgccc cctcgc DG01.28.Z CAR (SEQ ID NO: 220)
atggaatgga cctgggtgtt cctgtttctg ctgtccgtga ccgctggcgt gcacagccag gtgcagctgg tggaaagcgg
cggaggagtc gtgcagcctg gcagaagcct gaggctgagc tgtgccgcca gcggcttcgc cttcagctcc tacggcatgc
actgggtgag acaggcccct ggcaagggac tggagtgggt ggctgtgatc tggttcgacg gcaccaagaa gtactacacc
gacagcgtca agggcaggtt caccatctcc agggacaata gcaagaatac cctgtacctc caaatgaaca ccctgagggc
cgaggacacc gccgtgtatt actgcgccag ggatagggga atcggcgcca ggagaggccc ctactacatg gacgtgtggg
gcaagggcac aacagtgacc gtttcttctg ctggaggagg aggttctgga ggaggaggaa gcggaggagg aggctccgac
atccagatga cacagtcccc cagctccctg tccgccagcg tgggcgatag agtgaccatc acctgcaggg ccagccagag
catctccagc tacctgaact ggtatcaaca gaagcccggc aaagccccca aactgctgat ctacgctgcc agcagcctgc
agagcggcgt gccttccaga ttcagcggct ccggcagcgg caccgatttc acactgacca tctccagcct gcagcccgag
gacttcgcca cctactactg ccagcagagc tacagcaccc ccctgacctt tggcggaggc accaaggtgg agatcaaagc
tagcgtgaaa gggaaacacc tttgtccaag tcccctattt cccggacctt ctaagccctt ttgggtgctg gtggtggttg
gtggagtcct ggcttgctat agcttgctag taacagtggc ctttattatt ttctgggtga ggagtaagag gagcaggctc
ctgcacagtg actacatgaa catgactccc cgccgccccg ggcccacccg caagcattac cagccctatg ccccaccacg -continued

APPENDIX A-AMINO ACID AND NUCLEIC ACID SEQUENCES cgacttcgca gcctatcgct ccaagcttag agtgaagttc agcaggagcg cagacgcccc cgcgtaccag cagggccaga
accagctcta taacgagctc aatctaggac gaagagagga gtacgatgtt ttggacaaga gacgtggccg ggaccctgag
atggggggaa agccgagaag gaagaaccct caggaaggcc tgtacaatga actgcagaaa gataagatgg cggaggccta
cagtgagatt gggatgaaag gcgagcgccg gaggggcaag gggcacgatg gcctttacca gggtctcagt acagccacca
aggacaccta cgacgccctt cacatgcagg ccctgccccc t D002.28.Z CAR (SEQ ID NO: 221)
atggaatgga cctgggtgtt tctgttcctg ctgagcgtga cagccggcgt gcacagcgag gtgcagctgc tggagagcgg
aggaggactg gtgcaacccg gcggaagcct cagactgagc tgtgccgcca gcggcttcac cttcagcaac tatggcatga
gctgggtgag gcaggcccct ggcaaaggcc tcgaatgggt ggcttccatt aggagcggcg gcggcaggac ctattacagc
gacaacgtga agggcaggtt caccatctcc agggacaata gcaagaacac cctgtacctg cagatgaact ccctgagggc
cgaggatacc gccgtgtact actgcgtgag gtacgaccac tacagcggct ccagcgacta ttggggacag ggcaccctgg
tgacagtgtc cagcgccgga ggaggcggca gcggcggcgg cggcagcggc ggcggcggaa gcgatgtggt gatgacccag
tccccccctga gcctgcctgt gacacctgga gagcccgcca gcatcagctg taagagcagc cagagcctcc tggacagcga
cggcaaaacc tacctgaact ggctcctgca gaagcccgga caaagccccc agaggctgat ctacctggtg agcaaactgg
acagcggcgt gcctgacaga ttctccggct ccggcagcgg caccgacttc acactgaaga tcagcagagt ggaggctgag
gacgtgggcg tctactactg ctggcagggc acccacttcc ccaggacctt cggccaggga accaaggtgg agatcaaggc
tagcgtgaaa gggaaacacc tttgtccaag tcccctattt cccggacctt ctaagccctt ttgggtgctg gtggtggttg
gtggagtcct ggcttgctat agcttgctag taacagtggc ctttattatt ttctgggtga ggagtaagag gagcaggctc
ctgcacagtg actacatgaa catgactccc cgccgccccg ggcccacccg caagcattac cagccctatg ccccaccacg
cgacttcgca gcctatcgct ccaagcttag agtgaagttc agcaggagcg cagacgcccc cgcgtaccag cagggccaga
accagctcta taacgagctc aatctaggac gaagagagga gtacgatgtt ttggacaaga gacgtggccg ggaccctgag
atggggggaa agccgagaag gaagaaccct caggaaggcc tgtacaatga actgcagaaa gataagatgg cggaggccta
cagtgagatt gggatgaaag gcgagcgccg gaggggcaag gggcacgatg gcctttacca gggtctcagt acagccacca
aggacaccta cgacgccctt cacatgcagg ccctgccccc t DG03.28.Z CAR (SEQ ID NO: 222)
atggaatgga cctgggtgtt cctgtttctg ctctccgtga ccgccggagt gcacagcgag gtgcagctgg tcgaaagcgg
cggaggactg gtgcagcctg gcggcagcct gagactgagc tgtgccgcct ccggcttcac ctttagcagc tacggaatgt
cctgggtgag acaggctcct ggcaagggcc tggaactggt ggccagcatc aatagcaacg gcggcagcac ctactaccct
gatagcgtga agggcaggtt caccatctcc agggacaacg ccaagaacag cctgtacctg cagatgaaca gcctcagggc
cgaggacaca gccgtgtact actgcgccag cggcgactat tggggacagg gaacaaccgt gaccgtcagc agcgccggcg
gcggcggcag cggcggcggc ggcagcggcg gcggcggctc cgatatcgtg atgacccaga gcccccctgtc cctgcctgtc
acacctggcg aacccgccag cattagctgc aggtccagcc agagcctggt gtacagcaat ggcgacacct acctgcactg
gtacctgcag aagcctggcc agagccccca gctgctgatc tacaaggtga gcaacaggtt ctccggagtg cctgacaggt
tcagcggctc cggcagcgga accgatttca ccctcaagat cagcagagtg gaggccgagg acgtgggcgt ctactattgt
agccagagca cccacgtgcc ctggaccttt ggccagggca ccaaggtgga gatcaaagct agcgtgaaag ggaaacacct
ttgtccaagt cccctatttc ccggaccttc taagcccttt tgggtgctgg tggtggttgg tggagtcctg gcttgctata
gcttgctagt aacagtggcc tttattattt tctgggtgag gagtaagagg agcaggctcc tgcacagtga ctacatgaac
atgactcccc gccgccccgg gcccacccgc aagcattacc agccctatgc cccaccacgc gacttcgcag cctatcgctc
caagcttaga gtgaagttca gcaggagcgc agacgccccc gcgtaccagc agggccagaa ccagctctat aacgagctca
atctaggacg aagagaggag tacgatgttt tggacaagag acgtggccgg gaccctgaga tggggggaaa gccgagaagg
aagaaccctc aggaaggcct gtacaatgaa ctgcagaaag ataagatggc ggaggcctac agtgagattg ggatgaaagg
cgagcgccgg aggggcaagg ggcacgatgg cctttaccag ggtctcagta cagccaccaa ggacacctac gacgcccttc
acatgcaggc cctgcccccct DG04.28.Z CAR (SEQ ID NO: 223)
atggaatgga cctgggtgtt tctgttcctc ctgagcgtga ccgccggagt gcacagccaa gtggagctgg tggagagcgg
aggaggactg gtgcagcctg gaggctccct gaggctgagc tgtgctgcca gcggcttcac cttcagctcc tatgctatga
gctgggtgag acaggcccct ggcaaaggcc tggagtgggt gagcgccatc aacgcctccg gcaccaggac ctactatgcc
gactccgtga agggcaggtt caccatctcc agggacaaca gcaagaacac cctgtacctg cagatgaaca gcctgagggc
tgaagacacc gccgtgtact actgtgccag gggcaagggc aacacacaca agccctatgg ctacgtgaga tacttcgacg
tgtggggaca gggcaccctg gtgacagtga gcagcgccgg aggaggaggt tctggaggag gaggaagcgg cggaggagga
agcgacatcg tgctgacaca atcccccgcc acactgtccc tgtcccctgg cgagagggcc acactgagct gcagggccag
ccagagcgtg tcctcctcct acctggcctg gtaccagcag aaacctggcc aggcccccag gctgctgatc tatggcgcca
gcagcagagc cacaggagtg cctgccagat ttagcggcag cggcagcggc accgacttta ccctgaccat ttccagcctg
gagcccgagg acttcgccac ctactactgc ctgcagatct acaacatgcc tatcaccttc ggccagggca caaaagtgga
aatcaaggct agcgtgaaag ggaaacacct ttgtccaagt cccctatttc ccggaccttc taagcccttt tgggtgctgg
tggtggttgg tggagtcctg gcttgctata gcttgctagt aacagtggcc tttattattt tctgggtgag gagtaagagg
agcaggctcc tgcacagtga ctacatgaac atgactcccc gccgccccgg gcccacccgc aagcattacc agccctatgc
cccaccacgc gacttcgcag cctatcgctc caagcttaga gtgaagttca gcaggagcgc agacgccccc gcgtaccagc
agggccagaa ccagctctat aacgagctca atctaggacg aagagaggag tacgatgttt tggacaagag acgtggccgg
gaccctgaga tggggggaaa gccgagaagg aagaaccctc aggaaggcct gtacaatgaa ctgcagaaag ataagatggc
ggaggcctac agtgagattg ggatgaaagg cgagcgccgg aggggcaagg ggcacgatgg cctttaccag ggtctcagta
cagccaccaa ggacacctac gacgcccttc acatgcaggc cctgcccccct DG05.28.Z CAR (SEQ ID NO: 224)
atggaatgga cctgggtgtt tctgttcctc ctgtccgtga ccgccggagt gcactccgaa gtgcagctgg tgcagtccgg
cggaggactg gtgaaacccg gaggaagcct cagactgagc tgcgccggca gcggctttac cttctccagc tactccatgc
actggctgag acaggcccct ggcaagggcc tggaatgggt cagcgccatc ggcaccgccg gaggcacata ctatgccgac
agcgtgaagg gcaggttcac catcagcagg gacaacgcca agaacagcct gtacctgcag atgaactctc tgagggccga
ggataccgct gtgtactact gcgccaggga gtacttcttt ggcagcggca actacggata ctggggccag ggcaccctgg
tgacagtgag ctccgccgga ggaggaggaa gcggaggagg cggaagcgga ggaggcggca gcgaaatcgt gctgacccag
agccctgcca ccctgagcct gagccctggc gaaagggcca ccctgagctg cagagccagc cagagcgtga gcagctacct
ggcctggtac cagcagaagc ccggacaggc ccccagactg ctgatctacg acgccagcaa cagagccacc ggcattcccg
ccagattctc cggcagcggc agcggaaccg acttcacact gaccatcagc tccttagaac ccgaggactt cgccgtgtac
tactgtcagc agagaagcaa ctggcctccc accttcggcc agggcacaaa ggtggagatc aaggctagcg tgaaagggaa -continued

APPENDIX A-AMINO ACID AND NUCLEIC ACID SEQUENCES acacctttgt ccaagtcccc tatttcccgg accttctaag cccttttggg tgctggtggt ggttggtgga gtcctggctt
gctatagctt gctagtaaca gtggccttta ttattttctg ggtgaggagt aagaggagca ggctcctgca cagtgactac
atgaacatga ctccccgccg ccccgggccc acccgcaagc attaccagcc ctatgcccca ccacgcgact tcgcagccta
tcgctccaag cttagagtga agttcagcag gagcgcagac gcccccgcgt accagcaggg ccagaaccag ctctataacg
agctcaatct aggacgaaga gaggaglacg atgttttgga caagagacgt ggccgggacc ctgagatggg gggaaagccg
agaaggaaga accctcagga aggcctgtac aatgaactgc agaaagataa gatggcggag gcctacagtg agattgggat
gaaaggcgag cgccggaggg gcaaggggca cgatggcctt taccagggtc tcagtacagc caccaaggac acctacgacg
cccttcacat gcaggccctg ccccct DG06.28.Z CAR (SEQ ID NO: 225)
atggaatgga cctgggtgtt cctgttcctc ctgagcgtga ccgctggcgt ccacagccag gtgcagctgg tggaaagcgg
aggcggagtg gtgcagcctg gaaggtccct cagactgagc tgcgctgcca gcggcttcac cttcagcaac tacggcatcc
actgggtgag acaagccccc ggcaaaggcc tggagtgggt ggccatcatc tggcacgacg gcagcaactc ctactacgtg
gactccgtga agggcaggtt cacaatcagc agagacaaca gcaagaatac cctgtacctg cagatgaaca gcctcagggc
cgaagatacc gccgtgtact tctgcgccag gatcatcggc ggcgcctttg acatttgggg ccaaggcact atggttaccg
tgagcagcgc tggcggaggc ggcagcggcg gcggcggcag cggcggcggc ggaagcgaca tccagatgac ccagagccct
tccagcctca gcgcctccgt gggagacaga gtgaccatca cctgcagggc cagccagggc atctccagct ggctggcctg
gtaccagcag aagcctgaga aagccoccaa gagcctgatc tacgctgcct ccagcctgca gtccggcgtg ccttccagat
tctccggcag cggcagcggc accgacttta ccctgaccat ttccagcctg caacccgagg acttcgccac ctactactgc
cagcagtaca acagctaccc catcaccttt ggccagggca ccagactgga gatcaaggct agcgtgaaag ggaaacacct
ttgtccaagt cccctatttc ccggaccttc taagcccttt tgggtgctgg tggtggttgg tggagtcctg gcttgctata
gcttgctagt aacagtggcc tttattattt tctgggtgag gagtaagagg agcaggctcc tgcacagtga ctacatgaac
atgactcccc gccgccccgg gcccacccgc aagcattacc agccctatgc cccaccacgc gacttcgcag cctatcgctc
caagcttaga gtgaagttca gcaggagcgc agacgccccc gcgtaccagc agggccagaa ccagctctat aacgagctca
atctaggacg aagagaggag tacgatgttt tggacaagag acgtggccgg gaccctgaga tggggggaaa gccgagaagg
aagaaccctc aggaaggcct gtacaatgaa ctgcagaaag ataagatggc ggaggcctac agtgagattg ggatgaaagg
cgagcgccgg aggggcaagg ggcacgatgg cctttaccag ggtctcagta cagccaccaa ggacacctac gacgcccttc
acatgcaggc cctgcccccct DG07.28.Z CAR (SEQ ID NO: 226)
atggaatgga cctgggtgtt cctgttcctg ctgtccgtga ccgccggagt ccacagcgag gtgcagctgg tggaaagcgg
cggaggactg gtgcagcctg gaggcagcct gaggctgagc tgtgctgcca gcggcttctc catcagcggc tactggatgt
cctgggtgag gcaggcccct ggaaagggct tagaatgggt ggccaacatc aaacaggacg gcggcgagaa gtactacgga
gacagcgtca agggcagatt caccatcagc agggacaacg ccaagaacag cctgtacctg cagatgaaca gcctgagggc
cgaggacacc gctgtgtact actgcgtgat ggccggaggc ctggattatt ggggccaggg cacactggtg acagtgagca
gcgccggcgg cggcggcagc ggcggcggcg gcagcggcgg cggcggcagc gagatcgtgc tgacccagag ccctgccaca
ctgagcctga gccccggcga aagagccacc ctcagctgca gggccagcca gagcgtgagc agctacctgg cctggtacca
gcagaagccc ggacaggccc ctaggctgct gatctacgat gccagcaaca gagccaccgg catccctgct aggttcagcg
gttctggcag cggcaccgac ttcaccctga ccatcagcag cctggagcct gaggacttcg ctgtctacta ctgccagcag
aggagcaact ggtatacctt cggccaggga accaagctgg agatcaaggc tagcgtgaaa gggaaacacc tttgtccaag
tcccctattt cccggacctt ctaagccctt ttgggtgctg gtggtggttg gtggagtcct ggcttgctat agcttgctag
taacagtggc ctttattatt ttctgggtga ggagtaagag gagcaggctc ctgcacagtg actacatgaa catgactccc
cgccgccccg ggcccacccg caagcattac cagccctatg ccccaccacg cgacttcgca gcctatcgct ccaagcttag
agtgaagttc agcaggagcg cagacgcccc cgcgtaccag cagggccaga accagctcta taacgagctc aatctaggac
gaagagagga gtacgatgtt ttggacaaga gacgtggccg ggaccctgag atggggggaa agccgagaag gaagaaccct
caggaaggcc tgtacaatga actgcagaaa gataagatgg cggaggccta cagtgagatt gggatgaaag gcgagcgccg
gaggggcaag ggcacgatg gcctttacca gggtctcagt acagccacca aggacaccta cgacgccctt cacatgcagg
ccctgccccc t DG08.28.Z CAR (SEQ ID NO: 227)
atggaatgga cctgggtgtt cctgttcctg ctcagcgtga ccgccggagt gcactcccag gtgcagctgg tgcagagcgg
cgccgaagtg aaaaagcccg gcgccagcgt gagactctcc tgtagagcca gcggctacaa cttcatcgac ttccacatcc
actgggtgag acaggcccct ggagagggcc tggagtggat gggctggagc aacccccaga gcggcaatag cagcagcgcc
cagcagcgcc agggcagagt gaccatgacc accgatacct ccatgagcgc cgcctacatg gacctgaact ggctgaccct
ggacgacacc gccgtgtact actgcaccag gcctcacgac ggcgctggca actacaggtt cgacacctgg ggacagggaa
ccctgggtac agtcagcagc gcgggaggtg gtggtagcgg tggtgggggt tccggtggag gtggcagttc atatgagctt
acacaacccc caagtgtgag cgtggctcct ggccagacag ccaggatcac ctgcagcgga gacgccctgc ccaaacacta
cgcccactgg tatcagcaga aacccggcca ggtgcccatc gtggtgatct acaaggacac cgagagacct agcggcatcc
ccgagagatt cagcggcagc accagcggca ccacagtcac cctgaccatc tccggcgtgc aggccgagga tgaagcccac
tactactgcc aaagcgccga cgtgtcctcc acctatgtgg tgttcggcgg cggcaccaag ctgaccgtcc tcgctagcgt
gaaagggaaa cacctttgtc caagtcccct atttcccgga ccttctaagc ccttttgggt gctggtggtg gttggtggag
tcctggcttg ctatagcttg ctagtaacag tggcctttat tattttctgg gtgaggagta agaggagcag gctcctgcac
agtgactaca tgaacatgac tccccgccgc cccgggccca cccgcaagca ttaccagccc tatgccccac cacgcgactt
cgcagcctat cgctccaagc ttagagtgaa gttcagcagg agcgcagacg cccccgcgta ccagcagggc cagaaccagc
tctataacga gctcaatcta ggacgaagag aggagtacga tgttttggac aagagacgtg gccgggaccc tgagatgggg
ggaaagccga gaaggaagaa ccctcaggaa ggcctgtaca atgaactgca gaaagataag atggcggagg cctacagtga
gattgggatg aaaggcgagc gccggagggg caaggggcac gatggccttt accagggtct cagtacagcc accaaggaca
cctacgacgc ccttcacatg caggccctgc ccccct DG09.28.Z CAR (SEQ ID NO: 228)
atggagtgga cttgggtatt cctgtttttg ttgtccgtaa ctgctggggt acactcagag gtgcagctgg tagagtctgg
agggggctc gtcgaaccag gcggctctct caggctttcc tgtgccgtaa gcgggtttga ttttgagaaa gcatggatgt
cctgggtaag gcaagctcca gggcagggac tccagtgggt agcgcggata aagtcaacag ctgatggcgg aaccacctct
tatgcagcac cggttgaggg aaggttcatc atctcacgag acgattcccg caacatgttg tatctgcaga tgaacagttt
gaaaactgaa gacacagctg tttactactg tacttcagcg cattggggac agggtactct tgtgacggtc tctagcgccg
gggggggagg ctctggaggg gggggttcag gggtggtgg cagctcctat gagctgactc aaccgccttc agtaagcgta
agccctggtc agaccgctag aataacctgt agtggagagg ccctgccgat gcaattcgcc cactggtatc agcagaggcc -continued

APPENDIX A-AMINO ACID AND NUCLEIC ACID SEQUENCES tggaaaagcc ccagtgattg tcgtttacaa agattccgaa cgccctagcg gggttcccga acgctttagc ggtagttcaa
gcgggacaac agcaaccctt acgataaccg gtgtacaagc ggaagacgaa gcggattact attgccaatc acctgatagt
acaaatactt atgaggtatt tggcgggggga acgaagttga ctgtactggc tagcgtgaaa gggaaacacc tttgtccaag
tcccctattt cccggacctt ctaagccctt ttgggtgctg gtggtggttg gtggagtcct ggcttgctat agcttgctag
taacagtggc ctttattatt ttctgggtga ggagtaagag gagcaggctc ctgcacagtg actacatgaa catgactccc
cgccgccccg ggcccacccg caagcattac cagccctatg ccccaccacg cgacttcgca gcctatcgct ccaagcttag
agtgaagttc agcaggagcg cagacgcccc cgcgtaccag cagggccaga accagctcta taacgagctc aatctaggac
gaagagagga gtacgatgtt ttggacaaga gacgtggccg ggaccctgag atggggggaa agccgagaag gaagaaccct
caggaaggcc tgtacaatga actgcagaaa gataagatgg cggaggccta cagtgagatt gggatgaaag gcgagcgccg
gaggggcaag gggcacgatg gcctttacca gggtctcagt acagccacca aggacaccta cgacgccctt cacatgcagg
ccctgccccc t DG10.28.Z CAR (SEQ ID NO: 229)
atggaatgga cctgggtgtt cctcttcctc ctgtccgtca ccgctggcgt gcacagccag gtgcagctgg tccagagcgg
agccgaggtg aaaaagcccg gcgcctccgt gaaggtcagc tgcaaggcct ccggctacac cttcaccaac tacgccatgc
actgggtgag acaggcccct ggccagagac tggagtggat gggctggatc aacgccggca acggcaagag aaagtacagc
cagaagtttc aggacagggt gaccatcaac agggacacca gcgcctccac catctacatg gagctgtcca gcctgggcag
cgaggatacc gccgtgtact actgtgccag agaggaggat cacgctggca gcggcagcta cctgagcatg gacgtctggg
gacagggcag caccgtgaca gtgagcagcg ctggaggcgg cggctccggc ggcggaggaa gcggaggcgg aggctccgac
atcgtgatga cccagtcccc cgatagcctg gctgtgagcc tgggcgagag ggccacaatc aactgtaaga gcagccagaa
cgtgctgtac tcctccaaca acaagaacta cctggcctgg taccagcaga aacctggcca tccccccaag ctgctgatct
actgggccag caccagggag agcggagtgc ctgacaggtt tagcggcagc ggcagcggca cagactttac cctgaccatc
acctccctgc agaccgagga cgtggccgtg tactattgcc agcagtacta cagctcccct ctgaccttcg gcggcggcac
caaagtggag atcaaagcta gcgtgaaagg gaaacacctt tgtccaagtc ccctatttcc cggaccttct aagccctttt
gggtgctggt ggtggttggt ggagtcctgg cttgctatag cttgctagta acagtggcct ttattatttt ctgggtgagg
agtaagagga gcaggctcct gcacagtgac tacatgaaca tgactccccg ccgccccggg cccacccgca agcattacca
gccctatgcc ccaccacgcg acttcgcagc ctatcgctcc aagcttagag tgaagttcag caggagcgca gacgcccccg
cgtaccagca gggccagaac cagctctata acgagctcaa tctaggacga agagaggagt acgatgtttt ggacaagaga
cgtggccggg acccagagat gggggggaaag ccgagaagga agaaccctca ggaaggcctg tacaatgaac tgcagaaaga
taagatggcg gaggcctaca gtgagattgg gatgaaaggc gagcgccgga ggggcaaggg gcacgatggc ctttaccagg
gtctcagtac agccaccaag gacacctacg acgcccttca catgcaggcc ctgcccccct DGI1.28.Z CAR (SEQ ID NO: 230)
atggagtgga cttgggtatt ccttttcctc ctctccgtga cagcgggtgt gcactctgaa gtacaacttg tagagaccgg
tgggggattg gtgcaaccca agggttccct gaaactctca tgtgctacct ctggttttac tttcaacacc tatgcaatga
attgggttag gcaagcaccc ggtaaaggac ttgagtgggt ggcacggata cgcactaaga gtaatgacta tgctacgtac
tacgcagact ccgtaaaagg ccggatcacc atatctcgag acgatagcca gtctatgctg tatcttcaaa tgaacaacct
caaaacggaa gatacggcga tgtattactg cgtgcgagtt ggttataggc cttatgctat ggattactgg ggacagggca
cgtctgtcac ggtaagttct gccggagggg ggggcagcgg aggaggagga tctggcggag ggggctccga tgtccttatg
acacagactc ccctcagttt gcccgtgtcc ttgggggacc aggcttctat atcatgccgc agttcccaaa atatcgtcca
ttcaaatggc aatacttacc ttgagtggta tttgcagaag cctggacaga gcccgacgct tctgatctat aaggtaagca
acaggttcag tggtgtaccc gacagattta gtggaagtgg gtccggaact gatttcactc ttaagattag tcgggtagag
gctgaagacc ttggggtgta ttattgcttt caagggagtc acgtccctct tacatttggt gctgggacta agttggagct
gaaggctagc gtgaaaggga aacacctttg tccaagtccc ctatttcccg gaccttctaa gcccttttgg gtgctggtgg
tggttggtgg agtcctggct tgctatagct tgctagtaac agtggccttt attattttct gggtgaggag taagaggagc
aggctcctgc acagtgacta catgaacatg actccccgcc gccccgggcc cacccgcaag cattaccagc cctatgcccc
accacgcgac ttcgcagcct atcgctccaa gcttagagtg aagttcagca ggagcgcaga cgcccccgcg taccagcagg
gccagaacca gctctataac gagctcaatc taggacgaag agaggagtac gatgttttgg acaagagacg tggccgggac
cctgagatgg ggggaaagcc gagaaggaag aaccctcagg aaggcctgta caatgaactg cagaaagata agatggcgga
ggcctacagt gagattggga tgaaaggcga gcgccggagg ggcaaggggc acgatggcct ttaccagggt ctcagtacag
ccaccaagga cacctacgac gcccttcaca tgcaggccct gcccccct SIGNAL SEQUENCE (SEQ ID NO: 231)
atggaatgga cctgggtctt tctcttcctc ctgtcagtaa ctgcaggtgt ccac HUMAN CD28 HINGE (SEQ ID NO: 232)
gtgaaaggga aacacctttg tccaagtccc ctatttcccg gaccttctaa gccc MOUSE CD28 HINGE (SEQ ID NO: 233)
ataaaagaga aacatctttg tcatactcag tcatctccta agctg HUMAN CD8A HINGE (SEQ ID NO: 234)
accacgacgc cagcgccgcg accaccaaca ccggcgccca ccatcgcgtc gcagcccctg tccctgcgcc cagaggcgtg
ccggccagcg gcggggggcg cagtgcacac gagggggctg gacttcgcct gtgat HUMAN DAP10 HINGE (SEQ ID NO: 235)
cagacgaccc caggagagag atcatcactc cctgcctttt accctggcac ttcaggctcc tgttccggat gtgggtccct
ctctctgccg HUMAN CD28 TM (SEQ ID NO: 236)
ttttgggtgc tggtggtggt tggtggagtc ctggcttgct atagcttgct agtaacagtg gcctttatta ttttctgggt
g MOUSE CD28 TM (SEQ ID NO: 237)
ttttgggcac tggtcgtggt tgctggagtc ctgttttgtt atggcttgct agtgacagtg gctctttgtg ttatctggac
a -continued

APPENDIX A-AMINO ACID AND NUCLEIC ACID SEQUENCES

HUMAN CD8A TM (SEQ ID NO: 238)
atctacatct gggcgccctt ggccgggact tgtggggtcc ttctcctgtc actggttatc accattact gc HUMAN DAP10 TM (SEQ ID NO: 239)
ctcctggcag gcctcgtggc tgctgatgcg gtggcatcgc tgctcatcgt gggggcggtg ttc DG05-CD28tm-DAP10-CD3ζ (SEQ ID NO: 240)
ATGGAATGGACCTGGGTGTTTCTGTTCCTCCTGTCCGTGACCGCCGGAGTGCACTCCGAAGTGCAGCTGGTGCAGTCCGGCGGAGGA
CTGGTGAAACCCGGAGGAAGCCTCAGACTGAGCTGCGCCGGCAGCGGCTTTACCTTCTCCAGCTACTCCATGCACTGGCTGAGACAG
GCCCCTGGCAAGGGCCTGGAATGGGTCAGCGCCATCGGCACCGCCGGAGGCACATACTATGCCGACAGCGTGAAGGGCAGGTTCACC
ATCAGCAGGGACAACGCCAAGAACAGCCTGTACCTGCAGATGAACTCTCTGAGGGCCGAGGATACCGCTGTGTACTACTGCGCCAGG
GAGTACTTCTTTGGCAGCGGCAACTACGGATACTGGGGCCAGGGCACCCTGGTGACAGTGAGCTCCGCCGGAGGAGGAGGAAGCGGA
GGAGGCGGAAGCGGAGGAGGCGGCAGCGAAATCGTGCTGACCCAGAGCCCTGCCACCCTGAGCCTGAGCCCTGGCGAAAGGGCCACC
CTGAGCTGCAGAGCCAGCCAGAGCGTGAGCAGCTACCTGGCCTGGTACCAGCAGAAGCCCGGACAGGCCCCCAGACTGCTGATCTAC
GACGCCAGCAACAGAGCCACCGGCATTCCCGCCAGATTCTCCGGCAGCGGCAGCGGAACCGACTTCACACTGACCATCAGCTCCTTA
GAACCCGAGGACTTCGCCGTGTACTACTGTCAGCAGAGAAGCAACTGGCCTCCCACCTTCGGCCAGGGCACAAAGGTGGAGATCAAG
GCTAGCGTGAAAGGGAAACACCTTTGTCCAAGTCCCCTATTTCCCGGACCTTCTAAGCCCTTTTGGGTGCTGGTGGTGGTTGGTGGA
GTCCTGGCTTGCTATAGCTTGCTAGTAACAGTGGCCTTTATTATTTTCTGGGTGAGGAGTAAGAGGAGCCTGTGCGCACGCCCACGC
CGCAGCCCCGCCCAAGAAGATGGCAAAGTCTACATCAACATGCCAGGCAGGGGCAAGCTTAGAGTGAAGTTCAGCAGGAGCGCAGAC
GCCCCCGCGTACCAGCAGGGCCAGAACCAGCTCTATAACGAGCTCAATCTAGGACGAAGAGAGGAGTACGATGTTTTGGACAAGAGA
CGTGGCCGGGACCCTGAGATGGGGGGAAAGCCGAGAAGGAAGAACCCTCAGGAAGGCCTGTACAATGAACTGCAGAAAGATAAGATG
GCGGAGGCCTACAGTGAGATTGGGATGAAAGGCGAGCGCCGGAGGGGCAAGGGGCACGATGGCCTTTACCAGGGTCTCAGTACAGCC
ACCAAGGACACCTACGACGCCCTTCACATGCAGGCCCTGCCCCCTCGC DG05-CD28tm-CD44-CD3ζ (SEQ ID NO: 241)
ATGGAATGGACCTGGGTGTTTCTGTTCCTCCTGTCCGTGACCGCCGGAGTGCACTCCGAAGTGCAGCTGGTGCAGTCCGGCGGAGGA
CTGGTGAAACCCGGAGGAAGCCTCAGACTGAGCTGCGCCGGCAGCGGCTTTACCTTCTCCAGCTACTCCATGCACTGGCTGAGACAG
GCCCCTGGCAAGGGCCTGGAATGGGTCAGCGCCATCGGCACCGCCGGAGGCACATACTATGCCGACAGCGTGAAGGGCAGGTTCACC
ATCAGCAGGGACAACGCCAAGAACAGCCTGTACCTGCAGATGAACTCTCTGAGGGCCGAGGATACCGCTGTGTACTACTGCGCCAGG
GAGTACTTCTTTGGCAGCGGCAACTACGGATACTGGGGCCAGGGCACCCTGGTGACAGTGAGCTCCGCCGGAGGAGGAGGAAGCGGA
GGAGGCGGAAGCGGAGGAGGCGGCAGCGAAATCGTGCTGACCCAGAGCCCTGCCACCCTGAGCCTGAGCCCTGGCGAAAGGGCCACC
CTGAGCTGCAGAGCCAGCCAGAGCGTGAGCAGCTACCTGGCCTGGTACCAGCAGAAGCCCGGACAGGCCCCCAGACTGCTGATCTAC
GACGCCAGCAACAGAGCCACCGGCATTCCCGCCAGATTCTCCGGCAGCGGCAGCGGAACCGACTTCACACTGACCATCAGCTCCTTA
GAACCCGAGGACTTCGCCGTGTACTACTGTCAGCAGAGAAGCAACTGGCCTCCCACCTTCGGCCAGGGCACAAAGGTGGAGATCAAG
GCTAGCGTGAAAGGGAAACACCTTTGTCCAAGTCCCCTATTTCCCGGACCTTCTAAGCCCTTTTGGGTGCTGGTGGTGGTTGGTGGA
GTCCTGGCTTGCTATAGCTTGCTAGTAACAGTGGCCTTTATTATTTTCTGGGTGAGTCGAAGAAGGTGTGGGCAGAAGAAAAAGCTA
GTGATCAACAGTGGCAATGGAGCTGTGGAGGACAGAAAGCCAAGTGGACTCAACGGAGAGGCCAGCAAGTCTCAGGAAATGGTGCAT
TTGGTGAACAAGGAGTCGTCAGAAACTCCAGACCAGTTTATGACAGCTGATGAGACAAGGAACCTGCAGAATGTGGACATGAAGATT
GGGGTGAGAGTGAAGTTCAGCAGGAGCGCAGACGCCCCCGCGTACCAGCAGGGCCAGAACCAGCTCTATAACGAGCTCAATCTAGGA
CGAAGAGAGGAGTACGATGTTTTGGACAAGAGACGTGGCCGGGACCCTGAGATGGGGGGAAAGCCGAGAAGGAAGAACCCTCAGGAA
GGCCTGTACAATGAACTGCAGAAAGATAAGATGGCGGAGGCCTACAGTGAGATTGGGATGAAAGGCGAGCGCCGGAGGGGCAAGGGG
CACGATGGCCTTTACCAGGGTCTCAGTACAGCCACCAAGGACACCTACGACGCCCTTCACATGCAGGCCCTGCCCCCTCGC DG05-CD28tm-CD3ζ (SEQ ID NO: 242)
ATGGAATGGACCTGGGTGTTTCTGTTCCTCCTGTCCGTGACCGCCGGAGTGCACTCCGAAGTGCAGCTGGTGCAGTCCGGCGGAGGA
CTGGTGAAACCCGGAGGAAGCCTCAGACTGAGCTGCGCCGGCAGCGGCTTTACCTTCTCCAGCTACTCCATGCACTGGCTGAGACAG
GCCCCTGGCAAGGGCCTGGAATGGGTCAGCGCCATCGGCACCGCCGGAGGCACATACTATGCCGACAGCGTGAAGGGCAGGTTCACC
ATCAGCAGGGACAACGCCAAGAACAGCCTGTACCTGCAGATGAACTCTCTGAGGGCCGAGGATACCGCTGTGTACTACTGCGCCAGG
GAGTACTTCTTTGGCAGCGGCAACTACGGATACTGGGGCCAGGGCACCCTGGTGACAGTGAGCTCCGCCGGAGGAGGAGGAAGCGGA
GGAGGCGGAAGCGGAGGAGGCGGCAGCGAAATCGTGCTGACCCAGAGCCCTGCCACCCTGAGCCTGAGCCCTGGCGAAAGGGCCACC
CTGAGCTGCAGAGCCAGCCAGAGCGTGAGCAGCTACCTGGCCTGGTACCAGCAGAAGCCCGGACAGGCCCCCAGACTGCTGATCTAC
GACGCCAGCAACAGAGCCACCGGCATTCCCGCCAGATTCTCCGGCAGCGGCAGCGGAACCGACTTCACACTGACCATCAGCTCCTTA
GAACCCGAGGACTTCGCCGTGTACTACTGTCAGCAGAGAAGCAACTGGCCTCCCACCTTCGGCCAGGGCACAAAGGTGGAGATCAAG
GCTAGCGTGAAAGGGAAACACCTTTGTCCAAGTCCCCTATTTCCCGGACCTTCTAAGCCCTTTTGGGTGCTGGTGGTGGTTGGTGGA
GTCCTGGCTTGCTATAGCTTGCTAGTAACAGTGGCCTTTATTATTTTCTGGGTGAGGAGTAAGAGGAGCAGGAGAGTGAAGTTCAGC
AGGAGCGCAGACGCCCCCGCGTACCAGCAGGGCCAGAACCAGCTCTATAACGAGCTCAATCTAGGACGAAGAGAGGAGTACGATGTT
TTGGACAAGAGACGTGGCCGGGACCCTGAGATGGGGGGAAAGCCGAGAAGGAAGAACCCTCAGGAAGGCCTGTACAATGAACTGCAG
AAAGATAAGATGGCGGAGGCCTACAGTGAGATTGGGATGAAAGGCGAGCGCCGGAGGGGCAAGGGGCACGATGGCCTTTACCAGGGT
CTCAGTACAGCCACCAAGGACACCTACGACGCCCTTCACATGCAGGCCCTGCCCCCTCGC DG05-CD28 (SEQ ID NO: 243)
ATGGAATGGACCTGGGTGTTTCTGTTCCTCCTGTCCGTGACCGCCGGAGTGCACTCCGAAGTGCAGCTGGTGCAGTCCGGCGGAGGA
CTGGTGAAACCCGGAGGAAGCCTCAGACTGAGCTGCGCCGGCAGCGGCTTTACCTTCTCCAGCTACTCCATGCACTGGCTGAGACAG
GCCCCTGGCAAGGGCCTGGAATGGGTCAGCGCCATCGGCACCGCCGGAGGCACATACTATGCCGACAGCGTGAAGGGCAGGTTCACC
ATCAGCAGGGACAACGCCAAGAACAGCCTGTACCTGCAGATGAACTCTCTGAGGGCCGAGGATACCGCTGTGTACTACTGCGCCAGG
GAGTACTTCTTTGGCAGCGGCAACTACGGATACTGGGGCCAGGGCACCCTGGTGACAGTGAGCTCCGCCGGAGGAGGAGGAAGCGGA
GGAGGCGGAAGCGGAGGAGGCGGCAGCGAAATCGTGCTGACCCAGAGCCCTGCCACCCTGAGCCTGAGCCCTGGCGAAAGGGCCACC
CTGAGCTGCAGAGCCAGCCAGAGCGTGAGCAGCTACCTGGCCTGGTACCAGCAGAAGCCCGGACAGGCCCCCAGACTGCTGATCTAC
GACGCCAGCAACAGAGCCACCGGCATTCCCGCCAGATTCTCCGGCAGCGGCAGCGGAACCGACTTCACACTGACCATCAGCTCCTTA
GAACCCGAGGACTTCGCCGTGTACTACTGTCAGCAGAGAAGCAACTGGCCTCCCACCTTCGGCCAGGGCACAAAGGTGGAGATCAAG
GCTAGCGTGAAAGGGAAACACCTTTGTCCAAGTCCCCTATTTCCCGGACCTTCTAAGCCCTTTTGGGTGCTGGTGGTGGTTGGTGGA
GTCCTGGCTTGCTATAGCTTGCTAGTAACAGTGGCCTTTATTATTTTCTGGGTGAGGAGTAAGAGGAGCAGGCTCCTGCACAGTGAC
TACATGAACATGACTCCCCGCCGCCCCGGGCCCACCCGCAAGCATTACCAGCCCTATGCCCCACCACGCGACTTCGCAGCCTATCGC
TCC -continued

APPENDIX A-AMINO ACID AND NUCLEIC ACID SEQUENCES

DG05-CD28tm (SEQ ID NO: 244)
ATGGAATGGACCTGGGTGTTTCTGTTCCTCCTGTCCGTGACCGCCGGAGTGCACTCCGAAGTGCAGCTGGTGCAGTCCGGCGGAGGA
CTGGTGAAACCCGGAGGAAGCCTCAGACTGAGCTGCGCCGGCAGCCGCTTTACCTTCTCCAGCTACTCCATGCACTCGCTGAGACAG
GCCCCTGGCAAGGGCCTGGAATGGGTCAGCGCCATCGGCACCGCCGGAGGCACATACTATGCCGACAGCGTGAAGGGCAGGTTCACC
ATCAGCAGGGACAACGCCAAGAACAGCCTGTACCTGCAGATGAACTCTCTGAGGGCCGAGGATACCGCTGTGTACTACTGCGCCAGG
GAGTACTTCTTTGGCAGCGGCAACTACGGATACTGGGGCCAGGGCACCCTGGTGACAGTGAGCTCCGCCGGAGGAGGAGGAAGCGGA
GGAGGCGGAAGCGGAGGAGGCGGCAGCGAAATCGTGCTGACCCAGAGCCCTGCCACCCTGAGCCTGAGCCCTGGCGAAAGGGCCACC
CTGAGCTGCAGAGCCAGCCAGAGCGTGAGCAGCTACCTGGCCTGGTACCAGCAGAAGCCCGGACAGGCCCCCAGACTGCTGATCTAC
GACGCCAGCAACAGAGCCACCGGCATTCCCGCCAGATTCTCCGGCAGCGGCAGCGGAACCGACTTCACACTGACCATCAGCTCCTTA
GAACCCGAGGACTTCGCCGTGTACTACTGTCAGCAGAGAAGCAACTGGCCTCCCACCTTCGGCCAGGGCACAAAGGTGGAGATCAAG
GCTAGCGTGAAAGGGAAACACCTTTGTCCAAGTCCCCTATTTCCCGGACCTTCTAAGCCCTTTTGGGTGCTGGTGGTGGTTGGTGGA
GTCCTGGCTTGCTATAGCTTGCTAGTAACAGTGGCCTTTATTATTTTCTGGGTGAQGAGTAAGAGGAGCAGGCTCCTGCACAGTGAC

DG03-CD28tm-DAP10-CD3ζ (SEQ ID NO: 245)
ATGGAATGGACCTGGGTGTTCCTGTTTCTGCTCTCCGTGACCGCCGGAGTGCACAGCGAGGTGCAGCTGGTCGAAAGCGGCGGAGGA
CTGGTGCAGCCTGGCGGCAGCCTGAGACTGAGCTGTGCCGCCTCCGGCTTCACCTTTAGCAGCTACGGAATGTCCTGGGTGAGACAG
GCTCCTGGCAAGGGCCTGGAACTGGTGGCCAGCATCAATAGCAACGGCGGCAGCACCTACTACCCTGATAGCGTGAAGGGCAGGTTC
ACCATCTCCAGGGACAACGCCAAGAACAGCCTGTACCTGCAGATGAACAGCCTCAGGGCCGAGGACACAGCCGTGTACTACTGCGCC
AGCGGCGACTATTGGGGACAGGGAACAACCGTGACCGTCAGCAGCGCCGGCGGCGGCGGCAGCGGCGGCGGCGGCAGCGGCGGCGGC
GGCTCCGATATCGTGATGACCCAGAGCCCCCTGTCCCTGCCTGTCACACCTGGCGAACCCGCCAGCATTAGCTGCAGGTCCAGCCAG
AGCCTGGTGTACAGCAATGGCGACACCTACCTGCACTGGTACCTGCAGAAGCCTGGCCAGAGCCCCCAGCTGCTGATCTACAAGGTG
AGCAACAGGTTCTCCGGAGTGCCTGACAGGTTCAGCGGCTCCGGCAGCGGAACCGATTTCACCCTCAAGATCAGCAGAGTGGAGGCC
GAGGACGTGGGCGTCTACTATTGTAGCCAGAGCACCCACGTGCCCTGGACCTTTGGCCAGGGCACCAAGGTGGAGATCAAAGCTAGC
GTGAAAGGGAAACACCTTTGTCCAAGTCCCCTATTTCCCGGACCTTCTAAGCCCTTTTGGGTGCTGGTGGTGGTTGGTGGAGTCCTG
GCTTGCTATAGCTTGCTAGTAACAGTGGCCTTTATTATTTTCTGGGTGAGGAGTAAGAGGAGCCTGTGCGCACGCCCACGCCGCAGC
CCCGCCCAAGAAGATGGCAAAGTCTACATCAACATGCCAGGCAGGGGCAAGCTTAGAGTGAAGTTCAGCAGGAGCGCAGACGCCCCC
GCGTACCAGCAGGGCCAGAACCAGCTCTATAACGAGCTCAATCTAGGACGAAGAGAGGAGTACGATGTTTTGGACAAGAGACGTGGC
CGGGACCCTGAGATGGGGGGAAAGCCGAGAAGGAAGAACCCTCAGGAAGGCCTGTACAATGAACTGCAGAAAGATAAGATGGCGGAG
GCCTACAGTGAGATTGGGATGAAAGGCGAGCGCCGGAGGGGCAAGGGGCACGATGGCCTTTACCAGGGTCTCAGTACAGCCACCAAG
GACACCTACGACGCCCTTCACATGCAGGCCCTGCCCCCTCGC

DG03-CD28tm-CD44-CD3ζ (SEQ ID NO: 246)
ATGGAATGGACCTGGGTGTTCCTGTTTCTGCTCTCCGTGACCGCCGGAGTGCACAGCGAGGTGCAGCTGGTCGAAAGCGGCGGAGGA
CTGGTGCAGCCTGGCGGCAGCCTGAGACTGAGCTGTGCCGCCTCCGGCTTCACCTTTAGCAGCTACGGAATGTCCTGGGTGAGACAG
GCTCCTGGCAAGGGCCTGGAACTGGTGGCCAGCATCAATAGCAACGGCGGCAGCACCTACTACCCTGATAGCGTGAAGGGCAGGTTC
ACCATCTCCAGGGACAACGCCAAGAACAGCCTGTACCTGCAGATGAACAGCCTCAGGGCCGAGGACACAGCCGTGTACTACTGCGCC
AGCGGCGACTATTGGGGACAGGGAACAACCGTGACCGTCAGCAGCGCCGGCGGCGGCGGCAGCGGCGGCGGCGGCAGCGGCGGCGGC
GGCTCCGATATCGTGATGACCCAGAGCCCCCTGTCCCTGCCTGTCACACCTGGCGAACCCGCCAGCATTAGCTGCAGGTCCAGCCAG
AGCCTGGTGTACAGCAATGGCGACACCTACCTGCACTGGTACCTGCAGAAGCCTGGCCAGAGCCCCCAGCTGCTGATCTACAAGGTG
AGCAACAGGTTCTCCGGAGTGCCTGACAGGTTCAGCGGCTCCGGCAGCGGAACCGATTTCACCCTCAAGATCAGCAGAGTGGAGGCC
GAGGACGTGGGCGTCTACTATTGTAGCCAGAGCACCCACGTGCCCTGGACCTTTGGCCAGGGCACCAAGGTGGAGATCAAAGCTAGC
GTGAAAGGGAAACACCTTTGTCCAAGTCCCCTATTTCCCGGACCTTCTAAGCCCTTTTGGGTGCTGGTGGTGGTTGGTGGAGTCCTG
GCTTGCTATAGCTTGCTAGTAACAGTGGCCTTTATTATTTTCTGGGTGAGTCGAAGAAGGTGTGGGCAGAAGAAAAAGCTAGTGATC
AACAGTGGCAATGGAGCTGTGGAGGACAGAAAGCCAAGTGGACTCAACGGAGAGGCCAGCAAGTCTCAGGAAATGGTGCATTTGGTG
AACAAGGAGTCGTCAGAAACTCCAGACCAGTTTATGACAGCTGATGAGACAAGGAACCTGCAGAATGTGGACATGAAGATTGGGGTG
AGAGTGAAGTTCAGCAGGAGCGCAGACGCCCCCGCGTACCAGCAGGGCCAGAACCAGCTCTATAACGAGCTCAATCTAGGACGAAGA
GAGGAGTACGATGTTTTGGACAAGAGACGTGGCCGGGACCCTGAGATGGGGGGAAAGCCGAGAAGGAAGAACCCTCAGGAAGGCCTG
TACAATGAACTGCAGAAAGATAAGATGGCGGAGGCCTACAGTGAGATTGGGATGAAAGGCGAGCGCCGGAGGGGCAAGGGGCACGAT
GGCCTTTACCAGGGTCTCAGTACAGCCACCAAGGACACCTACGACGCCCTTCACATGCAGGCCCTGCCCCCTCGC

DG03-CD28tm-4-1-BB-CD3ζ (SEQ ID NO: 247)
ATGGAATGGACCTGGGTGTTCCTGTTTCTGCTCTCCGTGACCGCCGGAGTGCACAGCGAGGTGCAGCTGGTCGAAAGCGGCGGAGGA
CTGGTGCAGCCTGGCGGCAGCCTGAGACTGAGCTGTGCCGCCTCCGGCTTCACCTTTAGCAGCTACGGAATGTCCTGGGTGAGACAG
GCTCCTGGCAAGGGCCTGGAACTGGTGGCCAGCATCAATAGCAACGGCGGCAGCACCTACTACCCTGATAGCGTGAAGGGCAGGTTC
ACCATCTCCAGGGACAACGCCAAGAACAGCCTGTACCTGCAGATGAACAGCCTCAGGGCCGAGGACACAGCCGTGTACTACTGCGCC
AGCGGCGACTATTGGGGACAGGGAACAACCGTGACCGTCAGCAGCGCCGGCGGCGGCGGCAGCGGCGGCGGCGGCAGCGGCGGCGGC
GGCTCCGATATCGTGATGACCCAGAGCCCCCTGTCCCTGCCTGTCACACCTGGCGAACCCGCCAGCATTAGCTGCAGGTCCAGCCAG
AGCCTGGTGTACAGCAATCGCGACACCTACCTGCACTGGTACCTGCAGAAGCCTGGCCAGAGCCCCCAGCTGCTGATCTACAAGGTG
AGCAACAGGTTCTCCGGAGTGCCTGACAGGTTCAGCGGCTCCGGCAGCGGAACCGATTTCACCCTCAAGATCAGCAGAGTGGAGGCC
GAGGACGTGGGCGTCTACTATTGTAGCCAGAGCACCCACGTGCCCTGGACCTTTGGCCAGGGCACCAAGGTGGAGATCAAAGCTAGC
GTGAAAGGGAAACACCTTTGTCCAAGTCCCCTATTTCCCGGACCTTCTAAGCCCTTTTGGGTGCTGGTGGTGGTTGGTGGAGTCCTG
GCTTGCTATAGCTTGCTAGTAACAGTGGCCTTTATTATTTTCTGGGTGAGGAGTAAGAGGAGCCTCGAGAAACGGGGCAGAAAGAAA
CTCCTGTATATATTCAAACAACCATTTATGAGACCAGTACAAACTACTCAAGAGGAAGATGGCTGTAGCTGCCGATTTCCAGAAGAA
GAAGAAGGAGGATGTGAACTGAAGCTTAGAGTGAAGTTCAGCAGGAGCGCAGACGCCCCCGCGTACCAGCAGGGCCAGAACCAGCTC
TATAACGAGCTCAATCTAGGACGAAGAGAGGAGTACGATGTTTTGGACAAGAGACGTGGCCGGGACCCTGAGATGGGGGGAAAGCCG
AGAAGGAAGAACCCTCAGGAAGGCCTGTACAATGAACTGCAGAAAGATAAGATGGCGGAGGCCTACAGTGAGATTGGGATGAAAGGC
GAGCGCCGGAGGGGCAAGGGGCACGATGGCCTTTACCAGGGTCTCAGTACAGCCACCAAGGACACCTACGACGCCCTTCACATGCAG
GCCCTGCCCCCTCGC

DG03-CD28tm-CD3ζ (SEQ ID NO: 248)
ATGGAATGGACCTGGGTGTTCCTGTTTCTGCTCTCCGTGACCGCCGGAGTGCACAGCGAGGTGCAGCTGGTCGAAAGCGGCGGAGGA
CTGGTGCAGCCTGGCGGCAGCCTGAGACTGAGCTGTGCCGCCTCCGGCTTCACCTTTAGCAGCTACGGAATGTCCTGGGTGAGACAG
GCTCCTGGCAAGGGCCTGGAACTGGTGGCCAGCATCAATAGCAACGGCGGCAGCACCTACTACCCTGATAGCGTGAAGGGCAGGTTC
ACCATCTCCAGGGACAACGCCAAGAACAGCCTGTACCTGCAGATGAACAGCCTCAGGGCCGAGGACACAGCCGTGTACTACTGCGCC
AGCGGCGACTATTGGGGACAGGGAACAACCGTGACCGTCAGCAGCGCCGGCGGCGGCGGCAGCGGCGGCGGCGGCAGCGGCGGCGGC
GGCTCCGATATCGTGATGACCCAGAGCCCCCTGTCCCTGCCTGTCACACCTGGCGAACCCGCCAGCATTAGCTGCAGGTCCAGCCAG

-continued

APPENDIX A-AMINO ACID AND NUCLEIC ACID SEQUENCES

AGCCTGGTGTACAGCAATGGCGACACCTACCTGCACTGGTACCTGCAGAAGCCTGGCCAGAGCCCCCAGCTGCTGATCTACAAGGTG
AGCAACAGGTTCTCCGGAGTGCCTGACAGGTTCAGCGGCTCCGGCAGCGGAACCGATTTCACCCTCAAGATCAGCAGAGTGGAGGCC
GAGGACGTGGGCGTCTACTATTGTAGCCAGAGCACCCACGTGCCCTGGACCTTTGGCCAGGGCACCAAGGTGGAGATCAAAGCTAGC
GTGAAAGGGAAACACCTTTGTCCAAGTCCCCTATTTCCCGGACCTTCTAAGCCCTTTTGGGTGCTGGTGGTGGTTGGTGGAGTCCTG
GCTTGCTATAGCTTGCTAGTAACAGTGGCCTTTATTATTTTCTGGGTGAGGAGTAAGAGGAGCAGGAGAGTGAAGTTCAGCAGGAGC
GCAGACGCCCCCGCGTACCAGCAGGGCCAGAACCAGCTCTATAACGAGCTCAATCTAGGACGAAGAGAGGAGTACGATGTTTTGGAC
AAGAGACGTGGCCGGGACCCTGAGATGGGGGGAAAGCCGAGAAGGAAGAACCCTCAGGAAGGCCTGTACAATGAACTGCAGAAAGAT
AAGATGGCGGAGGCCTACAGTGAGATTGGGATGAAAGGCGAGCGCCGGAGGGGCAAGGGGCACGATGGCCTTTACCAGGGTCTCAGT
ACAGCCACCAAGGACACCTACGACGCCCTTCACATGCAGGCCCTGCCCCCTCGC

DG03-CD28 (SEQ ID NO: 249)
ATGGAATGGACCTGGGTGTTCCTGTTTCTGCTCTCCGTGACCGCCGGAGTGCACAGCGAGGTGCAGCTGGTCGAAAGCGGCGGAGGA
CTGGTGCAGCCTGGCGGCAGCCTGAGACTGAGCTGTGCCGCCTCCGGCTTCACCTTTAGCAGCTACGGAATGTCCTGGGTGAGACAG
GCTCCTGGCAAGGGCCTGGAACTGGTGGCCAGCATCAATAGCAACGGCGGCAGCACCTACTACCCTGATAGCGTGAAGGGCAGGTTC
ACCATCTCCAGGGACAACGCCAAGAACAGCCTGTACCTGCAGATGAACAGCCTCAGGGCCGAGGACACAGCCGTGTACTACTGCGCC
AGCGGCGACTATTGGGGACAGGGAACAACCGTGACCGTCAGCAGCGCCGGCGGCGGCGGCAGCGGCGGCGGCGGCAGCGGCGGCGGC
GGCTCCGATATCGTGATGACCCAGAGCCCCCTGTCCCTGCCTGTCACACCTGGCGAACCCGCCAGCATTAGCTGCAGGTCCAGCCAG
AGCCTGGTGTACAGCAATGGCGACACCTACCTGCACTGGTACCTGCAGAAGCCTGGCCAGAGCCCCCAGCTGCTGATCTACAAGGTG
AGCAACAGGTTCTCCGGAGTGCCTGACAGGTTCAGCGGCTCCGGCAGCGGAACCGATTTCACCCTCAAGATCAGCAGAGTGGAGGCC
GAGGACGTGGGCGTCTACTATTGTAGCCAGAGCACCCACGTGCCCTGGACCTTTGGCCAGGGCACCAAGGTGGAGATCAAAGCTAGC
GTGAAAGGGAAACACCTTTGTCCAAGTCCCCTATTTCCCGGACCTTCTAAGCCCTTTTGGGTGCTGGTGGTGGTTGGTGGAGTCCTG
GCTTGCTATAGCTTGCTAGTAACAGTGGCCTTTATTATTTTCTGGGTGAGGAGTAAGAGGAGCAGGCTCCTGCACAGTGACTACATG
AACATGACTCCCCGCCGCCCCGGGCCCACCCGCAAGCATTACCAGCCCTATGCCCCACCACGCGACTTCGCAGCCTATCGCTCC

DG03-CD28tm (SEQ ID NO: 250)
ATGGAATGGACCTGGGTGTTCCTGTTTCTGCTCTCCGTGACCGCCGGAGTGCACAGCGAGGTGCAGCTGGTCGAAAGCGGCGGAGGA
CTGGTGCAGCCTGGCGGCAGCCTGAGACTGAGCTGTGCCGCCTCCGGCTTCACCTTTAGCAGCTACGGAATGTCCTGGGTGAGACAG
GCTCCTGGCAAGGGCCTGGAACTGGTGGCCAGCATCAATAGCAACGGCGGCAGCACCTACTACCCTGATAGCGTGAAGGGCAGGTTC
ACCATCTCCAGGGACAACGCCAAGAACAGCCTGTACCTGCAGATGAACAGCCTCAGGGCCGAGGACACAGCCGTGTACTACTGCGCC
AGCGGCGACTATTGGGGACAGGGAACAACCCTGACCGTCAGCAGCGCCGGCGGCCGCGGCAGCGGCGGCGGCGGCAGCGGCGGCGGC
GGCTCCGATATCGTGATGACCCAGAGCCCCCTGTCCCTGCCTGTCACACCTGGCGAACCCGCCAGCATTAGCTGCAGGTCCAGCCAG
AGCCTGGTGTACAGCAATGGCGACACCTACCTGCACTGGTACCTGCAGAAGCCTGGCCAGAGCCCCCAGCTGCTGATCTACAAGGTG
AGCAACAGGTTCTCCGGAGTGCCTGACAGGTTCAGCGGCTCCGGCAGCGGAACCGATTTCACCCTCAAGATCAGCAGAGTGGAGGCC
GAGGACGTGGGCGTCTACTATTGTAGCCAGAGCACCCACGTGCCCTGGACCTTTGGCCAGGGCACCAAGGTGGAGATCAAAGCTAGC
GTGAAAGGGAAACACCTTTGTCCAAGTCCCCTATTTCCCGGACCTTCTAAGCCCTTTTGGGTGCTGGTGGTGGTTGGTGGAGTCCTG
GCTTGCTATAGCTTGCTAGTAACAGTGGCCTTTATTATTTTCTGGGTG

Construct for expression of the NDMM Nrf2 (Keap1 inhibitor peptide) (SEQ ID NO: 251)
ATGATGGATTTGGAACTTCCCCCCCCAGGGCTCCCATCCCAACAAGACATGGATCTCATAGACATACTGTGGAGACAGGACATCGAT
CTGGGGGTCAGCCGCGAAGTTTTCGACTTTTCACAAAGGCGGAAAGAATATGAATTGGAAAAGCAGAAAAAAATTGGAAAAAGAACGC
CAGGAACAGCTTCAGAAGGAGCAGGAAAAAGCCTTTTTTGCCCAGCTTCAGCTGGACGAGGAAACAGGGGAATTTCTCCCCATCCAA
CCAGCCCAG Construct for expression of the NDMM human catalase (SEQ ID NO: 252)
ATGGCAGACAGTCGAGACCCTGCTagcGACCAAATGCAACATTGGAAAGAGCAACGGGCGGCCCAGAAAGCCGACGTTTTGACCACT
GGGGCAGGTAATCCTGTTGGAGATAAGCTGAACGTcATcACGGTTGGACCCCGGGGACCGCTGCTCGTTCAAGACGTGGTTTTTACG
GATGAGATGGCCCATTTTGATCGAGAGAGGATACCAGAAAGGGTTGTGCACGCTAAGGGCGCAGGTGCCTTCGGATATTTCGAGGTA
ACTCACGACATTACTAAGTATAGCAAGGCCAAGGTATTTGAACACATTGGCAAGAAGACGCCGATAGCGGTCCGATTCAGTACAGTG
GCGGGCGAGTCAGGTTCAGCCGATACCGTGAGAGATCCGAGAGGATTTGCCGTGAAATTTTATACAGAGGACGGCAACTGGGACTTG
GTAGGAAACAATACCCCAATATTTTTCATAAGGGACCCAATCCTTTTTCCCAGCTTTATTCATTCACAGAAGCGGAACCCACAAACG
CACTTGAAAGATCCTGACATGGTGTGGGATTTTTGGAGCTTGAGGCCAGAGAGCCTGCACCAAGTGAGCTTCTTGTTCAGCGACAGA
GGCATACCGGACGGTCATAGACACATGAACGGTTACGGTAGTCACACCTTCAAACTGGTGAACGCCAACGGAGAGGCTGTCTATTGT
AAGTTCCACTATAAAACCGATCAAGGCATCAAAAACCTGAGCGTAGAGGACGCAGCCCGCCTTTCTCAAGAAGATCCAGACTATGGG
ATCCGGGATCTCTTTAACGCCATAGCTACGGGTAAATATCCCTCTTGGACGTTCTATATCCAGGTAATGACATTCAATCAAGCAGAG
ACTTTCCCCTTTAACCCGTTTGACCTTACTAAAGTATGGCCGCATAAGGACTACCCTCTGATTCCCGTCGGCAAACTCGTGCTTAAC
AGGAATCCAGTCAACTATTTCGCAGAAGTCGAGCAAATCGCCTTTGACCCTTCTAACATGCCGCCGGGAATCGAAGCGTCACCGGAC
AAGATGCTTCAAGGTCGGCTTTTCGCATACCCCGACACTCACCGACACAGACTGGGTCCGAATTATCTTCACATACCTGTCAACTGC
CCATATAGAGCACGCGTTGCGAACTACCAGCGCGATGGTCCGATGTGCATGCAGGACAACCAGGGGGGGGCACCCAACTATTATCCA
AATTCATTTGGGGCGCCGGAACAACAACCGTCAGCCCTTGAACACTCCATCCAGTATTCTGGCGAAGTAAGACGCTTCAACACGGCT
AATGATGACAACGTTACACAGGTTAGAGCGTTTTATGTGAACGTCTTGAACGAGGAACAACGGAAACGACTTTGCGAAAACATAGCG
GGTCATTTGAAAGATGCTCAGATTTTTATCCAAAAAAAAGCCGTCAAAAATTTTACCGAAGTCCACCCCGATTACGGTTCACATATT
CAGGCCCTGTTGGATAAGTACAACGCGGAAAAGCCCAAGAATGCAATACACACGTTTGTTCAGAGCGGGAGCCACCTCGCTGCTCGA
GAGAAAGCAAATCTG Construct for expression of the NDMM BDNF (SEQ ID NO: 253)
ATGACGATCCTGTTTCTGACAATGGTGATTAGCTATTTCGGATGTATGAAAGCCGCCCCGATGAAGGAGGCCAATATCAGGGGACAA
GGTGGGCTGGCTTATCCGGGCGTAAGGACACACGGCACACTGGAGAGTGTGAACGGCCCGAAGGCCGGATCACGAGGATTGACGAGC
CTCGCAGATACGTTTGAGCATGTAATCGAAGAGCTCTTGGATGAAGACCAAAAGGTCCGCCCCAATGAGGAGAACAACAAAGACGCA
GACCTGTACACATCACGAGTTATGCTGTCAAGTCAAGTGCCGCTCGAACCACCACTCCTCTTTCTGCTGGAGGAGTACAAAAACTAT
TTGGACGCTGCTAACATGTCTATGCGAGTGCGCAGACATAGTGACCCTGCCAGACGCGGTGAGCTTTCAGTCTGTGATTCTATAAGT
GAGTGGGTAACCGCAGCAGATAAGAAGACTGCCGTAGACATGTCAGGGGGAACTGTGACTGTACTTGAAAAGGTTCCCGTTTCTAAA
GGGCAGCTCAAACAGTATTTCTATGAAACAAAGTGTAATCCAATGGGGTACACCAAGGAAGGTTGCAGGGGAATCGACAAGCGACAT
TGGAACAGTCAATGTCGGACCACTCAGAGCTACGTCCGCGCTCTCACGATGGATAGTAAGAAACGCATCGGGTGGAGATTCATCAGA
ATCGACACCTCTTGCGTCTGTACTCTTACAATTAAGCGAGGGCGA -continued

APPENDIX A-AMINO ACID AND NUCLEIC ACID SEQUENCES

Construct for expression of the NDMM IGF-1 (SEQ ID NO: 254)
ATGGGGAAAATCTCCTCTCTCCCTACCCAGTTGTTCAAGTGTTGCTTTTGTGACTTCTTGAAGGTAAAAATGCACACTATGTCATCC
AGTCACCTTTTTTATTTGGCTCTGTGCCTCCTCACATTCACCAGTTCAGCTACTGCCGGGCCTGAAACACTCTGCGGCGCCGAACTC
GTTGATGCGCTTCAATTCGTGTGTGGAGATAGGGGGTTTTACTTTAACAAGCCGACGGGTTATGGTAGCTCAAGTAGACGAGCGCCA
CAGACTGGAATAGTAGATGAATGCTGTTTCCGCTCATGCGACCTTCGCAGATTGGAAATGTACTGCGCTCCTCTTAAACCAGCAAAG
AGTGCGCGGTCCGTGCGAGCCCAACGACATACCGATATGCCAAAAACCCAGAAATATCAGCCGCCGTCTACCAACAAGAACACCAAG
AGTCAGAGGAGAAAGGGTTGGCCCAAGACGCACCCGGGTGGCGAACAAAAAGAAGGTACTGAGGCAAGTTTGCAAATTCGAGGAAAG
AAGAAAGAACAACGAAGAGAGATAGGTTCTCGCAATGCGGAATGTCGAGGCAAAAAAGGTAAG Forward primer human β-actin (SEQ ID NO: 255)
GGC CGA GGA CTT TGA TTG C Reverse primer human β-actin (SEQ ID NO: 256)
TGG GGT GGC TTT TAG GAT GG Forward primer human IL-4 (SEQ ID NO: 257)
GCT TCC CCC TCT GTT CTT CC Reverse primer human IL-4 (SEQ ID NO: 258)
GAT GTC TGT TAC GGT CAA CTC G Forward primer human IL-10 (SEQ ID NO: 259)
TCA AGC CGC ATG TGA ACT CC Reverse primer human IL-10 (SEQ ID NO: 260)
CAG GGA AGA AAT CGA TGA CAG C

The invention claimed is:

1. A nucleic acid which comprises a first nucleic acid which encodes a chimeric antigen receptor (CAR) comprising (i) at least one ligand binding moiety which binds to a misfolded or aggregated protein expressed in the central nervous system at site(s) of neurodegeneration which protein is selected from an amyloid beta protein, a mutant superoxide dismutase and human alpha-synuclein;

(ii) at least one signaling domain;

wherein the expression of (i) and (ii) are controlled by the same or different inducible or constitutive promoters; further wherein (i) the ligand binding moiety is DG05 (SEQ ID NO: 5); or (2) a polypeptide that comprises at least 90% sequence identity to DG05 (SEQ ID NO: 5), which comprises the same binding specificity and complementarity determining regions (CDRs) as DG05 (SEQ ID NO: 5)

and (ii) the signaling domain is selected from CD28-CD3ζ, 4-1BB-CD3ζ, DAP10-CD3ζ, CD44-CD3ζ, CTLA4-CD3ζ, CD28, DAP1ζ, 4-1BB and CD3ζ.

2. The nucleic acid of claim 1, wherein the ligand binding moiety in the CAR is DG05 (SEQ ID NO: 5).

3. The nucleic acid of claim 1, wherein the ligand binding moiety in the CAR is a polypeptide that comprises at least 95% sequence identity to DG05 (SEQ ID NO: 5), which comprises the same binding specificity and CDRs as DG05 (SEQ ID NO: 5).

4. The nucleic acid of claim 1, wherein the encoded CAR is selected from DG05-CD28-CD3ζ (SEQ ID NO: 24); DG05-CD28tm-DAP10-CD3ζ (SEQ ID NO: 40); DG05-CD28tm-CD44-CD3ζ (SEQ ID NO: 41); DG05-CD28tm-CD3ζ (SEQ ID NO: 42; DG05-CD28 (SEQ ID NO: 43); and DG05-CD28tm (SEQ ID NO: 44) or is a CAR that is identical to one of DG05-CD28-CD3ζ (SEQ ID NO: 24); DG05-CD28tm-DAP10-CD3ζ (SEQ ID NO: 40); DG05-CD28tm-CD44-CD3ζ (SEQ ID NO: 41); DG05-CD28tm-CD3ζ (SEQ ID NO: 42); DG05-CD28 (SEQ ID NO: 43); and DG05-CD28tm (SEQ ID NO: 44), except that the CAR does not comprise a nucleic acid encoding a ligand binding moiety which is identical to DG05 (SEQ ID NO: 5), and instead comprises a nucleic acid encoding a ligand binding moiety which comprises at least 90% sequence identity to DG05 (SEQ ID NO: 5), which ligand binding moiety comprises the same binding specificity and complementarity determining regions (CDRs) as DG05 (SEQ ID NO: 5).

5. The nucleic acid of claim 1, which is contained on a nucleic acid construct.

6. The nucleic acid of claim 5, wherein the nucleic acid construct comprises a plasmid or a virus.

7. The nucleic acid of claim 5, wherein the nucleic acid construct comprises a retroviral construct.

8. The nucleic acid of claim 1, which further comprises a second nucleic acid which encodes (i) at least one of a pro-neuronal factor, a nerve growth factor, or a neurotrophic factor;

(ii) at least one of a pro-neuronal factor, neurotrophic factor, or nerve growth factor selected from brain-derived neurotrophic factor (BDNF), ciliary neurotrophic factor (CNTF), glial cell-line derived neurotrophic factor (GDNF), interleukin-1 receptor antagonist (IL-1ra); interleukin-6 (IL-6); activated protein C (APC); thrombomodulin; tissue plasminogen activator (tPA); Protein deglycase DJ-1; a tissue inhibitor of metalloproteinases (TIMP), insulin-like growth factor-1 (IGF-1), vascular endothelial growth factor (VEGF), fibroblast growth factor (FGF), a bone morphogenetic protein (BMP), erythropoietin (EPO), thrombopoietin (TPO), and granulocyte-colony stimulating factor (G-CSF) and/or (iii) NDMM Nrf2 (Keap1 inhibitor peptide) (SEQ ID NO: 51); NDMM human catalase (SEQ ID NO: 52); NDMM BDNF (SEQ ID NO: 53); NDMM IGF-1 (SEQ ID NO: 54), and/or a construct comprising at least 90%, at least 95%, at least 98%, or at least 99% sequence identity to any one or more of the foregoing.

9. The nucleic acid of claim 2, which further comprises a second nucleic acid which encodes (i) at least one of a pro-neuronal factor, a nerve growth factor, or a neurotrophic factor;

(ii) at least one of a pro-neuronal factor, neurotrophic factor, or nerve growth factor selected from brain-derived neurotrophic factor (BDNF), ciliary neurotrophic factor (CNTF), glial cell-line derived neurotrophic factor (GDNF), interleukin-1 receptor antagonist (IL-1ra); interleukin-6 (IL-6); activated protein C (APC); thrombomodulin; tissue plasminogen activator (tPA); Protein deglycase DJ-1; a tissue inhibitor of metalloproteinases (TIMP), insulin-like growth factor-1 (IGF-1), vascular endothelial growth factor (VEGF), fibroblast growth factor (FGF), a bone morphogenetic protein (BMP), erythropoietin (EPO), thrombopoietin (TPO), and granulocyte-colony stimulating factor (G-CSF) and/or (iii) NDMM Nrf2 (Keap1 inhibitor peptide) (SEQ ID NO: 51); NDMM human catalase (SEQ ID NO: 52); NDMM BDNF (SEQ ID NO: 53); NDMM IGF-1 (SEQ ID NO: 54), and/or a construct comprising at least 90%, at least 95%, at least 98%, or at least 99% sequence identity to any one or more of the foregoing.

10. The nucleic acid of claim 4, which further comprises a second nucleic acid which encodes (i) at least one of a pro-neuronal factor, a nerve growth factor, or a neurotrophic factor;

(ii) at least one of a pro-neuronal factor, neurotrophic factor, or nerve growth factor selected from brain-derived neurotrophic factor (BDNF), ciliary neurotrophic factor (CNTF), glial cell-line derived neurotrophic factor (GDNF), interleukin-1 receptor antagonist (IL-1ra); interleukin-6 (IL-6); activated protein C (APC); thrombomodulin; tissue plasminogen activator (tPA); Protein deglycase DJ-1; a tissue inhibitor of metalloproteinases (TIMP), insulin-like growth factor-1 (IGF-1), vascular endothelial growth factor (VEGF), fibroblast growth factor (FGF), a bone morphogenetic protein (BMP), erythropoietin (EPO), thrombopoietin (TPO), and granulocyte-colony stimulating factor (G-CSF) and/or (iii) NDMM Nrf2 (Keap1 inhibitor peptide) (SEQ ID NO: 51); NDMM human catalase (SEQ ID NO: 52); NDMM BDNF (SEQ ID NO: 53); NDMM IGF-1 (SEQ ID NO: 54), and/or a construct comprising at least 90%, at least 95%, at least 98%, or at least 99% sequence identity to any one or more of the foregoing.

11. A recombinant cell which comprises a nucleic acid according to claim 1.

12. A recombinant cell which comprises a nucleic acid according to claim 2.

13. A recombinant cell which comprises a nucleic acid according to claim 3.

14. A recombinant cell which comprises a nucleic acid according to claim 4.

15. A recombinant cell according to claim 11, which is selected from:

(i) a human immune cell;

(ii) a T cell or T cell progenitor or an NK cell; and (iii) a Treg.

16. A recombinant cell according to claim 12, which is selected from:

(i) a human immune cell;

(ii) a T cell or T cell progenitor or an NK cell; and (iii) a Treg.

17. A recombinant cell according to claim 13, which is selected from:

(i) a human immune cell;

(ii) a T cell or T cell progenitor or an NK cell; and (iii) a Treg.

18. A recombinant cell according to claim 14, which is selected from:

(i) a human immune cell;

(ii) a T cell or T cell progenitor or an NK cell; and (iii) a Treg.

19. A recombinant cell according to claim 11, which is engineered to express (i) at least one nerve growth factor or neurotrophic factor and/or expresses IL-10 or a viral variant of IL-10;

(ii) at least one of a pro-neuronal factor, neurotrophic factor, or nerve growth factor selected from brain-derived neurotrophic factor (BDNF), ciliary neurotrophic factor (CNTF), glial cell-line derived neurotrophic factor (GDNF), interleukin-1 receptor antagonist (IL-1ra); interleukin-6 (IL-6); activated protein C (APC); thrombomodulin; tissue plasminogen activator (tPA); Protein deglycase DJ-1; a tissue inhibitor of metalloproteinases (TIMP), insulin-like growth factor-1 (IGF-1), vascular endothelial growth factor (VEGF), fibroblast growth factor (FGF), a bone morphogenetic protein (BMP), erythropoietin (EPO), thrombopoietin (TPO), and granulocyte-colony stimulating factor (G-CSF) and/or (iii) NDMM Nrf2 (Keap1 inhibitor peptide) (SEQ ID NO: 51); NDMM human catalase (SEQ ID NO: 52); NDMM BDNF (SEQ ID NO: 53); NDMM IGF-1 (SEQ ID NO: 54), and/or a construct comprising at least 90%, at least 95%, at least 98%, or at least 99% sequence identity to any one or more of the foregoing.

* * * * *